United States Patent
Beste et al.

(10) Patent No.: US 9,346,884 B2
(45) Date of Patent: May 24, 2016

(54) BIOLOGICAL MATERIALS RELATED TO C-MET

(71) Applicant: Ablynx N.V., Zwijnaarde (BE)

(72) Inventors: Gerald Beste, Ghent (BE); Guy Hermans, Merelbeke (BE); Soren Steffensen, Woluwe-Saint-Pierre (BE); Alexander Szyroki, Oldenburg (DE); Cedric Jozef Neotere Ververken, Merelbeke (BE); Tinneke Denayer, De Pinte (BE)

(73) Assignee: Ablynx N.V., Zwijnaarde (BE)

( * ) Notice: Subject to any disclaimer, the term of this patent is extended or adjusted under 35 U.S.C. 154(b) by 0 days.

(21) Appl. No.: 14/347,697

(22) PCT Filed: Oct. 1, 2012

(86) PCT No.: PCT/EP2012/069373
§ 371 (c)(1),
(2) Date: Mar. 27, 2014

(87) PCT Pub. No.: WO2013/045707
PCT Pub. Date: Apr. 4, 2013

(65) Prior Publication Data

US 2014/0341903 A1    Nov. 20, 2014
US 2015/0307612 A9    Oct. 29, 2015

Related U.S. Application Data

(63) Continuation-in-part of application No. 13/435,567, filed on Mar. 30, 2012, now Pat. No. 8,703,135.

(60) Provisional application No. 61/541,368, filed on Sep. 30, 2011.

(51) Int. Cl.
*A61K 39/395* (2006.01)
*C07K 16/28* (2006.01)
*G01N 33/574* (2006.01)
*A61K 39/00* (2006.01)

(52) U.S. Cl.
CPC ...... *C07K 16/2863* (2013.01); *G01N 33/57423* (2013.01); *G01N 33/57426* (2013.01); *G01N 33/57438* (2013.01); *G01N 33/57492* (2013.01); *A61K 2039/505* (2013.01); *C07K 2317/22* (2013.01); *C07K 2317/34* (2013.01); *C07K 2317/55* (2013.01); *C07K 2317/565* (2013.01); *C07K 2317/567* (2013.01); *C07K 2317/569* (2013.01); *C07K 2317/73* (2013.01); *C07K 2317/76* (2013.01); *C07K 2317/92* (2013.01); *G01N 2800/52* (2013.01)

(58) Field of Classification Search
None
See application file for complete search history.

(56) References Cited

U.S. PATENT DOCUMENTS

| 7,741,273 | B2 | 6/2010 | McKay |
| 8,337,845 | B2 | 12/2012 | Park et al. |
| 8,703,135 | B2 | 4/2014 | Beste et al. |
| 2008/0057063 | A1 | 3/2008 | Rinkenberger et al. |
| 2012/0244164 | A1 | 9/2012 | Beste et al. |
| 2014/0199295 | A1 | 7/2014 | Baumeister et al. |
| 2014/0205597 | A1 | 7/2014 | Baumeister et al. |
| 2014/0228546 | A1 | 8/2014 | Dombrecht et al. |
| 2014/0294847 | A1 | 10/2014 | Beste et al. |

FOREIGN PATENT DOCUMENTS

| WO | WO 2004/041862 A2 | 5/2004 |
| WO | WO 2004/041865 A2 | 5/2004 |
| WO | WO 2006/015371 A2 | 2/2006 |
| WO | WO 2006/122786 A2 | 11/2006 |
| WO | WO 2006/122787 A1 | 11/2006 |
| WO | WO 2006/129843 A2 | 12/2006 |
| WO | WO 2007/085814 A1 | 8/2007 |
| WO | WO 2007/126799 A2 | 11/2007 |
| WO | WO 2008/020079 A1 | 2/2008 |
| WO | WO 2008/028977 A2 | 3/2008 |
| WO | WO 2008/043821 A1 | 4/2008 |
| WO | WO 2008/096158 A2 | 8/2008 |
| WO | WO 2008/122787 A1 | 10/2008 |
| WO | WO 2008/142164 A2 | 11/2008 |
| WO | WO 2009/007427 A2 | 1/2009 |
| WO | WO 2009/068627 A2 | 6/2009 |
| WO | WO 2009/138519 A1 | 11/2009 |
| WO | WO 2009/147248 A2 | 12/2009 |
| WO | WO 2010/042815 A2 | 4/2010 |
| WO | WO 2010/108937 A2 | 9/2010 |
| WO | WO 2011/073954 A2 | 6/2011 |

(Continued)

OTHER PUBLICATIONS

Birchmeier et al., Met, metastasis, motility and more. Nat Rev Mol Cell Biol. Dec. 2003;4(12):915-25.
Bottaro et al., Identification of the hepatocyte growth factor receptor as the c-met proto-oncogene product. Science. Feb. 15, 1991;251(4995):802-4.
Burgess et al., Fully human monoclonal antibodies to hepatocyte growth factor with therapeutic potential against hepatocyte growth factor/c-Met-dependent human tumors. Cancer Res. Feb. 1, 2006;66(3):1721-9. Erratum in: Cancer Res. Jun. 1, 2006;66(11):5976.

(Continued)

*Primary Examiner* — Marianne P Allen
(74) *Attorney, Agent, or Firm* — Wolf, Greenfield & Sacks, P.C.

(57) ABSTRACT

The present invention relates to biological materials related to c-Met possibly in combination with VEGF and/or EGFR, and more in particular to polypeptides, nucleic acids encoding such polypeptides; to methods for preparing such polypeptides; to host cells expressing or capable of expressing such polypeptides; to compositions and in particular to pharmaceutical compositions that comprise such polypeptides, for prophylactic, therapeutic or diagnostic purposes. Methods and kits for assessing the responsiveness of a patient to c-Met therapy are also described and provided.

5 Claims, 7 Drawing Sheets

(56) References Cited

FOREIGN PATENT DOCUMENTS

| WO | WO 2011/110642 | * | 9/2011 |
|---|---|---|---|
| WO | WO 2012/042026 A2 | | 4/2012 |
| WO | WO 2013/024059 A2 | | 2/2013 |

OTHER PUBLICATIONS

Cao et al., Neutralizing monoclonal antibodies to hepatocyte growth factor/scatter factor (HGF/SF) display antitumor activity in animal models. Proc Natl Acad Sci U S A. Jun. 19, 2001;98(13):7443-8.

Cooper et al., Molecular cloning of a new transforming gene from a chemically transformed human cell line. Nature. Sep. 6-11, 1984;311(5981):29-33.

Deffar et al., Nanobodies—the new concept in antibody engineering. African Journal of Biotechnology. 2009;8(12):2645-2652.

Gibbs, Nanobodies. Sci Am. Aug. 2005;293(2):78-83.

Holliger et al., Engineered antibody fragments and the rise of single domains. Nat Biotechnol. Sep. 2005;23(9):1126-36.

Kakkar et al., Pharmacokinetics and safety of a fully human hepatocyte growth factor antibody, AMG 102, in cynomolgus monkeys. Pharm Res. Oct. 2007;24(10):1910-8. Epub May 23, 2007.

Klimov, Spontaneous emission of an atom in the presence of nanobodies. Quantum Electronics. 2001;31(7):569-586.

Liu et al, Targeting the c-MET signaling pathway for cancer therapy. Expert Opin Investig Drugs. Jul. 2008;17(7):997-1011.

Loyet et al., Technology comparisons for anti-therapeutic antibody and neutralizing antibody assays in the context of an anti-TNF pharmacokinetic study. J Immunol Methods. Jun. 30, 2009;345(1-2):17-28. doi: 10.1016/j.jim.2009.03.012. Epub Apr. 2, 2009.

Matsumoto et al., NK4 (HGF-antagonist/angiogenesis inhibitor) in cancer biology and therapeutics. Cancer Sci. Apr. 2003;94(4):321-7.

Mire-Sluis et al., Recommendations for the design and optimization of immunoassays used in the detection of host antibodies against biotechnology products. J Immunol Methods. Jun. 2004;289(1-2):1-16.

Nguyen et al., Improved gene transfer selectivity to hepatocarcinoma cells by retrovirus vector displaying single-chain variable fragment antibody against c-Met. Cancer Gene Ther. Nov. 2003;10(11):840-9.

Nieba et al., Disrupting the hydrophobic patches at the antibody variable/constant domain interface: improved in vivo folding and physical characterization of an engineered scFv fragment. Protein Eng. Apr. 1997;10(4):435-44.

Peng et al., Clinical immunogenicity specificity assessments: a platform evaluation. J Pharm Biomed Anal. Feb. 20, 2011;54(3):629-35. doi: 10.1016/j.jpba.2010.09.035. Epub Oct. 29, 2010.

Poelmans et al., Immunogenicity monitoring during preclinical development of Nanobodies®: comparing assay formats and species matrices. The AAPS Journal. vol. 12. No. 51. Jan. 1, 2010.

Ponzetto et al., A novel recognition motif for phosphatidylinositol 3-kinase binding mediates its association with the hepatocyte growth factor/scatter factor receptor. Mol Cell Biol. Aug. 1993;13(8):4600-8.

Revets et al., Nanobodies as novel agents for cancer therapy. Expert Opin Biol Ther. Jan. 2005;5(1):111-24.

Routledge et al., Reshaping antibodies for therapy—5. Prospects for producing non-immunogenic monoclonal antibodies. 1996. last accessed at http://www.path.cam.ac.uk/~mrc7/reshaping/index.html on Apr. 23, 2014.

Shankar et al., Recommendations for the validation of immunoassays used for detection of host antibodies against biotechnology products. J Pharm Biomed Anal. Dec. 15, 2008;48(5):1267-81. doi: 10.1016/j.jpba.2008.09.020. Epub Sep. 19, 2008.

Skottrup et al., Diagnostic evaluation of a nanobody with picomolar affinity toward the protease RgpB from Porphyromonas gingivalis. Anal Biochem. Aug. 15, 2011;415(2):158-67. doi: 10.1016/j.ab.2011.04.015. Epub Apr. 20, 2011.

Strothmeyer et al., Comparative analysis of predicted HLA binding of immunoglobulin idiotype sequences indicates T cell mediated immunosurveillance in follicular lymphoma. Blood. Sep. 9, 2010;116(10):1734-6. doi: 10.1182/blood-2010-02-270199. Epub Jun. 3, 2010.

Trojan et al., Immunoglobulin framework-derived peptides function as cytotoxic T-cell epitopes commonly expressed in B-cell malignancies. Nat Med. Jun. 2000;6(6):667-72.

Muyldermans et al., Recognition of antigens by single-domain antibody fragments: the superfluous luxury of paired domains. Trends Biochem Sci. Apr. 2001;26(4):230-5.

* cited by examiner

BIOLOGICAL MATERIALS RELATED TO C-MET

RELATED APPLICATIONS

This application is a national stage filing under 35 U.S.C. §371 of international application PCT/EP2012/069373, filed Oct. 1, 2012, which was published under PCT Article 21(2) in English, claims the benefit under 35 U.S.C. §§120 and 365(c) of U.S. application Ser. No. 13/435,567, filed Mar. 30, 2012, and claims the benefit under 35 U.S.C. §119(e) of U.S. provisional application Ser. No. 61/541,368, filed Sep. 30, 2011, the disclosures of which are incorporated by reference herein in their entireties.

FIELD OF THE INVENTION

The present invention relates to biological materials related to c-Met and more in particular to polypeptides, nucleic acids encoding such polypeptides; to methods for preparing such polypeptides; to host cells expressing or capable of expressing such polypeptides; to compositions and in particular to pharmaceutical compositions that comprise such polypeptides, for prophylactic, therapeutic or diagnostic purposes. Methods and kits for assessing the responsiveness of a patient to c-Met therapy are also described and provided.

BACKGROUND OF THE INVENTION

Receptor tyrosine kinases (RTKs) are key regulators of critical cellular processes such as cell growth, differentiation, neo-vascularization, and tissue repair. In addition to their importance in normal physiology, aberrant expression of certain RTKs has been implicated in the development and progression of many types of cancer. These RTKs have emerged as promising drug targets for cancer therapy.

The RTK c-Met is the cell surface receptor for hepatocyte growth factor (HGF), also known as scatter factor (Cooper et al. Nature 1984; 311:29-33; Bottaro et al. Science 1991; 251:802-4). HGF is a 90 kD multidomain glycoprotein that is highly related to members of the plasminogen serine protease family. It is secreted as a single-chain, inactive polypeptide by mesenchymal cells and is cleaved to its active α/β heterodimer extracellular form by a number of proteases (Birchmeier et al. Nat Rev Mol Cell Biol 2003; 4:915-25). The a chain $NH_2$-terminal portion contains the high-affinity c-Met receptor-binding domain, but the β chain is required to interact with the c-Met receptor for receptor activation (Matsumoto & Nakamura Cancer Sci 2003; 94:321-7). The c-Met receptor, like its ligand, is a disulfide-linked heterodimer consisting of extracellular α and β chains. The a chain, heterodimerized to the amino-terminal portion of the β chain, forms the major ligand-binding site in the extracellular domain. The carboxy-terminal tail of c-Met includes tyrosines Y1349 and Y1356, which, when phosphorylated, serve as docking sites for intracellular adaptor proteins, leading to downstream signaling (Ponzetto et al. Mol Cell Biol 1993; 13:4600-8). The c-Met/HGF pathway is the main driver of the invasive growth program, a series of events including cell proliferation, scattering, migration, survival, and invasion of tissues. Under normal circumstances, the invasive growth program is essential for correct organ formation during embryogenesis and in adult homeostasis. Importantly, it is also involved in tumorigenesis, tumor angiogenesis and metastasis.

The use of HGF- or c-Met-specific antibodies that prevent ligand/receptor binding result in growth inhibition and tumor regression by inhibiting proliferation and enhancing apoptosis. A combination of three monoclonal antibodies displayed high neutralizing activity to HGF in vitro and in vivo and showed significant tumor growth inhibition against autocrine HGF-Met-expressing glioma xenograft tumors (Cao et al. Proc Natl Acad Sci USA 2001; 98:7443-8). The strategy of using monoclonal antibodies allows for exclusive specificity against HGF/c-Met, a relatively long half-life compared to small-molecule kinase inhibitors, and the potential to elicit a host immune response against tumor cells (Liu et al. Expert Opin Investig Drugs 2008; 17:997-1011).

AMG102 (Amgen, Inc.) is a fully human $IgG_2$ monoclonal antibody that selectively binds and neutralizes HGF, thereby preventing its binding to c-Met and subsequent activation (Kakkar et al. Pharm Res 2007; 24:1910-8; Burgess et al. Cancer Res 2006; 66:1721-9).

One-armed 5D5 (OA5D5, MetMAb; Genentech) is a humanized, monovalent, antagonistic anti-c-Met antibody derived from the agonistic monoclonal antibody 5D5 (Nguyen et al, Cancer Gene Ther 2003; 10:840-9). MetMAb binds to c-Met with high affinity and remains on the cell surface with c-Met, preventing HGF binding and subsequent c-Met phosphorylation as well as downstream signaling activity and cellular responses.

Unfortunately, the use of large monoclonal and/or heavily engineered antibodies also carries a high manufacturing cost and results in suboptimal tumor penetration compared to other strategies.

According to the current biomedical understanding, drug resistance is caused by a complex network of proteins responsible for the regulation of cell proliferation, apoptosis, migration and invasion. Currently, no systematic description of growth factor receptor dependent signaling pathways is available. Indeed, the molecular pathways by which c-Met abnormalities drive cancer development are extremely complex and involve many interconnected signaling pathways, including both signaling molecules (such as Ras and PI3K), receptors (such as EGFR), and growth factors (such as VEGF).

Targeting serum albumin to extend the half-life of biological molecules such as e.g. immunoglobulin single variable domains has been described e.g. in WO2008/028977, WO04/041865 and WO08/122787, and non-published US application U.S. 61/500,464 of 23 Jun. 2011.

SUMMARY OF THE INVENTION

The art is in need of more potent c-Met (or herein also referred to as c-MET) antagonists having superior selectivity and specificity over small molecule drugs, an ability to modulate half life, and/or a superior tumor targeting, i.e., are smaller than conventional antibodies and have an albumin-based tumor targeting strategy. Furthermore, the art is in need of diagnostically, preventatively, and/or therapeutically suitable c-Met antagonists such as provided herein.

Immunoglobulin sequences, such as antibodies and antigen binding fragments derived therefrom (e.g. immunoglobulin single variable domains) are used to specifically target their respective antigens in research and therapeutic applications. The generation of immunoglobulin single variable domains such as e.g. VHHs may involve the immunization of an experimental animal such as a Llama, construction of phage libraries from immune tissue, selection of phage displaying antigen binding immunoglobulin single variable domains and screening of said domains and engineered constructs thereof for the desired specificities (WO 94/04678). Alternatively, similar immunoglobulin single variable domains such as e.g. dAbs can be generated by selecting phage displaying antigen binding immunoglobulin single variable domains directly from naive or synthetic libraries and subsequent screening of said domains and engineered constructs thereof for the desired specificities (Ward et al., Nature, 1989, 341: 544-6); Holt et al., Trends Biotechnol., 2003, 21(11):484-490; as well as for example WO 06/030220, WO 06/003388 and other published patent applications of Domantis Ltd.).

The present invention relates to particular polypeptides, also referred to as "polypeptide(s) of the invention" or "immunoglobulin single variable domain(s) of the invention" or "ISVD(s) of the invention" that comprise or, more preferably, essentially consist of (i) a first building block consisting essentially of one or more (preferably one) immunoglobulin single variable domain(s), wherein said immunoglobulin single variable domain(s) is (are) directed against c-Met and in particular against human c-Met; (ii) optionally a second building block consisting essentially of one or more (preferably one) immunoglobulin single variable domain(s), wherein said immunoglobulin single variable domain(s) is (are) directed against serum albumin and in particular against human serum albumin (and even more preferably wherein said immunoglobulin single variable domain is Alb11 or Alb23 (as herein defined)); (iii) optionally a third and/or fourth building block consisting essentially of one or more (preferably one) immunoglobulin single variable domain(s), wherein said immunoglobulin single variable domain(s) is (are) directed against EGFR, in particular human EGFR, and/or is (are) directed against VEGF, in particular human VEGF. Furthermore, the invention also relates to nucleic acids encoding such polypeptides; to methods for preparing such polypeptides; to host cells expressing or capable of expressing such polypeptides; to compositions and in particular to pharmaceutical compositions that comprise such polypeptides, nucleic acids and/or host cells; and to uses of such polypeptides, nucleic acids, host cells and/or compositions for prophylactic, therapeutic or diagnostic purposes. Methods and kits for assessing the responsiveness of a patient to c-Met therapy are also described and provided. Other aspects, embodiments, advantages and applications of the invention will become clear from the further description herein.

As already mentioned, in some specific, but non-limiting aspects (described in more detail herein), the invention provides: amino acid sequences that are directed against (as defined herein) c-Met and that are capable of inhibiting or blocking (fully, or partially, as further described herein) ligand binding, and in particular of inhibiting or blocking (fully or partially, as further described herein) the binding of HGF to c-Met (as further described herein). These amino acid sequences are also referred to herein as "c-Met-blocking amino acid sequences" or "c-Met-blocking building blocks". Preferably, these c-Met-blocking amino acid sequences are ISVD's (as described herein), in which case they are also referred to as "c-Met-blocking ISVD's". Preferably, any c-Met-blocking amino acid sequences, c-Met-blocking building blocks or c-Met-blocking ISVD's are such that they have blocking activity, i.e. block HGF binding to c-Met partially or completely, which can be determined by any suitable assay known to the person skilled in the art, such as, for instance, by an Alphascreen assay or by a FACS competition assay (such as described herein, e.g. Example 2.3.2 HGF/c-Met competition assay based on flow cytometric assay). Preferably, the blocking activity is determined by a FACS competition assay as described in Example 2.3.2. Preferably, the ISVD has a blocking activity or competition capacity in A549 cells of blocking or competing HGF binding c-Met with an $IC_{50}$ of less than 600 nM, but preferably, 500 nM, 400 nM, 300 nM, 200 nM, 100 nM or even less. For instance, the 04E09-like ISVD has a blocking activity or competition capacity in this assay with an IC50 of less than 100 nM, more preferably, less than 75 nM, 50 nM or even less, such as less than 20 nM or 15 nM, 10 nM, 5 nM, 4 nM, 3 nM, 2 nM, 1 nM or even more preferably of less than 0.75 nM or even less than 0.5 nM.

For instance, the 33H10-like ISVD has a blocking activity or competition capacity in this assay with an IC50 of less than 100 nM, more preferably, less than 75 nM, 50 nM or even less, such as less than 20 nM or 15 nM, 10 nM, 5 nM, 4 nM, 3 nM, 2 nM, 1 nM or even more preferably of less than 075 nM, 0.5 nM, 0.25 nM or even less than 0.1 nM. In one specific, but non-limiting aspect, (some of the) "c-Met-blocking amino acid sequences" or "c-Met-blocking building blocks" may be (and preferably also are) such that they are capable of inhibiting or blocking c-Met signalling (see e.g. Examples 2.4-2.6 and 22), for example in the phosphorylation assay used in Example 2.4, the proliferation assay of Example 2.5 and/or chemotaxis assay of Example 2.6. Preferably, any c-Met-blocking amino acid sequences, c-Met-blocking building blocks or c-Met-blocking ISVD's are such that they have blocking activity, i.e. block or inhibit HGF mediated c-Met phosphorylation partially or completely, which can be determined by any suitable assay known to the person skilled in the art, such as, for instance, by any suitable phosphorylation assay, such as, for instance, an HGF-induced c-Met phosphorylation assay as described herein. Preferably, the blocking activity or inhibiting capacity of phosphorylation is determined by an HGF mediated c-Met phosphorylation as described in Examples 1.6, 2.4 and 22. Preferably, the ISVD has a blocking activity or an inhibition capacity of ligand (e.g. HGF) induced Tyr 1349-phosphorylated c-Met in A549 tumor cells with an $IC_{50}$ of less than 600 nM, but preferably, 500 nM, 400 nM, 300 nM, 200 nM, 100 nM or even less. For instance, the 04E09-like ISVD has a blocking activity or competition capacity of in this assay with an IC50 of less than 100 nM, more preferably, less than 75 nM, 50 nM or even less, such as less than 40 nM or 30 nM, 25 nM, 20 nM, 15 nM, 14 nM, 13 nM or 12 nM or even more preferably of less than 11, 10, 9, 8 or 7 nM. For instance, the 33H10-like ISVD has a blocking activity or competition capacity of in this assay with an IC50 of less than 100 nM, more preferably, less than 75 nM, 50 nM or even less, such as less than 40 nM or 30 nM, 25 nM, 20 nM, 15 nM, 14 nM, 13 nM or 12 nM or even more preferably of less than 11, 10, 9, 8, 7, 6, 5, 4 or 3 nM.

Preferably, the blocking activity or inhibiting capacity of signalling is determined by an HGF-induced proliferation assay as described in Example 2.5 and 22. Preferably, the ISVD has a blocking activity or an inhibition capacity of ligand (e.g. HGF) induced proliferation of BxPC-3 cells with an IC50 of less than 600 nM, but preferably, 500 nM, 400 nM, 300 nM, 200 nM, 100 nM or even less. For instance, the 04E09-like ISVD has a blocking activity or competition capacity of in this assay with an IC50 of less than 100 nM, more preferably, less than 80 nM, 70 nM or even less, such as less than 60 nM or 50 nM, 45 nM, 40 nM, 35 nM, 30 nM or even more preferably of less than 20 nM, such as 15, 12, 10, 8, 7, 6, 5, 4, 3, or even less than 2 nM. For instance, the 33H10-like ISVD has a blocking activity or competition capacity of in this assay with an IC50 of less than 100 nM, more preferably, less than 80 nM, 70 nM or even less, such as less than 60 nM or 50 nM, 45 nM, 40 nM, 35 nM, 30 nM or even more preferably of less than 20 nM, such as 15, 12, 10, 8, 7, 6, 5, 4, 3, or even less than 2 nM.

Preferably, the blocking activity or inhibiting capacity of signalling is determined by an HGF-dependent chemotaxis assay as described in Example 2.6. Preferably, the ISVD has a blocking activity or an inhibition capacity of ligand (e.g. HGF) induced chemotaxis of A549 cells with an IC50 of less than 600 nM, but preferably, 500 nM, 400 nM, 300 nM, 200 nM, 150 nM or even less. For instance, the 04E09-like ISVD has a blocking activity or competition capacity of in this assay with an IC50 of less than 150 nM, more preferably, less than 100 nM, 90 nM, 80 nM or even less, such as less than 80 nM, 70 nM or 60 nM, 55 nM or 50 nM or even less, such as less than 60 nM or 50 nM, 45 nM, 40 nM, 35 nM, 30 nM or even more preferably of less than 20 nM, such as 15, 12, 10, 8, 7, 6, 5, 4, 3, or even less than 2 nM.

DESCRIPTION OF THE INVENTION

Figure 1:
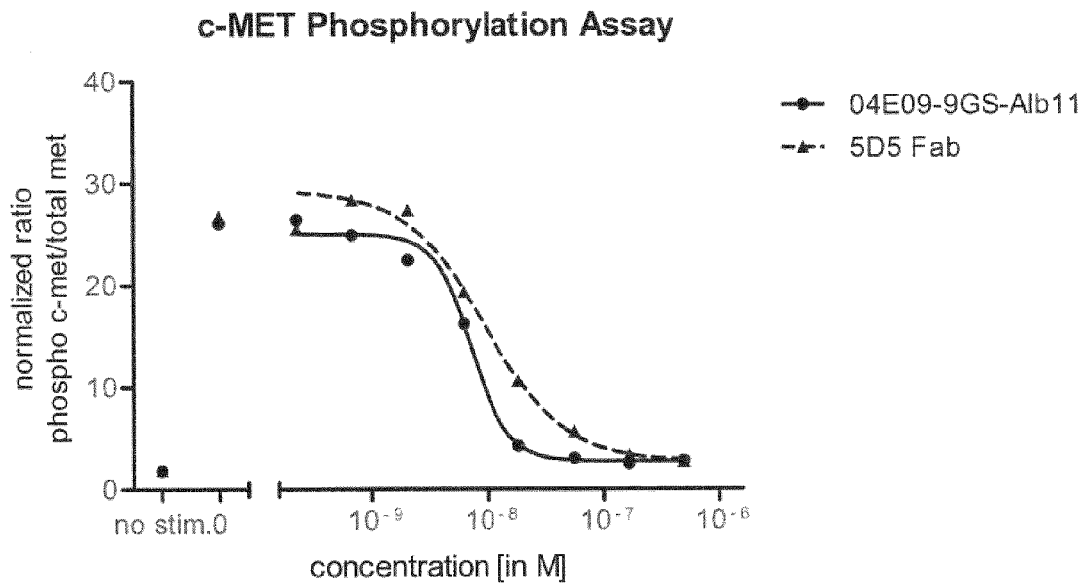
FIG. 1 shows that Nanobodies of the invention inhibit HGF-dependent c-Met phosphorylation. The normalized ratio (as described in Example 1, heading 1.6) is plotted against the concentration of the Nanobody or the 5D5 Fab (triangle). The tagged Nanobody 04E09-9G5-Alb11 (SEQ ID NO: 7) was plotted as closed circles (closed circles). The Nanobody was assayed together with 5D5 Fab, and plotted in the graph with full (SEQ ID NO: 7) and dotted (5D5 Fab) lines.

Definitions:
a) Unless indicated or defined otherwise, all terms used have their usual meaning in the art, which will be clear to the skilled person. Reference is for example made to the standard handbooks mentioned in paragraph a) on page 46 of WO 08/020079.

b) Unless indicated otherwise, the term "immunoglobulin single variable domain" or "ISVD" is used as a general term to include but not limited to antigen-binding domains or fragments such as $V_{HH}$ domains or $V_H$ or $V_L$ domains, respectively. The terms antigen-binding molecules or antigen-binding protein are used interchangeably and include also the term Nanobodies. The immunoglobulin single variable domains can be light chain variable domain sequences (e.g. a $V_L$-sequence), or heavy chain variable domain sequences (e.g. a $V_H$-sequence); more specifically, they can be heavy chain variable domain sequences that are derived from a conventional four-chain antibody or heavy chain variable domain sequences that are derived from a heavy chain antibody. Accordingly, the immunoglobulin single variable domains can be domain antibodies, or immunoglobulin sequences that are suitable for use as domain antibodies, single domain antibodies, or immunoglobulin sequences that are suitable for use as single domain antibodies, "dAbs", or immunoglobulin sequences that are suitable for use as dAbs, or Nanobodies, including but not limited to $V_{HH}$ sequences. The invention includes immunoglobulin sequences of different origin, comprising mouse, rat, rabbit, donkey, human and camelid immunoglobulin sequences. The immunoglobulin single variable domain includes fully human, humanized, otherwise sequence optimized or chimeric immunoglobulin sequences. The immunoglobulin single variable domain and structure of an immunoglobulin single variable domain can be considered—without however being limited thereto—to be comprised of four framework regions or "FR's", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively. It is noted that the terms Nanobody or Nanobodies are registered trademarks of Ablynx N.V. and thus may also be referred to as Nanobody® or Nanobodies®, respectively.

c) Unless indicated otherwise, the terms "immunoglobulin sequence", "sequence", "nucleotide sequence" and "nucleic acid" are as described in paragraph b) on page 46 of WO 08/020079.

d) Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta, Adv. Drug Deilv. Rev. 2006, 58 (5-6): 640-56; Levin and Weiss, Mol. Biosyst. 2006, 2(1): 49-57; Irving et al., J. Immunol. Methods, 2001, 248(1-2), 31-45; Schmitz et al., Placenta, 2000, 21 Suppl. A, S106-12, Gonzales et al., Tumour Biol., 2005, 26(1), 31-43, which describe techniques for protein engineering, such as affinity maturation and other techniques for improving the specificity and other desired properties of proteins such as immunoglobulins.

e) Amino acid residues will be indicated according to the standard three-letter or one-letter amino acid code. Reference is made to Table A-2 on page 48 of the International application WO 08/020079 of Ablynx N.V. entitled "Immunoglobulin single variable domains directed against IL-6R and polypeptides comprising the same for the treatment of diseases and disorders associated with Il-6 mediated signalling".

f) For the purposes of comparing two or more nucleotide sequences, the percentage of "sequence identity" between a first nucleotide sequence and a second nucleotide sequence may be calculated or determined as described in paragraph e) on page 49 of WO 08/020079 (incorporated herein by reference), such as by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position); or using a suitable computer algorithm or technique, again as described in paragraph e) on pages 49 of WO 08/020079 (incorporated herein by reference).

g) For the purposes of comparing two or more immunoglobulin single variable domains or other amino acid sequences such e.g. the polypeptides of the invention etc, the percentage of "sequence identity" between a first amino acid sequence and a second amino acid sequence (also referred to herein as "amino acid identity") may be calculated or determined as described in paragraph 1) on pages 49 and 50 of WO 08/020079 (incorporated herein by reference), such as by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e. as an "amino acid difference" as defined herein; or using a suitable computer algorithm or technique, again as described in paragraph f) on pages 49 and 50 of WO 08/020079 (incorporated herein by reference).

Also, in determining the degree of sequence identity between two immunoglobulin single variable domains, the skilled person may take into account so-called "conservative" amino acid substitutions, as described on page 50 of WO 08/020079.

Any amino acid substitutions applied to the polypeptides described herein may also be based on the analysis of the frequencies of amino acid variations between homologous proteins of different species developed by Schulz et al., Principles of Protein Structure, Springer-Verlag, 1978, on the analyses of structure forming potentials developed by Chou and Fasman, Biochemistry 13: 211, 1974 and Adv. Enzymol., 47: 45-149, 1978, and on the analysis of hydrophobicity patterns in proteins developed by Eisenberg et al., Proc. Natl. Acad Sci. USA 81: 140-144, 1984; Kyte & Doolittle; J Molec. Biol. 157: 105-132, 1981, and Goldman et al., Ann. Rev. Biophys. Chem. 15: 321-353, 1986, all incorporated herein in their entirety by reference. Information on the primary, secondary and tertiary structure of Nanobodies is given in the description herein and in the general background art cited above. Also, for this purpose, the crystal structure of a $V_{HH}$ domain from a llama is for example given by Desmyter et al., Nature Structural Biology, Vol. 3, 9, 803 (1996); Spinelli et al., Natural Structural Biology (1996); 3, 752-757; and Decanniere et al., Structure, Vol. 7, 4, 361 (1999). Further information about some of the amino acid residues that in conventional $V_H$ domains form the $V_H/V_L$ interface and potential camelizing substitutions on these positions can be found in the prior art cited above.

h) Immunoglobulin single variable domains and nucleic acid sequences are said to be "exactly the same" if they have 100% sequence identity (as defined herein) over their entire length.

i) When comparing two immunoglobulin single variable domains, the term "amino acid difference" refers to an insertion, deletion or substitution of a single amino acid residue on a position of the first sequence, compared to the second sequence; it being understood that two immunoglobulin single variable domains can contain one, two or more such amino acid differences.

j) When a nucleotide sequence or amino acid sequence is said to "comprise" another nucleotide sequence or amino acid sequence, respectively, or to "essentially consist of" another nucleotide sequence or amino acid sequence, this has the meaning given in paragraph i) on pages 51-52 of WO 08/020079.

k) The term "in essentially isolated form" has the meaning given to it in paragraph j) on pages 52 and 53 of WO 08/020079.

l) The terms "domain" and "binding domain" have the meanings given to it in paragraph k) on page 53 of WO 08/020079.

m) The terms "antigenic determinant" and "epitope", which may also be used interchangeably herein, have the meanings given to it in paragraph l) on page 53 of WO 08/020079.

n) As further described in paragraph m) on page 53 of WO 08/020079, an amino acid sequence (such as an antibody, a polypeptide of the invention, or generally an antigen binding protein or polypeptide or a fragment thereof) that can (specifically) bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

o) The term "specificity" has the meaning given to it in paragraph n) on pages 53-56 of WO 08/020079; and as mentioned therein refers to the number of different types of antigens or antigenic determinants to which a particular antigen-binding molecule or antigen-binding protein (such as a polypeptide of the invention) molecule can bind. The specificity of an antigen-binding protein can be determined based on affinity and/or avidity, as described on pages 53-56 of WO 08/020079 (incorporated herein by reference), which also describes some preferred techniques for measuring binding between an antigen-binding molecule (such as a polypeptide of the invention) and the pertinent antigen. Typically, antigen-binding proteins (such as the immunoglobulin single variable domains, and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^{-4}$ mol/liter (or any $K_A$ value lower than 10 liter/mol) is generally considered to indicate non-specific binding. Preferably, a monovalent immunoglobulin single variable domain of the invention will bind to the desired antigen with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein. As will be clear to the skilled person, and as described on pages 53-56 of WO 08/020079, the dissociation constant may be the actual or apparent dissociation constant. Methods for determining the dissociation constant will be clear to the skilled person, and for example include the techniques mentioned on pages 53-56 of WO 08/020079.

p) The half-life of an amino acid sequence, compound or polypeptide of the invention can generally be defined as described in paragraph o) on page 57 of WO 08/020079 and as mentioned therein refers to the time taken for the serum concentration of the amino acid sequence, compound or polypeptide to be reduced by 50%, in vivo, for example due to degradation of the sequence or compound and/or clearance or sequestration of the sequence or compound by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally be as described in paragraph o) on page 57 of WO 08/020079. As also mentioned in paragraph o) on page 57 of WO 08/020079, the half-life can be expressed using parameters such as the t1/2-alpha, t1/2 beta and the area under the curve (AUC). Reference is for example made to the Experimental Part below, as well as to the standard handbooks, such as Kenneth, A et al: Chemical Stability of Pharmaceuticals: A Handbook for Pharmacists and Peters et al, Pharmacokinete analysis: A Practical Approach (1996). Reference is also made to "Pharmacokinetics", M Gibaldi & D Perron, published by Marcel Dekker, 2nd Rev. edition (1982). The terms "increase in half-life" or "increased half-life" as also as defined in paragraph o) on page 57 of WO 08/020079 and in particular refer to an increase in the t1/2-beta, either with or without an increase in the t1/2-alpha and/or the AUC or both.

q) In respect of a target or antigen, the term "interaction site" on the target or antigen means a site, epitope, antigenic determinant, part, domain or stretch of amino acid residues on the target or antigen that is a site for binding to a ligand, receptor or other binding partner, a catalytic site, a cleavage site, a site for allosteric interaction, a site involved in multimerisation (such as homomerization or heterodimerization) of the target or antigen; or any other site, epitope, antigenic determinant, part, domain or stretch of amino acid residues on the target or antigen that is involved in a biological action or mechanism of the target or antigen. More generally, an "interaction site" can be any site, epitope, antigenic determinant, part, domain or stretch of amino acid residues on the target or antigen to which an amino acid sequence or polypeptide of the invention can bind such that the target or antigen (and/or any pathway, interaction, signalling, biological mechanism or biological effect in which the target or antigen is involved) is modulated (as defined herein).

r) An immunoglobulin single variable domain or polypeptide is said to be "specific for" a first target or antigen compared to a second target or antigen when it binds to the first antigen with an affinity/avidity (as described above, and suitably expressed as a $K_D$ value, $K_A$ value, $K_{off}$ rate and/or $K_{on}$ rate) that is at least 10 times, such as at least 100 times, and preferably at least 1000 times, and up to 10.000 times or more better than the affinity with which said amino acid sequence or polypeptide binds to the second target or polypeptide. For example, the first antigen may bind to the target or antigen with a $K_D$ value that is at least 10 times less, such as at least 100 times less, and preferably at least 1000 times less, such as 10.000 times less or even less than that, than the $K_D$ with which said amino acid sequence or polypeptide binds to the second target or polypeptide. Preferably, when an immunoglobulin single variable domain or polypeptide is "specific for" a first target or antigen compared to a second target or antigen, it is directed against (as defined herein) said first target or antigen, but not directed against said second target or antigen.

s) The terms "cross-block", "cross-blocked" and "cross-blocking" are used interchangeably herein to mean the ability of an immunoglobulin single variable domain or polypeptide to interfere with the binding of the natural ligand HGF to c-Met or with the binding of the natural ligand EGF to EGFR, or with the binding of the natural ligand VEGF to VEGF receptors (such as VEGFR-1R (Flt-1), VEGFR-2 (KDR/Flk-1) and/or VEGFR-3 (Flt-4)), respectively. The extent to which an immunoglobulin single variable domain or polypeptide of the invention is able to interfere with the binding of another compound such as the natural ligand to its target, e.g. c-Met, VEGF or EGFR, and therefore whether it can be said to cross-block according to the invention, can be determined using competition binding assays. One particularly suitable quantitative cross-blocking assay uses a FACS- or an ELISA-based approach or Alphascreen to measure competition between the labelled (e.g. His tagged or biotinylated) immunoglobulin single variable domain or polypeptide according to the invention and the other binding agent in terms of their binding to the target. The experimental part generally describes suitable FACS-, ELISA- or Alphascreen-displacement-based assays for determining whether a binding molecule cross-blocks or is capable of cross-blocking an immunoglobulin single variable domain or polypeptide according to the invention. It will be appreciated that the assay can be used with any of the immunoglobulin single variable domains or other binding agents described herein. Thus, in general, a cross-blocking amino acid sequence or other binding agent according to the invention is for example one which will bind to the target in the above cross-blocking assay such that, during the assay and in the presence of a second amino acid sequence or other binding agent of the invention, the recorded displacement of the immunoglobulin single variable domain or polypeptide according to the invention is between 60% and 100% (e.g. in ELISA/Alphascreen based competition assay) or between 80% to 100% (e.g. in FACS based competition assay) of the maximum theoretical displacement (e.g. displacement by cold (e.g. unlabeled) immunoglobulin single variable domain or polypeptide that needs to be cross-blocked) by the to be tested potentially cross-blocking agent that is present in an amount of 0.01 mM or less (cross-blocking agent may be another conventional monoclonal antibody such as IgG, classic monovalent antibody fragments (Fab, scFv)) and engineered variants (e.g. diabodies, triabodies, minibodies, VHHs, dAbs, VHs, VLs).

t) An amino acid sequence such as e.g. an immunoglobulin single variable domain or polypeptide according to the invention is said to be a "VHH1 type immunoglobulin single variable domain" or "VHH type 1 sequence", if said VHH1 type immunoglobulin single variable domain or VHH type 1 sequence has 85% identity (using the VHH1 consensus sequence as the query sequence and use the blastp algorithm with standard setting, i.e. blosom62 scoring matrix) to the VHH1 consensus sequence (SEQ ID NO: 99: QVQLVESGGGLVQPGGSLRLSCAASG- FTLDYYAIGWFRQAPGKEREGVSCISSS- DGSTYYADSVK GRFTISRDNAKNTVYLQMNSLK- PEDTAVYYCAA) and optionally has a cysteine in position 50, i.e. C50 (using Kabat numbering).

u) An amino acid sequence such as e.g. an immunoglobulin single variable domain or polypeptide according to the invention is said to be "cross-reactive" for two different antigens or antigenic determinants (such as serum albumin from two different species of mammal, such as human serum albumin and cynomolgus monkey serum albumin) if it is specific for (as defined herein) both these different antigens or antigenic determinants.

v) As further described in paragraph q) on pages 58 and 59 of WO 08/020079 (incorporated herein by reference), the amino acid residues of an immunoglobulin single variable domain are numbered according to the general numbering for $V_H$ domains given by Kabat et al. ("Sequence of proteins of immunological interest", US Public Health Services, NIH Bethesda, Md., Publication No. 91), as applied to $V_{HH}$ domains from Camelids in the article of Riechmann and Muyldermans, J. Immunol. Methods 2000 Jun. 23; 240 (1-2): 185-195 (see for example FIG. 2 of this publication), and accordingly FR1 of an immunoglobulin single variable domain comprises the amino acid residues at positions 1-30, CDR1 of an immunoglobulin single variable domain comprises the amino acid residues at positions 31-35, FR2 of an immunoglobulin single variable domain comprises the amino acids at positions 36-49, CDR2 of an immunoglobulin single variable domain comprises the amino acid residues at positions 50-65, FR3 of an Immunoglobulin single variable domain comprises the amino acid residues at positions 66-94, CDR3 of an immunoglobulin single variable domain comprises the amino acid residues at positions 95-102, and FR4 of an immunoglobulin single variable domain comprises the amino acid residues at positions 103-113.

w) The Figures, Sequence Listing and the Experimental Part/ Examples are only given to further illustrate the invention and should not be interpreted or construed as limiting the scope of the invention and/or of the appended claims in any way, unless explicitly indicated otherwise herein.

1. Polypeptides of the Invention and Uses Thereof 1.1 Anti-c-Met Building Blocks The polypeptides of the present invention can generally be used to modulate, and in particular inhibit and/or prevent, binding of c-Met and in particular human c-Met (SEQ ID NO: 1) to HGF and in particular human HGF (Swiss Prot database: P14210), and thus to modulate, and in particular inhibit or prevent, the signalling that is mediated by c-Met and in particular human c-Met (SEQ ID NO: 1) and/or HGF and in particular human HGF (Swiss Prot database: P14210), to modulate the biological pathways in which c-Met and in particular human c-Met (SEQ ID NO: 1) and/or HGF and in particular human HGF are involved, and/or to modulate the biological mechanisms, responses and effects associated with such signalling or these pathways.

As such, the polypeptides and compositions of the present invention can be used for the diagnosis, prevention and treatment of diseases and disorders of the present invention (herein also "diseases and disorders of the present invention") and include, but are not limited to cancer, e.g., carcinomas, gliomas, mesotheliomas, melanomas, lymphomas, leukemias, adenocarcinomas: breast cancer, ovarian cancer, cervical cancer, glioblastoma, multiple myeloma (including monoclonal gammopathy of undetermined significance, asymptomatic and symptomatic myeloma), prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, vaginal cancer, uterine cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma, Kaposi's sarcoma, multicentric Castleman's disease or AIDS-associated primary effusion lymphoma, neuroectodermal tumors, rhabdomyosarcoma (see e.g. Cancer, Principles and practice (DeVita, V. T. et al. eds 1997) for additional cancers); as well as any metastasis of any of the above cancers, as well as non-cancer indications such as nasal polyposis; as well as other disorders and diseases described herein. In particular, the polypeptides and compositions of the present invention can be used for the diagnosis, prevention and treatment of diseases involving c-Met mediated metastasis, chemotaxis, cell adhesion, trans endothelial migration, cell proliferation and/or survival, in particular non-small cell lung cancer and multiple myeloma. The polypeptides and compositions of the present invention can also be used for the diagnosis, prevention and/or treatment of bone disease in bone metastatic cancer, including multiple myeloma. The polypeptides and compositions of the present invention can also be used for the diagnosis, prevention and/or treatment of osteolytic lesions in bone metastatic cancer, including multiple myeloma.

Generally, said "diseases and disorders of the present invention" can be defined as diseases and disorders that can be diagnosed, prevented and/or treated, respectively, by suitably administering to a subject in need thereof (i.e. having the disease or disorder or at least one symptom thereof and/or at risk of attracting or developing the disease or disorder) of either a polypeptide or composition of the invention (and in particular, of a pharmaceutically active amount thereof) and/ or of a known active principle active against c-Met and in particular human c-Met (SEQ ID NO: 1) or a biological pathway or mechanism in which c-Met and in particular human c-Met (SEQ ID NO: 1) is involved (and in particular, of a pharmaceutically active amount thereof).

In particular, the polypeptides of the present invention can be used for the diagnosis, prevention and treatment of diseases and disorders of the present invention which are characterized by excessive and/or unwanted HGF and in particular human HGF signalling mediated by c-Met and in particular human c-Met (SEQ ID NO: 1) or by the pathway(s) in which c-Met and in particular human c-Met (SEQ ID NO: 1) is involved (e.g. HGF/c-Met axis). Examples of such diseases and disorders of the present invention will again be clear to the skilled person based on the disclosure herein.

Thus, without being limited thereto, the immunoglobulin single variable domains and polypeptides of the invention can for example be used to diagnose, prevent and/or to treat all diseases and disorders that are currently being diagnosed, prevented or treated with active principles that can modulate c-Met and in particular human c-Met (SEQ ID NO: 1)-mediated signalling, such as those mentioned in the diseases and prior art cited above. It is also envisaged that the polypeptides of the invention can be used to diagnose, prevent and/or to treat all diseases and disorders for which treatment with such active principles is currently being developed, has been proposed, or will be proposed or developed in the future. In addition, it is envisaged that, because of their favourable properties as further described herein, the polypeptides of the present invention may be used for the diagnosis, prevention and treatment of other diseases and disorders than those for which these known active principles are being used or will be proposed or developed; and/or that the polypeptides of the present invention may provide new methods and regimens for treating the diseases and disorders described herein.

The present invention thus relates to immunoglobulin single variable domains and/or polypeptides of the invention for use in therapy.

Other applications and uses of the immunoglobulin single variable domains and polypeptides of the invention will become clear to the skilled person from the further disclosure herein.

Generally, it is an object of the invention to provide pharmacologically active agents, as well as compositions comprising the same, that can be used in the diagnosis, prevention and/or treatment of diseases and/or disorders of the invention; and to provide methods for the diagnosis, prevention and/or treatment of such diseases and disorders that involve the administration and/or use of such agents and compositions.

In particular, it is an object of the invention to provide such pharmacologically active agents, compositions and/or methods that have certain advantages compared to the agents, compositions and/or methods that are currently used and/or known in the art. These advantages will become clear from the further description below.

More in particular, it is an object of the invention to provide therapeutic proteins that can be used as pharmacologically active agents, as well as compositions comprising the same, for the diagnosis, prevention and/or treatment of diseases and/or disorders of the invention and of the further diseases and disorders mentioned herein; and to provide methods for the diagnosis, prevention and/or treatment of such diseases and disorders that involve the administration and/or the use of such therapeutic proteins and compositions.

Accordingly, it is a specific object of the present invention to provide immunoglobulin single variable domains that are directed against c-Met, in particular against c-Met from a warm-blooded animal, more in particular against c-Met from a mammal such as e.g. mouse, and especially against human c-Met (SEQ ID NO: 1); and to provide proteins and polypeptides comprising or essentially consisting of at least one such immunoglobulin single variable domain.

In particular, it is a specific object of the present invention to provide such immunoglobulin single variable domains and such proteins and/or polypeptides that are suitable for prophylactic, therapeutic and/or diagnostic use in a warm-blooded animal, and in particular in a mammal, and more in particular in a human being.

More in particular, it is a specific object of the present invention to provide such immunoglobulin single variable domains and such proteins and/or polypeptides that can be used for the prevention, treatment, alleviation and/or diagnosis of one or more diseases, disorders or conditions associated with c-Met and/or mediated by c-Met (such as the diseases, disorders and conditions mentioned herein) in a warm-blooded animal, in particular in a mammal, and more in particular in a human being.

It is also a specific object of the invention to provide such immunoglobulin single variable domains and such proteins and/or polypeptides that can be used in the preparation of pharmaceutical or veterinary compositions for the prevention and/or treatment of one or more diseases, disorders or conditions associated with and/or mediated by c-Met (such as the diseases, disorders and conditions mentioned herein) in a warm-blooded animal, in particular in a mammal, and more in particular in a human being.

In the invention, generally, these objects are achieved by the use of the immunoglobulin single variable domains, proteins, polypeptides and compositions that are described herein.

In general, the invention provides immunoglobulin single variable domains that are directed against (as defined herein) and/or can specifically bind (as defined herein) to c-Met and in particular human c-Met (SEQ ID NO: 1); as well as compounds and constructs, and in particular proteins and polypeptides, that comprise at least one such amino acid sequence.

More in particular, the invention provides immunoglobulin single variable domains and polypeptides that can bind to c-Met and in particular human c-Met (SEQ ID NO: 1) with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein; as well as compounds and constructs, and in particular proteins and polypeptides, that comprise at least one such amino acid sequence.

In particular aspect, the immunoglobulin single variable domains and/or polypeptides of the invention are such that they:
  bind to human c-Met (SEQ ID NO: 1) with an IC50 of 1.2 nM or lower, more preferably of 500 pM or lower, even more preferably of 200 pM or lower, most preferably of 150 pM or lower in an Alphascreen assay as e.g. described in the experimental part (see Example 2.3.1), and wherein the polypeptides comprise only one human c-Met binding immunoglobulin single variable domain unit, and wherein full displacement means an average HGF displacement of about 60% to 80% and more, preferably 95% or more (e.g. when measured according to the ligand displacement assay in Example 2.3.1);
and/or such that they:
  fully displace human HGF from human c-Met (SEQ ID NO: 1) at an average IC50 value of 2.5 nM or less, more preferably at an average IC50 value of 2 nM or less, even more preferably at an average IC50 value of 1.5 nM or less in an assay as e.g. described in the experimental part (Example 2.3), and wherein the polypeptides comprise only one human c-Met binding immunoglobulin single variable domain unit, and wherein full displacement means an average HGF displacement of about 60% to 80% and more, preferably 95% or more (e.g. when measured according to the ligand displacement assay in Example 2.3.2);

Some preferred technical values for binding, displacing, migration or other in vivo and/or in vitro potency of the immunoglobulin single variable domains or polypeptides of the invention to c-Met and in particular human c-Met (SEQ ID NO: 1) will become clear from the further description and examples herein.

For binding to c-Met and in particular human c-Met (SEQ ID NO: 1), an amino acid sequence of the invention will usually contain within its amino acid sequence one or more amino acid residues or one or more stretches of amino acid residues (i.e. with each "stretch" comprising two or amino acid residues that are adjacent to each other or in close proximity to each other, i.e. in the primary or tertiary structure of the amino acid sequence) via which the amino acid sequence of the invention can bind to c-Met and in particular human c-Met (SEQ ID NO: 1), which amino acid residues or stretches of amino acid residues thus form the "site" for binding to c-Met and in particular human c-Met (SEQ ID NO: 1) (also referred to herein as the "antigen binding site").

The immunoglobulin single variable domains provided by the invention are preferably in essentially isolated form (as defined herein), or form part of a protein or polypeptide of the invention (as defined herein), which may comprise or essentially consist of one or more immunoglobulin single variable domains of the invention and which may optionally further comprise one or more further immunoglobulin single variable domains (all optionally linked via one or more suitable linkers). For example, and without limitation, a preferred aspect of the invention provides a polypeptide consisting essentially of one immunoglobulin single variable domain directed against human c-Met and an immunoglobulin single variable domain directed against human serum albumin linked by a peptide linker (as defined herein), so as to provide a bispecific polypeptide of the invention, respectively, and/or an immunoglobulin single variable domain directed against human EGFR also linked by a peptide linker (as defined herein), so as to provide a further bispecific or a trispecific polypeptide of the invention, all as described herein. Such a protein or polypeptide may also be in essentially isolated form (as defined herein).

The immunoglobulin single variable domains and polypeptides of the invention as such preferably essentially consist of a single amino acid chain that is not linked via disulphide bridges to any other amino acid sequence or chain (but that may or may not contain one or more intramolecular disulphide bridges. For example, it is known that agent of the invention—as described herein—may sometimes contain a disulphide bridge between CDR3 and CDR1 or FR2). However, it should be noted that one or more immunoglobulin single variable domains of the invention may be linked to each other and/or to other immunoglobulin single variable domains (e.g. via disulphide bridges) to provide peptide constructs that may also be useful in the invention (for example Fab' fragments, F(ab')$_2$ fragments, ScFv constructs, "diabodies" and other multispecific constructs. Reference is for example made to the review by Holliger and Hudson, Nat Biotechnol. 2005; 23:1126-36 (incorporated by reference).

Generally, when an amino acid sequence of the invention (or a compound, construct or polypeptide comprising the same) is intended for administration to a subject (for example for therapeutic and/or diagnostic purposes as described herein), it is preferably either an amino acid sequence that does not occur naturally in said subject; or, when it does occur naturally in said subject, is in essentially isolated form (as defined herein).

It will also be clear to the skilled person that for pharmaceutical use, the immunoglobulin single variable domains of the invention (as well as compounds, constructs and polypeptides comprising the same) are preferably directed against human c-Met and in particular human c-Met (SEQ ID NO: 1); whereas for veterinary purposes, the immunoglobulin single variable domains and polypeptides of the invention are preferably directed against c-Met from the species to be treated, or at least cross-reactive with c-Met from the species to be treated.

Furthermore, an amino acid sequence of the invention may optionally, and in addition to the at least one binding site for binding against c-Met and in particular human c-Met (SEQ ID NO: 1), contain one or more further binding sites for binding against other antigens, proteins or targets.

The efficacy of the immunoglobulin single variable domains and polypeptides of the invention, and of compositions comprising the same, can be tested using any suitable in vitro assay, cell-based assay, in vivo assay and/or animal model known per se, or any combination thereof, depending on the specific disease or disorder involved. Suitable assays and animal models will be clear to the skilled person, and for example include ligand displacement assays (Burgess et al., Cancer Res 2006 66:1721-9), dimerization assays (WO2009/007427A2, Goetsch, 2009), signaling assays (Burgess et al., Mol Cancer Ther 9:400-9), proliferation/survival assays (Pacchiana et al., J Biol Chem 2010 September M110.134031), cell adhesion assays (Holt et al, Haematologica 2005 90:479-88) and migration assays (Kong-Beltran et al, Cancer Cell 6:75-84), endothelial cell sprouting assays (Wang et al, J Immunol. 2009; 183:3204-11), osteoblast differentiation assay, ALP assay (Standal et al., Blood 2007 Apr. 1; 109(7): 3024-30), and in vivo xenograft models (Jin et al, Cancer Res. 2008 68:4360-8), as well as the assays and animal models used in the experimental part below and in the prior art cited herein.

Also, according to the invention, immunoglobulin single variable domains and polypeptides that are directed against c-Met from a first species of warm-blooded animal may or may not show cross-reactivity with c-Met from one or more other species of warm-blooded animal. For example, immunoglobulin single variable domains and polypeptides directed against human c-Met and in particular human c-Met (SEQ ID NO: 1) may or may not show cross reactivity with c-Met from one or more other species of primates (such as, without limitation, monkeys from the genus *Macaca* (such as, and in particular, cynomolgus monkeys (*Macaca foscicularis*) and/or rhesus monkeys (*Macaca mulatta*)) and baboon (*Papio ursinus*)) and/or with c-Met from one or more species of animals that are often used in animal models for diseases (for example mouse, rat, rabbit, pig or dog), and in particular in animal models for diseases and disorders associated with c-Met and in particular human c-Met (SEQ ID NO: 1) (such as the species and animal models mentioned herein). In this respect, it will be clear to the skilled person that such cross-reactivity, when present, may have advantages from a drug development point of view, since it allows the immunoglobulin single variable domains and polypeptides against human c-Met and in particular human c-Met (SEQ ID NO: 1) to be tested in such disease models.

More generally, immunoglobulin single variable domains and polypeptides of the invention that are cross-reactive with c-Met from multiple species of mammal will usually be advantageous for use in veterinary applications, since it will allow the same amino acid sequence or polypeptide to be used across multiple species. Thus, it is also encompassed within the scope of the invention that immunoglobulin single variable domains and polypeptides directed against c-Met from one species of animal (such as immunoglobulin single variable domains and polypeptides against human c-Met (SEQ ID NO: 1)) can be used in the treatment of another species of animal, as long as the use of the immunoglobulin single variable domains and/or polypeptides provide the desired effects in the species to be treated.

The present invention is in its broadest sense also not particularly limited to or defined by a specific antigenic determinant, epitope, part, domain, subunit or confirmation (where applicable) of c-Met and in particular human c-Met (SEQ ID NO: 1) against which the immunoglobulin single variable domains and polypeptides of the invention are directed. For example, the immunoglobulin single variable domains and polypeptides may or may not be directed against the HGF/c-Met interaction site, cell internalization site of c-Met, shedding site of c-Met and/or c-Met/c-Met homodimerization site, and are as further defined herein.

Furthermore, immunoglobulin single variable domains with dual specificity to c-Met and RON, and in particular to human c-Met (SEQ ID NO: 1) and human RON ((Ming-Hai Wang et al., *Acta Pharmocologica Sinica* (2010) 31: 1181-1188) are within the scope of this invention.

As further described herein, a polypeptide of the invention may contain (although not preferred) two or more immunoglobulin single variable domains of the invention that are directed against c-Met and in particular human c-Met (SEQ ID NO: 1). Generally, such polypeptides will bind to c-Met and in particular human c-Met (SEQ ID NO: 1) with increased avidity compared to a single amino acid sequence of the invention. Such a polypeptide may for example comprise two immunoglobulin single variable domains of the invention that are directed against the same antigenic determinant, epitope, part, domain, subunit or confirmation (where applicable) of c-Met and in particular human c-Met (SEQ ID NO: 1) (which may or may not be an interaction site); or comprise at least one "first" amino acid sequence of the invention that is directed against a first antigenic determinant, epitope, part, domain, subunit or conformation (where applicable) of c-Met and in particular human c-Met (SEQ ID NO: 1) (which may or may not be an interaction site); and at least one "second" amino acid sequence of the invention that is directed against a second antigenic determinant, epitope, part, domain, subunit or conformation (where applicable) different from the first (and which again may or may not be an interaction site). Preferably, in such "biparatopic" polypeptides of the invention, at least one amino acid sequence of the invention is directed against an interaction site (as defined herein), although the invention in its broadest sense is not limited thereto. For instance, polypeptides of the invention may be formatted e.g. in a biparatopic way such as to combine monovalent building blocks directed against different epitopes as characterized in the experimental part.

Also, when the target is part of a binding pair (for example, a receptor-ligand binding pair), the immunoglobulin single variable domains and polypeptides may be such that they compete with the cognate binding partners, e.g. HGF for binding to c-Met, and/or such that they (fully or partially) neutralize binding of the binding partner to the target.

It is also expected that the immunoglobulin single variable domains and polypeptides of the invention will generally bind to all naturally occurring or synthetic analogs, variants, mutants, alleles, parts and fragments of c-Met and in particular human c-Met (SEQ ID NO: 1); or at least to those analogs, variants, mutants, alleles, parts and fragments of c-Met and in particular human c-Met (SEQ ID NO: 1) that contain one or more antigenic determinants or epitopes that are essentially the same as the antigenic determinant(s) or epitope(s) to which the immunoglobulin single variable domains and polypeptides of the invention bind to c-Met and in particular to human c-Met (SEQ ID NO: 1). Again, in such a case, the immunoglobulin single variable domains and polypeptides of the invention may bind to such analogs, variants, mutants, alleles, parts and fragments with an affinity and/or specificity that are the same as, or that are different from (i.e. higher than or lower than), the affinity and specificity with which the immunoglobulin single variable domains of the invention bind to (wild-type) c-Met.

As c-Met and in particular human c-Met (SEQ ID NO: 1) exists in a monomeric form and in one or more multimeric forms, e.g. in homodimeric form, it is within the scope of the invention that the immunoglobulin single variable domains and polypeptides of the invention i) only bind to c-Met and in particular human c-Met (SEQ ID NO: 1) in monomeric form, ii) only bind to c-Met and in particular human c-Met (SEQ ID NO: 1) in multimeric/dimeric (homo- and/or heterodimeric) form, or iii) bind to both the monomeric and the multimeric form. In a preferred aspect of the invention, the polypeptides of the invention prevent formation of homodimeric human c-Met complexes. In another preferred aspect of the invention, the polypeptides of the invention do not induce (even at higher concentration such as 10 nM or less, 50 nM or less, 100 nM or less, or 500 nM or less) formation of homodimeric human c-Met complexes. Again, in such a case, the polypeptides of the invention may bind to the monomeric form with an affinity and/or specificity that are the same as, or that are different from (i.e. higher than or lower than), the affinity and specificity with which the immunoglobulin single variable domains of the invention bind to the multimeric form.

Also, when c-Met and in particular human c-Met (SEQ ID NO: 1) can associate with other proteins or polypeptides to form protein complexes (e.g. with HGF, but also with other receptors such as EGFR, HER3, plexins, integrins, CD44, RON), it is within the scope of the invention that the immunoglobulin single variable domains and polypeptides of the invention bind to c-Met and in particular human c-Met (SEQ ID NO: 1) in its non-associated state (and e.g. prevent ligand binding and/or prevent signalling), bind to c-Met and in particular human c-Met (SEQ ID NO: 1) in its associated state, or bind to both (preferably to the non-associated state). In all these cases, the immunoglobulin single variable domains and polypeptides of the invention may bind to such associated protein complexes with an affinity and/or specificity that may be the same as or different from (i.e. higher than or lower than) the affinity and/or specificity with which the immunoglobulin single variable domains and polypeptides of the invention bind to c-Met and in particular human c-Met (SEQ ID NO: 1) in its non-associated state.

Also, as will be clear to the skilled person, proteins or polypeptides that contain two or more immunoglobulin single variable domains directed against c-Met and in particular human c-Met (SEQ ID NO: 1), e.g. "biparatopic" polypeptides of the invention, may bind with higher avidity to c-Met and in particular human c-Met (SEQ ID NO: 1) than the corresponding monomeric amino acid sequence(s). For example, and without limitation, proteins or polypeptides that contain two or more immunoglobulin single variable domains directed against different epitopes of c-Met and in particular human c-Met (SEQ ID NO: 1) may (and usually will) bind with higher avidity than each of the different monomers, and proteins or polypeptides that contain two or more immunoglobulin single variable domains directed against c-Met and in particular human c-Met (SEQ ID NO: 1) may (and usually will) bind also with higher avidity to a multimer (e.g. homodimer) of c-Met and in particular to a multimer (e.g. homodimer) of human c-Met (SEQ ID NO: 1).

Generally, immunoglobulin single variable domains and polypeptides of the invention will at least bind to those forms of c-Met and in particular human c-Met (SEQ ID NO: 1) (including monomeric, multimeric, associated and different conformational forms) that are the most relevant from a biological and/or therapeutic point of view, as will be clear to the skilled person.

It is also within the scope of the invention to use parts, fragments, analogs, mutants, variants, alleles and/or derivatives of the immunoglobulin single variable domains and polypeptides of the invention, and/or to use proteins or polypeptides comprising or essentially consisting of one or more of such parts, fragments, analogs, mutants, variants, alleles and/or derivatives, as long as these are suitable for the uses envisaged herein. Such parts, fragments, analogs, mutants, variants, alleles and/or derivatives will usually contain (at least part of) a functional antigen-binding site for binding against c-Met and in particular human c-Met (SEQ ID NO: 1); and more preferably will be capable of specific binding to c-Met and in particular human c-Met (SEQ ID NO: 1), and even more preferably capable of binding to c-Met and in particular human c-Met (SEQ ID NO: 1) with an EC50 value, average Ki, $IC_{50}$ value concerning binding, migration, displacing and/or proliferation blocking and/or other measures for potency, as further described herein, (e.g. in the experimental part) that is as defined herein and such parts, fragments, analogs, mutants, variants, alleles and/or derivatives may be more potent, more stable, more soluble and may have the same epitope. Some non-limiting examples of such parts, fragments, analogs, mutants, variants, alleles, derivatives, proteins and/or polypeptides will become clear from the further description herein. Additional fragments or polypeptides of the invention may also be provided by suitably combining (i.e. by linking or genetic fusion) one or more (smaller) parts or fragments as described herein.

For a general description of immunoglobulin single variable domains, reference is made to the further description below, as well as to the prior art cited herein. In this respect, it should however be noted that this description and the prior art mainly describes immunoglobulin single variable domains of the so-called "$V_H3$ class" (i.e. immunoglobulin single variable domains with a high degree of sequence homology to human germline sequences of the $V_H3$ class such as DP-47, DP-51 or DP-29), which form a preferred aspect of this invention. It should, however, be noted that the invention in its broadest sense generally covers any type of immunoglobulin single variable domains directed against c-Met and in particular human c-Met (SEQ ID NO: 1), and for example also covers the immunoglobulin single variable domains belonging to the so-called "$V_H4$ class" (i.e. immunoglobulin single variable domains with a high degree of sequence homology to human germline sequences of the $V_H4$ class such as DP-78), as for example described in WO 07/118670.

Generally, immunoglobulin single variable domains (in particular $V_{HH}$ sequences and sequence optimized immunoglobulin single variable domains) can in particular be characterized by the presence of one or more "Hallmark residues" (as described herein) in one or more of the framework sequences (again as further described herein).

Thus, generally, an immunoglobulin single variable domain can be defined as an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively.

In a preferred aspect, the invention provides polypeptides comprising at least an immunoglobulin single variable domain that is an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:
i) at least one of the amino acid residues at positions 11, 37, 44, 45, 47, 83, 84, 103, 104 and 108 according to the Kabat numbering are chosen from the Hallmark residues mentioned in Table A-1 below; and in which:
ii) said amino acid sequence has at least 80%, more preferably 90%, even more preferably 95% amino acid identity with at least one of the immunoglobulin single variable domains as shown in WO 2009/138519 (see SEQ ID NOs: 1 to 125 in WO 2009/138519), in which for the purposes of determining the degree of amino acid identity, the amino acid residues that form the CDR sequences (indicated with X in the sequences) are disregarded; and in which:
iii) the CDR sequences are generally as further defined herein (e.g. the CDR1, CDR2 and CDR3 in a combination as provided in Table (8-2), note that the CDR definitions are calculated according to the Kabat numbering system).

maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein.

In a further preferred aspect, the invention provides polypeptides comprising one immunoglobulin single variable domain with amino acid sequence selected from the group consisting of amino acid sequences with SEQ ID NOs: 23 to 29, 102 and 187, preferably SEQ ID NO: 26 and/or 187 (see experimental part) and one immunoglobulin single variable domain with amino acid sequence selected from the group consisting of moieties providing an increased half-life (see below).

In a further preferred aspect, the invention provides polypeptides comprising at least an immunoglobulin single variable domain with amino acid sequence selected from the group consisting of amino acid sequences that essentially consist of 4 framework regions (FR1 to FR4, respectively) and 3 complementarity determining regions (CDR1 to CDR3, respectively), in which the CDR sequences of said amino acid sequences have at least 70% amino acid identity, preferably at

TABLE A-1

Hallmark Residues in VHHs

| Position | Human V$_H$3 | Hallmark Residues |
|---|---|---|
| 11 | L, V; predominantly L | L, S, V, M, W, F, T, Q, E, A, R, G, K, Y, N, P, I; preferably L |
| 37 | V, I, F; usually V | F$^{(1)}$, Y, V, L, A, H, S, I, W, C, N, G, D, T, P, preferably F$^{(1)}$ or Y |
| 44$^{(8)}$ | G | E$^{(3)}$, Q$^{(3)}$, G$^{(2)}$, D, A, K, R, L, P, S, V, H, T, N, W, M, I; preferably G$^{(2)}$, E$^{(3)}$ or Q$^{(3)}$; most preferably G$^{(2)}$ or Q$^{(3)}$ |
| 45$^{(8)}$ | L | L$^{(2)}$, R$^{(3)}$, P, H, F, G, Q, S, E, T, Y, C, I, D, V; preferably L$^{(2)}$ or R$^{(3)}$ |
| 47$^{(8)}$ | W, Y | F$^{(1)}$, L$^{(1)}$ or W$^{(2)}$ G, I, S, A, V, M, R, Y, E, P, T, C, H, K, Q, N, D; preferably W$^{(2)}$, L$^{(1)}$ or F$^{(1)}$ |
| 83 | R or K; usually R | R, K$^{(5)}$, T, E$^{(5)}$, Q, N, S, I, V, G, M, L, A, D, Y, H; preferably K or R; most preferably K |
| 84 | A, T, D; predominantly A | P$^{(5)}$, S, H, L, A, V, I, T, F, D, R, Y, N, Q, G, E; preferably P |
| 103 | W | W$^{(4)}$, R$^{(6)}$, G, S, K, A, M, Y, L, F, T, N, V, Q, P$^{(6)}$, E, C; preferably W |
| 104 | G | G, A, S, T, D, P, N, E, C, L; preferably G |
| 108 | L, M or T; predominantly L | Q, L$^{(7)}$, R, P, E, K, S, T, M, A, H; preferably Q or L$^{(7)}$ |

Notes:
$^{(1)}$In particular, but not exclusively, in combination with KERE or KQRE at positions 43-46.
$^{(2)}$Usually as GLEW at positions 44-47.
$^{(3)}$Usually as KERE or KQRE at positions 43-46, e.g. as KEREL, KEREF, KQREL, KQREF, KEREG, KQREW or KQREG at positions 43-47. Alternatively, also sequences such as TERE (for example TEREL), TQRE (for example TQREL), KECE (for example KECEL or KECER), KQCE (for example KQCEL), RERE (for example REREG), RQRE (for example RQREL, RQREF or RQREW), QERE (for example QEREG), QQRE, (for example QQREW, QQREL or QQREF), KGRE (for example KGREG), KDRE (for example KDREV) are possible. Some other possible, but less preferred sequences include for example DECKL and NVCEL.
$^{(4)}$With both GLEW at positions 44-47 and KERE or KQRE at positions 43-46.
$^{(5)}$Often as KP or EP at positions 83-84 of naturally occurring V$_{HH}$ domains.
$^{(6)}$In particular, but not exclusively, in combination with GLEW at positions 44-47.
$^{(7)}$With the proviso that when positions 44-47 are GLEW, position 108 is always Q in (non-humanized) V$_{HH}$ sequences that also contain a W at 103.
$^{(8)}$The GLEW group also contains GLEW-like sequences at positions 44-47, such as for example GVEW, EPEW, GLER, DQEW, DLEW, GIEW, ELEW, GPEW, EWLP, GPER, GLER and ELEW.

Again, such immunoglobulin single variable domains may be derived in any suitable manner and from any suitable source, and may for example be naturally occurring V$_{HH}$ sequences (i.e. from a suitable species of Camelid, e.g. llama) or synthetic or semi-synthetic VHs or VLs (e.g. from human). Such immunoglobulin single variable domains may include "humanized" or otherwise "sequence optimized" VHHs, "camelized" immunoglobulin sequences (and in particular camelized heavy chain variable domain sequences, i.e. camelized VHs), as well as human VHs, human VLs, camelid VHHs that have been altered by techniques such as affinity least 80% amino acid identity, more preferably at least 90% amino acid identity, such as 95% amino acid identity or more or even essentially 100% amino acid identity with the CDR sequences (see Table B-2) of at least one of the immunoglobulin single variable domains of SEQ ID NOs: 23 to 29, 102 and 187 preferably SEQ ID NO: 26 and/or 187 (see experimental part). This degree of amino acid identity can for example be determined by determining the degree of amino acid identity (in a manner described herein) between said amino acid sequence and one or more of the sequences of SEQ ID NOs: 23 to 29, 102 and 187 preferably SEQ ID NO:

26 and/or 187 (see experimental part), in which the amino acid residues that form the framework regions are disregarded. Such polypeptides and/or immunoglobulin single variable domains of the invention may further provide the following:

(i) polypeptides comprising at least one (preferably one) immunoglobulin single variable domain that is directed against (as defined herein) c-Met and in particular human c-Met (SEQ ID NO: 1) and that has at least 80%, preferably at least 85%, such as 90% or 95% or more sequence Identity with at least one of the immunoglobulin single variable domains of SEQ ID NOs: 23 to 29, 102 and 187 preferably SEQ ID NO: 26 and/or 187 (see experimental part); and/or (ii) polypeptides comprising at least one (preferably one) immunoglobulin single variable domain that is directed against (as defined herein) c-Met and in particular human c-Met (SEQ ID NO: 1) and that cross-block (as defined herein) the binding of at least one of the immunoglobulin single variable domains of SEQ ID NOs: 23 to 29, 102 and 187 preferably SEQ ID NO: 26 and/or 187 (see experimental part) to c-Met and in particular human c-Met (SEQ ID NO: 1) and/or that compete with at least one of the immunoglobulin single variable domains of SEQ ID NOs: 23 to 29, 102 and 187 preferably SEQ ID NO: 26 and/or 187 (see experimental part) for binding to c-Met and in particular human c-Met (SEQ ID NO: 1), and of which immunoglobulin single variable domains may be as further described herein; and/or (iii) polypeptides of the invention that comprise one or more (preferably one) of such immunoglobulin single variable domains (which may be as further described herein, and may for example be bispecific (e.g. also bind to serum albumin) and/or biparatopic polypeptides as described herein), and nucleic acid sequences that encode such immunoglobulin single variable domains and polypeptides. Such immunoglobulin single variable domains and polypeptides do not include any naturally occurring ligands.

The polypeptides of the invention comprise or essentially consist of at least one immunoglobulin single variable domain of the invention. Some preferred, but non-limiting examples of immunoglobulin single variable domains of the invention are given in SEQ ID NOs: 23 to 29, 102 and 187 preferably SEQ ID NO: 26 and/or 187 (see experimental part).

1.2 Anti-EGFR Building Blocks

EGFR consists of an extracellular ligand-binding domain, a transmembrane domain and an intracellular tyrosine kinase domain (Yarden et al. 2001, Nature Rev. Mol. Cell Biol. 2:127-137). Aberrant activation of EGFR mediated signalling has been implicated in processes involved in tumor growth and progression, including tumor cell proliferation, angiogenesis, metastasis, inhibition of apoptosis and resistance to radio- or chemotherapy (Grünwald, Hidalgo 2003 J. Natl. Cancer Inst. 95:851-867; and references therein). EGFR is expressed in a wide variety of tumors of epithelial origin, including >40% of NSCLC (non-small-cell-lung cancer), >95% of head and neck cancer, >30% of pancreatic cancer, >90% of renal carcinoma, >35% of ovarian cancer, >40% of glioma and >31% of bladder cancer (Salomon et al. 1995. Crit. Review Oncol. Hematol, 19:183-232). Since high levels of EGFR expression are correlated to disease progression, increased metastasis and poor prognosis, this provides a strong rationale for developing effective EGFR targeting antibodies for the treatment of various solid tumors.

Identification of MAbs inhibiting EGFR is an approach used in clinical development to target aberrant signalling of EGFR in malignant neoplasia. Examples of such EGFR targeting antibodies are IMC-C225 (Erbitux, Imclone), EMD72000 (Merck Darmstadt), ABX-EGF (Abgenix), h-R3 (theraCIM, YM Biosciences) and Humax-EGFR (Genmab). The mechanism of action of these antibodies relies on the inhibition with ligand binding to the receptor and subsequent inhibition of receptor transphosphorylation and the downstream signaling cascade. Mab 225 (of which Erbitux is the chimeric derivative), the 225-derived F(ab')$_2$ fragment are able to induce EGFR internalization and modest receptor sequestration but only after sustained incubation with EGFR expressing cells. The monovalent 225-derived Fab' fragment however only induces receptor downregulation after preincubation with a rabbit anti-mouse antibody (Fan et al 1993 J. Biol. Chem. 268:21073-21079; Fan et al., 1994 J. Biol. Chem. 269:27595-27602). These antibodies show an antitumoral activity against a broad panel of human tumor xenografts (reviewed in Grünwald & Hidalgo 2003 J. Natl. Cancer Inst. 95:851-867).

However, the known antibody-based therapeutics binding to the EGF receptor are cytostatic instead of cytotoxic. Indeed none of these antibodies or the presently available small molecule drugs is completely effective for the treatment of cancer. Moreover, for some patients therapeutic application of EGFR inhibitors is limited by serious toxicity.

WO 05/044858, WO 04/041867 and WO07/042289 already describe anti-EGFR Nanobodies and polypeptides with improved properties over standard antibodies.

However, multispecific constructs comprising the polypeptides of the present invention have improved efficacy in modulating signalling over a combination of the individual polypeptides of the present invention. In particular, a multispecific construct comprising (a) one or more polypeptides modulating c-Met signalling as described herein, and (b) one or more polypeptides modulating EGFR-mediated signalling is exceptionally useful in the diagnosis, prevention and treatment of diseases and disorders as set out above. The multispecific construct is particular useful in the diagnosis, prevention and treatment of cancer, in particular of non-small cell lung cancer.

The polypeptides and Nanobodies described in WO 05/044858, WO 04/041867, and/or WO07/042289 are particularly preferred as polypeptides modulating EGFR-mediated signalling in the multispecific constructs of the present invention. Accordingly, the present invention relates to a multispecific, such as for instance a bispecific or trispecific, construct comprising at least one ISVD against EGFR and at least one ISVD against c-Met, and optionally against VEGF. In such a multispecific, e.g. bispecific or trispecific, polypeptide construct, the Nanobodies and polypeptides against c-Met described herein can be combined with one or more of the anti-EGFR Nanobodies and polypeptides described in WO 05/044858, WO 04/041867, and WO07/042289 (all of which are specifically incorporated in its entirety herein).

Hence, the present invention relates to a multispecific construct of (a) one or more polypeptides modulating c-Met signalling and (b) one or more polypeptides modulating EGFR-mediated signalling, in particular EGFR-mediated signalling, for use in the diagnosis, prevention and treatment of diseases and disorders as set out above, in particular non-small cell lung cancer.

1.3 Anti-VEGF Building Blocks

Development of a vascular system is a fundamental requirement for many physiological and pathological processes. It is now well established that angiogenesis is implicated in the pathogenesis of a variety of disorders, including solid tumors and metastasis. In the case of tumor growth, angiogenesis appears to be crucial for the transition from hyperplasia to neoplasia, and for providing nourishment for the growth and metastasis of the tumor. Folkman et al., Nature 339:58 (1989). The process of vascular development is tightly regulated, in which vascular endothelial growth factor (VEGF) has been identified as the key factor involved in stimulating angiogenesis and in inducing vascular permeability. Ferrara et al., Endocr. Rev. 18:4-25 (1997). The term "VEGF" or "VEGF-A" is used to refer to the 165-amino acid human vascular endothelial cell growth factor and related 121-, 189-, and 206-amino acid human vascular endothelial cell growth factors, as described by Leung et al. Science, 246:1306 (1989), and Houck et al. Mol. Endocrin., 5:1806 (1991), together with the naturally occurring allelic and processed forms thereof. "VEGF biological activity" includes binding to any VEGF receptor or any VEGF signaling activity such as regulation of both normal and abnormal angiogenesis and vasculogenesis (Ferrara and Davis-Smyth (1997) Endocrine Rev. 18:4-25; Ferrara (1999) J. Mol. Med. 77:527-543).

Most clinical experience has been obtained with A4.6.1, also called bevacizumab (Avastin®; Genentech, San Francisco, Calif.). Avastin in combination with chemotherapy is, however, plagued by side-effects (hemorrhages, arterial thromboembolism, hypertension, gastrointestinal (GI) perforations, wound healing problems, proteinuria and congestive heart failure) which are primarily due to the fact that the anti-VEGF activity is not restricted to the site of the tumor, but persists in circulation over a long period of time. This results in a shift of physiological to pathophysiological activity of the peripheral endothelial cells. Anti-VEGF strategies using a recombinant humanized anti-VEGF Fab (rhuFab VEGF, Ranibizumab or Lucentis™) for the treatment of a chronic disease is, however, not ideal because of the risk of endophthalmitis, vitreous hemorrhage, and retinal detachment.

WO 08/101985 already describes anti-VEGF Nanobodies and polypeptides with improved properties over standard antibodies.

However, the multispecific constructs comprising the polypeptides of the present invention have improved efficacy in modulating signalling over a combination of the individual polypeptides of the present invention. In particular, a multispecific construct comprising (a) one or more polypeptides modulating c-Met signalling as described herein, and (b) one or more polypeptides modulating VEGF-mediated signalling, and optionally EGFR-mediated signalling is exceptionally useful in the diagnosis, prevention and treatment of diseases and disorders as set out above. The multispecific construct is particular useful in the diagnosis, prevention and treatment of cancer, in particular of non-small cell lung cancer.

The polypeptides and Nanobodies described in WO 08/101985 are particularly preferred as polypeptides modulating VEGF-mediated signalling in the multispecific constructs of the present invention. Accordingly, the present invention relates to a multispecific, such as for instance a bispecific, trispecific, or tetraspecific construct comprising at least one ISVD against c-Met and at least one ISVD against VEGF, and optionally against EGFR. In such a multispecific, e.g. bispecific, trispecific or tetraspecific, polypeptide construct, the Nanobodies and polypeptides against c-Met described herein can be combined with one or more of the anti-VEGF Nanobodies and polypeptides described in WO 08/101985 (which is specifically incorporated in its entirety herein).

Hence, the present invention relates to a multispecific construct of (a) one or more polypeptides modulating c-Met signalling and (b) one or more polypeptides modulating VEGF-mediated signalling, in particular human VEGF-mediated signalling, and optionally (c) one or more polypeptides modulating EGFR-mediated signalling, in particular human EGFR-mediated signalling, for use in the diagnosis, prevention and treatment of diseases and disorders as set out above, in particular non-small cell lung cancer. In particular aspects, the present invention provides combination therapies for treating a pathological condition, such as cancer, wherein a c-Met antagonist is combined with a VEGF antagonist, or wherein a c-Met antagonist is combined with a VEGF antagonist and an EGFR antagonist, thereby providing significant anti-tumor activity.

1.4 Valency

Generally, proteins or polypeptides that comprise or essentially consist of a single immunoglobulin single variable domain will be referred to herein as "monovalent" proteins or polypeptides or as "monovalent constructs". Proteins and polypeptides that comprise or essentially consist of two or more immunoglobulin single variable domains (such as at least two immunoglobulin single variable domains of the invention or at least one immunoglobulin single variable domain of the invention and at least one other immunoglobulin single variable domain) will be referred to herein as "multivalent" proteins or polypeptides or as "multivalent constructs", and these may provide certain advantages compared to the corresponding monovalent immunoglobulin single variable domains of the invention. Some non-limiting examples of such multivalent constructs will become clear from the further description herein.

For example a "bivalent" polypeptide of the invention comprises two ISVDs, optionally linked via a linker sequence, whereas a "trivalent" polypeptide of the invention comprises three ISVDs, optionally linked via two linker sequences, whereas a "tetravalent" polypeptide of the invention comprises four ISVDs, optionally linked via three linker sequences; etc.; in which at least one of the ISVDs present in the polypeptide or construct, and up to all of the ISVDs present in the polypeptide or construct, is/are an ISVD(s).

In a multivalent polypeptide of the invention the two or more ISVDs may be the same or different, and may be directed against the same antigen or antigenic determinant (for example against the same part(s) or epitope(s) or against different parts or epitopes) or may alternatively be directed against different antigens or antigenic determinants; or any suitable combination thereof. For example, a bivalent polypeptide of the invention may comprise (a) two identical ISVDs; (b) a first ISVD directed against a first antigenic determinant of a protein or antigen and a second ISVD directed against the same antigenic determinant of said protein or antigen which is different from the first ISVD; (c) a first ISVD directed against a first antigenic determinant of a protein or antigen and a second ISVD directed against another antigenic determinant of said protein or antigen; or (d) a first ISVD directed against a first protein or antigen and a second ISVD directed against a second protein or antigen (i.e. different from said first antigen). Similarly, a trivalent polypeptide of the invention may, for example and without being limited thereto, comprise (a) three identical ISVDs; (b) two identical ISVDs against a first antigenic determinant of an antigen and a third ISVD directed against a different antigenic determinant of the same antigen; (c) two identical ISVDs against a first antigenic determinant of an antigen and a third ISVD directed against a second antigen different from said first antigen; (d) a first ISVD directed against a first antigenic determinant of a first antigen, a second ISVD directed against a second antigenic determinant of said first antigen and a third ISVD directed against a second antigen different from said first antigen; or (e) a first ISVD directed against a first antigen, a second ISVD directed against a second antigen different from said first antigen, and a third ISVD directed against a third antigen different from said first and second antigen. Similarly, a tetravalent polypeptide of the invention may, for example and without being limited thereto, comprise (a) four identical ISVDs; (b) three identical ISVDs against a first antigenic determinant of a first antigen and one ISVD directed against a different antigenic determinant of the same antigen; (c) three identical ISVDs against a first antigenic determinant of a first antigen and one ISVD directed against a second antigen, different from said first antigen; (d) two identical ISVDs against a first antigenic determinant of an antigen and two ISVDs directed against a different antigenic determinant of the same antigen; (e) two identical ISVDs against a first antigenic determinant of an antigen, one ISVD directed against a different antigenic determinant of the same antigen, and one ISVDs directed against a second antigen different from said first antigen; (f) two identical ISVDs against a first antigenic determinant of an antigen, two ISVDs directed against a second antigen, wherein said second antigen is different from said first antigen; (g) two identical ISVDs against a first antigenic determinant of an antigen, one ISVD directed against a second antigen, wherein said second antigen is different from said first antigen, and one ISVD directed against a third antigen, wherein said third antigen is different from said first and second antigen; (h) a first ISVD directed against a first antigenic determinant of a first antigen, a second ISVD directed against a second antigenic determinant of said first antigen, a third and a fourth ISVD directed against a second antigen different from said first antigen; (i) a first ISVD directed against a first antigenic determinant of a first antigen, a second ISVD directed against a second antigenic determinant of said first antigen, a third ISVD directed against a second antigen different from said first antigen and a fourth ISVD directed against a third antigen different from said first antigen and said second antigen; or (j) a first ISVD directed against a first antigen, a second ISVD directed against a second antigen different from said first antigen, a third ISVD directed against a third antigen different from said first and second antigen, and a fourth ISVD directed against a fourth antigen different from said first, said second and said third antigen.

Polypeptides of the invention that contain at least two ISVDs, in which at least one ISVD is directed against a first antigen (i.e. against c-Met) and at least one ISVD is directed against a second antigen (i.e. different c-Met, e.g. EGFR or VEGF), will also be referred to as "multispecific" polypeptides of the invention, and the ISVDs present in such polypeptides will also be referred to herein as being in a "multivalent format". Thus, for example, a "bispecific" polypeptide of the invention is a polypeptide that comprises at least one ISVD directed against a first antigen (i.e. c-Met) and at least one further ISVD directed against a second antigen (i.e. different from c-Met, such as, for instance, EGFR or VEGF), whereas a "trispecific" polypeptide of the invention is a polypeptide that comprises at least one ISVD directed against a first antigen (i.e. c-Met), at least one further ISVD directed against a second antigen (i.e. different c-Met, such as for instance EGFR or VEGF) and at least one further ISVD directed against a third antigen (i.e. different from both c-Met and the second antigen, e.g. EGFR or VEGF), whereas a "tetraspecific" polypeptide of the invention is a polypeptide that comprises at least one ISVD directed against a first antigen (i.e. c-Met), at least one further ISVD directed against a second antigen (i.e. different c-Met, such as, for instance EGFR), at least one further ISVD directed against a third antigen (i.e. different from both c-Met and the second antigen EGFR, such as for instance VEGF), at least one further ISVD directed against a fourth antigen (i.e. different from the antigens c-Met, EGFR as well as VEGF, such as, for instance, serum albumin); etc.

Accordingly, in its simplest form, a bispecific polypeptide of the invention is a bivalent polypeptide of the invention (as defined herein), comprising a first ISVD directed against c-Met, and a second ISVD directed against a second antigen, such as EGFR or VEGF, in which said first and second ISVD may optionally be linked via a linker sequence (as defined herein); whereas a trispecific polypeptide of the invention in its simplest form is a trivalent polypeptide of the invention (as defined herein), comprising a first ISVD directed against c-Met, a second ISVD directed against a second antigen, such as, for instance, EGFR or VEGF, and a third ISVD directed against a third antigen, e.g. different form c-Met and said second antigen (e.g. EGFR or VEGF), in which said first, second and third ISVDs may optionally be linked via one or more, and in particular one and more in particular two, linker sequences; whereas a tetraspecific polypeptide of the invention in its simplest form is a tetravalent polypeptide of the invention (as defined herein), comprising a first ISVD directed against c-Met, a second ISVD directed against a second antigen, such as, for instance, EGFR, a third ISVD directed against a third antigen, such as VEGF, and a fourth ISVD directed against a fourth antigen different form c-Met, EGFR and VEGF, in which said first, second, third and fourth ISVDs may optionally be linked via one or more, and in particular one or more in particular three, linker sequences.

However, as will be clear from the description, the invention is not limited thereto, in the sense that a multispecific polypeptide of the invention may comprise at least one ISVD against c-Met and any number of ISVDs directed against one or more antigens different from c-Met, respectively.

According to a specific, but non-limiting embodiment, a polypeptide as described herein comprises at least one ISVD against c-Met and at least one ISVD against EGFR and/or VEGF, optionally linked using one or more suitable linkers. In such a bispecific polypeptide construct, the Nanobodies and polypeptides against c-Met described herein can be combined with one or more of the anti-EGFR Nanobodies and polypeptides described in WO 05/044858, WO 04/041867 and/or WO07/042289, and/or with one or more of the anti-VEGF Nanobodies and polypeptides described in WO08/101985.

Bispecific polypeptides that comprise two binding moieties, such as for instance two ISVDs, wherein each binding moiety is specific for a tumor associated antigen (i.e. an antigen expressed on a tumor cell, also called 'tumor marker'), are highly advantageous in tumor targeting. Such bispecific polypeptides are capable of simultaneously targeting two tumor associated antigens, resulting in enhanced tumor specificity. It is known that most tumor markers are not truly tumor specific but also occur (mostly at lower levels) on normal tissues or cells. Monospecific binding moieties, ISVDs or polypeptides against only one tumor marker will therefore also recognize those normal tissues or cells resulting in a non-specific cell arrest or killing. Polypeptides that are specific for two or more markers on one or more tumor cells will be much more tumor specific and provide a better specific binding. They can thus block simultaneously multiple receptor activation and downstream signal transduction pathways, and provide a better inhibition of tumor proliferation and arrest or killing of the tumor cells.

Accordingly, the present invention also relates to a bispecific or multispecific polypeptide, comprising or essentially consisting of at least two binding moieties, such as two ISVDs, wherein at least one of said at least two binding moieties is directed against c-Met, and the other binding moiety is directed against EGFR or VEGF. In a particular embodiment, said at least two binding moieties have a moderate or low affinity to their individual tumor associated antigen (such as, for instance, c-Met and EGFR or VEGF) and, accordingly, have only a reduced retention on normal tissues or cells expressing one of the tumor associated antigens. Those at least two binding moieties, however preferentially target (have a high avidity for) tumor cells that express both antigens (such as, for instance, c-Met and EGFR or VEGF) recognized by the bispecific or multispecific polypeptide.

Accordingly, the present invention also relates to a trispecific or multispecific polypeptide, comprising or essentially consisting of at least three binding moieties, such as three ISVDs, wherein at least one of said at least three binding moieties is directed against c-Met, one binding moiety is directed against EGFR and one binding moiety is directed against VEGF. In a particular embodiment, two of said at least three binding moieties have a moderate or low affinity to their individual tumor associated antigen (such as, for instance, c-Met and EGFR) and, accordingly, have only a reduced retention on normal tissues or cells expressing one of the tumor associated antigens. Those at least two binding moieties, however preferentially target (have a high avidity for) tumor cells that express both antigens (such as, for instance, c-Met and EGFR) recognized by the bispecific, trispecific or multispecific polypeptide.

EGFR, for example, is over-expressed on tumors in breast cancer, colon cancer, ovarian cancer, lung cancer and head and neck cancer.

By simultaneous targeting two of these tumor associated antigens, or different epitopes on one of these tumor associated antigens, a much more selective and/or enhanced tumor targeting is obtained.

Therefore, in a preferred embodiment, the invention also provides a bispecific or trispecific polypeptide comprising or essentially consisting of a Nanobody directed against c-Met and a Nanobody directed against EGFR and optionally against VEGF. The polypeptide of the invention may comprise or essentially consist of a Nanobody directed against c-Met and a Nanobody directed against EGFR. The polypeptide of the invention may comprise or essentially consist of a Nanobody directed against c-Met and a Nanobody directed against VEGF. Also, the polypeptide of the invention may comprise or essentially consist of a Nanobody directed against c-Met, a Nanobody directed against EGFR and a Nanobody directed against VEGF.

Also encompassed within the scope of the present invention are bispecific or multispecific polypeptides comprising or essentially consisting of at least two Nanobodies of which one of said at least two Nanobodies has a decreased or increased affinity for its antigen, upon binding by the other Nanobodies to its antigen. Such binding is called 'conditional bispecific or multispecific binding'. Such bispecific or multispecific polypeptide is also called 'a conditionally binding bispecific or multispecific polypeptide of the invention'.

Binding of the antigen by the first of said at least two Nanobodies may modulate, such as enhance, reduce or inhibit, binding of the antigen by the second of said at least two Nanobodies. In an embodiment, binding by the first of said at least two Nanobodies stimulates binding by the second of said at least two Nanobodies. In another embodiment, binding by the first of said at least two Nanobodies at least partially inhibits binding by the second of said at least two Nanobodies. In such an embodiment, the polypeptide of the invention may, for example, be maintained in the body of a subject organism in vivo through binding to a protein which increases the half-life of the polypeptide until such a time as it becomes bound to its second target antigen and dissociates from the half-life increasing protein.

Modulation of binding in the above context is achieved as a consequence of the structural proximity of the antigen binding sites of the Nanobodies relative to one another. Such structural proximity can be achieved by the nature of the structural components linking the two or more antigen binding sites, e.g. by the provision of a linker with a relatively rigid structure that holds the antigen binding sites in close proximity. Advantageously, the two or more antigen binding sites are in physically close proximity to one another such that one site modulates the binding of the antigen at another site by a process which involves steric hindrance and/or conformational changes within the polypeptide.

1.5 Serum Albumin Binding Building Blocks or Other Building Blocks Increasing Half-Life In another aspect, the invention relates to a compound or construct, and in particular to a protein or polypeptide (also referred to herein as a "compound of the invention" or "polypeptide of the invention", respectively) that comprises or essentially consists of one or more (preferably one) immunoglobulin single variable domains directed to human c-Met (or suitable fragments thereof), and optionally further comprises one or more other groups, residues, moieties or binding units. As will become clear to the skilled person from the further disclosure herein, such further groups, residues, moieties, binding units or immunoglobulin single variable domains may or may not provide further functionality to the amino acid sequence of the invention (and/or to the compound or construct in which it is present) and may or may not modify the properties of the amino acid sequence of the invention.

As will be clear from the further description above and herein, this means that the immunoglobulin single variable domains of the invention can be used as "building blocks" to form polypeptides of the invention, i.e. by suitably combining them with other groups, residues, moieties or binding units, in order to form compounds or constructs as described herein (such as, without limitations, the biparatopic, triparatopic, tetraparatopic, bi/tri/tetra/multivalent and bi/tri/tetra/multispecific polypeptides of the invention described herein) which combine within one molecule one or more desired properties or biological functions.

For a general description of multivalent and multispecific polypeptides containing one or more Nanobodies and their preparation, reference is also made to Conrath et al., J. Biol. Chem., Vol. 276, 10. 7346-7350, 2001; Muyldermans, Reviews in Molecular Biotechnology 74 (2001), 277-302; as well as to for example WO 96/34103, WO 99/23221, WO 04/041862, WO 2006/122786, WO 2008/020079, WO 2008/142164 or WO 2009/068627.

The compounds or polypeptides of the invention can generally be prepared by a method which comprises at least one step of suitably linking the one or more immunoglobulin single variable domains of the invention to the one or more further groups, residues, moieties or binding units, optionally via the one or more suitable linkers, so as to provide the compound or polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

The process of designing/selecting and/or preparing a compound or polypeptide of the invention, starting from an amino acid sequence of the invention, is also referred to herein as "formatting" said amino acid sequence of the invention; and an amino acid of the invention that is made part of a compound or polypeptide of the invention is said to be "formatted" or to be "in the format of" said compound or polypeptide of the invention. Examples of ways in which an amino acid sequence of the invention can be formatted and examples of such formats will be clear to the skilled person based on the disclosure herein; and such formatted immunoglobulin single variable domains form a further aspect of the invention.

For example, such further groups, residues, moieties or binding units may be one or more additional immunoglobulin single variable domains, such that the compound or construct is a (fusion) protein or (fusion) polypeptide. In a preferred but non-limiting aspect, said one or more other groups, residues, moieties or binding units are immunoglobulin sequences. Even more preferably, said one or more other groups, residues, moieties or binding units are chosen from the group consisting of domain antibodies, immunoglobulin single variable domains that are suitable for use as a domain antibody, single domain antibodies, immunoglobulin single variable domains (ISVDs) that are suitable for use as a single domain antibody, "dAb"'s, immunoglobulin single variable domains that are suitable for use as a dAb, or Nanobodies. Alternatively, such groups, residues, moieties or binding units may for example be chemical groups, residues, moieties, which may or may not by themselves be biologically and/or pharmacologically active. For example, and without limitation, such groups may be linked to the one or more immunoglobulin single variable domains of the invention so as to provide a "derivative" of an amino acid sequence or polypeptide of the invention, as further described herein.

Also within the scope of the present invention are compounds or constructs, which comprise or essentially consist of one or more derivatives as described herein, and optionally further comprise one or more other groups, residues, moieties or binding units, optionally linked via one or more linkers. Preferably, said one or more other groups, residues, moieties or binding units are immunoglobulin single variable domains. In the compounds or constructs described above, the one or more immunoglobulin single variable domains of the invention and the one or more groups, residues, moieties or binding units may be linked directly to each other and/or via one or more suitable linkers or spacers. For example, when the one or more groups, residues, moieties or binding units are immunoglobulin single variable domains, the linkers may also be immunoglobulin single variable domains, so that the resulting compound or construct is a fusion (protein) or fusion (polypeptide).

In a specific, but non-limiting aspect of the invention, which will be further described herein, the polypeptides of the invention have an increased half-life in serum (as further described herein) compared to the immunoglobulin single variable domain from which they have been derived. For example, an immunoglobulin single variable domain of the invention may be linked (chemically or otherwise) to one or more groups or moieties that extend the half-life (such as PEG), so as to provide a derivative of an amino acid sequence of the invention with increased half-life.

In a specific aspect of the invention, a compound of the invention or a polypeptide of the invention may have an increased half-life, compared to the corresponding amino acid sequence of the invention. Some preferred, but non-limiting examples of such compounds and polypeptides will become clear to the skilled person based on the further disclosure herein, and for example comprise immunoglobulin single variable domains or polypeptides of the invention that have been chemically modified to increase the half-life thereof (for example, by means of pegylation); immunoglobulin single variable domains of the invention that comprise at least one additional binding site for binding to a serum protein (such as serum albumin); or polypeptides of the invention which comprise at least one amino acid sequence of the invention that is linked to at least one moiety (and in particular at least one amino acid sequence) which increases the half-life of the amino acid sequence of the invention. Examples of polypeptides of the invention which comprise such half-life extending moieties or immunoglobulin single variable domains will become clear to the skilled person based on the further disclosure herein; and for example include, without limitation, polypeptides in which the one or more immunoglobulin single variable domains of the invention are suitably linked to one or more serum proteins or fragments thereof (such as (human) serum albumin or suitable fragments thereof) or to one or more binding units that can bind to serum proteins (such as, for example, domain antibodies, immunoglobulin single variable domains that are suitable for use as a domain antibody, single domain antibodies, immunoglobulin single variable domains that are suitable for use as a single domain antibody, "dAb"'s, immunoglobulin single variable domains that are suitable for use as a dAb, or Nanobodies that can bind to serum proteins such as serum albumin (such as human serum albumin), serum immunoglobulins such as IgG, or transferrin; reference is made to the further description and references mentioned herein); polypeptides in which an amino acid sequence of the invention is linked to an Fc portion (such as a human Fc) or a suitable part or fragment thereof; or polypeptides in which the one or more immunoglobulin single variable domains of the invention are suitable linked to one or more small proteins or peptides that can bind to serum proteins, such as, without limitation, the proteins and peptides described in WO 91/01743, WO 01/45746, WO 02/076489, WO2008/068280, WO2009/127691 and PCT/EP2011/051559.

Generally, the compounds or polypeptides of the invention with increased half-life preferably have a half-life that is at least 1.5 times, preferably at least 2 times, such as at least 5 times, for example at least 10 times or more than 20 times, greater than the half-life of the corresponding amino acid sequence of the invention per se. For example, the compounds or polypeptides of the invention with increased half-life may have a half-life e.g. in humans that is increased with more than 1 hours, preferably more than 2 hours, more preferably more than 6 hours, such as more than 12 hours, or even more than 24, 48 or 72 hours, compared to the corresponding amino acid sequence of the invention per se.

In a preferred, but non-limiting aspect of the invention, such compounds or polypeptides of the invention have a serum half-life e.g. in humans that is increased with more than 1 hours, preferably more than 2 hours, more preferably more than 6 hours, such as more than 12 hours, or even more than 24, 48 or 72 hours, compared to the corresponding amino acid sequence of the invention per se.

In another preferred, but non-limiting aspect of the invention, such compounds or polypeptides of the invention exhibit a serum half-life in human of at least about 12 hours, preferably at least 24 hours, more preferably at least 48 hours, even more preferably at least 72 hours or more. For example, compounds or polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In another aspect, the invention relates to a multispecific (and in particular bispecific) ISVD, such as a Nanobody construct that comprises Alb11 (SEQ ID NO: 5) or Alb23 [SEQ ID NO: 101] and at least one other ISVD such as a Nanobody (such as one or two other ISVDs, e.g. Nanobodies, which may be the same or different), in which said at least one other ISVD, e.g. Nanobody is preferably directed against a desired target (which is preferably a therapeutic target) and/or another ISVD, e.g. Nanobody that useful or suitable for therapeutic, prophylactic and/or diagnostic purposes. Again, Alb11 (SEQ ID NO: 5) or Alb23 [SEQ ID NO: 101] and the other Nanobodies may be suitably linked to each other either directly or optionally via one or more suitable linkers or spacers, and according to one specific but non-limiting aspect at least one (and up to all) of the other Nanobodies may be of the VHH-1 class.

Some other examples of some specific multispecific and/or multivalent polypeptide of the invention can be found in the applications by Ablynx N.V. mentioned herein. In particular, for a general description of multivalent and multispecific constructs comprising at least one Nanobody against a serum protein for increasing the half-life, of nucleic acids encoding the same, of compositions comprising the same, of the preparation of the aforementioned, and of uses of the aforementioned, reference is made to the International applications WO 04/041865 and WO 06/122787 mentioned above (Alb-23 [SEQ ID NO: 101] and the Alb-23 variants described herein can generally be used analogously to the half-life extending Nanobodies described therein such as Alb-8), as well as to the general description and specific examples of such constructs given in WO 04/041862, WO 2006/122786, WO 2008/020079, WO 2008/142164 or WO 2009/068627.

In one non-limiting embodiment, the one or more other Nanobodies present in such a polypeptide or protein construct may be directed against c-Met, and may in particular be Type I Nanobodies directed against c-Met.

One particularly preferred Type I Nanobody against c-Met that may be present in such a multivalent and/or multispecific polypeptide (next to Alb-23 [SEQ ID NO: 101] or an Alb-23 variant) is 04E09 (SEQ ID NO: 26) or variant thereof, e.g. 04E09-like ISVD.

Such a variant of 04E09 will generally have at least 80%, such as at least 85%, for example at least 90% or more such as 95% or more sequence identity with 04E09 and is preferably such that (i) it competes with 04E09 for binding to c-Met (in a suitable assay, such as the Alphascreen assay described in Example 7, but using 04E09 instead of HGF as used in Example 7); and/or (ii) it binds to the same epitope on c-Met as 04E09; and/or (iii) cross-blocks (as defined in WO 2009/068627) the binding of 04E09 to c-Met. Such a variant of 04E09 may for example be a humanized and/or sequence-optimized variant of 04E09 (as further described herein). Some preferred, but non-limiting examples of variants of 04E09 that could be present in such proteins or polypeptides are the following: 04E09 (L49S) (SEQ ID NO: 23); 04E09 (C50S/C100bG) (SEQ ID NO: 24); 04E09 (C22A/C92S) (SEQ ID NO: 25); A00790067=04E09 (Q108L) (SEQ ID NO: 114); A00790068=04E09 (A74S, K83R, Q108L) (SEQ ID NO: 115); A00790069=04E09 (A74S, K83R, G88A, Q108L) (SEQ ID NO: 116) and A00790105=04E09 (E1D, A74S, K83R, G88A, Q108L) (SEQ ID NO: 102), of which the latter is especially preferred.

Thus, in one specific but non-limiting aspect, the invention relates to a polypeptide or protein construct that comprises or essentially consists of Alb-23 [SEQ ID NO: 101](preferred) or an Alb-23 variant (as described herein), which is suitably linked (either directly or via one or more suitable linkers) to one or two Nanobodies against c-Met. As mentioned, according to a specific but non-limiting aspect, said one or two Nanobodies against c-Met comprise two disulphide bridges (i.e. are of "Class I").

In particular, the invention relates to a polypeptide or protein construct that comprises or essentially consists of Alb-23 [SEQ ID NO: 101](preferred) or an Alb-23 variant (as described herein), which is suitably linked (either directly or via one or more suitable linkers) to one or two (and preferably only one) Nanobodies against c-Met, which are 04E09 (SEQ ID NO: 26) or a variant of 04E09 (as described herein), and preferably a humanized or sequence optimized variant of 04E09 and more preferably A00790105 (SEQ ID NO: 102).

Some specific but non-limiting examples of such proteins and polypeptides are the constructs Alb23-9GS-4E09 (SEQ ID NO: 103), 4E09-9GS-Alb23 (SEQ ID NO: 104), Alb23-9GS-A00790105 (SEQ ID NO: 105), A00790105-9GS-Alb23 (SEQ ID NO: 106), Alb23-35GS-04E09 (SEQ ID NO: 107), 4E09-35GS-Alb23 (SEQ ID NO: 108), Alb23-35GS-A00790105 (SEQ ID NO: 109), A00790105-35GS-Alb23 (SEQ ID NO: 110), A00790105-35GS-A00790105-35GS-Alb23 (SEQ ID NO: 111), and A00790105-9GS-Alb23-A (SEQ ID NO: 188). Of these, the constructs A00790105-9GS-Alb23 (SEQ ID NO: 106) and A00790105-9GS-Alb23-A (SEQ ID NO: 188) are particularly preferred, and thus one aspect of the invention also relates to a polypeptide that has at least 80%, such as at least 85%, for example at least 90%, such as at least 95% or more sequence identity with the polypeptides of SEQ ID NO: 106 and 188.

A further particularly preferred Type I Nanobody against c-Met that may be present in a multivalent and/or multispecific polypeptide (next to Alb-11 [SEQ ID NO: 5] or an Alb-11 variant) is 33H10 (SEQ ID NO: 187) or variant thereof, e.g. an 33H10-like ISVD, which wholly unexpectedly was produced conveniently in different hosts. Such a variant of 33H10 will generally have at least 80%, such as at least 85%, for example at least 90% or more such as 95% or more sequence identity with 33H10 and is preferably such that (i) it competes with 33H10 for binding to c-Met (in a suitable assay, such as the Alphascreen assay described in Example 21 or 22, but using 33H10 instead of HGF as used in Example 1.5); and/or (ii) it binds to the same epitope on c-Met as 33H10; and/or (iii) cross-blocks (as defined in WO 2009/068627) the binding of 33H10 to c-Met. Such a variant of 33H10 may for example be a humanized and/or sequence-optimized variant of 33H10 (as further described herein). Some preferred, but non-limiting examples of variants of 33H10 that could be present in such proteins or polypeptides are the following: clones A007900184 (wt; SEQ ID NO: 151), A007900738-A007900753, A007901245-A007901253 and A007901255-A007901263 (SEQ ID NOs: 117-150, respectively), of which A007901256 (SEQ ID NO: 143), A007901259 (SEQ ID NO: 146) and A007901260 (SEQ ID NO: 147) are especially preferred.

Also in particular, the invention relates to a polypeptide or protein construct that comprises or essentially consists of Alb-11 [SEQ ID NO: 5] (preferred) or an Alb-11 variant (as described herein), which is suitably linked (either directly or via one or more suitable linkers) to one or two (and preferably only one) Nanobodies against c-Met, which are 33H10 (SEQ ID NO: 187) or a variant of 33H10 (as described herein), and preferably a humanized or sequence optimized variant of 33H10 and more preferably A007901256 (SEQ ID NO: 143), A007901259 (SEQ ID NO: 146) and A007901260 (SEQ ID NO: 147).

Some specific but non-limiting examples of such proteins and polypeptides are the constructs A007901255 (SEQ ID NO: 142); A007901256 (SEQ ID NO: 143); A007901257 (SEQ ID NO: 144); A007901258 (SEQ ID NO: 145); A007901259 (SEQ ID NO: 146); A007901260 (SEQ ID NO: 147); A007901261 (SEQ ID NO: 148); A007901262 (SEQ ID NO: 149); A007901263 (SEQ ID NO: 150). Of these, the constructs A007901256 (SEQ ID NO: 143), A007901259 (SEQ ID NO: 146) and A007901260 (SEQ ID NO: 147) are particularly preferred, and thus one aspect of the invention also relates to a polypeptide that has at least 80%, such as at least 85%, for example at least 90%, such as at least 95% or more sequence identity with the polypeptides of SEQ ID NOs: 143, 146 and 147.

In a particular preferred but non-limiting aspect of the invention, the invention provides a polypeptide of the invention comprising i) one c-Met binding immunoglobulin single variable domain as described herein; and ii) one or more (preferably one) serum albumin binding immunoglobulin single variable domain as described herein.

In a further preferred aspect, the invention provides a polypeptide of the invention comprising i) one c-Met binding immunoglobulin single variable domain as described herein; and ii) one or more (preferably one) serum albumin binding immunoglobulin single variable domain of SEQ ID NO: 5 or SEQ ID NO: 101 (cf. Table A-2 and B-1).

In a further preferred aspect, the invention provides a polypeptide of the invention comprising i) one c-Met binding immunoglobulin single variable domain as described herein; and ii) one or more (preferably one) serum albumin binding immunoglobulin single variable domain with CDRs (defined according to the Kabat numbering) of SEQ ID NO: 5 or SEQ ID NO: 101 (cf. Table A-2 and B-1).

Thus, for example, further reference (and thus incorporated by reference) is made in particular to the experimental part and further description of WO2008/068280, wherein further details on SEQ ID NO: 5 or SEQ ID NO: 101 is made and e.g. the half-life of a immunoglobulin single variable domain construct containing said sequence in rhesus monkeys is disclosed.

These may comprise of two immunoglobulin single variable domains, such as one immunoglobulin single variable domain directed against c-Met and one immunoglobulin single variable domain against serum albumin. Such multispecific constructs will be clear to the skilled person based on the disclosure herein; some preferred, but non-limiting examples of such multispecific immunoglobulin single variable domains are the constructs of SEQ ID NOs: 7 to 12, 103-111, 113, 188 and 142-150, preferably SEQ ID NOs: 7, 106, 113, 188, 143, 146 and 147 (see experimental part).

According to another specific, but non-limiting aspect, a polypeptide of the invention comprises or essentially consists of at least one immunoglobulin single variable domain of the invention and at least one other binding unit (i.e. directed against another epitope, antigen, target, protein or polypeptide), which is preferably also an immunoglobulin single variable domain. Such proteins or polypeptides are also referred to herein as "multispecific" proteins or polypeptides or as "multispecific constructs", and these may comprise or consist essentially of two immunoglobulin single variable domains, such as one immunoglobulin single variable domain of the invention directed against c-Met and one immunoglobulin single variable domain against serum albumin. Such multispecific constructs will be clear to the skilled person based on the disclosure herein; some preferred, but non-limiting examples of such multispecific immunoglobulin single variable domains are the constructs of SEQ ID NOs: 7 to 12, 103-111, 113, 188 and 142-150, preferably SEQ ID NOs: 7, 106, 113, 188, 143, 146 and 147 (see experimental part).

According to yet another specific, but non-limiting aspect, a polypeptide of the invention comprises or essentially consists of at least one immunoglobulin single variable domain of the invention, optionally one or more further immunoglobulin single variable domains, and at least one other amino acid sequence (such as a protein or polypeptide) that confers at least one desired property to the immunoglobulin single variable domain of the invention and/or to the resulting fusion protein. Again, such fusion proteins may provide certain advantages compared to the corresponding monovalent immunoglobulin single variable domains of the invention such as e.g. may provide an increased half-life.

In the above constructs, the one or more immunoglobulin single variable domains and/or other immunoglobulin single variable domains may be directly linked to each other and/or suitably linked to each other via one or more linker sequences. Some suitable but non-limiting examples of such linkers will become clear from the further description herein.

In one embodiment, the linker sequence joining the immunoglobulin single variable domains are chosen from SEQ ID NOs: 13 to 22, preferably SEQ ID NOs: 15 or 22, or as known in the art.

In another preferred embodiment, the invention relates to a trispecific, or multispecific polypeptide, comprising or essentially consisting of at least three ISVDs, wherein two of said at least three ISVDs are directed against a tumor associated antigen (such as, for instance, c-Met and EGFR or VEGF) and the other binding moiety is directed against another target or antigen. Preferably this target or antigen is a molecule which can increase the half-life of the polypeptide in vivo (as further described) or a molecule with an effector function such as CD3, the Fc receptor or a complement protein.

In an embodiment, the invention provides trispecific polypeptides comprising or essentially consisting of a Nanobody against EGFR or a Nanobody against VEGF, a Nanobody against c-Met and a Nanobody against human serum albumin.

In another preferred embodiment, the invention relates to a tetraspecific, or multispecific polypeptide, comprising or essentially consisting of at least four ISVDs, wherein three of said at least four ISVDs are directed against a tumor associated antigen (such as, for instance, c-Met, EGFR and VEGF) and the other binding moiety is directed against another target or antigen. Preferably this target or antigen is a molecule which can increase the half-life of the polypeptide in vivo (as further described) or a molecule with an effector function such as CD3, the Fc receptor or a complement protein.

In an embodiment, the invention provides tetraspecific polypeptides comprising or essentially consisting of a Nanobody against EGFR, a Nanobody against VEGF, a Nanobody against c-Met and a Nanobody against human serum albumin.

Furthermore, although it is encompassed within the scope of the invention that the specific order or arrangement of the various Nanobodies in the polypeptides of the invention may have some influence on the properties of the final polypeptide of the invention (including but not limited to the affinity, specificity or avidity for VEGF, EGFR or c-Met, respectively, or against the one or more other antigens), said order or arrangement is usually not critical and may be suitably chosen by the skilled person, optionally after some limited routine experiments based on the disclosure herein. Thus, when reference is made to a specific multispecific polypeptide of the invention, it should be noted that this encompasses any order or arrangements of the relevant Nanobodies, unless explicitly indicated otherwise.

According to yet another specific, but non-limiting aspect, a polypeptide of the invention may for example be chosen from the group consisting of immunoglobulin single variable domains that have more than 80%, preferably more than 90%, more preferably more than 95%, such as 99% or more "sequence identity" (as defined herein) with one or more of the immunoglobulin single variable domains of SEQ ID NOs: 23 to 29, 102 and 187, preferably SEQ ID NO: 26 and 187 (see experimental part), in which the polypeptides are preferably as further defined herein, i.e. in the preferred format of one immunoglobulin single variable domain directed against c-Met and one immunoglobulin single variable domain directed against serum albumin.

According to yet another specific, but non-limiting aspect, a polypeptide of the invention may for example be chosen from the group consisting of polypeptides that have more than 80%, preferably more than 90%, more preferably more than 95%, such as 99% or more "sequence identity" (as defined herein) with one or more of the polypeptides of SEQ ID NOs: 7 to 12, 103-111, 113, 188 and 142-150, preferably SEQ ID NOs: 7, 106, 113, 188, 143, 146 and 147.

1.6 Compositions and Pharmaceutical Compositions of the Invention

Generally, for pharmaceutical use, the polypeptides of the invention may be formulated as a pharmaceutical preparation or composition comprising at least one polypeptide of the invention and at least one pharmaceutically acceptable carrier, diluent or excipient and/or adjuvant, and optionally one or more further pharmaceutically active polypeptides and/or compounds. By means of non-limiting examples, such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc, wherein the parenteral administration is preferred. Such suitable administration forms—which may be solid, semi-solid or liquid, depending on the manner of administration—as well as Methods and carriers for use in the preparation thereof, will be clear to the skilled person, and are further described herein. Such a pharmaceutical preparation or composition will generally be referred to herein as a "pharmaceutical composition". A pharmaceutical preparation or composition for use in a non-human organism will generally be referred to herein as a "veterinary composition".

Thus, in a further aspect, the invention relates to a pharmaceutical composition that contains at least one amino acid of the invention, at least one polypeptide of the invention or at least one polypeptide of the invention and at least one suitable carrier, diluent or excipient (i.e., suitable for pharmaceutical use), and optionally one or more further active substances.

Generally, the polypeptides of the invention can be formulated and administered in any suitable manner known per se. Reference is for example made to the general background art cited above (and in particular to WO 04/041862, WO 04/041863, WO 04/041865, WO 04/041867 and WO 08/020079) as well as to the standard handbooks, such as Remington's Pharmaceutical Sciences, 18$^{th}$ Ed., Mack Publishing Company, USA (1990), Remington, the Science and Practice of Pharmacy, 21st Edition, Lippincott Williams and Wilkins (2005); or the Handbook of Therapeutic Antibodies (S. Dubel, Ed.), Wiley, Weinheim, 2007 (see for example pages 252-255).

The polypeptides of the invention may be formulated and administered in any manner known per se for conventional antibodies and antibody fragments (including ScFv's and diabodies) and other pharmaceutically active proteins. Such formulations and Methods for preparing the same will be clear to the skilled person, and for example include preparations suitable for parenteral administration (e.g. intravenous, intraperitoneal, subcutaneous, intramuscular, intraluminal, intra-arterial or intrathecal administration) or for topical (i.e., transdermal or intradermal) administration.

Preparations for parenteral administration may for example be sterile solutions, suspensions, dispersions or emulsions that are suitable for infusion or injection. Suitable carriers or diluents for such preparations for example include, without limitation, those mentioned on page 143 of WO 08/020079. In one embodiment, the preparation is an aqueous solution or suspension.

The polypeptides of the invention can be administered using methods of delivery known from gene therapy, see, e.g., U.S. Pat. No. 5,399,346, which is incorporated by reference for its gene therapy delivery methods. Using a gene therapy Method of delivery, primary cells transfected with the gene encoding an amino acid sequence, polypeptide of the invention can additionally be transfected with tissue specific promoters to target specific organs, tissue, grafts, tumors, or cells and can additionally be transfected with signal and stabilization sequences for subcellularly localized expression.

Thus, the polypeptides of the invention may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the polypeptides of the invention may be combined with one or more excipients and used in the form of ingestible tablets, buccal tablets, troches, capsules, elixirs, suspensions, syrups, wafers, and the like. Such compositions and preparations should contain at least 0.1% of the polypeptide of the invention. Their percentage in the compositions and preparations may, of course, be varied and may conveniently be between about 2 to about 60% of the weight of a given unit dosage form. The amount of the polypeptide of the invention in such therapeutically useful compositions is such that an effective dosage level will be obtained.

For local administration at the site of tumor resection, the polypeptides of the invention may be used in biodegradable polymeric drug delivery systems, slow release poly(lactic-co-glycolic acid) formulations and the like (Hart et al., Cochrane Database Syst Rev. 2008 Jul. 16; (3): CD007294).

In a further preferred aspect of the invention, the polypeptides of the invention, such as a polypeptide consisting essentially of one monovalent anti-human c-Met immunoglobulin single variable domain and of one monovalent anti-human serum albumin immunoglobulin single variable domain linked by a GS linker, may have a beneficial distribution and kinetics profile in solid tumors compared to conventional antibodies such as e.g. IgG.

The tablets, troches, pills, capsules, and the like may also contain binders, excipients, disintegrating agents, lubricants and sweetening or flavoring agents, for example those mentioned on pages 143-144 of WO 08/020079. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the polypeptides of the invention, sucrose or fructose as a sweetening agent, Methyl and propylparabens as preservatives, a dye and flavoring such as cherry or orange flavor. Of course, any material used in preparing any unit dosage form should be pharmaceutically acceptable and substantially non-toxic in the amounts employed. In addition, the polypeptides of the invention may be incorporated into sustained-release preparations and devices.

Preparations and formulations for oral administration may also be provided with an enteric coating that will allow the constructs of the invention to resist the gastric environment and pass into the Intestines. More generally, preparations and formulations for oral administration may be suitably formulated for delivery into any desired part of the gastrointestinal tract. In addition, suitable suppositories may be used for delivery into the gastrointestinal tract.

The polypeptides of the invention may also be administered intravenously or intraperitoneally by infusion or injection. Particular examples are as further described on pages 144 and 145 of WO 08/020079 or in PCT/EP2010/062975 (entire document).

For topical administration, the polypeptides of the invention may be applied in pure form, i.e., when they are liquids. However, it will generally be desirable to administer them to the skin as compositions or formulations, in combination with a dermatologic acceptable carrier, which may be a solid or a liquid. Particular examples are as further described on page 145 of WO 08/020079.

Generally, the concentration of the polypeptides of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the polypeptides of the invention required for use in treatment will vary not only with the particular polypeptide selected but also with the route of administration, the nature of the condition being treated and the age and condition of the patient and will be ultimately at the discretion of the attendant physician or clinician. Also the dosage of the polypeptides of the invention varies depending on the target cell, tumor, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication.

In another aspect, the invention relates to a method for the prevention and/or treatment of at least one disease or disorder associated with c-Met, said method comprising administering, to a subject in need thereof, a pharmaceutically active amount of a polypeptide of the invention, and/or of a pharmaceutical composition comprising the same.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk of, the diseases and disorders mentioned herein.

The invention relates to a method for the prevention and/or treatment of at least one disease or disorder that is associated with c-Met, with its biological or pharmacological activity, and/or with the biological pathways or signaling in which c-Met is involved, said method comprising administering, to a subject in need thereof, a pharmaceutically active amount of an amino acid sequence of the invention, of a polypeptide of the invention and/or of a pharmaceutical composition comprising the same. In an embodiment, the invention relates to a method for the prevention and/or treatment of at least one disease or disorder that can be treated by modulating c-Met, its biological or pharmacological activity, and/or the biological pathways or signaling in which c-Met is involved, said method comprising administering, to a subject in need thereof, a pharmaceutically active amount of a polypeptide of the invention, and/or of a pharmaceutical composition comprising the same. In an embodiment, said pharmaceutically effective amount may be an amount that is sufficient to modulate c-Met, its biological or pharmacological activity, and/or the biological pathways or signaling in which c-Met is involved; and/or an amount that provides a level of the polypeptide of the invention in the circulation that is sufficient to modulate c-Met, its biological or pharmacological activity, and/or the biological pathways or signaling in which c-Met is involved.

In an embodiment the invention relates to a method for the prevention and/or treatment of at least one disease or disorder that can be prevented and/or treated by administering a polypeptide of the invention, or a nucleotide construct of the invention encoding the same, and/or of a pharmaceutical composition comprising the same, to a patient. In an embodiment, the method comprises administering a pharmaceutically active amount of a polypeptide of the invention, or a nucleotide construct of the invention encoding the same, and/or of a pharmaceutical composition comprising the same to a subject in need thereof.

In an embodiment the invention relates to a method for the prevention and/or treatment of at least one disease or disorder that can be prevented and/or treated by inhibiting binding of HGF to c-Met in specific cells or in a specific tissue of a subject to be treated (and in particular, by inhibiting binding of HGF to c-Met in cancer cells, in a tumor or in the tumor microenvironment present in the subject to be treated), said method comprising administering a pharmaceutically active amount of a polypeptide of the invention, or a nucleotide construct of the invention encoding the same, and/or of a pharmaceutical composition comprising the same, to a subject in need thereof.

In an embodiment, the invention relates to a method for the prevention and/or treatment of at least one disease or disorder chosen from the group consisting of the diseases and disorders listed herein, said method comprising administering, to a subject in need thereof, a polypeptide of the invention, or a nucleotide construct of the invention encoding the same, and/or of a pharmaceutical composition comprising the same.

In an embodiment, the invention relates to a method for immunotherapy, and in particular for passive immunotherapy, which method comprises administering, to a subject suffering from or at risk of the diseases and disorders mentioned herein, a pharmaceutically active amount of a polypeptide of the invention, or a nucleotide construct of the invention encoding the same, and/or of a pharmaceutical composition comprising the same.

In the above methods, the amino acid sequences, polypeptides of the invention and/or the compositions comprising the same can be administered in any suitable manner, depending on the specific pharmaceutical formulation or composition to be used. Thus, the polypeptides of the invention and/or the compositions comprising the same can for example be administered orally, intraperitoneally (e.g. intravenously, subcutaneously, intramuscularly, or via any other route of administration that circumvents the gastrointestinal tract), intranasally, transdermally, topically, by means of a suppository, by inhalation, again depending on the specific pharmaceutical formulation or composition to be used. The clinician will be able to select a suitable route of administration and a suitable pharmaceutical formulation or composition to be used in such administration, depending on the disease or disorder to be prevented or treated and other factors well known to the clinician.

The polypeptides of the invention and/or the compositions comprising the same are administered according to a regime of treatment that is suitable for preventing and/or treating the disease or disorder to be prevented or treated. The clinician will generally be able to determine a suitable treatment regimen, depending on factors such as the disease or disorder to be prevented or treated, the severity of the disease to be treated and/or the severity of the symptoms thereof, the polypeptide of the invention to be used, the specific route of administration and pharmaceutical formulation or composition to be used, the age, gender, weight, diet, general condition of the patient, and similar factors well known to the clinician.

Generally, the treatment regimen will comprise the administration of one or more polypeptides of the invention, or of one or more compositions comprising the same, in one or more pharmaceutically effective amounts or doses. The specific amount(s) or doses to be administered can be determined by the clinician, again based on the factors cited above.

Generally, for the prevention and/or treatment of the diseases and disorders mentioned herein and depending on the specific disease or disorder to be treated, the potency of the specific polypeptide of the invention to be used, the specific route of administration and the specific pharmaceutical formulation or composition used, the polypeptides of the invention will generally be administered in an amount between 1 gram and 0.01 microgram per kg body weight per day, preferably between 0.1 gram and 0.1 microgram per kg body weight per day, such as about 1, 10, 100 or 1000 microgram per kg body weight per day, either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

In an embodiment, a single contiguous polypeptide of the invention will be used. In one embodiment two or more polypeptides of the invention are provided in combination.

The polypeptides of the invention may be used in combination with one or more further pharmaceutically active compounds or principles, i.e., as a combined treatment regimen, which may or may not lead to a synergistic effect. Again, the clinician will be able to select such further compounds or principles, as well as a suitable combined treatment regimen, based on the factors cited above and his expert judgment.

In particular, the polypeptides of the invention may be used in combination with other pharmaceutically active compounds or principles that are or can be used for the prevention and/or treatment of the diseases and disorders cited herein, as a result of which a synergistic effect may or may not be obtained. Examples of such compounds and principles, as well as routes, methods and pharmaceutical formulations or compositions for administering them will be clear to the clinician, and generally include the cytostatic and preferably cytotoxic active principles usually applied for the treatment of the tumor to be treated.

Specifically contemplated combinations for use with the polypeptides of the invention for oncology include, but are not limited to, e.g., RON antagonists, CXCR4 antagonists such as e.g. AMD3100, other chemokine receptor antagonists, taxol; gemcitabine; cisplatin; cIAP inhibitors (such as inhibitors to cIAP1, cIAP2 and/or XIAP); MEK inhibitors including but not limited to, e.g., U0126, PD0325901; bRaf inhibitors including but not limited to, e.g., RAF265; and mTOR inhibitors including but not limited to, e.g., RAD001; VEGF inhibitors including but not limited to e.g. bevacizumab, sutinib and sorafenib; ERBB inhibitors, such as, for instance, EGFR-inhibitors, including but not limited to specific small molecule kinase inhibitors, e.g. erlotinib, gefitinib; antibodies, e.g. cetuximab, nimotuzumab, panitumumab, necitumumab, IMC-C225 (Erbitux, Imclone), EMD72000 (Merck Darmstadt), ABX-EGF (Abgenix), h-R3 (theraCIM, YM Biosciences) and Humax-EGFR (Genmab); dual- or multispecific small molecule kinase inhibitors, e.g. lapatinib (EGFR&HER2), vandetanib (EGFR, RET, VEGFR2), neratinib (EGFR, HER2, HER4) and PF-299804 (EGFR, HER2, HER4), HER2-inhibitors including but not limited to e.g. trastuzumab and lapatinib; HER3-inhibitors; HER4 inhibitors; PDGFR, FGFR, src, JAK, STAT and/or GSK3 Inhibitors; selective estrogen receptor modulators including but not limited to tamoxifen; estrogen receptor downregulators including but not limited to fulvestrant. Specific contemplated combinations for use with the polypeptides of the invention for e.g. inflammatory and other conditions also include, but are not limited to, e.g., interferon beta 1 alpha and beta, IFN alpha 2b; natalizumab; TNF alpha antagonists including but not limited to e.g. infliximab, adalimumab, certolizumab pegol, etanercept; disease-modifying antirheumatic drugs such as e.g. Methotrexate (MTX); glucocorticoids including but not limited to e.g. dexamethasone, hydrocortisone; nonsteroidal anti-inflammatory drugs including but not limited to e.g. ibuprofen, sulindac; IL-6 or IL-6R inhibitors including but not limited to e.g. RoActemra, ALD518. In addition combinations for use with the polypeptides of the invention for oncology indications include but are not limited to non-targeted chemotherapeutics such as cytotoxics and/or cytostatics. The invention also comprises products and/or compositions comprising the polypeptides of the invention in combination with other antibodies and/or chemical compounds directed against other growth factors involved in tumor progression or metastasis and/or compounds and/or anti-cancer agents or agents conjugated with toxins and their use for the prevention and/or the treatment of certain cancers.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease or disorder involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

In another aspect, the invention relates to the use of polypeptide of the invention in the preparation of a pharmaceutical composition for prevention and/or treatment of at least one disease and disorder associated with c-Met; and/or for use in one or more of the methods of treatment mentioned herein.

The subject to be treated may be any warm-blooded animal, but is in particular a mammal, and more in particular a human being. In veterinary applications, the subject to be treated includes any animal raised for commercial purposes or kept as a pet. As will be clear to the skilled person, the subject to be treated will in particular be a person suffering from, or at risk of, the diseases and disorders mentioned herein.

The invention relates to the use of a polypeptide of the invention, or a nucleotide encoding the same, in the preparation of a pharmaceutical composition for the prevention and/or treatment of at least one disease or disorder that can be prevented and/or treated by administering a polypeptide of the invention, or a nucleotide encoding the same, and/or a pharmaceutical composition of the same to a patient.

More in particular, the invention relates to the use of a polypeptide of the invention, or a nucleotide encoding the same, in the preparation of a pharmaceutical composition for the prevention and/or treatment of diseases and disorders associated with c-Met, and in particular for the prevention and treatment of one or more of the diseases and disorders listed herein. The invention thus relates to a method for prevention and/or treatment of diseases and disorders associated with c-Met wherein an immunoglobulin single variable domain and/or polypeptide of the invention is administered. The present invention relates to an immunoglobulin single variable domain and/or polypeptide of the invention for use in prevention and/or treatment of diseases and disorders associated with c-Met.

The invention also relates to the use of a polypeptide of the invention, or a nucleotide encoding the same, in the preparation of a pharmaceutical composition for reducing and/or inhibiting myeloma cell proliferation in subjects suffering multiple myeloma. The invention thus relates to a method for reducing and/or inhibiting myeloma cell proliferation in subjects suffering multiple myeloma, wherein an immunoglobulin single variable domain and/or polypeptide of the invention is administered. The present invention relates to an immunoglobulin single variable domain and/or polypeptide of the invention for reducing and/or inhibiting myeloma cell proliferation in subjects suffering multiple myeloma. In a preferred aspect, myeloma cell proliferation is reduced by 30% or more, by 40% or more, by 50% or more, preferably by 60% or more, by 70% or more, or even by 80% or more, by 90% or more, most preferably by 100%.

The invention also relates to the use of a polypeptide of the invention, or a nucleotide encoding the same, in the preparation of a pharmaceutical composition for reducing and/or inhibiting migration of myeloma cells in subjects suffering multiple myeloma. The invention thus relates to a method for reducing and/or inhibiting migration of myeloma cells in subjects suffering multiple myeloma, wherein an immunoglobulin single variable domain and/or polypeptide of the invention is administered. The present invention relates to an immunoglobulin single variable domain and/or polypeptide of the invention for reducing and/or inhibiting migration of myeloma cells in subjects suffering multiple myeloma. In a preferred aspect, migration of myeloma cells is reduced by 30% or more, by 40% or more, by 50% or more, preferably by 60% or more, by 70% or more, or even by 80% or more, by 90% or more, most preferably by 100%.

In the present invention, the inventors for the first time observed that anti-c-Met ISVDs, such as anti-c-Met Nanobodies, could reverse HGF-induced osteoblastogenesis. Accordingly, the present invention is also devoted to this novel use of anti-c-Met ISVDs, including the polypeptides of the invention as well as previously described anti-c-Met ISVDs (e.g. as described in WO 2012/042026). The invention thus relates to the use of an anti-c-Met ISVD (such as e.g. a polypeptide of the invention), or a nucleotide encoding the same, in the preparation of a pharmaceutical composition for the prevention and/or treatment of bone disease in subjects suffering bone metastatic cancer, including multiple myeloma. The invention thus relates to a method for prevention and/or treatment of bone disease in subjects suffering bone metastatic cancer, including multiple myeloma, wherein an anti-c-Met ISVD (such as e.g. a polypeptide of the invention) is administered. The present invention relates to an anti-c-Met ISVD (such as e.g. a polypeptide of the invention) for use in prevention and/or treatment of bone disease in subjects suffering bone metastatic cancer, including multiple myeloma.

The invention also relates to the use of an anti-c-Met ISVD (such as e.g. a polypeptide of the invention), or a nucleotide encoding the same, in the preparation of a pharmaceutical composition for reversing and/or completely abolishing the inhibitory effect of HGF on bone formation in subjects suffering bone metastatic cancer, including multiple myeloma. The invention thus relates to a method for reversing and/or completely abolishing the inhibitory effect of HGF on bone formation in subjects suffering bone metastatic cancer, including multiple myeloma, wherein an anti-c-Met ISVD (such as e.g. a polypeptide of the invention) is administered. The present invention relates to an anti-c-Met ISVD (such as e.g. a polypeptide of the invention) for reversing and/or completely abolishing the inhibitory effect of HGF on bone formation in subjects suffering bone metastatic cancer, including multiple myeloma.

The invention also relates to the use of an anti-c-Met ISVD (such as e.g. a polypeptide of the invention), or a nucleotide encoding the same, in the preparation of a pharmaceutical composition for reversing and/or completely abolishing the inhibitory effect of HGF on (bone morphogenetic protein (BMP)-induced) osteoblastogenesis. The invention thus relates to a method for reversing and/or completely abolishing the inhibitory effect of HGF on (bone morphogenetic protein (BMP)-induced) osteoblastogenesis, wherein an anti-c-Met ISVD (such as e.g. a polypeptide of the invention) is administered. The present invention relates to an anti-c-Met ISVD (such as e.g. a polypeptide of the invention) for reversing and/or completely abolishing the inhibitory effect of HGF on (bone morphogenetic protein (BMP)-induced) osteoblastogenesis (as measured e.g. by an osteoblast differentiation assay or the ALP assay as described by Standal et al., Blood 2007 Apr. 1; 109(7): 3024-30). In a preferred aspect, the inhibitory effect of HGF on (bone morphogenetic protein (BMP)-induced) osteoblastogenesis is reversed by 30% or more, by 40% or more, by 50% or more, preferably by 60% or more, by 70% or more, or even by 80% or more, by 90% or more, most preferably by 100%.

The invention also relates to the use of an anti-c-Met ISVD (such as e.g. a polypeptide of the invention), or a nucleotide encoding the same, in the preparation of a pharmaceutical composition for reversing and/or completely abolishing the inhibitory effect of HGF on (BMP-induced expression of) alkaline phosphatase (ALP). The invention thus relates to a method for reversing and/or completely abolishing the inhibitory effect of HGF on (BMP-induced expression of) alkaline phosphatase (ALP), wherein an anti-c-Met ISVD (such as e.g. a polypeptide of the invention) is administered. The present invention relates to an anti-c-Met ISVD (such as e.g. a polypeptide of the invention) for reversing and/or completely abolishing the inhibitory effect of HGF on (BMP-induced expression of) alkaline phosphatase (ALP) (as measured e.g. by the ALP assay as described by Standal et al., Blood 2007 Apr. 1; 109(7): 3024-30). In a preferred aspect, the inhibitory effect of HGF on (BMP-induced expression of) alkaline phosphatase (ALP) is reversed by 30% or more, by 40% or more, by 50% or more, preferably by 60% or more, by 70% or more, or even by 80% or more, by 90% or more, most preferably by 100%.

The invention also relates to the use of an anti-c-Met ISVD (such as e.g. a polypeptide of the invention), or a nucleotide encoding the same, in the preparation of a pharmaceutical composition for reversing and/or completely abolishing the inhibitory effect of HGF on mineralization of osteoblasts. The invention thus relates to a method for reversing and/or completely abolishing the inhibitory effect of HGF on mineralization of osteoblasts, wherein an anti-c-Met ISVD (such as e.g. a polypeptide of the invention) is administered. The present invention relates to an anti-c-Met ISVD (such as e.g. a polypeptide of the invention) for reversing and/or completely abolishing the inhibitory effect of HGF on mineralization of osteoblasts (as measured e.g. by an osteoblast differentiation assay, the ALP assay, or quantification+ visualization by Alzarin Red-s (ARS), as described by Standal et al., Blood 2007 Apr. 1; 109(7): 3024-30). In a preferred aspect, the inhibitory effect of HGF on mineralization of osteoblasts is reversed by 30% or more, by 40% or more, by 50% or more, preferably by 60% or more, by 70% or more, or even by 80% or more, by 90% or more, most preferably by 100%.

The invention also relates to the use of an anti-c-Met ISVD (such as e.g. a polypeptide of the invention), or a nucleotide encoding the same, in the preparation of a pharmaceutical composition for reversing and/or completely abolishing the inhibitory effect of HGF on (BMP induced) expression of osteoblast-specific transcription factors Runx2 and/or Osterix. The invention thus relates to a method for reversing and/or completely abolishing the inhibitory effect of HGF on (BMP induced) expression of osteoblast-specific transcription factors Runx2 and/or Osterix, wherein an anti-c-Met ISVD (such as e.g. a polypeptide of the invention) is administered. The present invention relates to an anti-c-Met ISVD (such as e.g. a polypeptide of the invention) for reversing and/or completely abolishing the inhibitory effect of HGF on (BMP induced) expression of osteoblast-specific transcription factors Runx2 and/or Osterix (as measured e.g. by expression of RunX or Osterix mRNA in C2C12 cells, as described by Standal et al., Blood 2007 Apr. 1; 109(7): 3024-30). In a preferred aspect, the inhibitory effect of HGF on (BMP induced) expression of osteoblast-specific transcription factors Runx2 and/or Osterix is reversed by 30% or more, by 40% or more, by 50% or more, preferably by 60% or more, by 70% or more, or even by 80% or more, by 90% or more, most preferably by 100%.

The invention also relates to the use of an anti-c-Met ISVD (such as e.g. a polypeptide of the invention), or a nucleotide encoding the same, in the preparation of a pharmaceutical composition for reversing and/or completely abolishing the inhibitory effect of HGF on (BMP-induced) nuclear translocation of receptor-activated Smads. The invention thus relates to a method for reversing and/or completely abolishing the inhibitory effect of HGF on (BMP-induced) nuclear translocation of receptor-activated Smads, wherein an anti-c-Met ISVD (such as e.g. a polypeptide of the invention) is administered. The present invention relates to an anti-c-Met ISVD (such as e.g. a polypeptide of the invention) for reversing and/or completely abolishing the inhibitory effect of HGF on (BMP-induced) nuclear translocation of receptor-activated Smads (as measured e.g. by Confocal microscopy or the use of Smad-driven BMP-receptor constructs, as described by Standal et al., Blood 2007 Apr. 1; 109(7): 3024-30). In a preferred aspect, the inhibitory effect of HGF on (BMP-induced) nuclear translocation of receptor-activated Smads is reduced by 30% or more, by 40% or more, by 50% or more, preferably by 60% or more, by 70% or more, or even by 80% or more, by 90% or more, most preferably by 100%.

The invention also relates to the use of an anti-c-Met ISVD (such as e.g. a polypeptide of the invention), or a nucleotide encoding the same, in the preparation of a pharmaceutical composition for reversing and/or completely abolishing the inhibitory effect of HGF on BMP-2 signaling. The invention thus relates to a method for reversing and/or completely abolishing the inhibitory effect of HGF on BMP-2 signaling, wherein an anti-c-Met ISVD (such as e.g. a polypeptide of the invention) is administered. The present invention relates to an anti-c-Met ISVD (such as e.g. a polypeptide of the invention) for reversing and/or completely abolishing the inhibitory effect of HGF on BMP-2 signaling.

The invention also relates to the use of an anti-c-Met ISVD (such as e.g. a polypeptide of the invention), or a nucleotide encoding the same, in the preparation of a pharmaceutical composition for inhibiting the HGF-induced chemotaxis, proliferation and activation of osteoclast precursors or osteoclasts. The invention thus relates to a method for inhibiting the effects of HGF on osteoclasts wherein an anti-c-Met ISVD (such as e.g. a polypeptide of the invention) is administered. The present invention relates to an anti-c-Met ISVD (such as e.g. a polypeptide of the invention) for inhibiting the effects of HGF on osteoclasts (as described in Grano et al. 1996, Proc Natl Acad Sci USA 93(15): 7644-8).

Again, in such a pharmaceutical composition, the one or more polypeptide of the invention, or nucleotide encoding the same, and/or a pharmaceutical composition of the same, may also be suitably combined with one or more other active principles, such as those mentioned herein.

The invention also relates to a composition (such as, without limitation, a pharmaceutical composition or preparation as further described herein) for use, either in vitro (e.g. in an in vitro or cellular assay) or in vivo (e.g. in an a single cell or multicellular organism, and in particular in a mammal, and more in particular in a human being, such as in a human being that is at risk of or suffers from a disease or disorder of the invention).

In the context of the present invention, "modulating" or "to modulate" generally means reducing or inhibiting the activity of c-Met and in particular human c-Met (SEQ ID NO: 1), as measured using a suitable in vitro, cellular or in vivo assay (such as those mentioned herein). In particular, reducing or inhibiting the activity of c-Met and in particular human c-Met (SEQ ID NO: 1), as measured using a suitable in vitro, cellular or in vivo assay (such as those mentioned herein), by at least 1%, preferably at least 5%, such as at least 10% or at least 25%, for example by at least 50%, at least 60%, at least 70%, at least 80%, or 90% or more, compared to activity of c-Met and in particular human c-Met (SEQ ID NO: 1) in the same assay under the same conditions but without the presence of the polypeptide of the invention.

Modulating may for example involve reducing or inhibiting the binding c-Met to one of its substrates or ligands and/or competing with natural ligands (HGF), substrate for binding to c-Met. Alternatively, modulating may involve inhibiting the internalization, inducing internalization in order to reduce c-Met level and as such reducing signaling, homodimerization of c-Met and/or promoting of shedding of c-Met and thus may inhibit HGF dependent and/or HGF independent c-Met activation.

1.7 Generation of the Polypeptides and/or Other Biological Materials of the Invention The invention further relates to methods for preparing or generating the immunoglobulin single variable domains, polypeptides, nucleic acids, host cells, products and compositions described herein. Some preferred but non-limiting examples of such methods will become clear from the further description herein.

Generally, these methods may comprise the steps of:
a) providing a set, collection or library of immunoglobulin single variable domains; and
b) screening said set, collection or library of immunoglobulin single variable domains for immunoglobulin single variable domains that can bind to and/or have affinity for c-Met and in particular human c-Met (SEQ ID NO: 1); and
c) isolating the amino acid sequence(s) that can bind to and/or have affinity for c-Met and in particular human c-Met (SEQ ID NO: 1).

In such a method, the set, collection or library of immunoglobulin single variable domains may be any suitable set, collection or library of immunoglobulin single variable domains. For example, the set, collection or library of immunoglobulin single variable domains may be a set, collection or library of immunoglobulin sequences (as described herein), such as a naive set, collection or library of immunoglobulin sequences; a synthetic or semi-synthetic set, collection or library of immunoglobulin sequences; and/or a set, collection or library of immunoglobulin sequences that have been subjected to affinity maturation.

Also, in such a method, the set, collection or library of immunoglobulin single variable domains may be a set, collection or library of heavy or light chain variable domains (such as VL-, VH- or VHH domains, preferably VHH domains). For example, the set, collection or library of immunoglobulin single variable domains may be a set, collection or library of domain antibodies or single domain antibodies, or may be a set, collection or library of immunoglobulin single variable domains that are capable of functioning as a domain antibody or single domain antibody.

In a preferred aspect of this method, the set, collection or library of immunoglobulin single variable domains may be an immune set, collection or library of immunoglobulin sequences, for example derived from a mammal that has been suitably immunized with c-Met and in particular human c-Met (SEQ ID NO: 1) or with a suitable antigenic determinant based thereon (such as e.g. described in the experimental part, see human c-Met/Fc chimera (SEQ ID NO: 2) or derived therefrom, such as an antigenic part, fragment, region, domain, loop or other epitope thereof. In one particular aspect, said antigenic determinant may be an extracellular part, region, domain, loop or other extracellular epitope(s).

In the above methods, the set, collection or library of immunoglobulin single variable domains may be displayed on a phage, phagemid, ribosome or suitable micro-organism (such as yeast), such as to facilitate screening. Suitable methods, techniques and host organisms for displaying and screening (a set, collection or library of) immunoglobulin single variable domains will be clear to the person skilled in the art, for example on the basis of the further disclosure herein. Reference is also made to the review by Hoogenboom in Nature Biotechnology, 23:1105-1116 (2005).

In another aspect, the method for generating immunoglobulin single variable domains comprises at least the steps of:
a) providing a collection or sample of cells expressing immunoglobulin single variable domains;
b) screening said collection or sample of cells for cells that express an amino acid sequence that can bind to and/or have affinity for c-Met and in particular human c-Met (SEQ ID NO: 1); and
c) either (i) isolating said amino acid sequence; or (ii) isolating from said cell a nucleic acid sequence that encodes said amino acid sequence, followed by expressing said amino acid sequence.

In another aspect, the method for generating an amino acid sequence directed against c-Met and in particular human c-Met (SEQ ID NO: 1) may comprise at least the steps of:
a) providing a set, collection or library of nucleic acid sequences encoding immunoglobulin single variable domains;
b) screening said set, collection or library of nucleic acid sequences for nucleic acid sequences that encode an amino acid sequence that can bind to and/or has affinity for c-Met and in particular human c-Met (SEQ ID NO: 1); and
c) isolating said nucleic acid sequence, followed by expressing said amino acid sequence.

In such a method, the set, collection or library of nucleic acid sequences encoding immunoglobulin single variable domains may for example be a set, collection or library of nucleic acid sequences encoding a naive set, collection or library of immunoglobulin sequences; a set, collection or library of nucleic acid sequences encoding a synthetic or semi-synthetic set, collection or library of immunoglobulin sequences; and/or a set, collection or library of nucleic acid sequences encoding a set, collection or library of immunoglobulin sequences that have been subjected to affinity maturation.

In another aspect, the method for generating an amino acid sequence directed against c-Met and in particular human c-Met (SEQ ID NO: 1) may comprise at least the steps of:
a) providing a set, collection or library of nucleic acid sequences encoding immunoglobulin single variable domains;
b) screening said set, collection or library of nucleic acid sequences for nucleic acid sequences that encode an amino acid sequence that can bind to and/or has affinity for c-Met and in particular human c-Met (SEQ ID NO: 1) and that is cross-blocked or is cross blocking a immunoglobulin single variable domain or polypeptide of the invention, e.g. SEQ ID NOs: 7 to 12, 103-111, 113, 188 and 142-150, preferably SEQ ID NOs: 7, 106, 113, 188, 143, 146 and 147; and
c) isolating said nucleic acid sequence, followed by expressing said amino acid sequence.

In preferred aspect, the method for generating an amino acid sequence directed against c-Met and in particular human c-Met (SEQ ID NO: 1) may comprise at least the steps of:
a) providing a set, collection or library of VHH1 type immunoglobulin single variable domains; and
b) screening said set, collection or library of VHH1 type immunoglobulin single variable domains for immunoglobulin single variable domains that can bind to and/or have affinity for c-Met and in particular human c-Met (SEQ ID NO: 1); and
c) isolating the amino acid sequence(s) that can bind to and/or have affinity for c-Met and in particular human c-Met (SEQ ID NO: 1).

In such a method, the set, collection or library of VHH1 type immunoglobulin single variable domains may be any suitable set, collection or library of immunoglobulin single variable domains. For example, the set, collection or library of VHH1 type immunoglobulin single variable domains may be a set, collection or library of immunoglobulin sequences (as described herein), such as a naive set, collection or library of immunoglobulin sequences; a synthetic or semi-synthetic set, collection or library of immunoglobulin sequences; and/or a set, collection or library of VHH1 type immunoglobulin sequences that have been subjected to affinity maturation. In a preferred aspect, the set, collection or library of VHH1 type immunoglobulin single variable domains may be a set, collection or library of immunoglobulin sequences (as described herein), such as a synthetic set, collection or library of VHH1 type immunoglobulin sequences. In the above methods, the set, collection or library of VHH1 type immunoglobulin single variable domains may be displayed on a phage, phagemid, ribosome or suitable micro-organism (such as yeast), such as to facilitate screening. Suitable methods, techniques and host organisms for displaying and screening (a set, collection or library of) immunoglobulin single variable domains will be clear to the person skilled in the art such as e.g. described by Knappik, et al., J. Mol. Biol. 2000 Feb. 11, 296:57-86.

Suitable methods, techniques and host organisms for displaying and screening (a set, collection or library of) VHH1 type immunoglobulin single variable domains will be clear to the person skilled in the art, for example on the basis of the further disclosure herein. Reference is also made to the review by Hoogenboom in Nature Biotechnology, 23:1105-1116 (2005).

The invention also relates to immunoglobulin single variable domains that are obtained by the above methods, or alternatively by a method that comprises the one of the above methods and in addition at least the steps of determining the nucleotide sequence or amino acid sequence of said immunoglobulin sequence; and of expressing or synthesizing said amino acid sequence in a manner known per se, such as by expression in a suitable host cell or host organism or by chemical synthesis.

Also, following the steps above, one or more immunoglobulin single variable domains of the invention may be suitably humanized, camelized or otherwise sequence optimized (e.g. sequence optimized for manufacturability, stability and/or solubility); and/or the amino acid sequence(s) thus obtained may be linked to each other or to one or more other suitable immunoglobulin single variable domains (optionally via one or more suitable linkers) so as to provide a polypeptide of the invention. Also, a nucleic acid sequence encoding an amino acid sequence of the invention may be suitably humanized, camelized or otherwise sequence optimized (e.g. sequence optimized for manufacturability, stability and/or solubility) and suitably expressed; and/or one or more nucleic acid sequences encoding an amino acid sequence of the invention may be linked to each other or to one or more nucleic acid sequences that encode other suitable immunoglobulin single variable domains (optionally via nucleotide sequences that encode one or more suitable linkers), after which the nucleotide sequence thus obtained may be suitably expressed so as to provide a polypeptide of the invention.

The invention further relates to applications and uses of the immunoglobulin single variable domains, compounds, constructs, polypeptides, nucleic acids, host cells, products and compositions described herein, as well as to methods for the diagnosis, prevention and/or treatment for diseases and disorders associated with c-Met and in particular human c-Met (SEQ ID NO: 1). Some preferred but non-limiting applications and uses will become clear from the further description herein.

The invention also relates to the immunoglobulin single variable domains, compounds, constructs, polypeptides, nucleic acids, host cells, products and compositions described herein for use in therapy.

In particular, the invention also relates to the immunoglobulin single variable domains, compounds, constructs, polypeptides, nucleic acids, host cells, products and compositions described herein for use in therapy of a disease or disorder that can be prevented or treated by administering, to a subject in need thereof, of (a pharmaceutically effective amount of) an amino acid sequence, compound, construct or polypeptide as described herein.

More in particular, the invention relates to the immunoglobulin single variable domains, compounds, constructs, polypeptides, nucleic acids, host cells, products and compositions described herein for use in therapy of cancer.

1.8 Variants of Polypeptides and Other Biological Materials of the Invention

Polypeptides of the invention and immunoglobulin single variable domains (that form part of the polypeptides of the invention) may be altered in order to further improve potency or other desired properties.

Generally, an immunoglobulin single variable domain can be defined as a polypeptide with the formula 1

in which FR1 to FR4 refer to framework regions 1 to 4, respectively, and in which CDR1 to CDR3 refer to the complementarity determining regions 1 to 3, respectively.

Some particularly preferred, but non-limiting combinations of CDR sequences, as well as preferred combinations of CDR sequences and framework sequences, are mentioned in Table B-2 or A-2 below, which lists the CDR sequences and framework sequences that are present in a number of preferred (but non-limiting) immunoglobulin single variable domains of the invention. As will be clear to the skilled person, a combination of CDR1, CDR2 and CDR3 sequences that occur in the same clone (i.e. CDR1, CDR2 and CDR3 sequences that are mentioned on the same line or row in Table B-2 or A-2) will usually be preferred (although the invention in its broadest sense is not limited thereto, and also comprises other suitable combinations of the CDR sequences mentioned in Table B-2 or A-2). Also, a combination of CDR sequences and framework sequences that occur in the same clone (i.e. CDR sequences and framework sequences that are mentioned on the same line or row in Table B-2 or A-2) will usually be preferred (although the invention in its broadest sense is not limited thereto, and also comprises other suitable combinations of the CDR sequences and framework sequences mentioned in Table B-2 or A-2, as well as combinations of such CDR sequences and other suitable framework sequences, e.g. as further described herein).

Also, in the immunoglobulin single variable domains of the invention that comprise the combinations of CDRs mentioned in Table 8-2, each CDR can be replaced by a CDR chosen from the group consisting of immunoglobulin single variable domains that have at least 80%, preferably at least 90%, more preferably at least 95%, even more preferably at least 99% sequence identity (as defined herein) with the mentioned CDRs, in which:

i) any amino acid substitution in such a CDR is preferably, and compared to the corresponding CDR sequence mentioned in Table B-2, a conservative amino acid substitution (as defined herein); and/or ii) any such CDR sequence preferably only contains amino acid substitutions, and no amino acid deletions or insertions, compared to the corresponding CDR sequence mentioned in Table B-2; and/or iii) any such CDR sequence is a CDR that is derived by means of a technique for affinity maturation known per se, and in particular starting from the corresponding CDR sequence mentioned in Table B-2.

However, as will be clear to the skilled person, the (combinations of) CDR sequences, as well as (the combinations of) CDR sequences and framework sequences mentioned in Table 8-2 will generally be preferred.

Thus, in the immunoglobulin single variable domains of the invention, at least one of the CDR1, CDR2 and CDR3 sequences present is suitably chosen from the group consisting of the CDR1, CDR2 and CDR3 sequences, respectively, listed in Table B-2; or from the group of CDR1, CDR2 and CDR3 sequences, respectively, that have at least 80%, preferably at least 90%, more preferably at least 95%, even more preferably at least 99% "sequence identity" (as defined herein) with at least one of the CDR1, CDR2 and CDR3 sequences, respectively, listed in Table B-2; and/or from the group consisting of the CDR1, CDR2 and CDR3 sequences, respectively, that have 3, 2 or only 1 "amino acid difference(s)" (as defined herein) with at least one of the CDR1, CDR2 and CDR3 sequences, respectively, listed in Table B-2.

In this context, by "suitably chosen" is meant that, as applicable, a CDR1 sequence is chosen from suitable CDR1 sequences (i.e. as defined herein), a CDR2 sequence is chosen from suitable CDR2 sequences (i.e. as defined herein), and a CDR3 sequence is chosen from suitable CDR3 sequence (i.e. as defined herein), respectively. More in particular, the CDR sequences are preferably chosen such that the immunoglobulin single variable domains of the invention bind to c-Met and in particular human c-Met (SEQ ID NO: 1) with an affinity (suitably measured and/or expressed as a EC50 value, or alternatively as an $IC_{50}$ value, as further described herein in various in vitro and/or in vivo potency or other assays) that is as defined herein.

In particular, in the immunoglobulin single variable domains of the invention, at least the CDR3 sequence present is suitably chosen from the group consisting of the CDR3 sequences listed in Table B-2 or from the group of CDR3 sequences that have at least 80%, preferably at least 90%, more preferably at least 95%, even more preferably at least 99% sequence identity with at least one of the CDR3 sequences listed in Table B-2; and/or from the group consisting of the CDR3 sequences that have 3, 2 or only 1 amino acid difference(s) with at least one of the CDR3 sequences listed in Table B-2.

Preferably, in the immunoglobulin single variable domains of the invention, at least two of the CDR1, CDR2 and CDR3 sequences present are suitably chosen from the group consisting of the CDR1, CDR2 and CDR3 sequences, respectively, listed in Table B-2 or from the group consisting of CDR1, CDR2 and CDR3 sequences, respectively, that have at least 80%, preferably at least 90%, more preferably at least 95%, even more preferably at least 99% sequence identity with at least one of the CDR1, CDR2 and CDR3 sequences, respectively, listed in Table B-2; and/or from the group consisting of the CDR1, CDR2 and CDR3 sequences, respectively, that have 3, 2 or only 1 "amino acid difference(s)" with at least one of the CDR1, CDR2 and CDR3 sequences, respectively, listed in Table B-2.

In particular, in the immunoglobulin single variable domains of the invention, at least the CDR3 sequence present is suitably chosen from the group consisting of the CDR3 sequences listed in Table B-2 or from the group of CDR3 sequences that have at least 80%, preferably at least 90%, more preferably at least 95%, even more preferably at least 99% sequence identity with at least one of the CDR3 sequences listed in Table B-2, respectively; and at least one of the CDR1 and CDR2 sequences present is suitably chosen from the group consisting of the CDR1 and CDR2 sequences, respectively, listed in Table B-2 or from the group of CDR1 and CDR2 sequences, respectively, that have at least 80%, preferably at least 90%, more preferably at least 95%, even more preferably at least 99% sequence identity with at least one of the CDR1 and CDR2 sequences, respectively, listed in Table B-2; and/or from the group consisting of the CDR1 and CDR2 sequences, respectively, that have 3, 2 or only 1 amino acid difference(s) with at least one of the CDR1 and CDR2 sequences, respectively, listed in Table B-2.

Most preferably, in the immunoglobulin single variable domains of the invention, all three CDR1, CDR2 and CDR3 sequences present are suitably chosen from the group consisting of the CDR1, CDR2 and CDR3 sequences, respectively, listed in Table B-2 or from the group of CDR1, CDR2 and CDR3 sequences, respectively, that have at least 80%, preferably at least 90%, more preferably at least 95%, even more preferably at least 99% sequence identity with at least one of the CDR1, CDR2 and CDR3 sequences, respectively, listed in Table B-2; and/or from the group consisting of the CDR1, CDR2 and CDR3 sequences, respectively, that have 3, 2 or only 1 amino acid difference(s) with at least one of the CDR1, CDR2 and CDR3 sequences, respectively, listed in Table B-2.

Even more preferably, in the immunoglobulin single variable domains of the invention, at least one of the CDR1, CDR2 and CDR3 sequences present is suitably chosen from the group consisting of the CDR1, CDR2 and CDR3 sequences, respectively, listed in Table B-2. Preferably, in this aspect, at least one or preferably both of the other two CDR sequences present are suitably chosen from CDR sequences that have at least 80%, preferably at least 90%, more preferably at least 95%, even more preferably at least 99% sequence identity with at least one of the corresponding CDR sequences, respectively, listed in Table B-2; and/or from the group consisting of the CDR sequences that have 3, 2 or only 1 amino acid difference(s) with at least one of the corresponding sequences, respectively, listed in Table B-2.

In particular, in the immunoglobulin single variable domains of the invention, at least the CDR3 sequence present is suitably chosen from the group consisting of the CDR3 listed in Table B-2. Preferably, in this aspect, at least one and preferably both of the CDR1 and CDR2 sequences present are suitably chosen from the groups of CDR1 and CDR2 sequences, respectively, that have at least 80%, preferably at least 90%, more preferably at least 95%, even more preferably at least 99% sequence identity with the CDR1 and CDR2 sequences, respectively, listed in Table B-2; and/or from the group consisting of the CDR1 and CDR2 sequences, respectively, that have 3, 2 or only 1 amino acid difference(s) with at least one of the CDR1 and CDR2 sequences, respectively, listed in Table B-2.

Even more preferably, in the immunoglobulin single variable domains of the invention, at least two of the CDR1, CDR2 and CDR3 sequences present are suitably chosen from the group consisting of the CDR1, CDR2 and CDR3 sequences, respectively, listed in Table B-2. Preferably, in this aspect, the remaining CDR sequence present is suitably chosen from the group of CDR sequences that have at least 80%, preferably at least 90%, more preferably at least 95%, even more preferably at least 99% sequence identity with at least one of the corresponding CDR sequences listed in Table B-2; and/or from the group consisting of CDR sequences that have 3, 2 or only 1 amino acid difference(s) with at least one of the corresponding sequences listed in Table B-2.

In particular, in the immunoglobulin single variable domains of the invention, at least the CDR3 sequence is suitably chosen from the group consisting of the CDR3 sequences listed in Table B-2, and either the CDR1 sequence or the CDR2 sequence is suitably chosen from the group consisting of the CDR1 and CDR2 sequences, respectively, listed in Table B-2. Preferably, in this aspect, the remaining CDR sequence present is suitably chosen from the group of CDR sequences that have at least 80%, preferably at least 90%, more preferably at least 95%, even more preferably at least 99% sequence identity with at least one of the corresponding CDR sequences listed in Table B-2; and/or from the group consisting of CDR sequences that have 3, 2 or only 1 amino acid difference(s) with the corresponding CDR sequences listed in Table B-2.

Even more preferably, in the immunoglobulin single variable domains of the invention, all three CDR1, CDR2 and CDR3 sequences present are suitably chosen from the group consisting of the CDR1, CDR2 and CDR3 sequences, respectively, listed in Table B-2.

Also, generally, the combinations of CDR's listed in Table 8-2 (i.e. those mentioned on the same line or row in Table B-2) are preferred. Thus, it is generally preferred that, when a CDR in a immunoglobulin single variable domain of the invention is a CDR sequence mentioned in Table B-2 or is suitably chosen from the group of CDR sequences that have at least 80%, preferably at least 90%, more preferably at least 95%, even more preferably at least 99% sequence identity with a CDR sequence listed in Table B-2; and/or from the group consisting of CDR sequences that have 3, 2 or only 1 amino acid difference(s) with a CDR sequence listed in Table B-2, that at least one and preferably both of the other CDR's are suitably chosen from the CDR sequences that belong to the same combination in Table B-2 (i.e. mentioned on the same line or row in Table 8-2) or are suitably chosen from the group of CDR sequences that have at least 80%, preferably at least 90%, more preferably at least 95%, even more preferably at least 99% sequence identity with the CDR sequence(s) belonging to the same combination and/or from the group consisting of CDR sequences that have 3, 2 or only 1 amino acid difference(s) with the CDR sequence(s) belonging to the same combination. The other preferences indicated in the above paragraphs also apply to the combinations of CDRs mentioned in Table B-2, e.g. mentioned on the same row in Table B-2.

Thus, by means of non-limiting examples, a polypeptide of the invention can for example comprise a CDR1 sequence that has more than 80% sequence identity with one of the CDR1 sequences mentioned in Table 8-2, a CDR2 sequence that has 3, 2 or 1 amino acid difference with one of the CDR2 sequences mentioned in Table B-2 (but belonging to a different combination, e.g. mentioned on different rows in Table B-2), and a CDR3 sequence.

Some preferred immunoglobulin single variable domains of the invention may for example comprise: (1) a CDR1 sequence that has more than 80% sequence identity with one of the CDR1 sequences mentioned in Table B-2; a CDR2 sequence that has 3, 2 or 1 amino acid difference with one of the CDR2 sequences mentioned in Table B-2 (but belonging to a different combination, e.g. mentioned on different rows in Table 6-2); and a CDR3 sequence that has more than 80% sequence identity with one of the CDR3 sequences mentioned in Table B-2 (but belonging to a different combination, e.g. mentioned on different rows in Table B-2); or (2) a CDR1 sequence that has more than 80% sequence identity with one of the CDR1 sequences mentioned in Table B-2; a CDR2 sequence, and one of the CDR3 sequences listed in Table B-2; or (3) a CDR1 sequence; a CDR2 sequence that has more than 80% sequence identity with one of the CDR2 sequence listed in Table B-2; and a CDR3 sequence that has 3, 2 or 1 amino acid differences with the CDR3 sequence mentioned in Table B-2 that belongs to the same combination as the CDR2 sequence, e.g. mentioned on the same rows in Table B-2.

Some particularly preferred immunoglobulin single variable domains of the invention may for example comprise: (1)

a CDR1 sequence that has more than 80% sequence identity with one of the CDR1 sequences mentioned in Table B-2; a CDR2 sequence that has 3, 2 or 1 amino acid difference with the CDR2 sequence mentioned in Table B-2 that belongs to the same combination; and a CDR3 sequence that has more than 80% sequence identity with the CDR3 sequence mentioned in Table B-2 that belongs to the same combination; (2) a CDR1 sequence; a CDR2 listed in Table B-2 and a CDR3 sequence listed in Table B-2 (in which the CDR2 sequence and CDR3 sequence may belong to different combinations).

Some even more preferred immunoglobulin single variable domains of the invention may for example comprise: (1) a CDR1 sequence that has more than 80% sequence identity with one of the CDR1 sequences mentioned in Table B-2; the CDR2 sequence listed in Table B-1 that belongs to the same combination; and a CDR3 sequence mentioned in Table B-2 that belongs to a different combination (e.g. mentioned on different rows in Table B-2); or (2) a CDR1 sequence mentioned in Table B-2; a CDR2 sequence that has 3, 2 or 1 amino acid differences with the CDR2 sequence mentioned in Table B-2 that belongs to the same combination; and a CDR3 sequence that has more than 80% sequence identity with the CDR3 sequence listed in Table B-2 that belongs to the same or a different combination.

Particularly preferred immunoglobulin single variable domains of the invention may for example comprise a CDR1 sequence mentioned in Table B-2, a CDR2 sequence that has more than 80% sequence identity with the CDR2 sequence mentioned in Table B-2 that belongs to the same combination; and the CDR3 sequence mentioned in Table B-2 that belongs to the same combination.

In the most preferred immunoglobulin single variable domains of the invention, the CDR1, CDR2 and CDR3 sequences present are suitably chosen from one of the combinations of CDR1, CDR2 and CDR3 sequences, respectively, listed in Table B-2.

According to another preferred, but non-limiting aspect of the invention (a) CDR1 has a length of between 1 and 12 amino acid residues, and usually between 2 and 9 amino acid residues, such as 5, 6 or 7 amino acid residues; and/or (b) CDR2 has a length of between 13 and 24 amino acid residues, and usually between 15 and 21 amino acid residues, such as 16 and 17 amino acid residues; and/or (c) CDR3 has a length of between 2 and 35 amino acid residues, and usually between 3 and 30 amino acid residues, such as between 6 and 23 amino acid residues.

In another preferred, but non-limiting aspect, the invention relates to a immunoglobulin single variable domain in which the CDR sequences (as defined herein) have more than 80%, preferably more than 90%, more preferably more than 95%, such as 99% or more sequence identity (as defined herein) with the CDR sequences of at least one of the immunoglobulin single variable domains of SEQ ID NOs: 23 to 29, 102 and 187, preferably SEQ ID NO: 26 and/or 187.

Another preferred, but non-limiting aspect of the invention relates to humanized variants of the immunoglobulin single variable domains of SEQ ID NOs: 23 to 29, 102 and 187, preferably SEQ ID NO: 26 and/or 187, that comprise, compared to the corresponding native $VH_M$ sequence, at least one humanizing substitution (as defined herein), and in particular at least one humanizing substitution in at least one of its framework sequences (as defined herein).

It will be clear to the skilled person that the immunoglobulin single variable domains that are mentioned herein as "preferred" (or "more preferred", "even more preferred", etc.) are also preferred (or more preferred, or even more preferred, etc.) for use in the polypeptides described herein.

Thus, polypeptides that comprise or essentially consist of one or more "preferred" immunoglobulin single variable domains of the invention will generally be preferred, and polypeptides that comprise or essentially consist of one or more "more preferred" immunoglobulin single variable domains of the invention will generally be more preferred, etc.

1.9 Nucleic Acid Sequences and Host Cells of the Invention

Another aspect of this invention relates to a nucleic acid that encodes an amino acid sequence of the invention (such as an immunoglobulin single variable domain of the invention) or a polypeptide of the invention comprising the same. Again, as generally described herein for the nucleic acids of the invention, such a nucleic acid may be in the form of a genetic construct, as defined herein. Specific embodiments of this aspect of the invention are provided in experimental part, SEQ ID NOs: 30 to 42, preferably SEQ ID NO: 30.

In another preferred, but non-limiting aspect, the invention relates to nucleic acid sequences of immunoglobulin single variable domain in which the sequences (as defined herein) have more than 80%, preferably more than 90%, more preferably more than 95%, such as 99% or more sequence identity (as defined herein) with the sequences of at least one of nucleic acid sequence of the immunoglobulin single variable domains of SEQ ID NOs: 30 to 42, preferably SEQ ID NO: 30.

In another aspect, the invention relates to nucleic acid sequences that comprise the nucleic acid sequences of immunoglobulin single variable domain in which the sequences (as defined herein) have more than 80%, preferably more than 90%, more preferably more than 95%, such as 99% or more sequence identity (as defined herein) with the sequences of at least one of nucleic acid sequence of the immunoglobulin single variable domains of SEQ ID NOs: 30 to 42, preferably SEQ ID NO: 30.

In another aspect, the invention relates to a host or host cell which expresses or that is capable of expressing an amino acid sequence (such as an immunoglobulin single variable domain) of the invention and/or a polypeptide of the invention comprising the same; and/or which contains a nucleic acid of the invention. Some preferred but non-limiting examples of such hosts or host cells will become clear from the further description herein.

As will be clear to the skilled person, one particularly useful method for preparing a polypeptide of the invention generally comprises the steps of:
i) the expression, in a suitable host cell or host organism (also referred to herein as a "host of the invention") or in another suitable expression system of a nucleic acid that encodes said amino acid sequence, polypeptide of the invention (also referred to herein as a "nucleic acid of the invention"), optionally followed by:
ii) isolating and/or purifying the polypeptide of the invention thus obtained.

In particular, such a method may comprise the steps of:
i) cultivating and/or maintaining a host of the invention under conditions that are such that said host of the invention expresses and/or produces at least one polypeptide of the invention; optionally followed by:
ii) isolating and/or purifying the polypeptide of the invention thus obtained.

A nucleic acid of the invention can be in the form of single or double stranded DNA or RNA, and is preferably in the form of double stranded DNA. For example, the nucleotide sequences of the invention may be genomic DNA, cDNA or synthetic DNA (such as DNA with a codon usage that has been specifically adapted for expression in the intended host cell or host organism).

According to one aspect of the invention, the nucleic acid of the invention is in essentially isolated from, as defined herein.

The nucleic acid of the invention may also be in the form of, be present in and/or be part of a vector, such as for example a plasmid, cosmid or YAC, which again may be in essentially isolated form.

The nucleic acids of the invention can be prepared or obtained in a manner known per se, based on the information on the immunoglobulin single variable domains for the polypeptides of the invention given herein, and/or can be isolated from a suitable natural source. To provide analogs, nucleotide sequences encoding naturally occurring $V_{HH}$ domains can for example be subjected to site-directed mutagenesis, so at to provide a nucleic acid of the invention encoding said analog. Also, as will be clear to the skilled person, to prepare a nucleic acid of the invention, also several nucleotide sequences, such as at least one nucleotide sequence encoding a polypeptide of the invention and for example nucleic acids encoding one or more linkers can be linked together in a suitable manner.

Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers, using for example a sequence of a naturally occurring form of c-Met and in particular human c-Met (SEQ ID NO: 1) as a template. These and other techniques will be clear to the skilled person, and reference is again made to the standard handbooks, such as Sambrook et al. and Ausubel et al., mentioned above, as well as the Examples below.

The nucleic acid of the invention may also be in the form of, be present in and/or be part of a genetic construct, as will be clear to the person skilled in the art and as described on pages 131-134 of WO 08/020079 (incorporated herein by reference). Such genetic constructs generally comprise at least one nucleic acid of the invention that is optionally linked to one or more elements of genetic constructs known per se, such as for example one or more suitable regulatory elements (such as a suitable promoter(s), enhancer(s), terminator(s), etc.) and the further elements of genetic constructs referred to herein. Such genetic constructs comprising at least one nucleic acid of the invention will also be referred to herein as "genetic constructs of the invention".

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting aspect, a genetic construct of the invention comprises i) at least one nucleic acid of the invention; operably connected to
ii) one or more regulatory elements, such as a promoter and optionally a suitable terminator; and optionally also
iii) one or more further elements of genetic constructs known per se;

in which the terms "operably connected" and "operably linked" have the meaning given on pages 131-134 of WO 08/020079; and in which the "regulatory elements", "promoter", "terminator" and "further elements" are as described on pages 131-134 of WO 08/020079; and in which the genetic constructs may further be as described on pages 131-134 of WO 08/020079.

The nucleic acids of the invention and/or the genetic constructs of the invention may be used to transform a host cell or host organism, i.e. for expression and/or production of the polypeptide of the invention. Suitable hosts or host cells will be clear to the skilled person, and may for example be any suitable fungal, prokaryotic or eukaryotic cell or cell line or any suitable fungal, prokaryotic or eukaryotic organism, for example those described on pages 134 and 135 of WO 08/020079, as well as all other hosts or host cells known per se for the expression and production of antibodies and antibody fragments (including but not limited to (single) domain antibodies and ScFv fragments), which will be clear to the skilled person. Reference is also made to the general background art cited hereinabove, as well as to for example WO 94/29457, WO 96/34103 and WO 99/42077.

The immunoglobulin single variable domains, and polypeptides of the invention can for example also be produced in the milk of transgenic mammals, for example in the milk of rabbits, cows, goats or sheep (see for example U.S. Pat. No. 6,741,957, U.S. Pat. No. 6,304,489 and U.S. Pat. No. 6,849,992 for general techniques for introducing transgenes into mammals), in plants or parts of plants including but not limited to their leaves, flowers, fruits, seed, roots or tubers (for example in tobacco, maize, soybean or alfalfa) or in for example pupae of the silkworm *Bombyx mori*.

Furthermore, the immunoglobulin single variable domains, and polypeptides of the invention can also be expressed and/or produced in cell-free expression systems, and suitable examples of such systems will be clear to the skilled person. Some preferred, but non-limiting examples include expression in the wheat germ system; in rabbit reticulocyte lysates; or in the *E. coli* Zubay system.

As mentioned above, one of the advantages of the use of immunoglobulin single variable domains is that the polypeptides based thereon can be prepared through expression in a suitable bacterial system, and suitable bacterial expression systems, vectors, host cells, regulatory elements, etc., will be clear to the skilled person, for example from the references cited above. It should however be noted that the invention in its broadest sense is not limited to expression in bacterial systems.

Preferably, in the invention, an (in vivo or in vitro) expression system, such as a bacterial expression system, is used that provides the polypeptides of the invention in a form that is suitable for pharmaceutical use, and such expression systems will again be clear to the skilled person. As also will be clear to the skilled person, polypeptides of the invention suitable for pharmaceutical use can be prepared using techniques for peptide synthesis.

For production on industrial scale, preferred heterologous hosts for the (industrial) production of immunoglobulin single variable domains or immunoglobulin single variable domain-containing protein therapeutics include strains of *E. coli, Pichia pastoris, S. cerevisiae* that are suitable for large scale expression/production/fermentation, and in particular for large scale pharmaceutical (i.e. GMP grade) expression/production/fermentation. Suitable examples of such strains will be clear to the skilled person. Such strains and production/expression systems are also made available by companies such as Richter Helm (Hamburg, Germany) or CMC Biologics (Soeborg, Denmark).

Alternatively, mammalian cell lines, in particular Chinese hamster ovary (CHO) cells, can be used for large scale expression/production/fermentation, and in particular for large scale pharmaceutical expression/production/fermentation. Again, such expression/production systems are also made available by some of the companies mentioned above.

The choice of the specific expression system would depend in part on the requirement for certain post-translational modifications, more specifically glycosylation. The production of a immunoglobulin single variable domain-containing recombinant protein for which glycosylation is desired or required would necessitate the use of mammalian expression hosts that have the ability to glycosylate the expressed protein. In this respect, it will be clear to the skilled person that the glycosylation pattern obtained (i.e. the kind, number and position of residues attached) will depend on the cell or cell line that is used for the expression. Preferably, either a human cell or cell line is used (i.e. leading to a protein that essentially has a human glycosylation pattern) or another mammalian cell line is used that can provide a glycosylation pattern that is essentially and/or functionally the same as human glycosylation or at least mimics human glycosylation. Generally, prokaryotic hosts such as *E. coli* do not have the ability to glycosylate proteins, and the use of lower eukaryotes such as yeast usually leads to a glycosylation pattern that differs from human glycosylation. Nevertheless, it should be understood that all the foregoing host cells and expression systems can be used in the invention, depending on the desired polypeptide to be obtained.

Thus, according to one non-limiting aspect of the invention, the polypeptide of the invention is glycosylated. According to another non-limiting aspect of the invention, the polypeptide of the invention is non-glycosylated.

According to one preferred, but non-limiting aspect of the invention, the polypeptide of the invention is produced in a bacterial cell, in particular a bacterial cell suitable for large scale pharmaceutical production, such as cells of the strains mentioned above.

According to another preferred, but non-limiting aspect of the invention, the polypeptide of the invention is produced in a yeast cell, in particular a yeast cell suitable for large scale pharmaceutical production, such as cells of the species mentioned above.

According to yet another preferred, but non-limiting aspect of the invention, the polypeptide of the invention is produced in a mammalian cell, in particular in a human cell or in a cell of a human cell line, and more in particular in a human cell or in a cell of a human cell line that is suitable for large scale pharmaceutical production, such as the cell lines mentioned hereinabove.

As further described on pages 138 and 139 of WO 08/020079, when expression in a host cell is used to produce the immunoglobulin single variable domains, and the polypeptides of the invention, the immunoglobulin single variable domains, and polypeptides of the invention can be produced either intracellullarly (e.g. in the cytosol, in the periplasma or in inclusion bodies) and then isolated from the host cells and optionally further purified; or can be produced extracellularly (e.g. in the medium in which the host cells are cultured) and then isolated from the culture medium and optionally further purified. Thus, according to a non-limiting aspect of the invention, the polypeptide of the invention is an amino acid sequence, polypeptide that has been produced intracellularly and that has been isolated from the host cell, and in particular from a bacterial cell or from an inclusion body in a bacterial cell. According to another non-limiting aspect of the invention, the amino acid sequence, or polypeptide of the invention is an amino acid sequence, or polypeptide that has been produced extracellularly, and that has been isolated from the medium in which the host cell is cultivated.

Some preferred, but non-limiting promoters for use with these host cells include those mentioned on pages 139 and 140 of WO 08/020079.

Some preferred, but non-limiting secretory sequences for use with these host cells include those mentioned on page 140 of WO 08/020079.

Suitable techniques for transforming a host or host cell of the invention will be clear to the skilled person and may depend on the intended host cell/host organism and the genetic construct to be used. Reference is again made to the handbooks and patent applications mentioned above.

After transformation, a step for detecting and selecting those host cells or host organisms that have been successfully transformed with the nucleotide sequence/genetic construct of the invention may be performed. This may for instance be a selection step based on a selectable marker present in the genetic construct of the invention or a step involving the detection of the amino acid sequence of the invention, e.g. using specific antibodies.

The transformed host cell (which may be in the form or a stable cell line) or host organisms (which may be in the form of a stable mutant line or strain) form further aspects of the present invention.

Preferably, these host cells or host organisms are such that they express, or are (at least) capable of expressing (e.g. under suitable conditions), a polypeptide of the invention (and in case of a host organism: in at least one cell, part, tissue or organ thereof). The invention also includes further generations, progeny and/or offspring of the host cell or host organism of the invention, that may for instance be obtained by cell division or by sexual or asexual reproduction.

To produce/obtain expression of the immunoglobulin single variable domains of the invention, the transformed host cell or transformed host organism may generally be kept, maintained and/or cultured under conditions such that the (desired) amino acid sequence, or polypeptide of the invention is expressed/produced. Suitable conditions will be clear to the skilled person and will usually depend upon the host cell/host organism used, as well as on the regulatory elements that control the expression of the (relevant) nucleotide sequence of the invention. Again, reference is made to the handbooks and patent applications mentioned above in the paragraphs on the genetic constructs of the invention.

Generally, suitable conditions may include the use of a suitable medium, the presence of a suitable source of food and/or suitable nutrients, the use of a suitable temperature, and optionally the presence of a suitable inducing factor or compound (e.g. when the nucleotide sequences of the invention are under the control of an inducible promoter); all of which may be selected by the skilled person. Again, under such conditions, the immunoglobulin single variable domains of the invention may be expressed in a constitutive manner, in a transient manner, or only when suitably induced.

It will also be clear to the skilled person that the amino acid sequence, or polypeptide of the invention may (first) be generated in an immature form (as mentioned above), which may then be subjected to post-translational modification, depending on the host cell/host organism used. Also, the amino acid sequence, or polypeptide of the invention may be glycosylated, again depending on the host cell/host organism used.

The amino acid sequence, or polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the amino acid sequence, or polypeptide of the invention) and/or preparative immunological techniques (i.e. using antibodies against the amino acid sequence to be isolated).

1.10 Methods and Kits for Assessing the Responsiveness to Therapy

The invention further relates to methods for assessing the responsiveness of a patient suffering from a c-Met associated disease or disorder to a given therapy. The inventors surprisingly found that the quantification of soluble c-Met levels in a patient sample taken prior to and post initiation of therapy are an indication of the responsiveness of a patient to said therapy. Accordingly, present invention provides an in vitro method for assessing the responsiveness of a patient suffering from a c-Met associated disease or disorder to a therapy, said method comprising the steps of:
a) providing from said patient a first sample prior to therapy and measuring the amount of soluble c-Met in said first sample,
b) providing from said patient a second sample post initiation of therapy and measuring the amount of soluble c-Met in said second sample,
c) comparing the amount of soluble c-Met present in the first sample to the amount of soluble c-Met found in the second sample;
wherein a decrease in the amount of soluble c-Met found in the second sample compared to the amount of soluble c-Met in the first sample indicates that the patient is responsive to said therapy.

A person skilled in the art will recognize that the term "therapy" in the above method may include any c-Met antagonist that can modulate c-Met and in particular human c-Met (SEQ ID NO: 1)-mediated signaling, such as those mentioned in the diseases and prior art as described herein. Preferably, the c-Met antagonist is an anti-c-Met antibody. More preferably, the c-Met antagonist is an amino acid sequence such as e.g. an immunoglobulin single variable domain or polypeptide according to the invention. In particular, the c-Met antagonist is a Nanobody of the invention, e.g. SEQ ID NO: 23 to 29, 102 and 187, preferably SEQ ID NO: 26 and/or 187 (Table B-3), or a polypeptide or construct of the invention, e.g. SEQ ID NO: 7 to 12, 103-111, 113, 188 and 142-150, preferably SEQ ID NO: 7, 106, 113, 188, 143, 146 and/or 147 (see Table B-4).

By "patient sample" is intended any sampling of cells, tissues, or bodily fluids from a patient in which the amount of soluble c-Met can be measured. Examples of such patient samples include but are not limited to tissue biopsies, blood, serum, plasma, cerebrospinal fluid, bronchoalveolar lavage fluid, fecal sample and urine sample. Such samples may be obtained from a patient by a variety of techniques, including for example by venipuncture. Methods for collecting various patient samples are well known in the art. In particular aspects of the invention, the patient sample is a plasma sample.

The methods of the invention may be used to evaluate a first patient sample prior to therapy or before initiation of such therapy, and a second sample from said patient taken post initiation of such therapy, e.g. during and/or after said therapy to evaluate, for example, a reduction in tumor burden. By measuring the amount of soluble c-Met in a first and a second sample of a patient as provided by the method of the invention, a clinician will be able to determine whether the disease (e.g. cancer) has, for example, regressed and whether the patient is responsive to the therapy. A patient whose cancer has regressed post initiation of therapy (e.g. during and/or after therapy) will have reduced amounts of soluble c-Met compared to the amounts of soluble c-Met he had before the treatment. Similarly, a patient whose cancer has remained stable during therapy will have similar levels of soluble c-Met as he did prior to therapy, and a patient whose cancer has progressed will have increased amounts of soluble c-Met. The clinician can further utilize these measurements for monitoring the status of the patient and for tailoring treatment appropriately, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand. The effectiveness of the treatment regimen used according to the invention may be determined and/or followed in any manner known per se for the disease or disorder involved, as will be clear to the clinician. The method of the invention can for example comprise recommending a specific treatment course to a patient, such as stopping the therapy, changing the drug being administered, changing the dosage of the drug being administered, or further monitoring the patient. Generally, the treatment regimen will be followed until the desired therapeutic effect is achieved and/or for as long as the desired therapeutic effect is to be maintained, as determined by the clinician.

Any method available in the art for measuring or quantifying soluble c-Met can be used to practice the invention. The amount of soluble c-Met according to the invention can be detected on a nucleic acid level or a protein level. Such methods are well known in the art and include but are not limited to western blots, northern blots, southern blots, immunoassays, such as, enzyme-linked immunosorbent assays (ELISAs), radioimmunoassay, immunocytochemistry, immunofluorescence, flow cytometry, chemiluminescent assays, electrochemiluminescent assays, nucleic acid hybridization techniques, nucleic acid reverse transcription methods, and nucleic acid amplification methods. Preferably, soluble c-Met levels are detected at the protein level using, for example, antibodies that are directed against c-Met and in particular human c-Met (SEQ ID NO: 1). Representative immunoassays involve the use of monoclonal or polyclonal antibodies which can be appropriately labelled to measure the amount of soluble c-Met in said patient samples. Most preferably, soluble c-Met levels are measured using a Meso Scale Discovery electrochemiluminescence assay or an ELISA format as exemplified herein (see Example 23).

As set forth above, the invention provides diagnostic methods for measuring the amount of soluble c-Met present in a patient sample. Accordingly the invention also provides kits for performing these methods. In particular, the invention provides for kits for assessing the responsiveness of a patient suffering from a c-Met associated disease or disorder to a therapy, comprising one or more reagents, e.g. an antibody, a nucleic acid probe, etc. for measuring the amount of soluble c-Met in a patient sample. Chemicals for the detection of antibody binding to soluble c-Met may also be included in the kit. Other reagents for measuring the amount of soluble c-Met using antibodies in an ELISA immunoassay format may be further included in the kit of the invention.

Alternatively, or in addition the kit may also be used to monitor the diseases as cited herein, and may comprise at least one immunoglobulin single variable domain, polypeptide or pharmaceutical composition according to the invention.

In a further aspect of the invention the kit may comprise at least one immunoglobulin single variable domain, polypeptide or pharmaceutical composition according to the invention and all the necessary means and reagents for measuring the amount of soluble c-Met in a patient sample. All kits according to the invention may comprise the stated items or combinations of items and packaging materials therefore. Kits may also include instructions for use.

The entire contents of all of the references (including literature references, issued patents, published patent applications, and co-pending patent applications) cited throughout this application are hereby expressly incorporated by reference, in particular for the teaching that is referenced herein.

The invention will now be further described by means of the following non-limiting preferred aspects, figures and examples:

Preferred Aspects:

Aspect A-1: An immunoglobulin single variable domain that is directed against and/or that can specifically bind to c-Met and in particular human c-Met (SEQ ID NO: 1).

Aspect A-2: An immunoglobulin single variable domain according to aspect A-1, that is in essentially isolated form.

Aspect A-3: An immunoglobulin single variable domain according to aspect A-1 or A-2, for administration to a subject, wherein said immunoglobulin single variable domain does not naturally occur in said subject.

Aspect A-4: An immunoglobulin single variable domain that can specifically bind to c-Met and in particular human c-Met (SEQ ID NO: 1) with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter. Such an immunoglobulin single variable domain may in particular be an immunoglobulin single variable domain according to any of the preceding aspects.

Aspect A-5: An immunoglobulin single variable domain that can specifically bind to c-Met and in particular human c-Met (SEQ ID NO: 1) with a rate of association ($k_{on}$-rate) of between $10^2$ $M^{-1}s^{-1}$ to about $10^7$ $M^{-1}s^{-}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$. Such an immunoglobulin single variable domain may in particular be an immunoglobulin single variable domain according to any of the preceding aspects.

Aspect A-6: An immunoglobulin single variable domain that can specifically bind to c-Met and in particular human c-Met (SEQ ID NO: 1) with a rate of dissociation ($k_{off}$-rate) between 1 $s^{-1}$ and $10^{-6}$ $s^{-1}$, preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$. Such an immunoglobulin single variable domain may in particular be an immunoglobulin single variable domain according to any of the preceding aspects.

Aspect A-7: An immunoglobulin single variable domain that can specifically bind to c-Met and in particular human c-Met (SEQ ID NO: 1) with an affinity less than 500 nM, preferably less than 200 nM, more preferably less than 10 nM, such as less than 500 pM. Such an immunoglobulin single variable domain may in particular be an immunoglobulin single variable domain according to any of the preceding aspects.

Aspect A-8: An immunoglobulin single variable domain that can specifically displace HGF and in particular human HGF on c-Met and in particular on human c-Met (SEQ ID NO: 1) with an average Ki of less than 500 nM, preferably less than 200 nM, more preferably less than 10 nM, such as less than 1 nM and an average HGF displacement of 50% or more, more preferably of 75% or more, even more preferably of 80% or more. Such an average Ki and/or average displacement value may be determined e.g. in an assay as described in the experimental part.

Aspect A-9: An immunoglobulin single variable domain that can specifically displace HGF and in particular human HGF on c-Met and in particular on human c-Met (SEQ ID NO: 1) with an average Ki of less than 20 nM and an average HGF displacement of 70% or more. Such an average Ki and/or average displacement value may be determined e.g. in an assay as described in the experimental part.

Aspect A-10: An immunoglobulin single variable domain according to any of the preceding aspects, that essentially consists of 4 framework regions (FR1 to FR4 respectively) and 3 complementarity determining regions (CDR1 to CDR3 respectively).

Aspect A-11: An immunoglobulin single variable domain according to any of the preceding aspects, that is an immunoglobulin sequence.

Aspect A-12: An immunoglobulin single variable domain according to any of the preceding aspects, that is a naturally occurring immunoglobulin sequence (from any suitable species) or a synthetic or semi-synthetic immunoglobulin sequence.

Aspect A-13: An immunoglobulin single variable domain according to any of the preceding aspects that is a humanized immunoglobulin sequence, a camelized immunoglobulin sequence or an immunoglobulin sequence that has been obtained by techniques such as affinity maturation.

Aspect A-14: An immunoglobulin single variable domain according to any of the preceding aspects, that essentially consists of a light chain variable domain sequence (e.g. a VL-sequence); or of a heavy chain variable domain sequence (e.g. a VH-sequence).

Aspect A-15: An immunoglobulin single variable domain according to any of the preceding aspects, that essentially consists of a heavy chain variable domain sequence that is derived from a conventional four-chain antibody or that essentially consist of a heavy chain variable domain sequence that is derived from a heavy chain antibody.

Aspect A-16: An immunoglobulin single variable domain according to any of the preceding aspects, that essentially consists of a domain antibody (or an immunoglobulin single variable domain that is suitable for use as a domain antibody), of a single domain antibody (or an immunoglobulin single variable domain that is suitable for use as a single domain antibody), of a "dAb" (or an immunoglobulin single variable domain that is suitable for use as a dAb), of a Nanobody (including but not limited to a VHH sequence), of a VHH sequence (including but not limited to a VHH type 1 sequence), or of a VHH type 1 sequence.

Aspect A-17: An immunoglobulin single variable domain according to any of the preceding aspects, that essentially consists of a Nanobody.

Aspect A-18: An immunoglobulin single variable domain according to any of the preceding aspects, that essentially consists of a Nanobody that
i) has at least 80% amino acid identity with at least one of the immunoglobulin single variable domains of SEQ ID NOs: 23 to 29, 102 and/or 187, in which for the purposes of determining the degree of amino acid identity, the amino acid residues that form the CDR sequences are disregarded;
and in which:
ii) preferably one or more of the amino acid residues at positions 11, 37, 44, 45, 47, 83, 84, 103, 104 and 108 according to the Kabat numbering are chosen from the Hallmark residues mentioned in Table A-1.

Aspect A-19: An immunoglobulin single variable domain according to any of the preceding aspects, that essentially consists of an immunoglobulin single variable domain that
i) has at least 80% amino acid identity with the immunoglobulin single variable domain of SEQ ID NO: 26, in which for the purposes of determining the degree of amino acid identity, the amino acid residues that form the CDR sequences are disregarded;
and in which:
ii) preferably one or more of the amino acid residues at positions 11, 37, 44, 45, 47, 83, 84, 103, 104 and 108 according to the Kabat numbering are chosen from the Hallmark residues mentioned in Table A-1.

Aspect A-20: An immunoglobulin single variable domain according to any of the preceding aspects, that essentially consists of a VHH that is a VHH that has at least 80% amino acid identity with an immunoglobulin single variable domain selected from the group of immunoglobulin single variable domain having SEQ ID NOs: 23 to 29, 102 and 187, preferably SEQ ID NO: 26 and/or 187, in which for the purposes of determining the degree of amino acid identity, the amino acid residues that form the CDR sequences are disregarded.

Aspect A-21: An immunoglobulin single variable domain according to any of the preceding aspects, that essentially consists of a humanized or otherwise sequence optimized immunoglobulin single variable domain.

Aspect A-22: An immunoglobulin single variable domain according to any of the preceding aspects, that in addition to the at least one binding site for binding against c-Met and in particular human c-Met (SEQ ID NO: 1), contains one or more further amino acid sequence(s).

Aspect A-23: A VHH that is directed against and/or that can specifically bind to c-Met and in particular to human c-Met (SEQ ID NO: 1).

Aspect A-24: A VHH according to aspect A-1, that is in essentially isolated form.

Aspect A-25: A VHH according to aspect A-1 or A-2, for administration to a subject, wherein said VHH does not naturally occur in said subject.

Aspect A-26: A VHH that can specifically bind to c-Met and in particular human c-Met (SEQ ID NO: 1) with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter. Such an VHH may in particular be an VHH according to any of the preceding aspects.

Aspect A-27: A VHH that can specifically bind to c-Met and in particular human c-Met (SEQ ID NO: 1) with a rate of association ($k_{on}$-rate) of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$. Such a VHH may in particular be a VHH according to any of the preceding aspects.

Aspect A-28: A VHH that can specifically bind to c-Met and in particular human c-Met (SEQ ID NO: 1) with a rate of dissociation ($k_{off}$ rate) between 1 $s^{-1}$ and $10^{-6}$ $s^{-1}$, preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$. Such a VHH may in particular be a VHH according to any of the preceding aspects.

Aspect A-29: A VHH that can specifically bind to c-Met and in particular human c-Met (SEQ ID NO: 1) with an affinity less than 500 nM, preferably less than 200 nM, more preferably less than 10 nM, such as less than 500 pM. Such a VHH may in particular be a VHH according to any of the preceding aspects.

Aspect A-30: A VHH that can specifically displace HGF and in particular human HGF on c-Met and in particular on human c-Met (SEQ ID NO: 1) with an average Ki of less than 500 nM, preferably less than 200 nM, more preferably less than 10 nM, such as less than 1 nM and an average HGF displacement of 50% or more, more preferably of 75% or more, even more preferably of 80% or more. Such an average Ki and/or average displacement value may be determined e.g. in an assay as described in the experimental part.

Aspect A-31: A VHH that can specifically displace HGF and in particular human HGF on c-Met and in particular on human c-Met (SEQ ID NO: 1) with an average Ki of less than 20 nM and an average HGF displacement of 70% or more. Such an average Ki and/or average displacement value may be determined e.g. in an assay as described in the experimental part.

Aspect A-32: A VHH according to any of the preceding aspects, that essentially consists of 4 framework regions (FR1 to FR4 respectively) and 3 complementarity determining regions (CDR1 to CDR3 respectively).

Aspect A-33: A VHH according to any of the preceding aspects that is an immunoglobulin sequence.

Aspect A-34: A VHH according to any of the preceding aspects that is a naturally occurring immunoglobulin sequence (from any suitable species) or a synthetic or semi-synthetic immunoglobulin sequence.

Aspect A-35: A VHH according to any of the preceding aspects which is a humanized VHH obtained by techniques such as affinity maturation.

Aspect A-36: A VHH according to any of the preceding aspects, which essentially consists of a Nanobody or of a VHH type 1 sequence.

Aspect A-37: A VHH according to any of the preceding aspects, that essentially consists of a VHH type 1 sequence.

Aspect A-38: A VHH according to any of the preceding aspects, that essentially consists of a VHH that
i) has at least 80% amino acid identity with at least one of the VHHs of SEQ ID NOs: 23 to 29, 102 and/or 187, in which for the purposes of determining the degree of amino acid identity, the amino acid residues that form the CDR sequences are disregarded;
and in which:
ii) preferably one or more of the amino acid residues at positions 11, 37, 44, 45, 47, 83, 84, 103, 104 and 108 according to the Kabat numbering are chosen from the Hallmark residues mentioned in Table A-1.

Aspect A-39: A VHH according to any of the preceding aspects, that essentially consists of a VHH that
i) has at least 80% amino acid identity with the VHH of SEQ ID NO: 26 and/or 187, in which for the purposes of determining the degree of amino acid identity, the amino acid residues that form the CDR sequences are disregarded;
and in which:
ii) preferably one or more of the amino acid residues at positions 11, 37, 44, 45, 47, 83, 84, 103, 104 and 108 according to the Kabat numbering are chosen from the Hallmark residues mentioned in Table A-1.

Aspect A-40: A VHH according to any of the preceding aspects, that essentially consists of a VHH that is either
i) A VHH that has at least 80% amino acid identity with a VHH selected from the group of VHH having SEQ ID NOs: 23 to 29, 102 and 187, preferably to SEQ ID NO: 26 and/or 187, in which for the purposes of determining the degree of amino acid identity, the amino acid residues that form the CDR sequences are disregarded; or
ii) A VHH that has at least 80% amino acid identity with the VHH having SEQ ID NO: 7, in which for the purposes of determining the degree of amino acid identity, the amino acid residues that form the CDR sequences are disregarded.

Aspect A-41: A VHH according to any of the preceding aspects, that essentially consists of a humanized or otherwise sequence optimized VHH.

Aspect A-42: A VHH according to any of the preceding aspects, that in addition to the at least one binding site for binding against c-Met and in particular human c-Met (SEQ ID NO: 1), contains one or more further amino acid sequence(s), such as for instance polypeptide(s) modulating EGFR signalling and/or polypeptide(s) modulating VEGF signalling.

CDR-Based Aspects

Aspect B-1: An immunoglobulin single variable domain that is directed against and/or that can specifically bind c-Met and in particular human c-Met (SEQ ID NO: 1), and that comprises one or more (preferably one) stretches of amino acid residues chosen from the group consisting of:
a) SEQ ID NOs: 51 to 57 and 158-161, preferably SEQ ID NO: 51, 160;
b) polypeptides that have at least 80% amino acid identity with SEQ ID NOs: 51 to 57 and 158-161, preferably SEQ ID NO: 51, 160;
c) polypeptides that have 3, 2, or 1 amino acid difference with SEQ ID NOs: 51 to 57 and 158-161, preferably SEQ ID NO: 51, 160;
d) SEQ ID NOs: 67 to 73 and 168-171, preferably SEQ ID NO: 67, 170;
e) polypeptides that have at least 80% amino acid identity with SEQ ID NOs: 67 to 73 and 168-171, preferably SEQ ID NO: 67, 170;
f) polypeptides that have 3, 2, or 1 amino acid difference with SEQ ID NOs: 67 to 73 and 168-171, preferably SEQ ID NO: 67, 170;
g) SEQ ID NOs: 83 to 89 and 178-181, preferably SEQ ID NO: 83, 180;
h) polypeptides that have at least 80% amino acid identity SEQ ID NOs: 83 to 89 and 178-181, preferably SEQ ID NO: 83, 180;
i) polypeptides that have 3, 2, or 1 amino acid difference with SEQ ID NOs: 83 to 89 and 178-181, preferably SEQ ID NO: 83, 180;
or any suitable combination thereof.

Such an immunoglobulin single variable domain may in particular be VHH (including a VHH type 1 sequence) or sequence optimized VHH such as humanized, stabilized and/or solubilized VHH.

Aspect B-2: An immunoglobulin single variable domain according to aspect B-1, in which at least one of said stretches of amino acid residues forms part of the antigen binding site for binding against c-Met and in particular human c-Met (SEQ ID NO: 1).

Aspect B-3: An immunoglobulin single variable domain sequence that is directed against and/or that can specifically bind c-Met and in particular human c-Met (SEQ ID NO: 1) and that comprises two or more stretches of amino acid residues chosen from the group consisting of:
a) SEQ ID NOs: 51 to 57 and 158-161, preferably SEQ ID NO: 51, 160;
b) polypeptides that have at least 80% amino acid identity with SEQ ID NOs: 51 to 57 and 158-161, preferably SEQ ID NO: 51, 160;
c) polypeptides that have 3, 2, or 1 amino acid difference with SEQ ID NOs: 51 to 57 and 158-161, preferably SEQ ID NO: 51, 160;
d) SEQ ID NOs: 67 to 73 and 168-171, preferably SEQ ID NO: 67, 170;
e) polypeptides that have at least 80% amino acid identity with SEQ ID NOs: 67 to 73 and 168-171, preferably SEQ ID NO: 67, 170;
f) polypeptides that have 3, 2, or 1 amino acid difference with SEQ ID NOs: 67 to 73 and 168-171, preferably SEQ ID NO: 67, 170;
g) SEQ ID NOs: 83 to 89 and 178-181, preferably SEQ ID NO: 83, 180;
h) polypeptides that have at least 80% amino acid identity with SEQ ID NOs: 83 to 89 and 178-181, preferably SEQ ID NO: 83, 180;
i) polypeptides that have 3, 2, or 1 amino acid difference with SEQ ID NOs: 83 to 89 and 178-181, preferably SEQ ID NO: 83, 180;
such that (i) when the first stretch of amino acid residues corresponds to one of the polypeptides according to a), b) or c), the second stretch of amino acid residues corresponds to one of the polypeptides according to d), e), f), g), h) or i); (ii) when the first stretch of amino acid residues corresponds to one of the polypeptides according to d), e) or f), the second stretch of amino acid residues corresponds to one of the polypeptides according to a), b), c), g), h) or i); or (iii) when the first stretch of amino acid residues corresponds to one of the polypeptides according to g), h) or i), the second stretch of amino acid residues corresponds to one of the polypeptides according to a), b), c), d), e) or f).

Such an immunoglobulin single variable domain may in particular be VHH (including a VHH type 1 sequence) or sequence optimized VHH such as humanized, stabilized and/or solubilized VHH.

Aspect B-4: An immunoglobulin single variable domain according to aspect B-3, in which the at least two stretches of amino acid residues forms part of the antigen binding site for binding against c-Met and in particular human c-Met (SEQ ID NO: 1).

Aspect B-5: An immunoglobulin single variable domain sequence that is directed against and/or that can specifically bind c-Met and in particular human c-Met (SEQ ID NO: 1) and that comprises three or more stretches of amino acid residues, in which the first stretch of amino acid residues is chosen from the group consisting of:
a) the polypeptides of SEQ ID NOs: 51 to 57 and 158-161, preferably SEQ ID NO: 51, 160;
b) polypeptides that have at least 80% amino acid identity with at least one of the polypeptides of SEQ ID NOs: 51 to 57 and 158-161, preferably SEQ ID NO: 51, 160;
c) polypeptides that have 3, 2, or 1 amino acid difference with at least one of the polypeptides of SEQ ID NOs: 51 to 57 and 158-161, preferably SEQ ID NO: 51, 160;
the second stretch of amino acid residues is chosen from the group consisting of:
d) the polypeptide of SEQ ID NOs: 67 to 73 and 168-171, preferably SEQ ID NO: 67, 170;

e) polypeptides that have at least 80% amino acid identity with at least one of the polypeptides of SEQ ID NOs: 67 to 73 and 168-171, preferably SEQ ID NO: 67, 170;
f) polypeptides that have 3, 2, or 1 amino acid difference with at least one of the polypeptides of SEQ ID NOs: 67 to 73 and 168-171, preferably SEQ ID NO: 67, 170;
and the third stretch of amino acid residues is chosen from the group consisting of:
g) the polypeptides of SEQ ID NOs: 83 to 89 and 178-181, preferably SEQ ID NO: 83, 180;
h) polypeptides that have at least 80% amino acid identity with at least one of the polypeptides of SEQ ID NOs: 83 to 89 and 178-181, preferably SEQ ID NO: 83, 180;
i) polypeptides that have 3, 2, or 1 amino acid difference with at least one of the polypeptides of SEQ ID NOs: 83 to 89 and 178-181, preferably SEQ ID NO: 83, 180.

Such an immunoglobulin single variable domain may in particular be VHH (including a VHH type 1 sequence) or sequence optimized VHH such as humanized, stabilized and/or solubilized VHH.

Aspect B-6: An immunoglobulin single variable domain according to aspect B-5, in which the at least three stretches of amino acid residues forms part of the antigen binding site for binding against c-Met and in particular human c-Met (SEQ ID NO: 1).

Aspect B-7: An immunoglobulin single variable domain that is directed against and/or that can specifically bind c-Met and in particular human c-Met (SEQ ID NO: 1) in which the CDR sequences of said immunoglobulin single variable domain have at least 70% amino acid identity, preferably at least 80% amino acid identity, more preferably at least 90% amino acid identity, such as 95% amino acid identity or more or even essentially 100% amino acid identity with the CDR sequences of at least one of the immunoglobulin single variable domains of SEQ ID NOs: 23 to 29, 102 and 187, preferably to SEQ ID NO: 26 and/or 187.

Such an immunoglobulin single variable domain may in particular be VHH (including a VHH type 1 sequence) or sequence optimized VHH such as humanized, stabilized and/or solubilized VHH.

Cross-Blocked or Cross-Blocking Variants

Aspect C-1: An immunoglobulin single variable domain or polypeptide that is directed against c-Met and in particular human c-Met (SEQ ID NO: 1) and that cross-blocks the binding of at least one of the Immunoglobulin single variable domains of SEQ ID NOs: 23 to 29, 102 and 187, preferably to SEQ ID NO: 26 and/or 187 or polypeptides of SEQ ID NOs: 7 to 12, 103-111, 113, 188 and 142-150, preferably SEQ ID NO: 7, 106, 113, 188, 143, 146 and/or 147 to c-Met and in particular human c-Met (SEQ ID NO: 1). Such an immunoglobulin single variable domain may in particular be an immunoglobulin single variable domain according to any of the aspects A-1 to A-22 and/or according to aspects B-1 to B-7. Also, preferably, such an immunoglobulin single variable domain is able to specifically bind to c-Met and in particular human c-Met (SEQ ID NO: 1).

Aspect C-2: An immunoglobulin single variable domain or polypeptide that is directed against c-Met and in particular human c-Met (SEQ ID NO: 1) and that is cross-blocked from binding to c-Met and in particular human c-Met (SEQ ID NO: 1) by at least one of i) the immunoglobulin single variable domains of SEQ ID NOs: 23 to 29, 102 and 187, preferably of SEQ ID NO: 26 and/or 187, or ii) the polypeptides of SEQ ID NOs: 7 to 12, 103-111, 113, 188 and 142-150, preferably SEQ ID NO: 7, 106, 113, 188, 143, 146 and/or 147. Such an immunoglobulin single variable domain may in particular be an immunoglobulin single variable domain according to any of the aspects A-1 to A-22 and/or according to aspects B-1 to B-7. Also, preferably, such an immunoglobulin single variable domain is able to specifically bind to c-Met and in particular human c-Met (SEQ ID NO: 1).

Aspect C-3: An immunoglobulin single variable domain or polypeptide according to any of aspects C-1 or C-2, wherein the ability of said immunoglobulin single variable domain to cross-block or to be cross-blocked is detected in a displacement assay (e.g. as described in experimental part below).

Aspect C-4: An immunoglobulin single variable domain or polypeptide according to any of aspects C-1 to C-3 wherein the ability of said immunoglobulin single variable domain to cross-block or to be cross-blocked is detected in an EUSA assay and/or Alphascreen assay as shown in the experimental part.

Aspect D-1: An immunoglobulin single variable domain according to any of aspects B-1 to B-7 or C-1 to C-4, that is in essentially isolated form.

Aspect D-2: An immunoglobulin single variable domain according to any of aspects B-1 to B-7, C-1 to C-4, and/or D-1 for administration to a subject, wherein said immunoglobulin single variable domain does not naturally occur in said subject.

Aspect D-3: An immunoglobulin single variable domain according to any of aspects B-1 to B-7, C-1 to C-4, and/or D-1 to D-2 that can specifically bind to c-Met and in particular human c-Met (SEQ ID NO: 1) with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter.

Aspect D-4: An immunoglobulin single variable domain according to any of aspects B-1 to B-7, C-1 to C-4, and/or D-1 to D-3 that can specifically bind to c-Met and in particular human c-Met (SEQ ID NO: 1) with a rate of association ($k_{on}$-rate) of between $10^2 M^{-1}s^{-1}$ to about $10^7 M^{-1}s^{-1}$, preferably between $10^3 M^{-1}s^{-1}$ and $10^7 M^{-1}s^{-1}$, more preferably between $10^4 M^{-1}s^{-1}$ and $10^7 M^{-1}s^{-1}$, such as between $10^5 M^{-1}s^{-1}$ and $10^7 M^{-1}s^{-1}$.

Aspect D-5: An immunoglobulin single variable domain according to any of aspects B-1 to B-7, C-1 to C-4, and/or D-1 to D-4 that can specifically bind to c-Met and in particular human c-Met (SEQ ID NO: 1) with a rate of dissociation ($k_{off}$-rate) between $1\ s^{-1}$ and $10^{-6}\ s^{-1}$ preferably between $10^{-2}\ s^{-1}$ and $10^{-6}\ s^{-1}$, more preferably between $10^{-3}\ s^{-1}$ and $10^{-6}\ s^{-1}$, such as between $10^{-4}\ s^{-1}$ and $10^{-6}\ s^{-1}$.

Aspect D-6: An immunoglobulin single variable domain according to any of aspects B-1 to B-7, C-1 to C-4, and/or D-1 to D-5 that can specifically bind to c-Met and in particular human c-Met (SEQ ID NO: 1) with an affinity less than 500 nM, preferably less than 200 nM, more preferably less than 10 nM, such as less than 500 pM.

The immunoglobulin single variable domains according to aspects D-1 to D-6 may in particular be an immunoglobulin single variable domain according to any of the aspects A-1 to A-22.

Aspect E-1: An immunoglobulin single variable domain according to any of aspects 8-1 to B-7, C-1 to C-4 and/or D-1 to D-6, that is a naturally occurring immunoglobulin single variable domain (from any suitable species) or a synthetic or semi-synthetic immunoglobulin single variable domain.

Aspect E-2: An immunoglobulin single variable domain according to any of aspects B-1 to B-7, C-1 to C-4, D-1 to D-6, and/or E-1 that is sequence optimized Aspect E-3: An immunoglobulin single variable domain according to any of aspects B-1 to B-7, C-1 to C-4, D1 to D-6, and/or E-1 or E-2 that is stabilized.

Aspect E-4: An immunoglobulin single variable domain according to any of aspects B-1 to B-7, C-1 to C-4, D-1 to D-6, and/or E-1 to E-3, that is a naturally occurring immunoglobulin sequence (from any suitable species) or a synthetic or semi-synthetic immunoglobulin sequence.

Aspect E-5: An immunoglobulin single variable domain according to any of aspects B-1 to B-7, C-1 to C-4, D-1 to D-6, and/or E-1 to E-4 that is a humanized immunoglobulin sequence, a camelized immunoglobulin sequence or an immunoglobulin sequence that has been obtained by techniques such as affinity maturation.

Aspect E-6: An immunoglobulin single variable domain according to any of aspects B-1 to 8-7, C-1 to C-4, D1 to D-6, and/or E-1 to E-5 that essentially consists of a light chain variable domain sequence (e.g. a $V_L$-sequence); or of a heavy chain variable domain sequence (e.g. a $V_H$-sequence).

Aspect E-7: An immunoglobulin single variable domain according to any of aspects B-1 to B-7, C-1 to C-4, D-1 to D-6, and/or E-1 to E-6, that essentially consists of a heavy chain variable domain sequence that is derived from a conventional four-chain antibody or that essentially consist of a heavy chain variable domain sequence that is derived from heavy chain antibody.

Aspect E-8: An immunoglobulin single variable domain according to any of aspects B-1 to B-7, C-1 to C-4, D-1 to D-6, and/or E-1 to E-7, that essentially consists of a domain antibody (or an immunoglobulin single variable domain that is suitable for use as a domain antibody), of a single domain antibody (or an that is suitable for use as a single domain antibody), of a "dAb" (or an immunoglobulin single variable domain that is suitable for use as a dAb) or of a Nanobody (including but not limited to a $V_{HH}$ sequence or a VHH type 1 sequence).

Aspect E-9: An immunoglobulin single variable domain according to any of aspects B-1 to B-7, C-1 to C-4, D-1 to D-6, and/or E-1 to E-8 that essentially consists of a Nanobody (including but not limited to a $V_{HH}$ sequence or a VHH type 1 sequence).

Aspect E-10: An immunoglobulin single variable domain according to any of aspects B-1 to B-7, C-1 to C-4, D-1 to D-6, and/or E-1 to E-9 that essentially consists of a Immunoglobulin single variable domain that
 i) has at least 80% amino acid identity with at least one of the immunoglobulin single variable domains described herein, in which for the purposes of determining the degree of amino acid identity, the amino acid residues that form the CDR sequences are disregarded;
 and in which:
 ii) preferably one or more of the amino acid residues at positions 11, 37, 44, 45, 47, 83, 84, 103, 104 and 108 according to the Kabat numbering are chosen from the Hallmark residues mentioned in Table A-1.

Aspect E-11: An immunoglobulin single variable domain according to any of aspects B-1 to B-7, C-1 to C-4, D-1 to D-6, and/or E-1 to E-10, that essentially consists of an immunoglobulin single variable domain that
 i) has at least 80% amino acid identity with at least one of the immunoglobulin single variable domains of SEQ ID NOs: 23 to 29, 102 and/or 187, preferably SEQ ID NO: 26 and/or 187, in which for the purposes of determining the degree of amino acid identity, the amino acid residues that form the CDR sequences are disregarded;
 and in which:
 ii) preferably one or more of the amino acid residues at positions 11, 37, 44, 45, 47, 83, 84, 103, 104 and 108 according to the Kabat numbering are chosen from the Hallmark residues mentioned in Table A-1.

Aspect E-12: An immunoglobulin single variable domain according to any of aspects B-1 to B-7, C-1 to C-4, D-1 to D-6, and/or E-1 to E-11 that essentially consists of a humanized immunoglobulin single variable domain.

Aspect E-13: An immunoglobulin single variable domain according to any of the aspects B-1 to B-7, C-1 to C-4, D-1 to D-6, and/or E-1 to E-11, that in addition to the at least one binding site for binding formed by the CDR sequences, contains one or more further binding sites for binding against other antigens, proteins or targets.

The immunoglobulin single variable domains according to aspects E-1 to E-13 may in particular be an immunoglobulin single variable domain according to any of the aspects A-1 to A-22.

Polypeptides

Aspect K-1: Polypeptide that comprises of one or more (preferably one) immunoglobulin single variable domains according to any of aspects A-1 to A-22, B-1 to B-7, C-1 to C-4, D-1 to D-6, and/or E-1 to E-13, and optionally further comprises one or more peptidic linkers.

Aspect K-2: Polypeptide according to aspect K-1, which additionally comprises one or more (preferably one) immunoglobulin single variable domain directed against serum albumin.

Aspect K-3: Polypeptide according to any of aspects K-1 or K-2, in which said immunoglobulin single variable domain directed against serum albumin is directed against human serum albumin.

Aspect K-4: Polypeptide according to any of aspects K-1 to K-3, in which said one or more immunoglobulin single variable domain directed against serum albumin is an immunoglobulin single variable domain with SEQ ID NO: 5 or 101.

Nucleic Acids

Aspect M-1: Nucleic acid or nucleotide sequence, that encodes an immunoglobulin single variable domain according to any of aspects A-1 to A-22, B-1 to B-7, C-1 to C-4, D-1 to D-6, E-1 to E-13, a polypeptide according to any of aspects K-1 to K-4.

Aspect M-2: Nucleic acid or nucleotide sequence with SEQ ID NO: 30 to 42, preferably SEQ ID NO: 30 (Table B-6).

Host Cells

Aspect N-1: Host or host cell that expresses, or that under suitable circumstances is capable of expressing, an immunoglobulin single variable domain according to any of aspects A-1 to A-22, B-1 to B-7, C-1 to C-4, D-1 to D-6, E-1 to E-13, a polypeptide according to any of aspects K-1 to K-4; and/or that comprises a nucleic acid or nucleotide sequence according to aspect M-1 or M-2.

Compositions

Aspect O-1: Composition comprising at least one immunoglobulin single variable domain according to any of aspects A-1 to A-22, B-1 to B-7, C-1 to C-4, D-1 to D-6, E-1 to E-13, or at least one polypeptide according to any of aspects K-1 to K-4, or nucleic acid or nucleotide sequence according to aspects M-1 or M-2.

Aspect O-2: Composition according to aspect O-1, which is a pharmaceutical composition.

Aspect O-3: Composition according to aspect O-2, which is a pharmaceutical composition, that further comprises at least one pharmaceutically acceptable carrier, diluent or excipient and/or adjuvant, and that optionally comprises one or more further pharmaceutically active polypeptides and/or compounds.

Making of Agent and Composition of the Invention

Aspect P-1: Method for producing an immunoglobulin single variable domain according to any of aspects A-1 to A-22, B-1 to B-7, C-1 to C-4, D-1 to D-6, E-1 to E-13, a polypeptide according to any of aspects K-1 to K-4, said method at least comprising the steps of:
 a) expressing, in a suitable host cell or host organism or in another suitable expression system, a nucleic acid or nucleotide sequence according to aspect M-1, or aspect M-2;
 optionally followed by:
 b) isolating and/or purifying the immunoglobulin single variable domain according to any of aspects A-1 to A-22, B-1 to B-7, C-1 to C-4, D-1 to D-6, E-1 to E-13, a polypeptide according to any of aspects K-1 to K-4.

Aspect P-2: Method for producing an immunoglobulin single variable domain according to any of aspects A-1 to A-22, B-1 to B-7, C-1 to C-4, D-1 to D-6, E-1 to E-13, a polypeptide according to any of aspects K-1 to K-4, said method at least comprising the steps of:
 a) cultivating and/or maintaining a host or host cell according to aspect N-1 under conditions that are such that said host or host cell expresses and/or produces at least one immunoglobulin single variable domain according to any of aspects A-1 to A-22, B-1 to B-7, C-1 to C-4, D-1 to D-6, E-1 to E-13, a polypeptide according to any of aspects K-1 to K-4;
 optionally followed by:
 b) isolating and/or purifying the immunoglobulin single variable domain according to any of aspects A-1 to A-22, B-1 to B-7, C-1 to C-4, D-1 to D-6, E-1 to E-13, a polypeptide according to any of aspects K-1 to K-4.

Method of Screening

Aspect Q-1: Method for screening immunoglobulin single variable domains directed against c-Met and in particular human c-Met (SEQ ID NO: 1) that comprises at least the steps of:
 a) providing a set, collection or library of nucleic acid sequences encoding immunoglobulin single variable domains; and
 b) screening said set, collection or library of nucleic acid sequences for nucleic acid sequences that encode an immunoglobulin single variable domain that can bind to and/or has affinity for c-Met and in particular human c-Met (SEQ ID NO: 1) and that is cross-blocked or is cross blocking a Nanobody of the invention, e.g. SEQ ID NO: 23 to 29, 102 and 187, preferably SEQ ID NO: 26 and/or 187 (Table B-3), or a polypeptide or construct of the invention, e.g. SEQ ID NO: 7 to 12, 103-111, 113, 188 and 142-150, preferably SEQ ID NO: 7, 106, 113, 188, 143, 146 and/or 147 (see Table B-4); and
 c) isolating said nucleic acid sequence, followed by expressing said immunoglobulin single variable domain.

Aspect Q-2: Method for screening immunoglobulin single variable domains directed against c-Met and in particular human c-Met (SEQ ID NO: 1) that comprises at least the steps of:
 a) providing a set, collection or library of amino acid sequences encoding immunoglobulin single variable domains; and
 b) screening said set, collection or library of immunoglobulin single variable domains that can bind to and/or has affinity for c-Met and in particular human c-Met (SEQ ID NO: 1) and that is cross-blocked or is cross blocking an immunoglobulin single variable domain of the invention, e.g. SEQ ID NO: 23 to 29, 102 and 187, preferably SEQ ID NO: 26 and/or 187 (Table B-3), or a polypeptide or construct of the invention, e.g. SEQ ID NO: 7 to 12, 103-111, 113, 188 and 142-150, preferably SEQ ID NO: 7, 106, 113, 188, 143, 146 and/or 147 (see Table B-4); and
 c) isolating said amino acid sequence(s) that can bind to and/or have affinity for c-Met and in particular human c-Met (SEQ ID NO: 1).

Aspect Q-3: Method for screening immunoglobulin single variable domains directed against c-Met and in particular human c-Met (SEQ ID NO: 1) that comprises at least the steps of:
 a) providing a set, collection or library of VHH1 type immunoglobulin single variable domains; and
 b) screening said set, collection or library of VHH1 type immunoglobulin single variable domains for immunoglobulin single variable domains that can bind to and/or have affinity for c-Met and in particular human c-Met (SEQ ID NO: 1); and
 c) isolating the amino acid sequence(s) that can bind to and/or have affinity for c-Met and in particular human c-Met (SEQ ID NO: 1).

Use of Agents of the Invention

Aspect R-1: Method for the prevention and/or treatment of cancer and/or inflammatory diseases (such as e.g. mentioned herein), said method comprising administering, to a subject in need thereof, a pharmaceutically active amount of at least one immunoglobulin single variable domain according to any of aspects A-1 to A-22, B-1 to B-7, C-1 to C-4, D-1 to D-6, E-1 to E-13, a polypeptide according to any of aspects K-1 to K-4; or composition according to aspect O-2 or O-3.

Aspect R-2: Method for the prevention and/or treatment of at least one disease or disorder that is associated with c-Met and in particular human c-Met (SEQ ID NO: 1), with its biological or pharmacological activity, and/or with the biological pathways or signalling in which c-Met and in particular human c-Met (SEQ ID NO: 1) is involved, said method comprising administering, to a subject in need thereof, a pharmaceutically active amount of at least one immunoglobulin single variable domain according to any of aspects A-1 to A-22, B-1 to B-7, C-1 to C-4, D-1 to D-6, E-1 to E-13, a polypeptide according to any of aspects K-1 to K-4; or composition according to aspect O-2 or O-3.

Aspect R-3: Method for the prevention and/or treatment of at least one disease or disorder that can be prevented and/or treated by administering, to a subject in need thereof, at least one immunoglobulin single variable domain according to any of aspects A-1 to A-22, B-1 to B-7, C-1 to C-4, D-1 to D-6, E-1 to E-13, a polypeptide according to any of aspects K-1 to K-4; or composition according to aspect O-2 or O-3, said method comprising administering, to a subject in need thereof, a pharmaceutically active amount of at least one at least one immunoglobulin single variable domain according to any of aspects A-1 to A-22, B-1 to B-7, C-1 to C-4, D-1 to D-6, E-1 to E-13, a polypeptide according to any of aspects K-1 to K-4; or composition according to aspect O-2 or O-3.

Aspect R-4: Method for immunotherapy, said method comprising administering, to a subject in need thereof, a pharmaceutically active amount of at least one immunoglobulin single variable domain according to any of aspects A-1 to A-22, B-1 to B-7, C-1 to C-4, D-1 to D-6, E-1 to E-13, a polypeptide according to any of aspects K-1 to K-4; or composition according to aspect O-2 or O-3.

Aspect R-5: Method for the prevention and/or treatment of bone disease and/or osteolytic lesions in subjects suffering bone metastatic cancer, including multiple myeloma, said method comprising administering, to the subject in need thereof, a pharmaceutically active amount of at least one immunoglobulin single variable domain against c-Met, and/or according to any of aspects A-1 to A-22, B-1 to B-7, C-1 to C-4, D-1 to D-6, E-1 to E-13, a polypeptide according to any of aspects K-1 to K-4; or composition according to aspect O-2 or O-3.

Aspect R-6: An immunoglobulin single variable domain according to any of aspects A-1 to A-22, B-1 to B-7, C-1 to C-4, D-1 to D-6, E-1 to E-13, a polypeptide according to any of aspects K-1 to K-4, a pharmaceutical composition according to aspect O-2 or O-3 for use in one or more of the methods according to aspects R-1 to R-5.

Aspect R-7: A polypeptide according to any of aspects K-1 to K-4, for the diagnosis, prevention and/or treatment of cancer.

Aspect R-8: ISVDs against c-Met and/or polypeptide according to any of aspects K-1 to K-4, for the diagnosis, prevention and/or treatment of bone disease and/or osteolytic lesion in bone metastatic cancer, including multiple myeloma.

Aspect S-1 A multispecific construct comprising an immunoglobulin single variable domain according to any one of aspects A-1 to A-22, B-1 to B-7, C-1 to C-4, D-1 to D-6 and E-1 to E-13 and a polypeptide modulating VEGF signalling.

Aspect S-2 A multispecific construct comprising a VHH according to any one of aspects A-23 to A-44 and a polypeptide modulating VEGF signalling.

Aspect S-3 A multispecific construct according to aspect S-1 or S-2, wherein said polypeptide modulating VEGF signalling, is an immunoglobulin single variable domain, preferably a domain antibody, more preferably a dAb.

Aspect S-4 A multispecific construct according to aspect S-1 or S-2, wherein said polypeptide modulating VEGF signalling, is a VHH and even more preferably a Nanobody.

Aspect S-5 A multispecific construct according to aspect S-3 or S-4, wherein said polypeptide modulating VEGF signalling, is a polypeptide described in WO 08/101985, in particular any one of SEQ ID NOs: 441-677.

Aspect S-6 A multispecific construct according to any of aspects S-1 to S-5 further comprising one or more peptidic linkers.

Aspect S-7 A multispecific construct according to any of aspects S-1 to S-6, further comprising one or more (preferably one) immunoglobulin single variable domain directed against serum albumin.

Aspect S-8 A multispecific construct according to aspect S-7, wherein said immunoglobulin single variable domain directed against serum albumin is directed against human serum albumin.

Aspect S-9 A multispecific construct according to any of aspects S-7 to S-8, wherein said one or more immunoglobulin single variable domain directed against serum albumin is an immunoglobulin single variable domain with SEQ ID NO: 5 or 101.

Aspect S-10 A multispecific construct according to any one of aspects S-1 to S-9 for use in diagnosing, preventing or treating cancer, preferably multiple myeloma or non-small cell lung cancer.

Aspect S-11 A nucleic acid or nucleotide sequence encoding a multispecific construct according to any one of aspects S-1 to S-9.

Aspect S-12 A host cell expressing a multispecific construct according to any one of aspects S-1 to S-9.

Aspect S-13 A composition, preferably a pharmaceutical composition, comprising a multispecific construct according to any one of aspects S-1 to S-9.

Aspect S-14 A composition, preferably a pharmaceutical composition, comprising a nucleic acid or nucleotide sequence according to aspect S-11.

Aspect S-15 A composition, preferably a pharmaceutical composition, comprising a host cell according to aspect S-12.

Aspect S-16 Method for diagnosing, treating and/or preventing cancer, preferably multiple myeloma or non-small cell lung cancer, as described herein, comprising as essential step the use of a multispecific construct according to any one of aspects S-1 to S-9.

Aspect X-1 A multispecific construct comprising an immunoglobulin single variable domain according to any one of aspects A-1 to A-22, B-1 to B-7, C-1 to C-4, D-1 to D-6 and E-1 to E-13 and a polypeptide modulating EGFR signalling.

Aspect X-2 A multispecific construct comprising a VHH according to any one of aspects A-23 to A-44 and a polypeptide modulating EGFR signalling.

Aspect X-3 A multispecific construct according to aspect X-1 or X-2, wherein said polypeptide modulating EGFR signalling, is an immunoglobulin single variable domain, preferably a domain antibody, more preferably a dAb.

Aspect X-4 A multispecific construct according to aspect X-1 or X-2, wherein said polypeptide modulating EGFR signalling, is a VHH and even more preferably a Nanobody.

Aspect X-5 A multispecific construct according to aspect X-3 or X-4, wherein said polypeptide modulating EGFR signalling, is a polypeptide described in WO 04/041867, in particular SEQ ID NOs: 23-44, WO 05/044858, and in particular SEQ ID NOs: 1-56 and 62-71 and/or WO 07/042289, in particular SEQ ID NOs: 80-93 and 110-143.

Aspect X-6 A multispecific construct according to any of aspects X-1 to X-5 further comprising one or more peptidic linkers.

Aspect X-7 A multispecific construct according to any of aspects X-1 to X-6, further comprising one or more (preferably one) immunoglobulin single variable domain directed against serum albumin.

Aspect X-8 A multispecific construct according to aspect X-7, wherein said immunoglobulin single variable domain directed against serum albumin is directed against human serum albumin.

Aspect X-9 A multispecific construct according to any of aspects X-7 to X-8, wherein said one or more immunoglobulin single variable domain directed against serum albumin is an immunoglobulin single variable domain with SEQ ID NO: 5 or 101.

Aspect X-10 A multispecific construct according to any one of aspects X-1 to X-9 for use in diagnosing, preventing or treating cancer, preferably multiple myeloma or non-small cell lung cancer.

Aspect X-11 A nucleic acid or nucleotide sequence encoding a multispecific construct according to any one of aspects X-1 to X-9.

Aspect X-12 A host cell expressing a multispecific construct according to any one of aspects X-1 to X-9.

Aspect X-13 A composition, preferably a pharmaceutical composition, comprising a multispecific construct according to any one of aspects X-1 to X-9.

Aspect X-14 A composition, preferably a pharmaceutical composition, comprising a nucleic acid or nucleotide sequence according to aspect X-11.

Aspect X-15 A composition, preferably a pharmaceutical composition, comprising a host cell according to aspect X-12.

Aspect X-16 Method for diagnosing, treating and/or preventing cancer, preferably multiple myeloma or non-small cell lung cancer, as described herein, comprising as essential step the use of a multispecific construct according to any one of aspects X-1 to X-9

Aspect Y-1 A multispecific construct comprising an immunoglobulin single variable domain according to any one of aspects A-1 to A-22, B-1 to B-7, C-1 to C-4, D-1 to D-6 and E-1 to E-13, a polypeptide modulating VEGF signalling and a polypeptide modulating EGFR signalling.

Aspect Y-2 A multispecific construct comprising a VHH according to any one of aspects A-23 to A-44, a polypeptide modulating VEGF signalling and a polypeptide modulating EGFR signalling.

Aspect Y-3 A multispecific construct according to aspect Y-1 or Y-2, wherein said polypeptide modulating VEGF signalling, is an immunoglobulin single variable domain, preferably a domain antibody, more preferably a dAb, and wherein said polypeptide modulating EGFR signalling, is an immunoglobulin single variable domain, preferably a domain antibody, more preferably a dAb.

Aspect Y-4 A multispecific construct according to aspect Y-1 or Y-2, wherein said polypeptide modulating VEGF signalling, is a VHH and even more preferably a Nanobody and wherein said polypeptide modulating EGFR signalling, is a VHH and even more preferably a Nanobody Aspect Y-5 A multispecific construct according to aspect Y-3 or Y-4, wherein said polypeptide modulating VEGF signalling, is a polypeptide described in WO 08/101985, in particular by any one of SEQ ID NOs: 441-677, and wherein said polypeptide modulating EGFR signalling, is a polypeptide described in WO 04/041867, in particular by any one of SEQ ID NOs: 23-44, WO 05/044858, and in particular by any one of SEQ ID NOs: 1-56 and 62-71 and/or WO 07/042289, in particular by any one of SEQ ID NOs: 80-93 and 110-143.

Aspect Y-6 A multispecific construct according to any of aspects Y-1 to Y-5 further comprising one, two or more peptidic linkers.

Aspect Y-7 A multispecific construct according to any of aspects Y-1 to Y-6, further comprising one or more (preferably one) immunoglobulin single variable domain directed against serum albumin.

Aspect Y-8 A multispecific construct according to aspect Y-7, wherein said immunoglobulin single variable domain directed against serum albumin is directed against human serum albumin.

Aspect Y-9 A multispecific construct according to any of aspects Y-7 to Y-8, wherein said one or more immunoglobulin single variable domain directed against serum albumin is an immunoglobulin single variable domain with SEQ ID NO: 5 or 101.

Aspect Y-10 A multispecific construct according to any one of aspects Y-1 to Y-9 for use in diagnosing, preventing or treating cancer, preferably multiple myeloma or non-small cell lung cancer.

Aspect Y-11 A nucleic acid or nucleotide sequence encoding a multispecific construct according to any one of aspects Y-1 to Y-9.

Aspect Y-12 A host cell expressing a multispecific construct according to any one of aspects Y-1 to Y-9.

Aspect Y-13 A composition, preferably a pharmaceutical composition, comprising a multispecific construct according to any one of aspects Y-1 to Y-9.

Aspect Y-14 A composition, preferably a pharmaceutical composition, comprising a nucleic acid or nucleotide sequence according to aspect Y-11.

Aspect Y-15 A composition, preferably a pharmaceutical composition, comprising a host cell according to aspect Y-12.

Aspect Y-16 Method for diagnosing, treating and/or preventing cancer, preferably multiple myeloma or non-small cell lung cancer, as described herein, comprising as essential step the use of a multispecific construct according to any one of aspects Y-1 to Y-9.

Further Aspects:

1. An immunoglobulin single variable domain that can specifically displace HGF on human c-Met (SEQ ID NO: 1) with an IC50 of less than 10 nM, more preferably less than 5 nM, more preferably less than 1 nM, even more preferably less than 500 pM, most preferably less than 100 pM and an average HGF displacement of 60% to 80% or more, more preferably 90% or more (e.g. under the condition as outlined in example part).

2. The immunoglobulin single variable domain of aspect 1, wherein the immunoglobulin single variable domain comprises an amino acid sequence with the formula 1

FR1-CDR1-FR2-CDR2-FR3-CDR3-FR4     (1);

wherein FR1 to FR4 refer to framework regions 1 to 4 and are framework regions of an immunoglobulin single variable domain; and wherein CDR1 is chosen from the group consisting of:
    a) SEQ ID NO: 160 and 51,
    b) polypeptides that have at least 80% amino acid identity with SEQ ID NO: 160 and 51,
    c) polypeptides that have 3, 2, or 1 amino acid difference with SEQ ID NO: 160 and 51,
    and wherein CDR2 is chosen from the group consisting of:
    d) SEQ ID NO: 170 and 67;
    e) polypeptides that have at least 80% amino acid identity with SEQ ID NO: 170 and 67;
    f) polypeptides that have 3, 2, or 1 amino acid difference with SEQ ID NO: 170 and 67;
    and wherein CDR3 is chosen from the group consisting of:
    g) SEQ ID NO: 180 and 83;
    h) polypeptides that have at least 80% amino acid identity with SEQ ID NO: 180 and 83;
    i) polypeptides that have 3, 2, or 1 amino acid difference with SEQ ID NO: 180 and 83.

3. The immunoglobulin single variable domain according to any of aspects 1 to 2, wherein the framework regions (FRs) have a sequence identity of more than 80% (more preferably 85%, even more preferably 90%, most preferred 95%) with the FRs of SEQ ID NOs: 189, 59, 190 and/or 185.

4. The immunoglobulin single variable domain of aspect 1, wherein the immunoglobulin single variable domain comprises an amino acid sequence with the formula 1

FR1-CDR1-FR2-CDR2-FR3-CDR3-FR4     (1);

wherein FR1 to FR4 refer to framework regions 1 to 4 and are framework regions of an immunoglobulin single variable domain; wherein CDR1 is SEQ ID NO: 160 or 51, CDR2 is SEQ ID NO: 170 or 67; and CDR3 is SEQ ID NO: 180 or 83.

5. A polypeptide comprising an immunoglobulin single variable domain of any of aspects 1 to 4.

6. The polypeptide according to aspect 5, wherein the polypeptide is selected from the group consisting of polypeptides that have an amino acid sequence with a sequence identity of more than 80% (more preferably 85%, even more preferably 90%, most preferred 95%) with SEQ ID NOs: 23 to 29, 102 or 187.

7. The polypeptide to any of aspects 5 or 6, wherein the polypeptide is selected from the group consisting of polypeptides that have an amino acid sequence with a sequence identity of more than 80% (more preferably 85%, even more preferably 90%, most preferred 95%) with SEQ ID NO: 26 or 187.

8. The polypeptide according to any of aspects 5 to 7 and additionally comprising an immunoglobulin single variable domain that binds human serum albumin such as e.g. Alb11 (SEQ ID NO: 5) or Alb23 (SEQ ID NO: 101).

9. The polypeptides according to any of aspects 5 to 8, wherein the polypeptide is selected from the group consisting of polypeptides that have an amino acid sequence with a sequence identity of more than 80% (more preferably 85%, even more preferably 90%, most preferred 95%) with SEQ ID NOs: 7 to 12, 103-111, 113, 188 or 142 to 150.

10. The polypeptides according to any of aspects 5 to 9, wherein the polypeptide is selected from the group consisting of polypeptides that have an amino acid sequence with a sequence identity of more than 80% (more preferably 85%, even more preferably 90%, most preferred 95%) with SEQ ID NO: 7, 106, 113, 188, 143, 146 or 147.

11. The immunoglobulin single variable domain according to any of aspect 1 to 4 or the polypeptide according to any of aspect 5 to 10, wherein the IC50 in the Alphascreen assay (such as in example 2.3.1) is 1.2 nM or lower.

12. The immunoglobulin single variable domain according to any of aspect 1 to 4 or the polypeptide according to any of aspect 5 to 10, wherein the IC50 in the Alphascreen assay (such as in example 2.3.1) is 500 pM or lower.

13. A nucleic acid sequence encoding i) an immunoglobulin single variable domain according to any of aspects 1 to 4, 11, or 12; or ii) a polypeptide according to any of aspects 5 to 10.

14. A pharmaceutical composition comprising i) an immunoglobulin single variable domain according to any of aspects 1 to 4, 11, or 12; or ii) a polypeptide according to any of aspects 5 to 10; and optionally a pharmaceutically acceptable excipient.

15. An immunoglobulin single variable domain according to any of aspects 1 to 4, 11, or 12; or ii) a polypeptide according to any of aspects 5 to 10, for use in cancer.

16. Method for producing an immunoglobulin single variable domain according to any of aspects 1 to 4, 11, or 12; or ii) a polypeptide according to any of aspects 5 to 10, said method at least comprising the steps of:

a) expressing, in a suitable host cell or host organism or in another suitable expression system, a nucleic acid or nucleotide sequence according to aspect 13; optionally followed by:

b) isolating and/or purifying said immunoglobulin single variable domain or said polypeptide.

17. Method for screening immunoglobulin single variable domains directed against c-Met and in particular human c-Met (SEQ ID NO: 1) that comprises at least the steps of:

a) providing a set, collection or library of VHH1 type immunoglobulin single variable domains; and b) screening said set, collection or library of VHH1 type immunoglobulin single variable domains for immunoglobulin single variable domains that can bind to and/or have affinity for c-Met and in particular human c-Met (SEQ ID NO: 1); and c) isolating the amino acid sequence(s) that can bind to and/or have affinity for c-Met and in particular human c-Met (SEQ ID NO: 1).

18. An in vitro method for assessing the responsiveness of a patient suffering from a c-Met associated disease or disorder to a therapy, said method comprising the steps of:

a) providing from said patient a first sample prior to therapy and measuring the amount of soluble c-Met in said first sample, b) providing from said patient a second sample post Initiation of therapy and measuring the amount of soluble c-Met in said second sample, c) comparing the amount of soluble c-Met present in the first sample to the amount of soluble c-Met found in the second sample;

wherein a decrease in the amount of soluble c-Met found in the second sample compared to the amount of soluble c-Met in the first sample indicates that the patient is responsive to said therapy.

19. The method of claim 18, wherein said sample is a blood sample, a serum sample, a plasma sample, a urine sample, a fecal sample, a bronchoalveolar lavage fluid, a cerebrospinal fluid, or a tissue biopsy.

20. The method of claim 18, wherein the amount of soluble c-Met is measured using immunoassays, chemiluminescent assays or electrochemiluminescent assays.

21. The method of claim 18, wherein the therapy comprises administering i) an immunoglobulin single variable domain according to any of claims 1 to 4, 11, or 12; ii) a polypeptide according to any of claims 5 to 10; or iii) a pharmaceutical composition according to claim 14.

22. A method for treatment of at least one disease or disorder associated with c-Met, said method comprising administering to a subject in need thereof, a pharmaceutical composition according to claim 14.

23. A kit for assessing the responsiveness of a patient suffering from a c-Met associated disease or disorder to a therapy, said kit comprising one or more reagents for measuring the amount of soluble c-Met in a patient according to the method of claim 18.

24. The kit of claim 22, further comprising i) an immunoglobulin single variable domain according to any of claims 1 to 4, 11, or 12; or ii) a polypeptide according to any of claims 5 to 10; or iii) a pharmaceutical composition according to claim 14.

EXPERIMENTAL PART

Sequences

TABLE B-1

Prior art sequences

| Name | SEQ ID NO | Amino acid sequences |
|---|---|---|
| Human c-Met or hc-Met | 1 | MKAPAVLAPGILVLLFTLVQRSNGECKEALAKSEMNVNMKYQLPNFTAE<br>TPIQNVILHEHHIFLGATNYIYVLNEEDLQKVAEYKTGPVLEHPDCFPCQD<br>CSSKANLSGGVWKDNINMALVVDTYYDDQLISCGSVNRGTCQRHVFPH<br>NHTADIQSEVHCIFSPQIEEPSQCPDCVVSALGAKVLSSVKDRFINFFVGN<br>TINSSYFPDHPLHSISVRRLKETKDGFMFLTDQSYIDVLPEFRDSYPIKYVH<br>AFESNNFIYFLTVQRETLDAQTFHTRIIRFCSINSGLHSYMEMPLECILTEK<br>RKKRSTKKEVFNILQAAYVSKPGAQLARQIGASLNDDILFGVFAQSKPDS<br>AEPMDRSAMCAFPIKYVNDFFNKIVNKNNVRCLQHFYGPNHEHCFNRT<br>LLRNSSGCEARRDEYRTEFTTALQRVDLFMGQFSEVLLTSISTFIKGDLTIA<br>NLGTSEGRFMQVVVSRSGPSTPHVNFLLDSHPVSPEVIVEHTLNQNGYT<br>LVITGKKITKIPLNGLGCRHFQSCSQCLSAPPFVQCGWCHDKCVRSEECLS<br>GTWTQQICLPAIYKVFPNSAPLEGGTRLTICGWDFGFRRNNKFDLKKTR<br>VLLGNESCTLTLSESTMNTLKCTVGPAMNKHFNMSIIISNGHGTTQYSTF<br>SYVDPVITSISPKYGPMAGGTLLTLTGNYLNSGNSRHISIGGKTCTLKSVS<br>NSILECYTPAQTISTEFAVKLKIDLANRETSIFSYREDPIVYEIHPTKSFISGGS<br>TITGVGKNLNSVSVPRMVINVHEAGRNFTVACQHRSNSEIICCTTPSLQQ<br>LNLQLPLKTKAFFMLDGILSKYFDLIYVHNPVFKPFEKPVMISMGNENVLE<br>IKGNDIDPEAVKGEVLKVGNKSCENIHLHSEAVLCTVPNDLLKLNSELNIE<br>WKQAISSTVLGKVIVQPDQNFTGLIAGVVSISTALLLLLGFFLWLKKRKQIK<br>DLGSELVRYDARVHTPHLDRLVSARSVSPTTEMVSNESVDYRATFPEDQ<br>FPNSSQNGSCRQVQYPLTDMSPILTSGDSDISSPLLQNTVHIDLSALNPEL<br>VQAVQHVVIGPSSLIVHFNEVIGRGHFGCVYHGTLLDNDGKKIHCAVKSL<br>NRITDIGEVSQFLTEGIIMKDFSHPNVLSLLGICLRSEGSPLVVLPYMKHG<br>DLRNFIRNETHNPTVKDLIGFGLQVAKGMKYLASKKFVHRDLAARNCML<br>DEKFTVKVADFGLARDMYDKEYYSVHNKTGAKLPVKWMALESLQTQKF<br>TTKSDVWSFGVLLWELMTRGAPPYPDVNTFDITVYLLQGRRLLQPEYCP<br>DPLYEVMLKCWHPKAEMRPSFSELVSRISAIFSTFIGEHYVHVNATYVNV<br>KCVAPYPSLLSSEDNADDEVDTRPASFWETS |
| recombinant human cMet/Fc chimera (R&D systems) | 2 | ECKEALAKSEMNVNMKYQLPNFTAETPIQNVIHEHHIFLGATNYIYVLN<br>EEDLQKVAEYKTGPVLEHPDCFPCQDCSSKANLSGGVWKDNINMALVV<br>DTYYDDQLISCGSVNRGTCQRHVFPHNHTADIQSEVHCIFSPQIEEPSQC<br>PDCVVSALGAKVLSSVKDRFINFFVGNTINSSYFPDHPLHSISVRRLKETKD<br>GFMFLTDQSYIDVLPEFRDSYPIKYVHAFESNNFIYFLTVQRETLDAQTFH<br>TRIIRFCSINSGLHSYMEMPLECILTEKRKKRSTKKEVFNILQAAYVSKPGA<br>QLARQIGASLNDDILFGVFAQSKPDSAEPMDRSAMCAFPIKYVNDFFNKI<br>VNKNNVRCLQHFYGPNHEHCFNRTLLRNSSGCEARRDEYRTEFTTALQR<br>VDLFMGQFSEVLLTSISTFIKGDLTIANLGTSEGRFMQVVVSRSGPSTPHV<br>NFLLDSHPVSPEVIVEHTLNQNGYTLVITGKKTKIPLNGLGCRHFQSCSQ<br>CLSAPPFVQCGWCHDKCVRSEECLSGTWTQQICLPAIYKVFPNSAPLEG<br>GTRLTICGWDFGFRRNNKFDLKKTRVLLGNESCTLTLSESTMNTLKCTVG<br>PAMNKHFNMSIIISNGHGTTQYSTFSYVDPVITSISPKYGPMAGGTLLTLT<br>GNYLNSGNSRHISIGGKTCTLKSVSNSILECYTPAQTISTEFAVKLKIDLANR<br>ETSIFSYREDPIVYEIHPTKSFISGGSTITGVGKNLNSVSVPRMVINVHEAG<br>RNFTVACQHRSNSEIICCTTPSLQQLNLQLPLKTKAFFMLDGILSKYFDLIY<br>VHNPVFKPFEKPVMISMGNENVLEIKGNDIDPEAVKGEVLKVGNKSCEN<br>IHLHSEAVLCTVPNDLLKLNSELNIEWKQAISSTVLGKVIVQPDQNFTHIE<br>GRMDPKSCDKTHTCPPCPAPELLGGPSVFLFPPKPKDTLMISRTPEVTCV<br>VVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSRDELTK<br>NQVSLTCLVKGFYPSDIAVEWESNGQPENNYKTTPPVLDSDGSFFLYSKL<br>TVDKSRWQQGNVFSCSVMHEALHNHYTQKSLSLSPGKHHHHHH |
| recombinant human SEMA/Fc | 100 | MKAPAVLAPGILVLLFTLVQRSNGECKEALAKSEMNVNMKYQLPNFTAE<br>TPIQNVILHEHHIFLGATNYIYVLNEEDLQKVAEYKTGPVLEHPDCFPCQD<br>CSSKANLSGGVWKDNINMALVVDTYYDDQLISCGSVNRGTCQRHVFPH<br>NHTADIQSEVHCIFSPQIEEPSQCPDCVVSALGAKVLSSVKDRFINFFVGN<br>TINSSYFPDHPLHSISVRRLKETKDGFMFLTDQSYIDVLPEFRDSYPIKYVH<br>AFESNNFIYFLTVQRETLDAQTFHTRIIRFCSINSGLHSYMEMPLECILTEK<br>RKKRSTKKEVFNILQAAYVSKPGAQLARQIGASLNDDILFGVFAQSKPDS<br>AEPMDRSAMCAFPIKYVNDFFNKIVNKNNVRCLQHFYGPNHEHCFNRT<br>LLRNSSGCEARRDEYRTEFTTALQRVDLFMGQFSEVLLTSISTFIKGDLTIA<br>NLGTSEGRFMQVVVSRSGPSTPHVNFLLDSHPVSPEVIVEHTLNQNGYT<br>LVITGKKITKIPLNGLGHIEGRMDPKSCDKTHTCPPCPAPELLGGPSVFLFP<br>PKPKDTLMISRTPEVTCVVVDVSHEDPEVKFNWYVDGVEVHNAKTKPR<br>EEQYNSTYRVVSVLTVLHQDWLNGKEYKCKVSNKALPAPIEKTISKAKGQ<br>PREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSL<br>SLSPGKHHHHHH |

TABLE B-1 -continued

Prior art sequences

| Name | SEQ ID NO | Amino acid sequences |
|---|---|---|
| cynomolgus c-Met | 3 | MKAPAVLVPGILVLLFTLVQRSNGECKEALAKSEMNVNMKYQLPNFTAE<br>TAIQNVILHEHHIFLGATNYIYVLNEEDLQKVAEYKTGPVLEHPDCFPCQD<br>CSSKANLSGGVWKDNINMALVVDTYYDDQLISCGSVNRGTCQRHVFPH<br>NHTADIQSEVHCIFSPQIEEPNQCPDCVVSALGAKVLSSVKDRFINFFVG<br>NTINSSYFPHHPLHSISVRRLKETKDGFMFLTDQSYIDVLPEFRDSYPIKYIH<br>AFESNNFIYFLTVQRETLNAQTFHTRIIRFCSLNSGLHSYMEMPLECILTEK<br>RKKRSTKKEVFNILQAAYVSKPGAQLARQIGASLNDDILFGVFAQSKPDS<br>AEPMDRSAMCAFPIKYVNDFFNKIVNKNNVRCLQHFYGPNHEHCFNRT<br>LLRNSSGCEARRDEYRAEFTTALQRVDLFMGQFSEVLLTSISTFVKGDLTI<br>ANLGTSEGRFMQVVVSRSGPSTPHVNFLLDSHPVSPEVIVEHPLNQNGY<br>TLVVTGKKITKIPLNGLGCRHFQSCSQCLSAPPFVQCGWCHDKCVRSEEC<br>PSGTWTQQICLPAIYKVFPTSAPLEGGTRLTICGWDFGFRRNNKFDLKKT<br>RVLLGNESCTLTLSESTMNTLKCTVGPAMNKHFNMSIIISNGHGTTQYST<br>FSYVDPIITSISPKYGPMAGGTLLTLTGNYLNSGNSRHISIGGKTCTLKSVS<br>NSILECYTPAQTISTEFAVKLKIDLANRETSIFSYREDPIVYEIHPTKSFISGGS<br>TITGVGKNLHSVSVPRMVINVHEAGRNFTVACQHRSNSEIICCTTPSLQQ<br>LNLQLPLKTKAFFMLDGILSKYFDLIYVHNPVFKPFEKPVMISMGNENVLE<br>IKGNDIDPEAVKGEVLKVGNKSCENIHLHSEAVLCTVPNDLLKLNSELNIE<br>WKQAISSTVLGKVIVQPDQNFTGLIAGVVSISIALLLLLGLFLWLKKRKQIK<br>DLGSELVRYDARVHTPHLDRLVSARSVSPTTEMVSNESVDYRATFPEDQ<br>FPNSSQNGSCRQVQYPLTDMSPILTSGDSDISSPLLQNTVHIDLSALNPEL<br>VQAVQHVVIGPSSLIVHFNEVIGRGHFGCVYHGTLLDNDGKKIHCAVKSL<br>NRITDIGEVSQFLTEGIIMKDFSHPNVLSLLGICLRSEGSPLVVLPYMKHG<br>DLRNFIRNETHNPTVKDLIGFGLQVAKGMKYLASKKFVHRDLAARNCML<br>DEKFTVKVADFGLARDMYDKEYYSVHNKTGAKLPVKWMALESLQTQKF<br>TTKSDVWSFGVLLWELMTRGAPPYPDVNTFDITVYLLQGRRLLQPEYCP<br>DPLYEVMLKCWHPKAEMRPSFSELVSRISAIFSTFIGEHYVHVNATYVNV<br>KCVAPYPSLLSSEDNADDEVDT |
| recombinant cynomolgus c-Met/Fc chimera | 4 | MKAPAVLVPGILVLLFTLVQRSNGECKEALAKSEMNVNMKYQLPNFTAE<br>TAIQNVILHEHHIFLGATNYIYVLNEEDLQKVAEYKTGPVLEHPDCFPCQD<br>CSSKANLSGGVWKDNINMALVVDTYYDDQLISCGSVNRGTCQRHVFPH<br>NHTADIQSEVHCIFSPQIEEPNQCPDCVVSALGAKVLSSVKDRFINFFVG<br>NTINSSYFPHHPLHSISVRRLKETKDGFMFLTDQSYIDVLPEFRDSYPIKYIH<br>AFESNNFIYFLTVQRETLNAQTFHTRIIRFCSLNSGLHSYMEMPLECILTEK<br>RKKRSTKKEVFNILQAAYVSKPGAQLARQIGASLNDDILFGVFAQSKPDS<br>AEPMDRSAMCAFPIKYVNDFFNK1VNKNNVRCLQHFYGPNHEHCFNRT<br>LLRNSSGCEARRDEYRAEFTTALQRVDLFMGQFSEVLLTSISTFVKGDLTI<br>ANLGTSEGRFMQVVVSRSGPSTPHVNFLLDSHPVSPEVIVEHPLNQNGY<br>TLVVTGKKITKIPLNGLGCRHFQSCSQCLSAPPFVQCGWCHDKCVRSEEC<br>PSGTWTQQICLPAIYKVFPTSAPLEGGTRLTICGWDFGFRRNNKFDLKKT<br>RVLLGNESCTLTLSESTMNTLKCTVGPAMNKHFNMSIIISNGHGTTQYST<br>FSYVDPIITSISPKYGPMAGGTLLTLTGNYLNSGNSRHISIGGKTCTLKSVS<br>NSILECYTPAQTISTEFAVKLKIDLANRETSIFSYREDPIVYEIHPTKSFISGGS<br>TITGVGKNLHSVSVPRMVINVHEAGRNFTVACQHRSNSEIICCTTPSLQQ<br>LNLQLPLKTKAFFMLDGILSKYFDLIYVHNPVFKPFEKPVMISMGNENVLE<br>IKGNDIDPEAVKGEVLKVGNKSCENIHLHSEAVLCTVPNDLLKLNSELNIE<br>WKQAISSTVLGKVIVQPDQNFTHIEGRMDPKSCDKTHTCPPCPAPELLG<br>GPSVFLFPPKPKDTLMISRTPEVTCVVVDVSHEDPEVKFNWYVDGVEVH<br>NAKTKPREEQYNSTYRVVSVLTVLHQDWLNGKEYKCKVSNKALPAPIEK<br>TISKAKGQPREPQVYTLPPSRDELTKNQVSLTCLVKGFYPSDIAVEWESN<br>GQPENNYKTTPPVLDSDGSFFLYSKLTVDKSRWQQGNVFSCSVMHEAL<br>HNHYTQKSLSLSPGKHHHHHH |
| Alb11 | 5 | EVQLVESGGGLVQPGNSLRLSCAASGFTFSSFGMSWVRQAPGKGLEW<br>VSSISGSGSDTLYADSVKGRFTISRDNAKTTLYLQMNSLRPEDTAVYYCTI<br>GGSLSRSSQGTLVTVSS |
| Alb23 | 101 | EVQLLESGGGLVQPGGSLRLSCAASGFTFRSFGMSWVRQAPGKGPEW<br>VSSISGSGSDTLYADSVKGRFTISRDNSKNTLYLQMNSLRPEDTAVYYCTI<br>GGSLSRSSQGTLVTVSS |
| Tag-1 or 3xFLAG-His$_6$ | 6 | GAADYKDHDGDYKDHDIDYKDDDDKGAAHHHHHH |

TABLE B-2

Sequences for CDRs and frameworks, plus preferred combinations as provided in for formula I, namely FR1-CDR1-FR2-CDR2-FR3-CDR3-FR4 (the following terms: "ID" refers to the given SEQ ID NO. Preferred combinations of FR and CDR sequences for each Nanobody construct are used interchangeably through-out the application)

| Clone* | ID FR1 | ID CDR1 | ID FR2 | ID CDR2 | ID FR3 | ID CDR3 | ID FR4 |
|---|---|---|---|---|---|---|---|
| A | 43 EVQLVESGGGLVQPGGSLRLSCAASGFILD | 51 YYAIG | 59 WFRQAPGKEREGVL | 67 CIDASDDITYYADSVKG | 75 RFTISRDNAKNTVYLQMNSLKPEDTGVYYCAT | 83 PIGLSSSCLLEYDYDY | 91 WGQGTLVTVSS |
| B | 44 EVQLVESGGGLVQAGGSLRLSCAASGRTIS | 52 RYTMG | 60 WFRQAPGKEREFVA | 68 AISWSGDNTNYADSVKG | 76 RFTISRPNTKNTMYLQMNSLKPEDTAVYYCAT | 84 DYRSGSYYQASEWTRPSGYDY | 92 WGQGTLVTVSS |
| C | 45 EVQLVESGGGLVQPGGSLRLSCAASGFSLD | 53 YFAIG | 61 WFRQAPGKEREEIS | 69 CISNSDGSTYYANSVKG | 77 RFTISIDNAKNTVYLQMTSLKPEDTAVYYCAT | 85 PVGLGPFCKTTNDYDY | 93 SGQGTLVTVSS |
| D | 46 EVQLVESGGGLVQPGGSLRLSCAASGFTLD | 54 YYAIN | 62 WFRQAPGKEREGVS | 70 CISGGDGSTYYADSVKG | 78 RFTISRDNAKNTVYLQMNSLKPEDTGVYYCAT | 86 ALGLSSSCHGDGYDY | 94 WGQGTLVTVSS |
| E | 47 EVQLVESGGGLVQPGGSLRLSCAASGFILD | 55 YYAIG | 63 WFRQAPGKEREGVS | 71 CIDASDDITYYADSVKG | 79 RFTISRDNAKNTVYLQMNSLKPEDTGVYYCAT | 87 PIGLSSSCLLEYDYDY | 95 WGQGTLVTVSS |
| F | 48 EVQLVESGGGLVQPGGSLRLSCAASGFILD | 56 YYAIG | 64 WFRQAPGKEREGVL | 72 SIDASDDITYYADSVKG | 80 RFTISRDNAKNTVYLQMNSLKPEDTGVYYCAT | 88 PIGLSSSGLLEYDYDY | 96 WGQGTLVTVSS |
| G | 49 EVQLVESGGGLVQPGGSLRLSAAASGFILD | 57 YYAIG | 65 WFRQAPGKEREGVL | 73 CIDASDDITYYADSVKG | 81 RFTISRDNAKNTVYLQMNSLKPEDTGVYYSAT | 89 PIGLSSSCLLEYDYDY | 97 WGQGTLVTVSS |
| J | 153 EVQLVESGGGLVQAGGSLRLSCAASGFTFD | 158 DYAIG | 163 WFRQAPGEEREGVS | 168 SISSTYGLTYYADSVKG | 173 RFTISSSNAKNTVYLQMNNLKPEDTAVYYCAA | 178 TPIERLGLDAYEYDY | 183 WGQGTQVTVSS |
| K | 154 DVQLVESGGGLVQPGGSLRLSCAASGFAFD | 159 DYAIG | 164 WFRQAPGEEREGVS | 169 SISSTYGLTYYADSVKG | 174 RFTISSDNSKNTVYLQMNSLRPEDTAVYYCAA | 179 TPIGLIGLDAYEYDY | 184 WGQGTLVTVSS |
| L | 155 DVQLVESGGGLVQPGGSLRLSCAASGFTFD | 160 DYAIG | 165 WFRQAPGEERLGVS | 170 SISSTYGLTYYADSVKG | 175 RFTISSDNSKNTVYLQMNSLRPEDTAVYYCAA | 180 TPIGLIGLDAYEYDY | 185 WGQGTLVTVSS |
| M | 156 DVQLVESGGGLVQPGGSLRLSCAASGFAFD | 161 DYAIG | 166 WFRQAPGEERLGVS | 171 SISSTYGLTYYADSVKG | 176 RFTISSDNSKNTVYLQMNSLRPEDTAVYYCAA | 181 TPIGLIGLDAYEYDY | 186 WGQGTLVTVSS |
| N | 189 DVQLVESGGGLVQPGGSLRLSCAASGFILD | 51 YYAIG | 59 WFRQAPGKEREGVL | 67 CIDASDDITYYADSVKG | 190 RFTISRDNSKNTVYLQMNSLRPEDTAVYYCAT | 83 PIGLSSSCLLEYDYDY | 185 WGQGTLVTVSS |

*A: 04E09; B: 06B08; C: 06C12; D: 06F10; E: 04E09 (L49S); F: 04E09 (C50S/C100bG); G: 04E09 (C22A/C92S); J: 33H10; K: A007901256 (first building block); L: A007901259 (first building block); M: A007901260 (first building block); N: A00790105.

TABLE A-2

Sequences for ALB CDRs and frameworks, plus preferred combinations as provided in for formula I, namely FR1-CDR1-FR2-CDR2-F113-CDR3-FR4 (the following terms: "ID" refers to the given SEQ ID NO. Preferred combinations of FR and CDR sequences for each Nanobody construct are used interchangeably through-out the application)

| Clone* | ID FR1 | ID CDR1 | ID FR2 | ID CDR2 | ID FR3 | ID CDR3 | ID FR4 |
|---|---|---|---|---|---|---|---|
| H | 50 EVQLVESGGGLVQPGNSLRLSCAASGFTFS | 58 SFGMS | 66 WVRQAPGKGLEWVS | 74 SISGSGSDTLYADSVKG | 82 RFTISRDNAKTTLYLQMNSLRPEDTAVYYCTI | 90 GSLSR | 98 SSQGTLVTVSS |
| I | 152 EVQLLESGGGLVQPGGSLRLSCAASGFTFR | 157 SFGMS | 162 WVRQAPGKGLEWVS | 167 SISGSGSDTLYADSVKG | 172 RFTISRDNSKNTLYLQMNSLRPEDTAVYYCTI | 177 GSLSR | 182 SSQGTLVTVSS |

*H: Alb11; I: Alb23_;

TABLE B-3

Amino acid sequences of immunoglobulin single variable sequences of the invention

| Name of clone | SEQ ID NO: | Amino acid sequences |
|---|---|---|
| 4E09 | 26 | EVQLVESGGGLVQPGGSLRLSCAASGFILDYYAIGWFRQAPGKEREGVLCIDASDDITYYADSVKGRFTISRDNAKNTVYLQMNSLKPEDTGVYYCATPIGLSSSCLLEYDYDYWGQGTLVTVSS |

TABLE B-3 -continued

Amino acid sequences of immunoglobulin single variable sequences of the invention

| Name of clone | SEQ ID NO: | Amino acid sequences |
|---|---|---|
| 06B08 | 27 | EVQLVESGGGLVQAGGSLRLSCAASGRTISRYTMGWFRQAPGKEREFVAAISWSGDNTNYADSVKGRFTISRPNTKNTMYLQMNSLKPEDTAVYYCAADYRSGSYYQASEWTRPSGYDYWGQGTLVTVSS |
| 06C12 | 28 | EVQLVESGGGLVQPGGSLRLSCAASGFSLDYFAIGWFRQAPGKEREEISCISNSDGSTYYANSVKGRFTISIDNAKNTVYLQMTSLKPEDTAVYYCATPVGLGPFCKTTNDYDYSGQGTLVTVSS |
| 06F10 | 29 | EVQLVESGGGLVQPGGSLRLSCAASGFTLDYYAINWFRQAPGKEREGVSCISGGDGSTYYADSVKGRFTISRDNAKNTVYLQMNSLKPEDTAVYYCATALGLSSSCHGDGYDYWGQGTLVTVSS |
| 04E09 (L49S) | 23 | EVQLVESGGGLVQPGGSLRLSCAASGFILDYYAIGWFRQAPGKEREGVSCIDASDDITYYADSVKGRFTISRDNAKNTVYLQMNSLKPEDTGVYYCATPIGLSSSCLLEYDYDYWGQGTLVTVSS |
| 04E09 (C50S/C100bG) | 24 | EVQLVESGGGLVQPGGSLRLSCAASGFILDYYAIGWFRQAPGKEREGVLSIDASDDITYYADSVKGRFTISRDNAKNTVYLQMNSLKPEDTGVYYCATPIGLSSSGLLEYDYDYWGQGTLVTVSS |
| 04E09 (C22A/C92S) | 25 | EVQLVESGGGLVQPGGSLRLSAAASGFILDYYAIGWFRQAPGKEREGVLCIDASDDITYYADSVKGRFTISRDNAKNTVYLQMNSLKPEDTGVYYSATPIGLSSSCLLEYDYDYWGQGTLVTVSS |
| 33H10 | 187 | EVQLVESGGGLVQAGGSLRLSCAASGFTFDDYAIGWFRQAPGEEREGVSSISSTYGLTYYADSVKGRFTISSSNAKNTVYLQMNNLKPEDTAVYYCAATPIERLGLDAYEYDYWGQGTQVTVSS |

TABLE B-4

Polypeptide sequences of the invention

| Name of clone | SEQ ID NO: | Amino acid sequences |
|---|---|---|
| 04E09-9GS-Alb11 | 7 | EVQLVESGGGLVQPGGSLRLSCAASGFILDYYAIGWFRQAPGKEREGVLCIDASDDITYYADSVKGRFTISRDNAKNTVYLQMNSLKPEDTGVYYCATPIGLSSSCLLEYDYDYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| 06B08-9GS-Alb11 | 8 | EVQLVESGGGLVQAGGSLRLSCAASGRTISRYTMGWFRQAPGKEREFVAAISWSGDNTNYADSVKGRFTISRPNTKNTMYLQMNSLKPEDTAVYYCAADYRSGSYYQASEWTRPSGYDYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| 06C12-9GS-Alb11 | 9 | EVQLVESGGGLVQPGGSLRLSCAASGFSLDYFAIGWFRQAPGKEREEISCISNSDGSTYYANSVKGRFTISIDNAKNTVYLQMTSLKPEDTAVYYCATPVGLGPFCKTTNDYDYSGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| 06F10-9GS-Alb11 | 10 | EVQLVESGGGLVQPGGSLRLSCAASGFTLDYYAINWFRQAPGKEREGVSCISGGDGSTYYADSVKGRFTISRDNAKNTVYLQMNSLKPEDTAVYYCATALGLSSSCHGDGYDYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| A007900031 (Alb11-35GS-04E09) | 11 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGGGGSGGGGSGGGGSGGGGSGGGGSGGGGSGGGGSEVQLVESGGGLVQPGGSLRLSCAASGFILDYYAIGWFRQAPGKEREGVLCIDASDDITYYADSVKGRFTISRDNAKNTVYLQMNSLKPEDTGVYYCATPIGLSSSCLLEYDYDYWGQGTLVTVSS |

TABLE B-4 -continued

Polypeptide sequences of the invention

| Name of clone | SEQ ID NO: | Amino acid sequences |
|---|---|---|
| A007900032 (Alb11-9GS-04E09) | 12 | EVQLVESGGGLVQPGNSLRLSCAASGFTFSSFGMSWVRQAPG KGLEWVSSISGSGSDTLYADSVKGRFTISRDNAKTTLYLQMNSL RPEDTAVYYCTIGGSLSRSSQGTLVTVSSGGGGSGGGGSEVQLVE SGGGLVQPGGSLRLSCAASGFILDYYAIGWFRQAPGKEREGVL CIDASDDITYYADSVKGRFTISRDNAKNTVYLQMNSLKPEDTGV YYCATPIGLSSSCLLEYDYDYWGQGTLVTVSS |
| A00790105 4E09 = (E1D, A74S, K83R, G88A, Q108L) | 102 | DVQLVESGGGLVQPGGSLRLSCAASGFILDYYAIGWFRQAPGK EREGVLCIDASDDITYYADSVKGRFTISRDNSKNTVYLQMNSLR PEDTAVYYCATPIGLSSSCLLEYDYDYWGQGTLVTVSS |
| Alb23-9GS-4E09 | 103 | EVQLLESGGGLVQPGGSLRLSCAASGFTFRSFGMSWVRQAPG KGPEWVSSISGSGSDTLYADSVKGRFTISRDNSKNTLYLQMNSL RPEDTAVYYCTIGGSLSRSSQGTLVTVSSGGGGSGGGGSEVQLVE SGGGLVQPGGSLRLSCAASGFILDYYAIGWFRQAPGKEREGVL CIDASDDITYYADSVKGRFTISRDNAKNTVYLQMNSLKPEDTGV YYCATPIGLSSSCLLEYDYDYWGQGTLVTVSS |
| 4E09-9GS-Alb23 (A007900057) | 104 | EVQLVESGGGLVQPGGSLRLSCAASGFILDYYAIGWFRQAPGK EREGVLCIDASDDITYYADSVKGRFTISRDNAKNTVYLQMNSLK PEDTGVYYCATPIGLSSSCLLEYDYDYWGQGTLVTVSSGGGGS GGGSEVQLLESGGGLVQPGGSLRLSCAASGFTFRSFGMSWVR QAPGKGPEWVSSISGSGSDTLYADSVKGRFTISRDNSKNTLYLQ MNSLRPEDTAVYYCTIGGSLSRSSQGTLVTVSS |
| Alb23-9GS-A00790105 | 105 | EVQLLESGGGLVQPGGSLRLSCAASGFTFRSFGMSWVRQAPG KGPEWVSSISGSGSDTLYADSVKGRFTISRDNSKNTLYLQMNSL RPEDTAVYYCTIGGSLSRSSQGTLVTVSSGGGGSGGGGSDVQLV ESGGGLVQPGGSLRLSCAASGFILDYYAIGWFRQAPGKEREGVL CIDASDDITYYADSVKGRFTISRDNSKNTVYLQMNSLRPEDTAV YYCATPIGLSSSCLLEYDYDYWGQGTLVTVSS |
| A0079105-9GS-Alb23 (A007901219) | 106 | DVQLVESGGGLVQPGGSLRLSCAASGFILDYYAIGWFRQAPGK EREGVLCIDASDDITYYADSVKGRFTISRDNSKNTVYLQMNSLR PEDTAVYYCATPIGLSSSCLLEYDYDYWGQGTLVTVSSGGGGSG GGSEVQLLESGGGLVQPGGSLRLSCAASGFTFRSFGMSWVRQ APGKGPEWVSSISGSGSDTLYADSVKGRFTISRDNSKNTLYLQ MNSLRPEDTAVYYCTIGGSLSRSSQGTLVTVSS |
| Alb23-35GS-4E09 | 107 | EVQLLESGGGLVQPGGSLRLSCAASGFTFRSFGMSWVRQAPG KGPEWVSSISGSGSDTLYADSVKGRFTISRDNSKNTLYLQMNSL RPEDTAVYYCTIGGSLSRSSQGTLVTVSSGGGGSGGGGSGGGG SGGGGSGGGGSGGGGSEVQLVESGGGLVQPGGSLRL SCAASGFILDYYAIGWFRQAPGKEREGVLCIDASDDITYYADSVK GRFTISRDNAKNTVYLQMNSLKPEDTGVYYCATPIGLSSSCLLEY DYDYWGQGTLVTVSS |
| 4E09-35GS-Alb23 (A007900058) | 108 | EVQLVESGGGLVQPGGSLRLSCAASGFILDYYAIGWFRQAPGK EREGVLCIDASDDITYYADSVKGRFTISRDNAKNTVYLQMNSLK PEDTGVYYCATPIGLSSSCLLEYDYDYWGQGTLVTVSSGGGGS GGGGSGGGGSGGGGSGGGGSGGGGSEVQLLESGGG LVQPGGSLRLSCAASGFTFRSEGMSWVRQAPGKGPEWVSSIS GSGSDTLYADSVKGRFTISRDNSKNTLYLQMNSLRPEDTAVYYC TIGGSLSRSSQGTLVTVSS |
| Alb23-35GS-A00790105 | 109 | EVQLLESGGGLVQPGGSLRLSCAASGFTFRSFGMSWVRQAPG KGPEWVSSISGSGSDTLYADSVKGRFTISRDNSKNTLYLQMNSL RPEDTAVYYCTIGGSLSRSSQGTLVTVSSGGGGSGGGGSGGGG SGGGGSGGGGSGGGGSDVQLVESGGGLVQPGGSLRL SCAASGFILDYYAIGWFRQAPGKEREGVLCIDASDDITYYADSVK GRFTISRDNSKNTVYLQMNSLRPEDTAVYYCATPIGLSSSCLLEY DYDYWGQGTLVTVSS |
| A00790105-35GS-Alb23 | 110 | DVQLVESGGGLVQPGGSLRLSCAASGFILDYYAIGWFRQAPGK EREGVLCIDASDDITYYADSVKGRFTISRDNSKNTVYLQMNSLR PEDTAVYYCATPIGLSSSCLLEYDYDYWGQGTLVTVSSGGGGSG GGGSGGGGSGGGGSGGGGSGGGGSEVQLLESGGGL VQPGGSLRLSCAASGFTFRSFGMSWVRQAPGKGPEWVSSISG SGSDTLYADSVKGRFTISRDNSKNTLYLQMNSLRPEDTAVYYCTI GGSLSRSSQGTLVTVSS |

TABLE B-4 -continued

Polypeptide sequences of the invention

| Name of clone | SEQ ID NO: | Amino acid sequences |
|---|---|---|
| A00790105-35GS-A00790105-35GS-Alb23 | 111 | DVQLVESGGGLVQPGGSLRLSCAASGFILDYYAIGWFRQAPGK EREGVLCIDASDDITYYADSVKGRFTISRDNSKNTVYLQMNSLR PEDTAVYYCATPIGLSSSCLLEYDYDYWGQGTLVTVSSGGGGSG GGSDVQLVESGGGLVQPGGSLRLSCAASGFILDYYAIGWFRQA PGKEREGVLCIDASDDITYYADSVKGRFTISRDNSKNTVYLQMN SLRPEDTAVYYCATPIGLSSSCLLEYDYDYWGQGTLVTVSSGGG GSGGGSEVQLLESGGGLVQPGGSLRLSCAASGFTFRSFGMSW VRQAPGKGPEWVSSISGSGSDTLYADSVKGRFTISRDNSKNTLY LQMNSLRPEDTAVYYCTIGGSLSRSSQGTLVTVSS |
| A007900009 (4E09-9GS-ALB11-Flag3-His6) | 112 | EVQLVESGGGLVQPGGSLRLSCAASGFILDYYAIGWFRQAPGK EREGVLCIDASDDITYYADSVKGRFTISRDNAKNTVYLQMNSLK PEDTGVYYCATPIGLSSSCLLEYDYDYWGQGTLVTVSSGGGGS GGGSEVQLVESGGGLVQPGNSLRLSCAASGFTFSSFGMSWVR QAPGKGLEWVSSISGSGSDTLYADSVKGRFTISRDNAKTTLYLQ MNSLRPEDTAVYYCTIGGSLSRSSQGTLVTVSSGAADYKDHDG DYKDHDIDYKDDDDKGAAHHHHHH |
| A007900171 (A00790105-9GS-Alb11) | 113 | DVQLVESGGGLVQPGGSLRLSCAASGFILDYYAIGWFRQAPGK EREGVLCIDASDDITYYADSVKGRFTISRDNSKNTVYLQMNSLR PEDTAVYYCATPIGLSSSCLLEYDYDYWGQGTLVTVSSGGGGSG GGSEVQLVESGGGLVQPGNSLRLSCAASGFTFSSFGMSWVRQ APGKGLEWVSSISGSGSDTLYADSVKGRFTISRDNAKTTLYLQM NSLRPEDTAVYYCTIGGSLSRSSQGTLVTVSS |
| A00790067 | 114 | VQLVESGGGLVQPGGSLRLSCAASGFILDYYAIGWFRQAPGKE REGVLCIDASDDITYYADSVKGRFTISRDNAKNTVYLQMNSLKP EDTGVYYCATPIGLSSSCLLEYDYDYWGQGTLVTVSSAAADYKD HDGDYKDHDIDYKDDDDKGAAHHHHHH |
| A00790068 | 115 | EVQLVESGGGLVQPGGSLRLSCAASGFILDYYAIGWFRQAPGK EREGVLCIDASDDITYYADSVKGRFTISRDNSKNTVYLQMNSLR PEDTGVYYCATPIGLSSSCLLEYDYDYWGQGTLVTVSSAAADYK DHDGDYKDHDIDYKDDDDKGAAHHHHHH |
| A00790069 | 116 | EVQLVESGGGLVQPGGSLRLSCAASGFILDYYAIGWFRQAPGK EREGVLCIDASDDITYYADSVKGRFTISRDNSKNTVYLQMNSLR PEDTAVYYCATPIGLSSSCLLEYDYDYWGQGTLVTVSSAAADYK DHDGDYKDHDIDYKDDDDKGAAHHHHHH |
| A007900738 | 117 | EVQLVESGGGLVQPGGSLRLSCAASGFTFDDYAIGWFRQAPGE EREGVSSISSTYGLTYYADSVKGRFTISSSNSKNTVYLQMNNLKP EDTAVYYCAATPIERLGLDAYEYDYWGQGTLVTVSSAAADYKD HDGDYKDHDIDYKDDDDKGAAHHHHHH |
| A007900739 | 118 | EVQLVESGGGLVQPGGSLRLSCAASGFTFDDYAIGWFRQAPGE EREGVSSISSTYGLTYYADSVKGRFTISSSNSKNTVYLQMNSLKP EDTAVYYCAATPIERLGLDAYEYDYWGQGTLVTVSSAAADYKD HDGDYKDHDIDYKDDDDKGAAHHHHHH |
| A007900740 | 119 | EVQLVESGGGLVQPGGSLRLSCAASGFTFDDYAIGWFRQAPGE EREGVSSISSTYGLTYYADSVKGRFTISSDNSKNTVYLQMNNLKP EDTAVYYCAATPIERLGLDAYEYDYWGQGTLVTVSSAAADYKD HDGDYKDHDIDYKDDDDKGAAHHHHHH |
| A007900741 | 120 | EVQLVESGGGLVQPGGSLRLSCAASGFTFDDYAIGWFRQAPGE EREGVSSISSTYGLTYYADSVKGRFTISSDNSKNTVYLQMNSLKP EDTAVYYCAATPIERLGLDAYEYDYWGQGTLVTVSSAAADYKD HDGDYKDHDIDYKDDDDKGAAHHHHHH |
| A007900742 | 121 | EVQLVESGGGLVQPGGSLRLSCAASGFTFDDYAIGWFRQAPGE EREGVSSISSTYGLTYYADSVKGRFTISRSNSKNTVYLQMNNLKP EDTAVYYCAATPIERLGLDAYEYDYWGQGTLVTVSSAAADYKD HDGDYKDHDIDYKDDDDKGAAHHHHHH |
| A007900743 | 122 | EVQLVESGGGLVQPGGSLRLSCAASGFTFDDYAIGWFRQAPGE EREGVSSISSTYGLTYYADSVKGRFTISRDNSKNTVYLQMNNLK PEDTAVYYCAATPIERLGLDAYEYDYWGQGTLVTVSSAAADYK DHDGDYKDHDIDYKDDDDKGAAHHHHHH |
| A007900744 | 123 | VQLVESGGGLVQPGGSLRLSCAASGFTFDDYAIGWFRQAPGEE REGVSSISSTYGLTYYADSVKGRFTISRSNSKNTVYLQMNSLKPE DTAVYYCAATPIERLGLDAYEYDYWGQGTLVTVSSAAADYKDH DGDYKDHDIDYKDDDDKGAAHHHHHH |

TABLE B-4 -continued

Polypeptide sequences of the invention

| Name of clone | SEQ ID NO: | Amino acid sequences |
|---|---|---|
| A007900745 | 124 | EVQLVESGGGLVQPGGSLRLSCAASGFTFDDYAIGWFRQAPGE<br>EREGVSSISSTYGLTYYADSVKGRFTISRDNSKNTVYLQMNSLKP<br>EDTAVYYCAATPIERLGLDAYEYDYWGQGTLVTVSSAAADYKD<br>HDGDYKDHDIDYKDDDDKGAAHHHHHH |
| A007900746 | 125 | EVQLVESGGGLVQPGGSLRLSCAASGFTFDDYAIGWFRQAPGK<br>EREGVSSISSTYGLTYYADSVKGRFTISSSNSKNTVYLQMNNLKP<br>EDTAVYYCAATPIERLGLDAYEYDYWGQGTLVTVSSAAADYKD<br>HDGDYKDHDIDYKDDDDKGAAHHHHHH |
| A007900747 | 126 | EVQLVESGGGLVQPGGSLRLSCAASGFTFDDYAIGWFRQAPGK<br>EREGVSSISSTYGLTYYADSVKGRFTISSSNSKNTVYLQMNSLKP<br>EDIAVYYCAATPIERLGLDAYEYDYWGQGTLVTVSSAAADYKD<br>HDGDYKDHDIDYKDDDDKGAAHHHHHH |
| A007900748 | 127 | EVQLVESGGGLVQPGGSLRLSCAASGFTFDDYAIGWFRQAPGK<br>EREGVSSISSTYGLTYYADSVKGRFTISSDNSKNTVYLQMNNLKP<br>EDTAVYYCAATPIERLGLDAYEYDYWGQGTLVTVSSAAADYKD<br>HDGDYKDHDIDYKDDDDKGAAHHHHHH |
| A007900749 | 128 | EVQLVESGGGLVQPGGSLRLSCAASGFTFDDYAIGWFRQAPGK<br>EREGVSSISSTYGLTYYADSVKGRFTISSDNSKNTVYLQMNSLKP<br>EDTAVYYCAATPIERLGLDAYEYDYWGQGTLVTVSSAAADYKD<br>HDGDYKDHDIDYKDDDDKGAAHHHHHH |
| A007900750 | 129 | EVQLVESGGGLVQPGGSLRLSCAASGFTFDDYAIGWFRQAPGK<br>EREGVSSISSTYGLTYYADSVKGRFTISRSNSKNTVYLQMNNLKP<br>EDTAVYYCAATPIERLGLDAYEYDYVVGQGTLVTVSSAAADYKD<br>HDGDYKDHDIDYKDDDDKGAAHHHHHH |
| A007900751 | 130 | EVQLVESGGGLVQPGGSLRLSCAASGFTFDDYAIGWFRQAPGK<br>EREGVSSISSTYGLTYYADSVKGRFTISRDNSKNTVYLQMNNLK<br>PEDTAVYYCAATPIERLGLDAYEYDYWGQGTLVTVSSAAADYK<br>DHDGDYKDHDIDYKDDDDKGAAHHHHHH |
| A007900752 | 131 | EVQLVESGGGLVQPGGSLRLSCAASGFTFDDYAIGWFRQAPGK<br>EREGVSSISSTYGLTYYADSVKGRFTISRSNSKNTVYLQMNSLKP<br>EDTAVYYCAATPIERLGLDAYEYDYWGQGTLVTVSSAAADYKD<br>HDGDYKDHDIDYKDDDDKGAAHHHHHH |
| A007900753 | 132 | EVQLVESGGGLVQPGGSLRLSCAASGFTFDDYAIGWFRQAPGK<br>EREGVSSISSTYGLTYYADSVKGRFTISRDNSKNTVYLQMNSLKP<br>EDTAVYYCAATPIERLGLDAYEYDYWGQGTLVTVSSAAADYKD<br>HDGDYKDHDIDYKDDDDKGAAHHHHHH |
| A007901245 | 133 | EVQLVESGGGLVQPGGSLRLSCAASGFTFDDYAIGWFRQAPGE<br>EREGVSSISSTYGLTYYADSVKGRFTISSDNSKNTVYLQMNSLRP<br>EDTAVYYCAATPIGLIGLDAYEYDYWGQGTLVTVSSAAADYKD<br>HDGDYKDHDIDYKDDDDKGAAHHHHHH |
| A007901246 | 134 | EVQLVESGGGLVQPGGSLRLSCAASGFAFDDYAIGWFRQAPG<br>EEREGVSSISSTYGLTYYADSVKGRFTISSDNSKNTVYLQMNSLR<br>PEDTAVYYCAATPIGLIGLDAYEYDYWGQGTLVTVSSAAADYK<br>DHDGDYKDHDIDYKDDDDKGAAHHHHHH |
| A007901247 | 135 | EVQLVESGGGLVQPGGSLRLSCAASGFTFDDYAIGWFRQAPGK<br>EREGVSSISSTYGLTYYADSVKGRFTISSDNSKNTVYLQMNSLRP<br>EDTAVYYCAATPIGLIGLDAYEYDYWGQGTLVTVSSAAADYKD<br>HDGDYKDHDIDYKDDDDKGAAHHHHHH |
| A007901248 | 136 | EVQLVESGGGLVQPGGSLRLSCAASGFAFDDYAIGWFRQAPG<br>KEREGVSSISSTYGLTYYADSVKGRFTISSDNSKNNYLQMNSLR<br>PEDTAVYYCAATPIGLIGLDAYEYDYWGQGTLVTVSSAAADYK<br>DHDGDYKDHDIDYKDDDDKGAAHHHHHH |
| A007901249 | 137 | EVQLVESGGGLVQPGGSLRLSCAASGFTFDDYAIGWFRQAPGE<br>ERLGVSSISSTYGLTYYADSVKGRFTISSDNSKNTVYLQMNSLRP<br>EDTAVYYCAATPIGLIGLDAYEYDYWGQGTLVTVSSAAADYKD<br>HDGDYKDHDIDYKDDDDKGAAHHHHHH |
| A007901250 | 138 | EVQLVESGGGLVQPGGSLRLSCAASGFAFDDYAIGWFIRQAPG<br>EERLGVSSISSTYGLTYYADSVKGRFTISSDNSKNTVYLQMNSLR<br>PEDTAVYYCAATPIGLIGLDAYEYDYWGQGTLVTVSSAAADYK<br>DHDGDYKDHDIDYKDDDDKGAAHHHHHH |

TABLE B-4 -continued

Polypeptide sequences of the invention

| Name of clone | SEQ ID NO: | Amino acid sequences |
|---|---|---|
| A007901251 | 139 | EVQLVESGGGLVQPGGSLRLSCAASGFTFDDYAIGWFRQAPGK ERLGVSSISSTYGLTYYADSVKGRFTISSDNSKNTVYLQMNSLRP EDTAVYYCAATPIGLIGLDAYEYDYWGQGTLVTVSSAAADYKD HDGDYKDHDIDYKDDDDKGAAHHHHHH |
| A007901252 | 140 | EVQLVESGGGLVQPGGSLRLSCAASGFAFDDYAIGWFRQAPG KERLGVSSISSTYGLTYYADSVKGRFTISSDNSKNTVYLQMNSLR PEDTAVYYCAATPIGLIGLDAYEYDYWGQGTLVTVSSAAADYK DHDGDYKDHDIDYKDDDDKGAAHHHHHH |
| A007901253 | 141 | EVQLVESGGGLVQPGGSLRLSCAASGFTFDDYAIGWFRQAPGE EREGVSSISSTYGLTYYADPVKGRFTISSDNSKNTVYLQMNSLRP EDTAVYYCAATPIGLIGLDAYEYDYWGQGTLVTVSSAAADYKD HDGDYKDHDIDYKDDDDKGAAHHHHHH |
| A007901255 | 142 | DVQLVESGGGLVQPGGSLRLSCAASGFTFDDYAIGWFRQAPG EEREGVSSISSTYGLTYYADSVKGRFTISSDNSKNTVYLQMNSLR PEDTAVYYCAATPIGLIGLDAYEYDYWGQGTLVTVSSGGGGSG GGSEVQLVESGGGLVQPGNSLRLSCAASGFTFSSFGMSWVRQ APGKGLEWVSSISGSGSDTLYADSVKGRFTISRDNAKTTLYLQM NSLRPEDTAVYYCTIGGSLSRSSQGTLVTVSSA |
| A007901256 | 143 | DVQLVESGGGLVQPGGSLRLSCAASGFAFDDYAIGWFRQAPG EEREGVSSISSTYGLTYYADSVKGRFTISSDNSKNTVYLQMNSLR PEDTAVYYCAATPIGLIGLDAYEYDYWGQGTLVTVSSGGGGSG GGSEVQLVESGGGLVQPGNSLRLSCAASGFTFSSFGMSWVRQ APGKGLEWVSSISGSGSDTLYADSVKGRFTISRDNAKTTLYLQM NSLRPEDTAVYYCTIGGSLSRSSQGTLVTVSSA |
| A007901257 | 144 | DVQLVESGGGLVQPGGSLRLSCAASGFTFDDYAIGWFRQAPG KEREGVSSISSTYGLTYYADSVKGRFTISSDNSKNTVYLQMNSLR PEDTAVYYCAATPIGLIGLDAYEYDYWGQGTLVTVSSGGGGSG GGSEVQLVESGGGLVQPGNSLRLSCAASGFTFSSFGMSWVRQ APGKGLEWVSSISGSGSDTLYADSVKGRFTISRDNAKTTLYLQM NSLRPEDTAVYYCTIGGSLSRSSQGTLVTVSSA |
| A007901258 | 145 | DVQLVESGGGLVQPGGSLRLSCAASGFAFDDYAIGWFRQAPG KEREGVSSISSTYGLTYYADSVKGRFTISSDNSKNTVYLQMNSLR PEDTAVYYCAATPIGLIGLDAYEYDYWGQGTLVTVSSGGGGSG GGSEVQLVESGGGLVQPGNSLRLSCAASGFTFSSFGMSWVRQ APGKGLEWVSSISGSGSDTLYADSVKGRFTISRDNAKTTLYLQM NSLRPEDTAVYYCTIGGSLSRSSQGTLVTVSSA |
| A007901259 | 146 | DVQLVESGGGLVQPGGSLRLSCAASGFTFDDYAIGWFRQAPG EERLGVSSISSTYGLTYYADSVKGRFTISSDNSKNTVYLQMNSLR PEDTAVYYCAATPIGLIGLDAYEYDYWGQGTLVTVSSGGGGSG GGSEVQLVESGGGLVQPGNSLRLSCAASGFTFSSFGMSWVRQ APGKGLEWVSSISGSGSDTLYADSVKGRFTISRDNAKTTLYLQM NSLRPEDTAVYYCTIGGSLSRSSQGTLVTVSSA |
| A007901260 | 147 | DVQLVESGGGLVQPGGSLRLSCAASGFAFDDYAIGWFRQAPG EERLGVSSISSTYGLTYYADSVKGRFTISSDNSKNTVYLQMNSLR PEDTAVYYCAATPIGLIGLDAYEYDYWGQGTLVTVSSGGGGSG GGSEVQLVESGGGLVQPGNSLRLSCAASGFTFSSFGMSWVRQ APGKGLEWVSSISGSGSDTLYADSVKGRFTISRDNAKTTLYLQM NSLRPEDTAVYYCTIGGSLSRSSQGTLVTVSSA |
| A007901261 | 148 | DVQLVESGGGLVQPGGSLRLSCAASGFTFDDYAIGWFRQAPG KERLGVSSISSTYGLTYYADSVKGRFTISSDNSKNTVYLQMNSLR PEDTAVYYCAATPIGLIGLDAYEYDYWGQGTLVTVSSGGGGSG GGSEVQLVESGGGLVQPGNSLRLSCAASGFTFSSFGMSWVRQ APGKGLEWVSSISGSGSDTLYADSVKGRFTISRDNAKTTLYLQM NSLRPEDTAVYYCTIGGSLSRSSQGTLVTVSSA |
| A007901262 | 149 | DVQLVESGGGLVQPGGSLRLSCAASGFAFDDYAIGWFRQAPG KERLGVSSISSTYGLTYYADSVKGRFTISSDNSKNTVYLQMNSLR PEDTAVYYCAATPIGLIGLDAYEYDYWGQGTLVTVSSGGGGSG GGSEVQLVESGGGLVQPGNSLRLSCAASGFTFSSFGMSWVRQ APGKGLEWVSSISGSGSDTLYADSVKGRFTISRDNAKTTLYLQM NSLRPEDTAVYYCTIGGSLSRSSQGTLVTVSSA |
| A007901263 | 150 | DVQLVESGGGLVQPGGSLRLSCAASGFTFDDYAIGWFRQAPG EEREGVSSISSTYGLTYYADPVKGRFTISSDNSKNTVYLQMNSLR PEDTAVYYCAATPIGLIGLDAYEYDYWGQGTLVTVSSGGGGSG GGSEVQLVESGGGLVQPGNSLRLSCAASGFTFSSFGMSWVRQ |

TABLE B-4 -continued

Polypeptide sequences of the invention

| Name of clone | SEQ ID NO: | Amino acid sequences |
|---|---|---|
| | | APGKGLEWVSSISGSGSDTLYADSVKGRFTISRDNAKTTLYLQM NSLRPEDTAVYYCTIGGSLSRSSQGTLVTVSSA |
| A007900184 (33H10-3×FLAG-His<sub>6</sub>) | 151 | EVQLVESGGGLVQAGGSLRLSCAASGFTFDDYAIGWFRQAPG EEREGVSSISSTYGLTYYADSVKGRFTISSSNAKNTVYLQMNNLK PEDTAVYYCAATPIERLGLDAYEYDYWGQGTLVTVSSAAADYK DHDGDYKDHDIDYKDDDDKGAAHHHHHH |
| A007901222 | 188 | DVQLVESGGGLVQPGGSLRLSCAASGFILDYYAIGWFRQAPGK EREGVLCIDASDDITYYADSVKGRFTISRDNSKNTVYLQMNSLR PEDTAVYYCATPIGLSSSCLLEYDYDWGQGTLVTVSSGGGGSG GGSEVQLLESGGGLVQPGGSLRLSCAASGFTFRSFGMSWVRQ APGKGPEWVSSISGSGSDTLYADSVKGRFTISRDNSKNTLYLQ MNSLRPEDTAVYYCTIGGSLSRSSQGTLVTVSSA |

TABLE B-5

Linker sequences of the invention

| Name of linker | SEQ ID NO: | Amimo acid sequences |
|---|---|---|
| 5GS | 13 | GGGGS |
| 6GS | 14 | SGGSGGS |
| 9GS | 15 | GGGGSGGGS |
| 10GS | 16 | GGGGSGGGGS |
| 15GS | 17 | GGGGSGGGGSGGGGS |
| 18GS | 18 | GGGGSGGGGSGGGGGGS |
| 20GS | 19 | GGGGSGGGGSGGGGSGGGGS |
| 25GS | 20 | GGGGSGGGGSGGGGSGGGGSGGGGS |
| 30GS | 21 | GGGGSGGGGSGGGGSGGGGSGGGGSGGGGS |
| 35GS | 22 | GGGGSGGGGSGGGGSGGGGSGGGGSGGGGSGGGGS |

TABLE B-6

Nucleic acid sequences of invention

| Name of clone | SEQ ID NO: | Nucleic acid sequences |
|---|---|---|
| 04E09 | 30 | GAGGTGCAATTGGTGGAGTCTGGGGGAGGCTTGGTGCAGC CTGGGGGGTCCCTGAGACTCTCCTGTGCAGCCTCTGGATTCA TTTTGGATTATTATGCCATAGGCTGGTTCCGCCAGGCCCCAG GGAAGGAGCGCGAGGGGGTCTTATGTATTGATGCTAGTGAT GATATTACATACTATGCAGACTCCGTGAAGGGCCGATTCACC ATCTCCAGAGACAATGCCAAGAACACGGTGTATCTGCAAAT GAACAGCCTGAAACCTGAGGACACGGGCGTTTATTACTGTG CGACCCCCATCGGACTGAGTAGTAGCTGCCTACTTGAATATG ATTATGACTACTGGGGCCAGGGGACCCTGGTCACGGTCTCC TCC |
| 06B08 | 31 | GAGGTGCAATTGGTGGAGTCTGGGGGAGGATTGGTGCAGG CTGGGGGCTCTCTGAGACTCTCCTGTGCAGCCTCTGGACGCA CCATCAGTAGGTATACCATGGGCTGGTTCCGCCAGGCTCCA GGGAAGGAGCGTGAGTTTGTAGCAGCTATTAGCTGGAGTG GTGATAACACAAACTATGCAGACTCCGTGAAGGGCCGATTC ACCATCTCCAGACCCAACACCAAGAACACGATGTATCTGCAA ATGAACAGCCTGAAACCTGAGGACACGGCCGTTTATTACTGT GCAGCAGATTACCGAAGTGGTAGTTACTACCAGGCATCAGA GTGGACACGGCCATCGGGTATGACTACTGGGGCCAGGG ACCCTGGTCACGGTCTCCTCC |
| 06C12 | 32 | GAGGTGCAATTGGTGGAGTCTGGGGGAGGCTTGGTGCAGC CTGGGGGGTCTCTGAGACTCTCCTGTGCAGCCTCTGGATTCT CTTTGGATTATTTTGCCATAGGCTGGTTCCGCCAGGCCCCAG GGAAGGAGCGCGAGGAAATCTCATGTATTAGTAACAGTGAT GGTAGCACATACTATGCAAACTCCGTGAAGGGCCGATTCAC CATCTCCATAGACAATGCCAAGAACACGGTGTATCTGCAAAT GACAAGCCTGAAACCTGAGGACACGGCCGTTTATTACTGT CGACCCCCGTGGGGTTGGGGCCATTCTGTAAGACGACCAAT GACTATGACTACAGCGGCCAGGGGACCCTGGTCACGGTCT CTCC |

TABLE B-6 -continued

Nucleic acid sequences of invention

| Name of clone | SEQ ID NO: | Nucleic acid sequences |
|---|---|---|
| 06F10 | 33 | GAGGTGCAATTGGTGGAGTCTGGGGGAGGCTTGGTGCAGC<br>CTGGGGGGTCTCTGAGACTCTCCTGTGCAGCCTCTGGATTCA<br>CTTTTGGATTATTATGCCATAAACTGGTTCCGCCAGGCCCCAG<br>GGAAGGAGCGCGAGGGGGTCTCATGTATTAGTGGTGGTGA<br>TGGTAGCACATACTATGCAGACTCCGTGAAGGGCCGATTCA<br>CCATCTCCAGAGACAATGCCAAGAACACGGTGTATCTGCAA<br>ATGAACAGCCTGAAACCTGAGGACACGGCCGTTTATTACTGT<br>GCGACAGCCTTAGGATTATCAAGTAGCTGCCACGGAGACGG<br>ATATGACTACTGGGGCCAGGGGACCCTGGTCACGGTCTCCT<br>CC |
| 04E09 (L49S) | 34 | GAGGTGCAATTGGTGGAGTCTGGGGGTGGTTTGGTTCAACC<br>AGGTGGTTCTTTGAGATTGTCCTGTGCTGCTTCCGGTTTCATC<br>TTGGACTACTACGCTATCGGTTGGTTCAGACAGGCTCCAGGT<br>AAAGAAAGAGAGGGAGTTTCCTGTATCGACGCTTCCGACGA<br>CATCACTTACTACGCTGACTCCGTTAAGGGTAGATTCACTAT<br>CTCCAGAGACAACGCTAAGAACACTGTTTACTTGCAGATGAA<br>CTCCTTGAAGCCAGAGGACACTGGTGTTTACTACTGTGCTAC<br>TCCAATCGGTTTGTCCTCCTCCTGTTTGTTGGAATACGACTAC<br>GACTACTGGGGTCAAGGGACCCTGGTCACCGTCTCCTCA |
| 04E09 (C50S/C100bG) | 35 | GAGGTGCAATTGGTGGAGTCTGGGGGTGGTTTGGTTCAACC<br>AGGTGGTTCTTTGAGATTGTCCTGTGCTGCTTCCGGTTTCATC<br>TTGGACTACTACGCTATCGGTTGGTTCAGACAGGCTCCAGGT<br>AAAGAAAGAGAGGGAGTTTTGTCCATCGACGCTTCCGACGA<br>CATCACTTACTACGCTGACTCCGTTAAGGGTAGATTCACTAT<br>CTCCAGAGACAACGCTAAGAACACTGTTTACTTGCAGATGAA<br>CTCCTTGAAGCCAGAGGACACTGGTGTTTACTACTGTGCTAC<br>TCCAATCGGTTTGTCCTCCTCCGGTTTGTTGGAATACGACTAC<br>GACTACTGGGGTCAAGGGACCCTGGTCACCGTCTCCTCA |
| 04E09 (C22A/C92S) | 36 | GAGGTGCAATTGGTGGAGTCTGGGGGTGGTTTGGTTCAACC<br>AGGTGGTTCTTTGAGATTGTCTGCTGCTGCTTCCGGTTTCATC<br>TTGGACTACTACGCTATCGGTTGGTTCAGACAGGCTCCAGGT<br>AAAGAAAGAGAAGGTGTTTTGTGTATCGACGCTTCCGACGA<br>CATCACTTACTACGCTGACTCCGTTAAGGGTAGATTCACTAT<br>CTCCAGAGACAACGCTAAGAACACTGTTTACTTGCAGATGAA<br>CTCCTTGAAGCCAGAGGACACTGGTGTTTACTACTCCGCTAC<br>TCCAATCGGTTTGTCCTCCTCCTGTTTGTTGGAATACGACTAC<br>GACTACTGGGGTCAAGGGACCCTGGTCACCGTCTCCTCA |
| 04E09-9GS-Alb11 | 37 | GAGGTGCAATTGGTGGAGTCTGGGGGAGGCTTGGTGCAGC<br>CTGGGGGGTCCCTGAGACTCTCCTGTGCAGCCTCTGGATTCA<br>TTTTTGGATTATTATGCCATAGGCTGGTTCCGCCAGGCCCCAG<br>GGAAGGAGCGCGAGGGGGTCTTATGTATTGATGCTAGTGAT<br>GATATTACATACTATGCAGACTCCGTGAAGGGCCGATTCACC<br>ATCTCCAGAGACAATGCCAAGAACACGGTGTATCTGCAAAT<br>GAACAGCCTGAAACCTGAGGACACGGCCGTTTATTACTGTG<br>CGACCCCCATCGGACTGAGTAGTAGCTGCCTACTTGAATATG<br>ATTATGACTACTGGGGCCAGGGGACCCTGGTCACGGTCTCC<br>TCCGGAGGCGGTGGATCTGGCGGTGGATCCGAGGTGCAGT<br>TGGTGGAGTCTGGGGGTGGCTTGGTGCAACCGGGTAACAG<br>TCTGCGCCTTAGCTGCGCAGCGTCTGGCTTTACCTTCAGCTCC<br>TTTGGCATGAGCTGGGTTCGCCAGGCTCCGGGAAAAGGACT<br>GGAATGGGTTTCGTCTATTAGCGGCAGTGGTAGCGATACGC<br>TCTACGCGGACTCCGTGAAGGGCCGTTTCACCATCTCCCGCG<br>ATAACGCCAAAACTACACTGTATCTGCAAATGAATAGCCTGC<br>GTCCTGAAGACACGGCCGTTTATTACTGTACTATTGGTGGCT<br>CGTTAAGCCGTTCTTCACAGGGGACCCTGGTCACCGTCTCCT<br>CA |
| 06B08-9GS-Alb11 | 38 | GAGGTGCAATTGGTGGAGTCTGGGGGAGGATTGGTGCAGG<br>CTGGGGGCTCTCTGAGACTCTCCTGTGCAGCCTCTGGACGCA<br>CCATCAGTAGGTATACCATGGGCTGGTTCCGCCAGGCTCCA<br>GGGAAGGAGCGTGAGTTTGTAGCAGCTATTAGCTGGAGTG<br>GTGATAACACAAACTATGCAGACTCCGTGAAGGGCCGATTC<br>ACCATCTCCAGACCCAACACCAAGAACACGATGTATCTGCAA<br>ATGAACAGCCTGAAACCTGAGGACACGGCCGTTTATTACTGT<br>GCAGCAGATTACCGAAGTGGTAGTTACTACCAGGCATCAGA<br>GTGGACACGGCCATCGGGGTATGACTACTGGGGCCAGGGG<br>ACCCTGGTCACGGTCTCCTCCGGAGGCGGTGGATCTGGCGG<br>TGGATCCGAGGTGCAGTTGGTGGAGTCTGGGGGTGGCTTG<br>GTGCAACCGGGTAACAGTCTGCGCCTTAGCTGCGCAGCGTC<br>TGGCTTTACCTTCAGCTCCTTTGGCATGAGCTGGGTTCGCCA<br>GGCTCCGGGAAAAGGACTGGAATGGGTTTCGTCTATTAGCG |

TABLE B-6 -continued

Nucleic acid sequences of invention

| Name of clone | SEQ ID NO: | Nucleic acid sequences |
|---|---|---|
| | | GCAGTGGTAGCGATACGCTCTACGCGGACTCCGTGAAGGGC<br>CGTTTCACCATCTCCCGCGATAACGCCAAAACTACACTGTAT<br>CTGCAAATGAATAGCCTGCGTCCTGAAGACACGGCCGTTTAT<br>TACTGTACTATTGGTGGCTCGTTAAGCCGTTCTTCACAGGGG<br>ACCCTGGTCACCGTCTCCTCA |
| 06C12-9GS-Alb11 | 39 | GAGGTGCAATTGGTGGAGTCTGGGGGAGGCTTGGTGCAGC<br>CTGGGGGGTCTCTGAGACTCTCCTGTGCAGCCTCTGGATTCT<br>CTTTTGGATTATTTTGCCATAGGCTGGTTCCGCCAGGCCCCAG<br>GGAAGGAGCGCGAGGAAATCTCATGTATTAGTAACAGTGAT<br>GGTAGCACATACTATGCAAACTCCGTGAAGGGCCGATTCAC<br>CATCTCCATAGACAATGCCAAGAACACGGTGTATCTGCAAAT<br>GACAAGCCTGAAACCTGAGGACACGGCCGTTTATTACTGTG<br>CGACCCCCGTGGGGTTGGGGCCATTCTGTAAGACGACCAAT<br>GACTATGACTACAGCGGCCAGGGGACCCTGGTCACGGTCTC<br>CTCCGGAGGCGGTGGATCTGGCGGTGGATCCGAGGTGCAG<br>TTGGTGGAGTCTGGGGGTGGCTTGGTGCAACCGGGTAACA<br>GTCTGCGCCTTAGCTGCGCAGCGTCTGGCTTTACCTTCAGCT<br>CCTTTGGCATGAGCTGGGTTCGCCAGGCTCCGGGAAAAGGA<br>CTGGAATGGGTTTCGTCTATTAGCGGCAGTGGTAGCGATAC<br>GCTCTACGCGGACTCCGTGAAGGGCCGTTTCACCATCTCCCG<br>CGATAACGCCAAAACTACACTGTATCTGCAAATGAATAGCCT<br>GCGTCCTGAAGACACGGCCGTTTATTACTGTACTATTGGTGG<br>CTCGTTAAGCCGTTCTTCACAGGGGACCCTGGTCACCGTCTC<br>CTCA |
| 06F10-9GS-Alb11 | 40 | GAGGTGCAATTGGTGGAGTCTGGGGGAGGCTTGGTGCAGC<br>CTGGGGGGTCTCTGAGACTCTCCTGTGCAGCCTCTGGATTCA<br>CTTTTGGATTATTATGCCATAAACTGGTTCCGCCAGGCCCCAG<br>GGAAGGAGCGCGAGGGGGTCTCATGTATTAGTGGTGGTGA<br>TGGTAGCACATACTATGCAGACTCCGTGAAGGGCCGATTCA<br>CCATCTCCAGAGACAATGCCAAGAACACGGTGTATCTGCAA<br>ATGAACAGCCTGAAACCTGAGGACACGGCCGTTTATTACTGT<br>GCGACAGCCTTAGGATTATCAAGTAGCTGCCACGGAGACGG<br>ATATGACTACTGGGGCCAGGGGACCCTGGTCACGGTCTCCT<br>CCCGGAGGCGGTGGATCTGGCGGTGGATCCGAGGTGCAGTT<br>GGTGGAGTCTGGGGGTGGCTTGGTGCAACCGGGTAACAGT<br>CTGCGCCTTAGCTGCGCAGCGTCTGGCTTTACCTTCAGCTCCT<br>TTGGCATGAGCTGGGTTCGCCAGGCTCCGGGAAAAGGACTG<br>GAATGGGTTTCGTCTATTAGCGGCAGTGGTAGCGATACGCT<br>CTACGCGGACTCCGTGAAGGGCCGTTTCACCATCTCCCGCGA<br>TAACGCCAAAACTACACTGTATCTGCAAATGAATAGCCTGCG<br>TCCTGAAGACACGGCCGTTTATTACTGTACTATTGGTGGCTC<br>GTTAAGCCGTTCTTCACAGGGGACCCTGGTCACCGTCTCCTCA |
| Alb11-35GS-04E09 | 41 | GAGGTGCAATTGGTGGAGTCTGGGGGTGGCTTGGTGCAAC<br>CGGGTAACAGTCTGCGCCTTAGCTGCGCAGCGTCTGGCTTTA<br>CCTTCAGCTCCTTTGGCATGAGCTGGGTTCGCCAGGCTCCGG<br>GAAAAGGACTGGAATGGGTTTCGTCTATTAGCGGCAGTGGT<br>AGCGATACGCTCTACGCGGACTCCGTGAAGGGCCGTTTCAC<br>CATCTCCCGCGATAACGCCAAAACTACACTGTATCTGCAAAT<br>GAATAGCCTGCGTCCTGAAGACACGGCCGTTTATTACTGTAC<br>TATTGGTGGCTCGTTAAGCCGTTCTTCACAGGGGACCCTGGT<br>CACGGTCTCCTCCGGAGGCGGTGGGTCAGGTGGCGGAGGC<br>AGCGGTGGAGGAGGTAGTGGCGGTGGCGGTAGTGGGGGT<br>GGAGGCAGCGGAGGCGGAGGCAGTGGGGGCGGTGGATCC<br>GAGGTGCAGTTGGTGGAGTCTGGGGGAGGCTTGGTGCAGC<br>CTGGGGGGTCCCTGAGACTCTCCTGTGCAGCCTCTGGATTCA<br>TTTTGGATTATTATGCCATAGGCTGGTTCCGCCAGGCCCCAG<br>GGAAGGAGCGCGAGGGGGTCTTATGTATTGATGCTAGTGAT<br>GATATTACATACTATGCAGACTCCGTGAAGGGCCGATTCACC<br>ATCTCCAGAGACAATGCCAAGAACACGGTGTATCTGCAAAT<br>GAACAGCCTGAAACCTGAGGACACGGGCGTTTATTACTGTG<br>CGACCCCCATCGGACTGAGTAGTAGCTGCCTACTTGAATATG<br>ATTATGACTACTGGGGCCAGGGGACCCTGGTCACCGTCTCCT<br>CA |
| Alb11-9GS-04E09 | 42 | GAGGTGCAATTGGTGGAGTCTGGGGGTGGCTTGGTGCAAC<br>CGGGTAACAGTCTGCGCCTTAGCTGCGCAGCGTCTGGCTTTA<br>CCTTCAGCTCCTTTGGCATGAGCTGGGTTCGCCAGGCTCCGG<br>GAAAAGGACTGGAATGGGTTTCGTCTATTAGCGGCAGTGGT<br>AGCGATACGCTCTACGCGGACTCCGTGAAGGGCCGTTTCAC<br>CATCTCCCGCGATAACGCCAAAACTACACTGTATCTGCAAAT<br>GAATAGCCTGCGTCCTGAAGACACGGCCGTTTATTACTGTAC<br>TATTGGTGGCTCGTTAAGCCGTTCTTCACAGGGGACCCTGGT<br>CACGGTCTCCTCCGGAGGCGGTGGATCTGGCGGTGGATCCG |

TABLE B-6 -continued

Nucleic acid sequences of invention

| Name of clone | SEQ ID NO: | Nucleic acid sequences |
|---|---|---|
| | | AGGTGCAGTTGGTGGAGTCTGGGGGAGGCTTGGTGCAGCC<br>TGGGGGGTCCCTGAGACTCTCCTGTGCAGCCTCTGGATTCAT<br>TTTGGATTATTATGCCATAGGCTGGTTCCGCCAGGCCCCAGG<br>GAAGGAGCGCGAGGGGGTCTTATGTATTGATGCTAGTGATG<br>ATATTACATACTATGCAGACTCCGTGAAGGGCCGATTCACCA<br>TCTCCAGAGACAATGCCAAGAACACGGTGTATCTGCAAATG<br>AACAGCCTGAAACCTGAGGACACGGGCGTTTATTACTGTGC<br>GACCCCCATCGGACTGAGTAGTAGCTGCCTACTTGAATATGA<br>TTATGACTACTGGGGCCAGGGGACCCTGGTCACCGTCTCCTCA |

Example 1

Identification of c-Met Blocking Nanobodies

Immunoglobulin single variable domains/domain are mostly referred to in the experimental part as Nanobodies/Nanobody.

1.1 Immunizations

Three llamas (No. 450, 451 and 452, llama glama) were immunized according to standard protocols with 4 intramuscular injections in the neck (100 or 50 µg/dose at 2 week intervals) of human (h; hu) c-Met/Fc (hc-Met/Fc or hu c-Met/Fc; c-Met extracellular domain genetically fused to human Fc and expressed in NS0 mouse myeloma cells; R&D Systems, Catalogue number 358-MT/CF, Minneapolis, Minn., USA, see also SEQ ID NO: 2), formulated in Complete Freund's Adjuvant (day 0) or Incomplete Freund's Adjuvant (following immunizations) (Difco, BD Biosciences, San Jose, Calif., USA).

At days 0 and 35, serum was collected from llamas immunized with recombinant protein to define antibody titers against hu c-Met by ELISA. 96-well Maxisorp plates (Nunc, Wiesbaden, Germany) were coated with hu c-Met/Fc or irrelevant Fc. After blocking and adding serial dilutions of serum samples, the presence of llama-anti-hu c-Met antibodies was demonstrated using mouse anti-llama IgG1, 2 and 3 monoclonal antibodies (Daley et al., Clin Diagn Lab Immunol. 2005 March; 12(3):380-6.) followed by HRP (horseradish peroxidase) conjugated rabbit anti-mouse IgG (Dako, Glostrup, Denmark) and a subsequent enzymatic reaction in the presence of the substrate TMB (3,3',5,5'-tetramentylbenzidine) (Promega, Madison, Wis., USA).

At days 0 and 50, serum was collected from llamas immunized with recombinant protein to define antibody titers against c-Met-expressing A549 lung tumor cells (ATCC number CCL-185) or c-Met negative control CHO K1 (ATCC number CCL-61) cells by FACS. Cells were cultured in RPMI 1640+10% Fetal Calf Serum+1% Penicillin/Streptomycin. Cells were resuspended in diluted serum samples. After washing, the presence of cell surface bound anti-c-Met llama antibodies was detected in FACSArray™ (BD Biosciences) using goat anti-llama IgG (Bethyl Laboratories, Montgomery, Tex., USA) and PE conjugated donkey anti-goat IgG (Jackson Immuno Research, West Grove, Pa., USA).

In ELISA, all 3 llamas showed a good and specific response in IgG1, IgG2 and IgG3 immunoglobulin classes towards hc-Met. In FACS, a serum response towards c-Met expressing A549 tumor cells was clearly detectable in all 3 llamas. Since the llamas were immunized with recombinant protein and not with cells, the observed signals can be considered specific for c-Met.

1.2 Library Construction

Blood samples from the immunized llamas were taken on days 46 and 50 and peripheral blood mononuclear cells were prepared using Ficoll-Paque Plus (GE Healthcare, Uppsala, Sweden) according to the manufacturer's instructions. Total RNA was extracted from the peripheral blood mononuclear cells using Rneasy Midi Kit (Qiagen, Venlo, The Netherlands) following manufacturer's instructions. The total RNA samples were used as starting material for RT-PCR to amplify Nanobody encoding gene fragments. These fragments were cloned into a house made phagemid vector (pAX50), allowing production of recombinant phage particles, after infection with helper phage, which display the Nanobodies as gene III fusion proteins on the surface of the phage particles. Phage was prepared according to standard methods and after filter sterilization stored in 20% glycerol at −80° C.

1.3 Selection

Phage libraries obtained from llamas 450, 451 and 452 were used for different selection strategies.

Strategy 1:

In a first selection round (or second round after selection on cells), 1 or 100 nM biotinylated human c-Met/Fc (R&D Systems; biotinylated in house according to the manufacturer's instructions using Sulfo-NHS-LC-Biotin (Pierce, Rockford, Ill., USA)) was incubated with the phage libraries and subsequently captured on Streptavidin Dynabeads (Invitrogen). Following extensive washing, bead bound phages were eluted with 1 mg/mL trypsin.

Strategy 2:

In a first selection round (or second round after selection on recombinant antigen), $10^6$ cells/mL human A549 cells endogenously expressing c-Met were incubated with the phage libraries. Following extensive cell washing, cell bound phages were eluted with 1 mg/mL trypsin.

The phage output from the selections of the different strategies was rescued in E. coli TG1 cells. Colonies were picked and grown in 96 deep well plates (1 mL/well volume). Expression of C-terminally c-myc and $His_6$ tagged soluble Nanobodies was induced by adding IPTG to the growth medium. Periplasmic extracts (volume: ~100 µl) were prepared according to standard methods (WO 94/04678).

1.4 Screening for c-Met Binding Nanobodies in a Flow Cytometry Assay

Periplasmic extracts were screened for cellularly expressed c-Met binding in a FACS assay using c-Met-expressing A549 tumor cells (ATCC No. CCL-185). $2 \times 10^5$ A549 cells were incubated in 1:10 diluted periplasmic extracts for 30 min at 4° C., and then thoroughly washed. Next, cells were incubated with 2 µg/ml anti c-myc antibody for 29 min at 4° C., washed again, and incubated for 30 min at 4° C. with goat anti-mouse PE labelled antibody (1:100). Samples were washed, resuspended in FACS Buffer (D-PBS from Gibco, with 10% FBS from Sigma and 0.05% sodium azide from Merck) supplemented with 5 nM TOPRO3 (Molecular Probes cat#T3605). Cell suspensions were then analyzed on a FACS Canto. Gating was set on live, intact cells using forward/side scatter and TOPRO3 channel fluorescence parameters. Live cell PE channel mean channel fluorescence values higher than those obtained in control experiments omitting Nanobody staining or including an irrelevant specificity binding Nanobody indicates that a clone bound the cell line.

1.5 Screening for HGF-Blocking Nanobodies in Alphascreen Assay

The periplasmic extracts were screened in an Alphascreen assay to evaluate the ligand blocking capacity of the Nanobodies. This assay relies on the use of Donor and Acceptor beads which can be conjugated to biological molecules. When a biological interaction between molecules brings the beads into proximity, excited singlet oxygen molecules produced by a photosensitizer in the Donor bead upon laser excitation at 680 nm, diffuse across to react with a chemiluminescer in the acceptor bead that further activates fluorophores emitting light at 520-620 nm. If the Nanobody inhibits binding of HGF to c-Met/Fc, fluorescence signal will decrease.

Acceptor beads (Perkin Elmer, Waltham, Mass., USA) were conjugated with anti-human Fc Nanobodies (prepared in house) according to the manufacturer's instructions. The periplasmic extracts were pre-incubated with 0.26 nM biotinylated HGF for 15 min at room temperature. Next, anti-human Fc conjugated acceptor beads and c-Met/Fc (0.26 nM final concentration) were added and incubated for 1 hour at room temperature. Second, streptavidin donor beads (Perkin Elmer) were added and incubated for an additional 1 hour. Fluorescence was measured by reading plates on the EnVision Multilabel Plate Reader (Perkin Elmer) using an excitation wavelength of 680 nm and an emission wavelength of 520 nm. A decrease in signal indicates that the binding of biotinylated HGF to c-Met is blocked by the Nanobody expressed in the periplasmic extract.

An arbitrary 50% cut-off was chosen to classify Nanobodies as blocking the interaction of c-Met with HGF or not.

Nanobodies which scored positive in either the flow cytometric screening or the Alphascreen assay were sequenced. Clones were clustered into sequence families based on their CDR3 sequence. 46 distinct families of c-Met binders and/or HGF blockers were identified.

1.6 Screening for Nanobodies Blocking HGF-Induced Phosphorylation of c-Met

Periplasmic extracts of Nanobodies which were positive in either the flow cytometric or Alphascreen assays were further screened in a phosphorylation assay. This assay allows the identification of Nanobodies inhibiting HGF-driven c-Met phosphorylation and downstream signaling. Inhibition of c-Met phosphorylation can occur by either inhibiting binding of HGF to c-Met or by inhibiting c-Met dimerization. Phosphorylated c-Met (Tyr 1349) was detected using a Mesoscale Discovery kit (MSD, Cat #K15126A-3, Mesoscale Discovery, Gaithersburg, Md.). This kit allows for the detection of both total c-Met as well as Tyr 1349-phosphorylated c-Met in a single well.

A549 tumor cells (ATCC No. CCL-185) were seeded at a density of 20.000 cells per well. After 2 days, the cell culture medium was changed to serum free medium and cells were serum starved overnight. The next day, cells were incubated with a 1/5 dilution of periplasmic extracts (20 µl in total volume of 100 µl) for 30 min prior to addition of 1 nM HGF (Peprotech) and another 15 minute incubation at 37° C. Cells were then washed and lysed in RIPA buffer (10×RIPA buffer, Cell Signaling Technology). The lysates were transferred to the c-Met MSD assay plates. After washing away unbound lysate material, bound phosphorylated and total c-Met were detected with sulfo-tagged antibody and plates were read on the Sector Imager 2400 (Meso Scale Discovery). As positive control, several replicates of anti-c-Met antibody h224G11 Pierre-Fabre Institute (WO 2009/007427, FIG. 65 and FIG. 72) were spiked into irrelevant periplasmic extracts (final 1/5 dilution) in each assay plate.

The percent phosphoprotein in a sample was then calculated as the recommended normalized ratio $$\text{Normalized ratio} = \frac{2 \cdot Phospho \text{ signal}}{Phospho \text{ signal} + \text{Total signal}} \cdot 100\%$$

The percentage inhibition is calculated as follows, with respect to the maximal signal (average of several replicates with 1 nM HGF+irrelevant periplasmic material at a 1/5 dilution) and the negative control (average of several replicates with no HGF stimulation+irrelevant periplasmic material at a 1/5 dilution):

$$\% \text{ inhibition} = 100\% - \left(\frac{NR(\text{sample}) - NR(\text{no } HGF)}{NR(\text{irrelevant } NB) | NR(\text{no } HGF)}\right) \cdot 100\%$$

88 of 196 screened clones were at least as efficacious as h224G11 in their ability to inhibit >30% of HGF-induced c-Met phosphorylation in A549 cells.

1.7 Formatted or Mutated Nanobodies of the Invention

Nanobodies 04E09-9GS-Alb11 (SEQ ID NO: 7), 06B08-9GS-Alb11 (SEQ ID NO: 8), 06C12-9GS-Alb11 (SEQ ID NO: 9), and 06F10-9GS-Alb11 (SEQ ID NO: 10) were cloned into an in-house constructed plasmid allowing expression in *Pichia pastoris* and secretion into the cultivation medium. Cloning was done such that said Nanobodies (04E09-9GS-Alb11 (SEQ ID NO: 7), 06808-9GS-Alb11 (SEQ ID NO: 8), 06C12-9GS-Alb11 (SEQ ID NO: 9), and 06F10-9GS-Alb11 (SEQ ID NO: 10)] were translationally fused at their C-terminus to an anti-human serum albumin (HSA) binding Nanobody (ALB11 also designated as Alb11), separated by a 9GS-linker (amino acid sequence GGGGSGGGS). Constructs had an additional C-terminal 3×FLAG and His$_6$-tag (SEQ ID NO: 6).

Nanobodies Alb11-35GS-04E09 (SEQ ID NO: 11) and Alb11-35GS-04E09 (SEQ ID NO: 12) were cloned into the same expression plasmid and fused to the same ALB11 Nanobody, but such that the c-Met binding Nanobodies were translationally fused at their N-terminus to ALB11, separated by a 35GS-linker (SEQ ID NO: 22) or 9GS-linker (SEQ ID NO: 15). As above, these constructs carried C-terminal 3×FLAG and His$_6$-tags (SEQ ID NO: 6).

Nanobodies 04E09-L49S (SEQ ID NO: 23), 04E09-C50S/C100bG (SEQ ID NO: 24) and 04E09-C22A/C92S (SEQ ID NO: 25) were also cloned into this plasmid. The Nanobody 04E09 was mutated at Kabat positions Leu49 to Ser (L49S), Cys50 to Ser and Cys100b to Gly (C50S/C100bG), or Cys22 to Ala and Cys92 to Ser (C22A/C92S) and fused at its C-terminus to 3×FLAG and His$_6$-tags (SEQ ID NO: 6).

Example 2

Characterization of c-Met Blocking Nanobodies in Proliferation Assay, Chemotaxis Assay, in Two HGF-Competition Assays, and in a Flow Cytometric Assay

2.1 Nanobody Expression and Purification

Nanobodies (SEQ ID NOs: 7 to 10) were cloned as described in 1.7 and expressed in *P. pastoris* in a culture volume of 250 mL Nanobody expression was induced by addition of methanol and allowed to continue for 48 hours at 30° C. The cleared supernatants were used as starting material for immobilized metal ion affinity chromatography (IMAC) using a HisTrap™ column (GE Healthcare). Nanobodies were eluted from the column using imidazole step gradient from 20 mM to 250 mM. In a next step, Nanobodies were buffer changed to D-PBS (Invitrogen) using HiPrep™ 26/10 desalting columns (GE Healthcare).

2.2 MET-Blocking Benchmark Molecules

2.2.1 Anti-c-Met Antibody 5D5

The murine hybridoma cell line 5D5.11.6 (ATCC HB-11895; lot no 3996831, LGC Standards, UK) was grown in DMEM+Glutamax-I (Gibco) supplemented with 10% FCS and 1% Penicillin/Streptomycin. The cultivation medium was changed for antibody production to CD Hybridoma (Lonza) supplemented with 6 mM L-glutamine and 1× cholesterol. Conditioned medium was harvested after ca. 1 week and centrifuged and filtered using a Stericup system with a 0.22 μm Express PLUS membrane (Millipore) prior to loading onto a HiTrap ProteinG column (GE Healthcare). The column was eluted with 0.1M Glycine-HCl, pH 2.7, and eluate was immediately neutralized with 0.2 volume of 1M Tris-HCl pH 9. The antibody solution was then buffer changed to D-PBS on a PD-10 desalting column (GE Healthcare).

2.2.2. Anti-c-Met Antibody Fragment 5D5 Fab from mAb

The Fab fragment of the anti-c-Met antibody 5D5 was prepared by ficin digestion of the murine IgG using the Pierce Mouse IgG1 Fab and F(ab')2 Micro Preparation Kit (Cat #44980, Thermo Scientific). Briefly, the IgG was incubated for 4 hours at 37° C. with agarose immobilized ficin in digestion buffer supplemented with 25 mM cysteine. Undigested IgG and Fc fragment were removed by 1 hour incubation with anti-murine Fc agarose (Europa Bioproducts; Cat #EU-AMIgGFc-AGA-1). The bead-free supernatant was concentrated on a membrane filter concentrator (20,000 MWCO, CAT #87750, Pierce—Thermo Scientific) to less than 1 mL volume. The preparation was size separated and buffer changed by gel filtration on a Superdex 75 10/300GL column (GE Healthcare). The eluted fractions were again concentrated on the same membrane filter concentrator.

2.2.3 Generation of 5D5 Fab v2

The 5D5 Fab v2 sequence was published in Dennis et al. (US patent application number US2007/0092520. The 5D5 Fab v2 differed from the parental murine hybridoma monoclonal antibody 5D5 in that it was humanized and affinity matured. The sequences of the variable heavy and light domains (synthetically generated, Geneart) have been genetically fused to the human IgG1 CH1 (tagged with the hemagglutinin- and a hexahistidine-tag), and the human kappa CL, respectively. The constructs were expressed from an in-house generated *E. coli* expression plasmid. *E. coli* TG1 cells were grown in a 2 L-fermenter in LB medium supplemented with 0.5% glucose and kanamycin, and expression induced with 1 mM IPTG. Cells were harvested by centrifugation (3600×g, 20 min), and periplasmic extracts were produced. The 5D5 Fab v2 was captured on a Ni-NTA column (HisTrap, GE Healthcare), and eluted in 250 mM imidazole. The eluate was further purified on an anti-human kappa affinity column (KappaSelect, GE Healthcare): The 5D5 Fab v2 was eluted in 100 mM glycine, pH2.5, and immediately neutralized by addition of 0.2 vol. 1M TRIS. pH7.5.

2.3 Nanobodies Block the Binding of the c-Met-Ligand HGF in Alphascreen Assay and in a Flow Cytometric Assay

2.3.1 Nanobodies Block the Binding of the c-Met Ligand HGF in Alphascreen Assay The purified Nanobodies were characterized in a HGF/c-Met competition Alphascreen assay to evaluate their blocking potency and efficacy and compare this with 5D5 Fab. Dilution series of anti-c-Met Nanobodies and 5D5 Fab starting from 250 nM down to 0.9 pM were incubated with 100 pM biotinylated hHGF (human HGF) for 15 minutes at room temperature. Next, anti-human Fc conjugated acceptor beads and c-Met/Fc (100 pM final concentration) were added and the mixture incubated for another 2 hours at room temperature. Then streptavidin donor beads were added and the mixture was incubated for 1 additional hour. Fluorescence was measured by reading plates on the EnVision Multilabel Plate Reader using an excitation wavelength of 680 nm and an emission wavelength of 520 nm.

The selected Nanobodies effectively inhibit the HGF binding to c-Met receptor in a dose-dependent manner. The calculated IC50 values and percentage inhibition are shown in Table 1. Percentage inhibition reflects the maximal degree of inhibition for a particular compound dilution series compared to the maximal concentration of cold (non-biotinylated) ligand (set as 100% reference point). For instance, Nanobody 06B08-9GS-Alb11 blocks the HGF/c-Met interaction up to 65%, whereas other Nanobodies and 5D5 Fab were able to inhibit to about 100%.

TABLE 1

Inhibition of HGF binding to c-Met as determined by Alphascreen (IC50 values and % inhibition; Nanobodies* were tagged with 3xFlag-His6 = SEQ ID NO: 6 as described in Example 1.7)

| ID | global IC50 [in nM] | % inhibition |
| --- | --- | --- |
| 5D5 Fab | 1.3 | 101% |
| 04E09-9GS-Alb11 (SEQ ID NO: 7)* | 0.11 | 102% |
| 06B08-9GS-Alb11 (SEQ ID NO: 8)* | 0.32 | 65% |
| 06C12-9GS-Alb11 (SEQ ID NO: 9)* | 0.20 | 101% |
| 06F10-9GS-Alb11 (SEQ ID NO: 10)* | 1.1 | 99% |

The purified Nanobodies were evaluated in the presence or absence of 5 μM of Human Serum Albumin (HSA).

Table 2 summarizes the potency ($IC_{50}$ values) of the Nanobodies in the presence or absence of HSA. For none of the Nanobodies, a signification shift in potency was observed in the presence of HSA.

TABLE 2

Influence of HSA on the ability of the Nanobodies to block HGF binding to c-Met (Nanobodies* were tagged with 3xFlag-His6 = SEQ ID NO: 6 as described in Example 1.7)

| ID | In absence of HSA IC50 [in nM] | In presence of 5 μM HSA IC50 [in nM] |
| --- | --- | --- |
| 5D5 Fab | 3.2 | 3.1 |
| 04E09-9GS-Alb11 (SEQ ID NO: 7)* | 0.34 | 0.26 |

TABLE 2-continued

Influence of HSA on the ability of the Nanobodies to block HGF binding to c-Met
(Nanobodies* were tagged with 3xFlag-His6 = SEQ ID NO: 6 as described in Example 1.7)

| ID | In absence of HSA IC50 [in nM] | In presence of 5 µM HSA IC50 [in nM] |
|---|---|---|
| 06B08-9GS-Alb11 (SEQ ID NO: 8)* | 0.50 | 0.36 |
| 06C12-9GS-Alb11 (SEQ ID NO: 9)* | 0.43 | 0.14 |
| 06F10-9GS-Alb11 (SEQ ID NO: 10)* | 0.55 | 0.30 |

2.3.2 Nanobodies Block the Binding of the c-MET Ligand HGF in a Flow Cytometric Assay The purified Nanobodies were characterized in an HGF/c-Met competition assay based on flow cytometric measurements to evaluate their blocking potency and efficacy and compare this with 5D5 mAb. A549 cells were washed and resuspended at $2 \times 10^6$/mL. A dilution series of anti-c-Met Nanobodies and 5D5 mAb starting from 1 µM down to 5.6 pM was pre-incubated with 1 nM biotinylated hHGF. Next, A549 cells and the Nanobody/HGF mixture were incubated for 2 hr at 4° C. After washing, cells were stained with streptavidin/PE (BD Bioscience) for 30 min at 4° C. Cells were then washed again, stained with 2.5 nM TOPRO3 (Invitrogen) and analyzed on a FACSArray instrument (BD Bioscience).

The data indicated that the Nanobodies 04E09-9GS-Alb11 (SEQ ID NO: 7), 06C12-9GS-Alb11 (SEQ ID NO: 9) and 06F10-9GS-Alb11 (SEQ ID NO: 10) show full competition with HGF. Nanobodies 04E09-9GS-Alb11 (SEQ ID NO: 7) and 06C12-9GS-Alb11 (SEQ ID NO: 9) had an IC50 value significantly lower than that of the 5D5 mAb. The IC50 value of the 5D5 Fab fragment was determined to be 11.3 nM in this assay.

TABLE 3

Inhibition of HGF binding to cell bound c-Met as determined by competition flow cytometry
(IC50 values and % inhibition; Nanobodies* were tagged with 3xFlag-His6 = SEQ ID NO: 6 as described in Example 1.7)

| Sample | IC50 [in nM] | % inhibition |
|---|---|---|
| 5D5 mAb | 2.72 (n = 4) | 100 (Reference) |
| 04E09-9GS-Alb11 (SEQ ID NO: 7)* | 1.13 | 99 |
| 06B08-9GS-Alb11 (SEQ ID NO: 8)* | 2.33 | 50 |
| 06C12-9GS-Alb11 (SEQ ID NO: 9)* | 1.30 | 97 |
| 06F10-9GS-Alb11 (SEQ ID NO: 10)* | 4.82 | 95 |

2.3.3 Binding of the C-Met-Ligand HGF in Alphascreen Assay

The anti-c-MET/anti-serum albumin Nanobody constructs were characterized in an HGF/c-MET competition Alphascreen assay to evaluate their blocking potency and efficacy and compare this with a benchmark antibody fragment (5D5 Fab v2). A dilution series of anti-c-MET Nanobodies and benchmark 5D5 Fab v2 starting from 250 nM up to 0.9 pM was pre-incubated with 100 pM biotinylated hHGF during 15 minutes at RT. To this mixture the anti-human Fc conjugated acceptor beads and c-MET/Fc (100 pM final concentration) were added and incubated for 2 hours at RT. Next, streptavidin donor beads were added and the mixture was incubated for 1 additional hour. Fluorescence was measured by reading plates on the EnVision Multilabel Plate Reader using an excitation wavelength of 680 nm and an emission wavelength of 520 nm.

The two constructs effectively inhibit the HGF binding to c-MET receptor in a dose-dependent manner. The calculated $IC_{50}$ values and corresponding 95% confidence intervals are shown in Table 3A. A007900171 and the two batches of A007901219 have similar IC50 values; their 95% CI are overlapping, which suggests that the difference is statistically not significant. The Nanobodies showed an >5-fold improved potency as compared to the benchmark 5D5 Fab v2.

In conclusion, the Nanobody constructs outperform the benchmark, irrespective of the particular anti-serum albumin moiety.

TABLE 3A

Inhibition of HGF binding to c-MET as determined by Alphascreen
(IC50 values and 95% confidence intervals)

| ID | $IC_{50}$ [in pM] | 95% CI [in pM] |
|---|---|---|
| 5D5 Fab v2 | 380 | 330 to 440 |
| A007900171 (Alb11) (SEQ ID NO: 113) | 58 | 50 to 66 |
| A007901219 (Alb23) (SEQ ID NO: 106) | 66 | 57 to 78 |

2.4 Nanobodies Block the HGF-Induced c-Met Phosphorylation in the A549 Cancer Cell Line The purified Nanobodies were characterized in the HGF-dependent phosphorylation assay as outlined in Example 1.6.

2.4.1 Nanobodies Block the HGF-Induced c-Met Phosphorylation in the A549 Cancer Cell Line In a first series of experiments, dilution series of formatted anti-c-Met Nanobodies or 5D5 Fab from 1 µM down to 0.23 nM were co-incubated with 1 nM HGF on A549 cells for 15 min at 37° C. ⅓ of cell lysate was then applied to the MSD phosphorylated c-Met assay plates. Lysates from duplicate samples were pooled prior to measurement. After washing away unbound lysate, a sulfo tagged antibody detecting both phosphorylated as well as unphosphorylated c-Met was added and plates were read using the Sector Imager 2400 (MSD).

The purified Nanobodies were shown to virtually completely block HGF-dependent c-Met-phosphorylation. Results are summarized in Table 4; see also FIG. 1.

In conclusion, tagged (SEQ ID NO: 6) Nanobody 04E09-9GS-Alb11 (SEQ ID NO: 7) outperforms the 5D5 Fab benchmark. Nanobodies 06B08-9GS-Alb11 (SEQ ID NO: 8) and 06C12-9GS-Alb11 (SEQ ID NO: 9) have a comparable IC50 (within 95% confidence intervals), whereas 06F10-9GS-Alb11 (SEQ ID NO: 10) is less potent.

TABLE 4

Inhibition of HGF-dependent c-Met phosphorylation in A549 tumor cells
(Nanobodies* were tagged with 3xFlag-His6 = SEQ ID NO: 6 as described in Example 1.7)

| Clone | Experiment 1 | | Experiment 2 | |
|---|---|---|---|---|
| | IC50 (NB)/IC50 (5D5 Fab) | % inhibition | IC50 (NB)/IC50 (5D5 Fab) | % inhibition |
| 5D5 Fab** | 1 (Reference) | 96.36 | 1 (Reference) | 95.86 |
| 04E09-9GS-Alb11 (SEQ ID NO: 7)* | 0.66 | 96.02 | 0.47 | 83.58 |
| 06B08-9GS-Alb11 (SEQ ID NO: 8)* | 3.45 | 91.25 | 1.33 | 91.52 |
| 06C12-9GS-Alb11 (SEQ ID NO: 9)* | 3.85 | 96.33 | 1.24 | 99.85 |

TABLE 4-continued

Inhibition of HGF-dependent c-Met phosphorylation in A549 tumor cells
(Nanobodies* were tagged with 3xFlag-His6 = SEQ ID NO: 6
as described in Example 1.7)

|  | Experiment 1 | | Experiment 2 | |
| --- | --- | --- | --- | --- |
| Clone | $\frac{\text{IC50 (NB)}}{\text{IC50 (5D5 Fab)}}$ | % inhibition | $\frac{\text{IC50 (NB)}}{\text{IC50 (5D5 Fab)}}$ | % inhibition |
| 06F10-9GS-Alb11 (SEQ ID NO: 10)* | 6.97 | 91.54 | 2.47 | 96.69 |

**5D5 Fab had an IC50 of 10.4 nM (experiment 1) and 9.09 nM (experiment 2).

Based on the results of the c-Met phosphorylation assay in A549 cells, Nanobody 04E09-9GS-Alb11 (SEQ ID NO: 7) was identified as the most potent Nanobody.

2.4.2 Alb23 Derived Nanobodies Block the HGF-Induced c-Met Phosphorylation in the A549 Cancer Cell Line In a second series of experiments, the purified anti-c-MET/anti-serum albumin Alb11 and Alb23 Nanobody constructs were characterized in the HGF-dependent phosphorylation assay. A dilution series of the anti-cMET constructs or the anti-cMET benchmark 5D5 Fab v2 starting from 1 µM up to 0.23 nM was co-incubated with 1 nM HGF on A549 cells during 15 min at 37° C. ⅓ of the lysed cell solution was then applied to the phospho c-MET MSD assay plates. Two duplicates on cell culture level were pooled on MSD level. After washing away unbound material, a sulfo tagged detection c-Met antibody detected both the phosphorylated as well as the non-phosphorylated receptor. The read out was performed with the sector imager 2400.

The two anti-c-MET/anti-serum albumin Nanobody constructs effectively inhibit the HGF-dependent c-MET receptor phosphorylation in a dose-dependent manner. The calculated $IC_{50}$ values and corresponding 95% confidence intervals are shown in Table 4A. A007900171 (SEQ ID NO: 113) and the two batches of A007901219 (SEQ ID NO: 106) have similar $IC_{50}$ values; their 95% CI are overlapping, which suggests that the differences are statistically not significant. The Nanobodies showed a ca. 2-fold improved potency as compared to the benchmark 5D5 Fab v2. Additionally, within 95% confidence intervals, the addition of human serum albumin to the stimulated cells did not alter $IC_{50}$ values of the tested Nanobodies.

In conclusion, the Nanobody constructs outperform the benchmark, irrespective of the particular anti-serum albumin moiety.

TABLE 4A

Inhibition of HGF binding to cMET as determined by cMET
phosphorylation assay (IC50 values and 95% confidence intervals)

|  | −HSA | | +HSA | |
| --- | --- | --- | --- | --- |
| ID | $IC_{50}$ [in nM] | 95% CI [in nM] | $IC_{50}$ [in nM] | 95% CI [in nM] |
| 5D5 Fab v2 | 11.9 | 8.57 to 16.5 | n.d. | |
| A007900171 (Alb11) | 5.97 | 5.08 to 7.00 | 6.28 | 5.35 to 7.36 |
| A007901219 (Alb23) | 5.41 | 4.61 to 6.35 | 4.20 | 3.60 to 4.91 |

2.5 Nanobodies Block the HGF-Induced Proliferation of BxPC-3 Cells

Nanobodies were evaluated for their ability to block HGF-induced proliferation of BxPC3 cells (pancreatic cancer cells, ATCC No CRL-1687). In this assay, $1 \times 10^4$ cells per well are seeded in E-plates (ACEA/Roche Applied Science) and their dynamics are monitored using the Xcelligence RTCA Analyser (Roche Applied Science) by measuring each well's impedance value and providing a calculated 'Normalized Cell Index' (NCI). After overnight incubation and 4 hours serum starvation, dilution series of formatted anti-c-Met Nanobodies or anti-c-Met 5D5 Fab benchmark from 0.8 µM down to 0.05 nM were added to BxPC3 cells. NCI values were recorded for 3 days.

Figure 3:
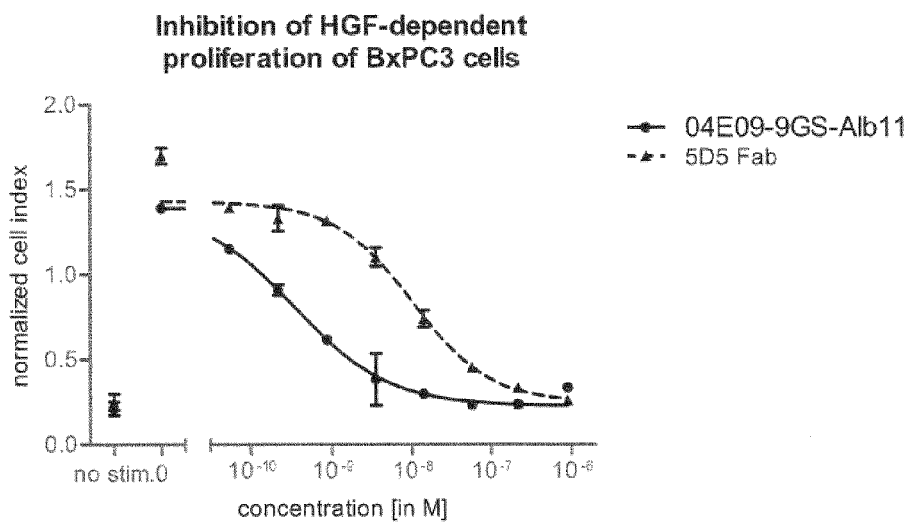
FIG. 3 shows that the Nanobody 04E09-9GS-Alb11 (SEQ ID NO: 7) of the invention inhibits HGF-dependent proliferation of BxPC3 cells. The impedance value of each well was used to calculate the 'Normalized Cell Index' (NCI), which is indicative of the cell proliferation. In this graph, the NCI of two samples is recorded after 3 days of growth. The Nanobody was plotted as closed circles. The Nanobody was assayed together with 5D5 Fab (triangles) and plotted in the graph with dotted lines.

After 3 days, all Nanobodies could almost completely block HGF-mediated NCI increases, indicating they efficiently block HGF-induced cell proliferation (Table 5). Tagged (SEQ ID NO: 6) Nanobody 04E09-9GS-Alb11 (SEQ ID NO: 7) had a potency superior to that of 5D5 Fab (see FIG. 3). Other Nanobodies had $IC_{50}$ values comparable to 5D5 Fab (data not shown).

TABLE 5

Inhibition of HGF-dependent proliferation of BxPC3 cells (Nanobodies*
were tagged with 3xFlag-His6 = SEQ ID NO: 6 as described in Example 1.7)

|  | Experiment | |
| --- | --- | --- |
| Clone | $\frac{\text{IC50 (NB)}}{\text{IC50 (5D5 Fab)}}$ | % inhibition |
| 5D5 Fab** | 1 (Reference) | 94.84 |
| 04E09-9GS-Alb11 (SEQ ID NO: 7)* | 0.03 | 89.49 |

**5D5 Fab had an IC50 of 34.3 nM 2.6 Nanobodies Block the HGF-Dependent Chemotaxis of A549 Cells The ability of anti-c-Met Nanobodies to block migration of A549 cells towards an HGF concentration gradient was tested in a chemotaxis assay.

The assay was based on FluoroBlok™ plates (BD Falcon™) which consist of a black multiwell insert plate with fluorescence-blocking, microporous PET (polyethylene terephthalate) membrane inserts (8 µm pore size) mounted on a transparent 96-well receiver plate. Sub-confluent A549 cells were serum starved overnight and stained with the fluorescent dye DilC12 (BD Biosciences). Next, 75.000 cells/well were seeded onto the membrane inserts and incubated with dilution series of anti-c-Met Nanobodies or anti-c-Met murine 5D5 Fab, starting from 0.4 µM down to 0.01 nM. The same concentration of Nanobody/antibody was also added to the lower compartment, as well as 2.5 nM of HGF. 24 hours later, the amount of cells having migrated to the bottom plate was quantified on a bottom-reading fluorescence plate reader (Envision, Perkin Elmer)

All tested Nanobodies could inhibit HGF-driven migration of A549 cells in the chemotaxis assay to a similar extent as the 5D5 Fab benchmark (complete block). Nanobody 06B08-9GS-Alb11 (SEQ ID NO: 8) seemed to decrease migration even below background level. Nanobodies 04E09-9GS-Alb11 (SEQ ID NO: 7) and 06C12-9GS-Alb11 (SEQ ID NO: 9) were more potent in this assay than 5D5 Fab. Results are summarized in Table 6, see also FIG. 4.

TABLE 6

Inhibition of HGF-dependent A549 cell migration (Nanobodies* were tagged with 3xFlag-His6 = SEQ ID NO: 6 as described in Example 1.7)

| sample ID | Experiment $\frac{\text{IC50 (NB)}}{\text{IC50 (5D5 Fab)}}$ | % inhibition |
|---|---|---|
| 5D5 Fab** | 1 (Reference) | 112.37 |
| 04E09-9G5-Alb11 (SEQ ID NO: 7) | 0.2 | 105.73 |

**5D5 Fab had an IC50 of 5.48 nM

2.7 A007901222 Inhibits HGF Binding to c-MET

The anti-c-Met Nanobody A007901222 (SEQ ID NO: 188) was produced in *P. pastoris* strain X33 on a 2 L scale in complex medium, pH6.0, 95 hai (hours after induction), and at 30° C. in a fermentor. The culture broth was first clarified by a high speed centrifugation step (7000 rpm, 4° C., 20 min, Sigma 8K10 rotor) and the supernatant was then made particle free by microfiltration using TFF. The material was subsequently loaded on a MEP HyperCel column (PALL). The Nanobody was eluted with sodium acetate pH 3.5 and the eluate was neutralized with 1/10 v/v 1M TRIS pH8.8. The Nanobody was further buffer-exchanged to the polish step-buffer on Sephadex G25 and subsequently purified by an anion exchange chromatographic polish step on Poros50 HQ. After OGP-treatment for LPS-removal, the material was buffer exchanged on Superdex 75 to D-PBS.

The purified Nanobody was tested in three different assays and compared to the 5D5 Fab v2 benchmark: (i) analysis of in vitro potency in HGF-competition Alphascreen, (ii) cell-based c-Met phosphorylation assay, (iii) cell-based proliferation assay.

The HGF-competition Alphascreen was performed as described in Example 2 (2.3.1). The cell-based cMet phosphorylation assay was performed as outlined in Example 1.6. The cell-based proliferation assay was performed as outlined in Example 2.5.

The calculated $IC_{50}$ values and corresponding 95% confidence intervals are shown in Table 7.

TABLE 7

Inhibition of HGF binding to c-MET as determined by Alphascreen, c-MET phosphorylation assay and proliferation assay

| Clone number | Alphascreen [in pM] | | c-Met phosphorylation [in nM] | | Proliferation assay [in nM] | |
|---|---|---|---|---|---|---|
| | $IC_{50}$ | 95% CI | $IC_{50}$ | 95% CI | $IC_{50}$ | 95% CI |
| A007901222 (SEQ ID NO: 188) | 72 | 64-82 | 3.97 | 3.18-4.96 | 1.37 | 1.03-1.81 |
| 5D5 Fab v2 | 320 | 280-360 | 7.13 | 5.65-9.00 | 2.88 | 1.76-4.71 |

Example 3

Binding Specificity of c-Met Blocking Nanobodies

3.1 c-Met Blocking Nanobodies Bind Specifically to Cell-Membrane Expressed Human and Cynomolgus c-Met A549 cells (ATCC No. CCL-185, LGC Standards, UK) were used as a source of endogenous human cell membrane expressed c-Met. Cynomolgus monkey c-Met was expressed on BAF3 cells as full length, membrane-bound protein. BAF3 cells (ABL157, DMSZ, Germany) were transfected with the expression plasmid DNA and a population with high c-Met expression levels was isolated by FACS sorting (FACSAria, BD Biosciences). Binding of Nanobodies to endogenously and ectopically cell surface expressed human and cynomolgus c-Met, respectively, was assessed by FACS analysis as described below.

Dilution series of anti-c-Met Nanobodies from 1 µM down to 0.5 pM were incubated for 30 min at 4° C. with $10^5$ A549, BAF3, or cynomolgus c-Met transfected BAF3 cells. After washing the cells, cell surface bound Nanobodies were detected in FACS Array™ using mouse anti-FLAG and PE conjugated goat anti-mouse IgG.

All Nanobodies showed a comparable dose-dependent binding to both cell expressed human c-Met and cynomolgus monkey c-Met. No binding to BAF3 cells was observed, indicating binding to transfected BAF3 cells was specific to the cyno c-Met transgene. The ratio of $EC_{50}$ values for binding to human over cynomolgus c-Met were all within 2.5-fold.

3.2 c-Met Blocking Nanobodies Bind to Recombinant Human and Cynomolgus c-Met/Fc Chimeras

3.2.1 Production of Cynomolgus Monkey c-Met/Fc

The cynomolgus monkey (*M. fasciculoris*) c-Met sequence was determined by PCR on pre-made cDNA from liver tissue (purchased both from BioChain Institute Inc., Cat #C1534149-CY, and Zyagen, Cat #KD-314). Primers were designed based on the publically available rhesus (*M. mulatta*) c-Met sequence (NCBI ref NM_001168629.1). Alignment of the sequenced products with the rhesus sequence revealed no deviation on the amino acid level.

The extracellular domain of cynomolgus monkey c-Met (mature protein from E25 to T932) was fused to human Fc (IgG1 subtype), including a factor Xa cleavage site between the c-Met extracellular domain and the Fc portion and a C-terminal His6 tag (SEQ ID NO: 4). Both fragments were cloned by 3-point-ligation into an in-house constructed, episomally replicating mammalian expression vector. Human embryonic kidney cells containing the Epstein-Barr nuclear antigen (HEK293-EBNA; LGC Standards, UK) were grown in Pro293a medium (Lonza, Cat #12-764Q) supplemented with 4 mM glutamine, 1% Penicillin/Streptomycin, and 0.25 mg/mL geneticin. HEK293-EBNA cells were transiently transfected with the plasmid expressing cynomolgus monkey c-Met/Fc using FuGene HD Transfection Reagent (Roche, Cat #04 709 713 001) and Pro293a medium according to manufacturer's instructions. The conditioned medium was harvested for five times every 2 to 3 days, while incubating at 37° C. in a humidified $CO_2$ incubator (Binder, Cat #9140-0012 CB150). The medium was centrifuged, filtered with a Stericup system with a 0.221 µm Express PLUS membrane (Millipore) and the supernatant was purified on a POROS MabCaptureA matrix column (Applied Biosystems, Cat #4374730), eluted with 50 mM $Na_3$Citrate pH 3.0, and immediately neutralized with 0.2×vol. 1M TRIS-HCl pH 9. The protein solution was buffer changed to D-PBS by sequential dilutions with D-PBS and concentrations using a membrane filter concentrator (Vivaspin2, 50,000 MWCO, Sartorius Stedium Cat #VS2031).

3.2.2 Cross-Reactivity Testing by Competition ELISA

The binding of anti-c-Met Nanobodies to cynomolgus monkey c-Met/Fc was tested in a competition ELISA.

Human recombinant c-Met/Fc (R&D Systems) was coated on a Maxisorp plate at a concentration of 2 µg/mL. A fixed concentration of 0.17 nM of the Nanobodies (corresponding to the $EC_{50}$ concentration as determined in a binding ELISA to coated human recombinant c-Met/Fc) was pre-incubated for 1 hr at room temperature with a dilution series of soluble human c-Met/Fc (starting at a 120-fold molar excess), cynomolgus c-Met/Fc (starting at a 120-fold molar excess) or human CTLA-4/Fc (as a control) before they were added to the c-Met/Fc coated ELISA plate. Binding of Nanobodies to the immobilized human c-Met/Fc was detected using mouse anti-FLAG monoclonal antibody (Sigma-Aldrich) and HRP conjugated rabbit anti-mouse IgG (Dako). Detection was done using TMB One solution (Promega). The reaction was stopped with 2N $H_2SO_4$, and absorbance was determined at 450 nm with correction at 620 nm.

Binding of the Nanobodies to directly coated human c-Met/Fc was inhibited by human c-Met/Fc but not CTLA-4/Fc. For all the selected Nanobody leads, binding was similarly inhibited by exogenously added cynomolgus c-Met/Fc, indicating a comparable affinity as to human c-Met/Fc.

In an additional experiment, species cross-reactivity was also tested against mouse c-Met/Fc (R&D Systems) and canine c-Met (R&D Systems) using the same competition ELISA set-up. Again, a fixed concentration of 0.17 nM of the Nanobodies was pre-incubated for 1 hr at room temperature with a concentration series of murine c-Met/Fc (at a 120-fold molar excess) or canine decoy c-Met (at a 240-fold molar excess). Only for Nanobodies 04E09-9GS-Alb11 (SEQ ID NO: 7), 06C12-9GS-Alb11 (SEQ ID NO: 9) and 06F10-9GS-Alb11 (SEQ ID NO: 10) some inhibition could be observed at very high concentrations of murine c-Met/Fc or (to an even lesser extent) with canine c-Met. A quantitative comparison between human and murine or canine c-Met cannot be done, but it is clear that cross-reactivity with murine and canine c-Met is very low.

3.3 c-Met Blocking Nanobodies Bind to the SEMA Domain of c-Met 3.3.1 Production of Recombinant Human SEMA/Fc For the determination of Nanobody subdomain binding, the SEMA domain (matured protein from E25 to G519; Uniprot ref P08581 (MET_HUMAN)) was fused to the human Fc (IgG1 subtype), including a C-terminal $His_6$ tag and a factor Xa cleavage site between SEMA and Fc (SEQ ID NO: 100). The chimera was generated by extension PCR and sub-cloned into an in-house constructed, episomally replicating mammalian expression vector.

Transfection of HEK-EBNA cells and production and purification of the recombinant protein was done as described under 3.2.1

3.3.2 Epitope Mopping by Competition ELISA

The binding of anti-c-Met Nanobodies to the extracellular SEMA subdomain was tested in a competition ELISA.

Human recombinant c-Met/Fc (R&D Systems) was coated on a Maxisorp plate at a concentration of 2 µg/mL A fixed concentration of 0.17 nM of the c-Met Nanobodies (corresponding to the $EC_{50}$ concentration as determined in binding ELISA to immobilized human recombinant c-Met/Fc) was pre-incubated for 1 hr at room temperature with a fixed concentration of human c-Met/Fc (120-fold molar excess), human SEMA/Fc (180-fold molar excess) or human CTLA-4/Fc (as a control) before adding to the c-Met/Fc coated ELISA plate. Binding of Nanobodies to the plate immobilized human c-Met/Fc was detected with mouse anti-FLAG monoclonal antibody (Sigma-Aldrich) and HRP conjugated rabbit anti-mouse IgG (Dako). Detection was done using TMB One solution (Promega). The reaction was stopped with 2N $H_2SO_4$, and absorbance was determined at 450 nm with correction at 620 nm.

Binding of the Nanobodies to directly coated human c-Met/Fc was inhibited by human c-Met/Fc and not by CTLA-4/Fc. For the selected Nanobody leads, binding to c-Met/Fc was inhibited by exogenously added SEMA/Fc, indicating that they bind to the SEMA domain of c-Met.

3.4 c-Met Blocking Nanobodies do not Bind to c-Met Human Homologues RON or Plexin D1

The cross-reactivity of tagged (SEQ ID NO: 6) anti-c-Met Nanobodies (SEQ ID NOs: 7 to 10) to two close homologues of c-Met was tested in a competition ELISA. RON (MSP-R, GenBank: X70040.1) shares 29% amino acid sequence identity with the extracellular domain of c-Met, the Plexin D1 (GenBank: AY116661.1) shares 16% identity.

Human recombinant c-Met/Fc (R&D Systems) was coated on a Maxisorp plate at a concentration of 2 µg/mL A fixed concentration of 0.17 nM of the c-Met Nanobodies (corresponding to the $EC_{50}$ concentration as determined in binding ELISA to coated human recombinant c-Met/Fc) was pre-incubated for 1 hr at room temperature with dilution series of human c-Met/Fc (starting at a 230-fold molar excess), RON (starting at a 990-fold molar excess) or Plexin D1 (starting at a 440-fold molar excess) before they were added to the c-Met/Fc coated ELISA plate. Binding of Nanobodies to immobilized human c-Met/Fc was detected with mouse anti-FLAG monoclonal antibody (Sigma-Aldrich) and HRP conjugated rabbit anti-mouse IgG (Dako). Detection was done using TMB One solution (Promega). The reaction was stopped with 2N $H_2SO_4$, and absorbance was determined at 450 nm with correction at 620 nm.

No cross-reactivity to RON or Plexin D1 was detected for anti-c-Met Nanobodies.

Example 4

Agonistic Activity of c-Met Blocking Nanobodies in a c-Met Phosphorylation Assay The HGF-independent c-Met activation capacity of two of the purified tagged (SEQ ID NO: 6) Nanobodies (04E09-9GS-Alb-11 (SEQ ID NO: 7) and 06C12-9GS-Alb11 (SEQ ID NO: 9)) was characterized in the phosphorylation assay as outlined in Example 1.6. A dilution series of anti-c-Met Nanobodies or 5D5 monoclonal antibody from 1 gIM down to 0.23 nM was applied to A549 cells for 30 min at 37° C. ⅓ of the cell lysate was applied to the MSD phosphorylated c-Met assay plates. Lysates from duplicate samples were pooled. After washing away unbound material, a sulfo tagged c-Met detection antibody was added and plates were read using the Sector Imager 2400 (MSD).

Figure 2:
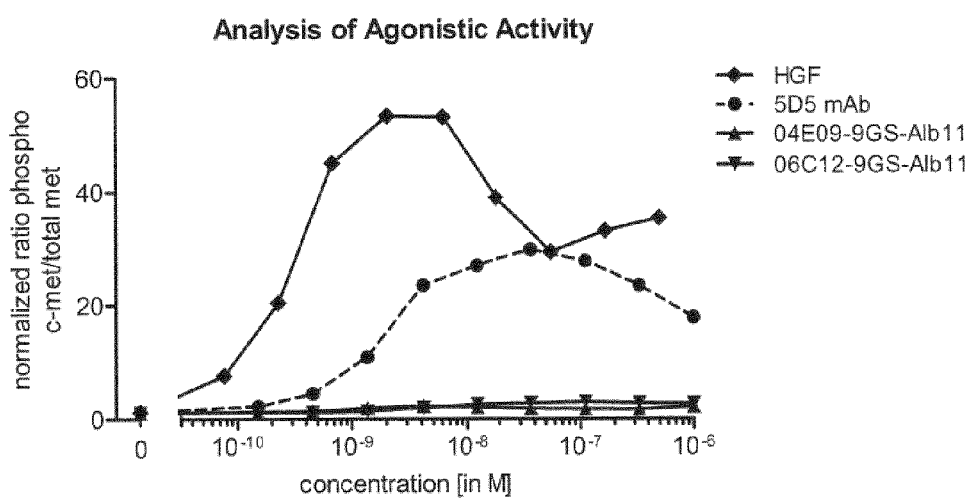
FIG. 2 shows the analysis of agonistic activity of Nanobody formats 04E09-9GS-Alb11 (SEQ ID NO: 7) and 06C12-9GS-Alb11 (SEQ ID NO: 9), and the comparison to 5D5 mAb and HGF. The normalized ratio (as described in Example 1, heading 1.6) is plotted against the concentration of the compound, which ability to phosphorylate c-Met was analyzed. The positive control HGF is plotted with diamonds, the 5D5 mAb with closed circles, 04E09-9GS-Alb11 with up-right triangles, and 06C12-9GS-Alb11 with inverse triangles.

It can be seen from FIG. 2 that neither 04E09-9GS-Alb-11 (SEQ ID NO: 7) nor 06C12-9GS-Alb11 (SEQ ID NO: 9) showed any agonistic activity up to a concentration of 1 µM. In contrast, 5D5 mAb induced c-Met phosphorylation with a maximum around 37 nM. As expected, HGF induced c-Met phosphorylation with a maximum efficiency between 2 nM and 6 nM.

Example 5

Affinity Determination Using Surface Plasmon Resonance

Kinetic analysis of the anti-c-Met Nanobody-Alb11 fusion construct 04E09-9GS-Alb-11 (SEQ ID NO: 7) was performed using Surface Plasmon Resonance on the ProteOn (BioRad). The experiment was performed in ProteOn PBS/Tween buffer (phosphate buffered saline, pH7.4, 0.005% Tween 20, cat. 176-2720, BioRad) at 25° C. Anti-human IgG(Fc) antibody (GE Healthcare) was immobilized on a ProteOn GLC Sensorchip (BioRad) via amine coupling on two ligand lanes at densities of approximately 5300RU and 2700RU. During kinetic analysis, 50 nM recombinant human c-Met/Fc chimera (R&D Systems) and 150 nM recombinant human CTLA4/Fc chimera (R&D Systems) were injected in the 2 separate lanes during 3 minutes at 25 μl/min, followed by injection of 04E09-9GS-Alb-11 (SEQ ID NO: 7) during 2 minutes at 45 μl/min. Nanobody concentrations of 100 nM, 25 nM, 6.25 nM, 1.56 nM and 0.39 nM were used for kinetic analysis. Regeneration of the surface was performed by an 80 seconds injection of 3M magnesium chloride at 25 μl/min (component of kit BR-1008-39, GE Healthcare).

Nanobody 04E09-9GS-Alb-11 (SEQ ID NO: 7) bound to c-Met/Fc with a $K_D$ of 13.5 pM. No binding to recombinant human CTLA4/Fc control chimera was observed. The kinetic constants for binding of 4E9-9GS-Alb111 are compared to the published affinity of the affinity matured 5D5 Fab v2 in Table 8.

TABLE 8

Affinity determination of Nanobodies by surface plasmon resonance (SPR)

| ID | ka 1/Ms | ka error | kd 1/s | kd error | KD M |
|---|---|---|---|---|---|
| 04E09-9GS-Alb11 | 2.89E+06 | 283.3 | 3.89E−05 | 10.7 | 1.35E−11 |
| 5D5 Fab v2 | 2.36E+05 | | 1.47E−04 | | 6.25E−10 |

Figure 4:
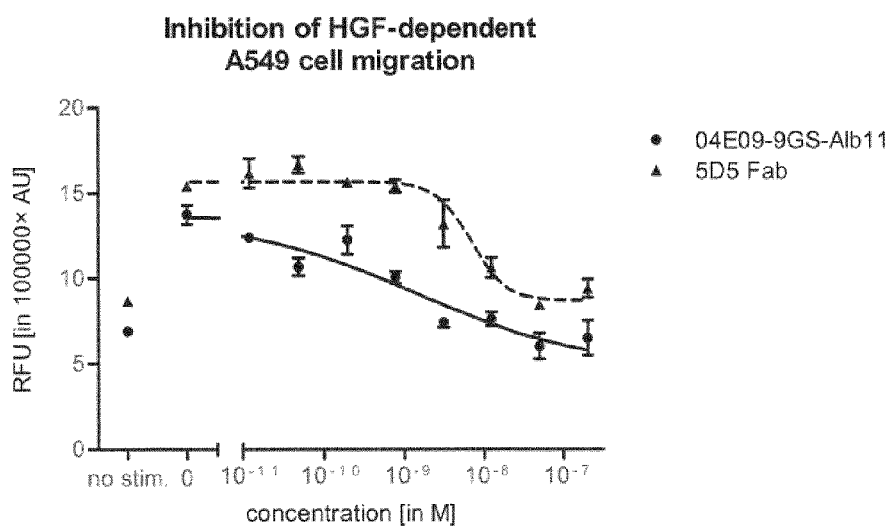
FIG. 4 shows that the c-Met blocking Nanobody 04E09-9GS-Alb11 inhibits HGF-dependent migration of A549 cells. The assay read-out 'Relative fluorescence units' is indicative of the A549 cells traversing the membrane into the HGF-containing lower compartment. The RFU is plotted against the concentration of the selected Nanobodies. The Nanobody was plotted as closed circles. The Nanobody was assayed together with 5D5 Fab (triangles) and plotted in the graph with full (SEQ ID NO: 7) and dotted (5D5 Fab) lines.

5D5 Fab v2 Affinity data acquired from published patent application US 2007/0092520 A1, FIG. 4, 5D5 variant #78

Example 6

Identification of Nanobodies Binding to a Similar Epitope as 04E09-9GS-Alb11

In order to increase the repertoire of Nanobodies binding to a similar epitope as 04E09-9GS-Alb$_{11}$, a new set of selections was performed.

Phage libraries obtained from llamas 450, 451 and 452 were used for 2 rounds of selection on cells (A549 cells and BAF3 cells over-expressing cynomolgus c-Met) as described in Example 1.3, with the modification that elution of bound phage was performed with 1 μM 04E09 Nanobody (SEQ ID NO: 26) instead of trypsin. This elution method was designed to result in a specific enrichment of phages that bind to the 04E09 epitope over phages that bind to other (non-overlapping) epitopes on the c-Met antigen.

The output from the selections was rescued in E. coli TG1 cells. Colonies were picked and grown in 96 deep well plates (1 mL volume). Nanobody production was induced by addition of IPTG. Nanobodies contained C-terminal c-myc and His$_6$ tags. Periplasmic extracts (volume: ~100 μl) were prepared according to standard methods.

Periplasmic extracts were screened in an Alphascreen assay to determine whether these Nanobodies inhibit the binding of Nanobody 04E09 to c-Met/Fc. The assay was performed essentially as described in Example 1.5, but biotinylated HGF was substituted with biotinylated 04E09 Nanobody (produced, purified and biotinylated in-house).

363 clones inhibiting the binding of Nanobody 04E09 to human c-Met were identified. After sequencing, these clones could be clustered into 26 different families, 14 of which were not identified previously. Thus, a total of 60 families binding to c-Met were identified using either trypsin or 04E09 for elution.

The 363 clones were also screened for their capacity to inhibit binding of HGF to c-Met/Fc in the Alphascreen assay (cf. Example 1.5). This screen confirmed that all Nanobodies binding epitopes similar to that of Nanobody 04E09 were also able to inhibit the binding of HGF to c-Met/Fc.

Of the 26 Nanobody families binding to the epitope of 04E09, 25 (96%) were derived from the VHH1 germline. Of the 34 families identified using trypsin elution that were not found to be binding to an epitope overlapping with 04E09, only 3 (9%) were of VHH1 type. This shows that binding to the epitope region targeted by Nanobody 04E09 is specifically favored for VHH1 type Nanobodies or VHH1 type immunoglobulin single variable domains.

Example 7

Evaluation of Different Variants of 04E09

A mutant of Nanobody 04E09 was constructed, in which Leu49 was replaced by a less bulky Ser residue (L49S, SEQ ID NO: 23). In addition, two variants of clone 04E09 were constructed to explore the importance of the VHH1-specific disulfide bridge (C5OS/C100bG, SEQ ID NO: 24) and the canonical disulfide bridge (C22A/C92S, SEQ ID NO: 25) to potency. Nanobodies with SEQ ID NOs: 23 to 25 were produced as described in Example 1.7.

7.1 Competition FACS

A dilution series from 1 μM down to 0.5 pM of tagged (SEQ ID NO: 6) anti-c-Met Nanobodies with SEQ ID NOs: 23 to 25 were mixed with 0.5 nM biotinylated HGF and incubated at 4° C. for 2 hr with $2 \times 10^5$ BAF3 cells stably transfected with cynomolgus monkey c-Met (cf. Example 3.1). Cells were extensively washed, after which biotinylated HGF bound to cell surface expressed c-Met was detected by streptavidin-PE. Cells were analyzed on a FACSarray flow cytometer as described in earlier examples.

SEQ ID NO: 23 and SEQ ID NO: 25 had an IC50 similar to the parental Nanobody SEQ ID NO: 7 (=04E09-9GS-Alb11). This indicates that the mutations at Kabat positions Leu49 to Ser (L49S, SEQ ID NO: 23) or Cys22 to Ala and Cys92 to Ser (C22A/C92S, SEQ ID NO: 25) had no effect on ligand binding blocking potency. However, the mutations of the Kabat positions Cys50 to Ser and Cys100b to Gly (SEQ ID NO: 24) decrease potency by a factor of ~35.

TABLE 9

Blocking activity of 04E09 mutants as determined by competitions FACS

| ID | IC50 [in M] | % inhibition |
|---|---|---|
| 5D5 mAb | 6.7E−09 (n = 3) | 100 (Reference) |
| 04E09-9GS-Alb11 (SEQ ID NO: 7) | 5.7E−10 | 100 |
| 04E09(L49S)-(SEQ ID NO: 23)* | 6.1E−10 | 100 |

TABLE 9-continued

Blocking activity of 04E09 mutants as determined by competitions FACS

| ID | IC50 [in M] | % inhibition |
|---|---|---|
| 04E09(C50S/C100bG)-(SEQ ID NO: 24)* | 2.0E−08 | 100 |
| 04E09(C22A/C92S)-(SEQ ID NO: 25)* | 4.9E−10 | 101 |

*tagged with 3xFlag-His6 (SEQ ID NO: 6) as described in Example 1.7.

7.2 Phosphorylation Assay

Purified tagged (SEQ ID NO: 6) anti-c-Met Nanobodies with SEQ ID NO: 23 to 25 were characterized in the HGF-dependent phosphorylation assay outlined in Example 1.6. Dilution series of from 1 μM down to 0.23 nM anti-c-Met Nanobodies were co-incubated with 1 nM HGF on A549 cells during 15 min at 37° C. ⅓ of the cell lysate was then applied to the MSD phosphorylated c-Met assay plates. Lysates from duplicate samples were pooled. After washing away unbound material, a sulfo tagged c-Met detection antibody was added and plates were read using the Sector Imager 2400 (MSD).

Mutations at Kabat positions Leu49 to Ser (L49S, SEQ ID NO: 23), or Cys22 to Ala and Cys92 to Ser (C22A/C92S, SEQ ID NO: 25) did not influence Nanobody 04E09 potency. The mutation of Kabat positions Cys50 to Ser and Cys100b to Gly (SEQ ID NO: 24) decreased potency such that barely any inhibitory effect remained (Table 10).

TABLE 10

Inhibition of HGF-dependent c-Met phosphorylation in A549 tumor cells

| ID | IC50 [in M] |
|---|---|
| 04E09-9GS-Alb11 (SEQ ID NO: 7) | 2.3E−09 |
| 04E09(L49S)-(SEQ ID NO: 23)* | 3.1E−09 |
| 04E09(C50S/C100bG)-(SEQ ID NO: 24)* | No curve fit |
| 04E09(C22A/C92S)-(SEQ ID NO: 25)* | 3.8E−09 |

*tagged with 3xFlag-His6 (SEQ ID NO: 6) as described in Example 1.7.

7.3 Affinity Determination of 04E09 Mutants Using Surface Plasmon Resonance

Kinetic analysis of the 04E09 mutants 04E09 (C50S/C100bG, SEQ ID NO: 24) and 04E09 (C22A/C92S, SEQ ID NO: 25) were performed using surface plasmon resonance on the ProteOn (BioRad). The experiment was performed as described in Example 5.

Affinities, on- and off-rates of Nanobodies 04E09-9GS-Alb11 (SEQ ID NO: 7) and 04E09 (C22A/C92S, SEQ ID NO: 25) to recombinant human c-Met/Fc were comparable. 04E09 (C50S/C100bG, SEQ ID NO: 24) had ten-fold lower on-rate and off-rates, which lead to significant lower affinity to recombinant human c-Met/Fc than either 04E09-9GS-Alb11 (SEQ ID NO: 7) or 04E09 (C22A/C92S, SEQ ID NO: 25). None of the analytes showed binding to control recombinant human CTLA4/Fc chimera (cf. Table 11).

TABLE 11

Affinity determination of Nanobodies by surface plasmon resonance

| ID | ka 1/Ms | ka ka error | kd 1/s | kd kd error | KD M |
|---|---|---|---|---|---|
| 04E09-9GS-Alb11 (SEQ ID NO: 7) | 2.89E+06 | 283.3 | 3.89E−05 | 10.7 | 1.35E−11 |
| 04E09(C50S/C100bG)-(SEQ ID NO: 24)* | 1.93E+05 | 88.1 | 7.88E−04 | 66.8 | 4.09E−09 |
| 04E09(C22A/C92S)-(SEQ ID NO: 25)* | 3.37E+06 | 208.0 | 7.90E−05 | 16.2 | 2.34E−11 |

Example 8

Sequence Optimization of Anti-c-Met Nanobodies

In general, during Nanobody® sequence optimization, parental wild type Nanobody® sequences are mutated to yield Nanobody® sequences that are more identical to human VH3-JH germline consensus sequences. Specific amino acids in the framework regions that differ between the Nanobody® and the human VH3-JH germline consensus are altered to the human counterpart in such a way that the protein structure, activity and stability are kept intact. To investigate this, all sequence optimization variants were compared with the parental Nanobody in three different assays: (i) determination of the melting temperature (Tm) in a Thermal Shift Assay (TSA), (ii) analysis of in vitro potency in HGF-competition Alphascreen, (iii) analysis of in vitro potency in the c-Met phosphorylation assay and (iv) analytical size exclusion (SEC) analysis.

In the TSA assay, Nanobodies were diluted to a concentration of 0.2 mg/ml and melting temperature (Tm) was determined at different pH by stepwise increase in temperature in presence of Sypro Orange, a dye that binds to Trp residues that become exposed upon unfolding of the protein, using the Lightcycler (Roche) for detection. The HGF-competition Alphascreen was performed as described in Example 2 (2.3.1). The c-Met phosphorylation assay was performed as described in Example 2 (2.4). In SEC analysis, the Nanobodies were analyzed on a Phenomenex matrix to allow detection of multimers or aggregates.

8.1 Sequence Optimization of 04E09

For sequence optimization, the following mutations were investigated: E1D, A74S, K83R and G88A. One additional mutation, which does not to have an effect on potency or Tm, was introduced during re-cloning: Q108L. 3 individual mutants were generated as depicted in Table 12:

TABLE 12

| Clone number | based on SEQ ID NO | Mutation introduced** |
|---|---|---|
| A00790067* | 114 | Q108L |
| A00790068* | 115 | A74S, K83R, Q108L |
| A00790069* | 116 | A74S, K83R, G88A, Q108L |
| A00790105* | 102 | E1D, A74S, K83R, G88A, Q108L |

*tagged with 3xFlag-His6 (SEQ ID NO: 6) as described in Example 1.7.
**relative to 04E09-9GS-Alb11 (SEQ ID NO: 7)

All constructs were cloned in an *E. coli* expression vector, and expressed in *E. coli* as 3×FLAG-His$_6$-tagged proteins (as described in Example 1.7) in a culture volume of 0.5 L to 1.5 L TB medium. Expression was induced by addition of 1 mM IPTG and allowed to continue for 4 hours at 37° C. and 250 rpm. Cells were pelleted, and periplasmic extracts were prepared by freeze-thawing and resuspension in dPBS. These extracts were used as starting material for immobilized metal affinity chromatography (IMAC) using Histrap FF crude columns (GE healthcare). Nanobodies were eluted from the column with 250 mM imidazole and subsequently desalted towards dPBS. The purity and integrity of Nanobodies was verified by reducing 5D5-PAGE and Western blot using anti-His$_6$ and anti-VHH detection.

As summarized in Table 13, A74S, K83R and Q108L mutations had no clear effect on potency or thermal stability. The G88A mutation led to a ca. 1® C. drop in Tm, but the potency remained rather unchanged. Similarly, the additional mutation E1D did not affect on Tm or potency.

TABLE 13

| | Clone | Tm at pH 7 [in ° C.] | Alphascreen [in pM] IC$_{50}$ | 95% CI | c-Met phosphorylation [in nM] IC$_{50}$ | 95% CI |
|---|---|---|---|---|---|---|
| EXP 1 | A00790067 | 78.1 | 69 | 55-87 | 2.21 | 1.99-2.46 |
| | | | 69 | 57-82 | | |
| | A00790068 | 78.5 | 104 | 85-127 | 1.96 | 1.78-2.15 |
| | | | 72 | 61-85 | | |
| | A00790069 | 76.9 | 107 | 87-131 | 2.05 | 1.83-2.29 |
| | | | 46 | 38-57 | | |
| EXP 2 | A00790069 | 76.5 | 71 | 60-85 | 2.45 | 2.02-2.95 |
| | A00790105 | 76.5 | 61 | 51-73 | 2.33 | 1.92-2.84 |

Furthermore, the behaviour of A00790068 (cf. SEQ ID NO: 115) and A00790069 (cf. SEQ ID NO: 116) in analytic SEC on Phenomenex matrix was similar to that of A00790067 (cf. SEQ ID NO: 114). The Nanobodies eluted at the expected molecular weight and no significant aggregation was observed. A00790105 (cf. SEQ ID NO: 102) showed a small post-peak, which might indicate a low degree of degradation.

In conclusion, Nanobody® sequence optimization resulted in Nanobodies in which protein structure, activity and stability were kept similar vis-à-vis the protein structure, activity and stability of the wildtype clone.

Example 9

In Vivo Efficacy of Nanobody 04E09-9GS-Alb11 in an U87MG Xenograft Model

The anti-tumor effect of the 04E09-9GS-Alb11 Nanobody (SEQ ID NO: 7) was evaluated in a model of human U87 MG (HTB-14, American Type Culture Collection) glioblastoma tumors xenografted in immunodeficient mice. U87MG expresses c-Met as well as the ligand HGF (autocrine loop). Female SWISS Nude mice were subcutaneously injected in the right flank with ten million ($10^7$) U87MG cells to induce tumor growth. Upon reaching a mean tumor volume of 195 mm$^3$, mice were randomized into the 3 treatment groups as outlined in Table 14 and the treatment was initiated. The mice were treated for 3 weeks in total, after which treatment was stopped and the mice were further monitored for tumor relapse for another 5 weeks. During the course of the study, the body weight and tumor volume (mm$^3$) (=(length×width$^2$)/2) were monitored and recorded twice a week. All mice were euthanized at the end of the study, or earlier if the tumor volume was larger than 2000 mm$^3$.

TABLE 14

Overview of the treatment groups, number of animals per group, dose, administration route and treatment schedule in the high dose U87MG xenograft study

| Group | No. Animals | Treatment | Dose | Route | Treatment Schedule |
|---|---|---|---|---|---|
| 1 | 12 | Vehicle (PBS) | 0.2 ml/20 g | IP | 3x/wk |
| 2 | 12 | Anti-c-Met Nanobody 04E09-9GS-Alb11 | 10 mg/kg/adm. | IP | 3x/wk |
| 3 | 8 | Temozolomide | 10 mg/kg/adm. | PO | Q1Dx5 |

Figure 5:
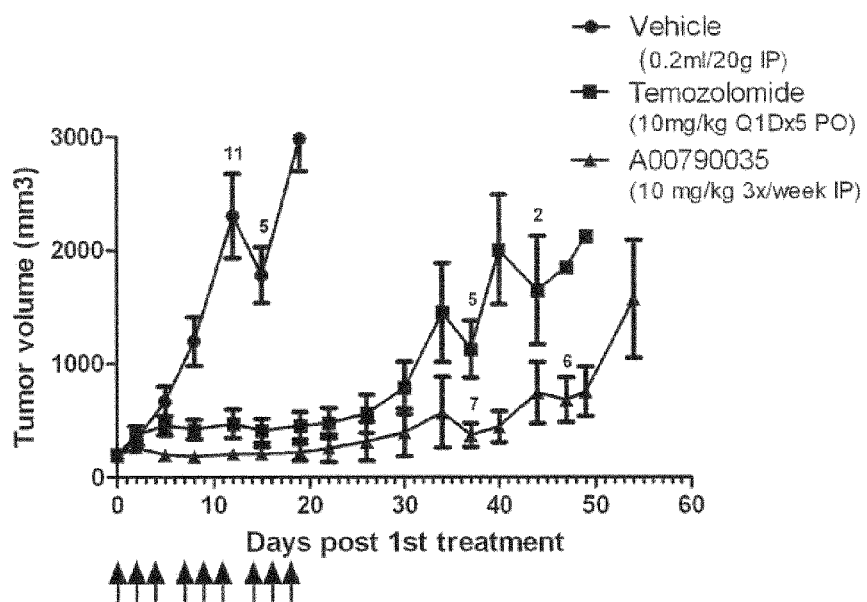
FIG. 5. The effect of A00790035 Nanobody treatment (10 mg/kg; 3x/week (P) on tumor growth in the HGF-dependent U87MG glioblastoma xenograft model. Temozolomide is used as reference compound in the positive control group. The vehicle group is included as negative control group. The arrows represent the different A00790035 administrations. The tumor volume is represented as the mean tumor volume±SE (mm$^3$). The numbers on top of the curves illustrate the number of remaining mice per group at different time points. (A00790035 or Nanobody 4E09-9GS-Alb11; SEQ ID NO: 7)

As shown in FIG. 5, the 04E09-9GS-Alb11 Nanobody (indicated by A00790035 in the figure) showed tumor growth inhibition in the HGF-dependent U87MG xenograft model. This tumor inhibition was shown to be significantly different between the treatment and vehicle group (longitudinal analysis tumor volume, LS means difference at last treatment day; p<0.0001). The T(reated)/C(ontrol) % ratio was analysed, which is a measure of tumor growth inhibition and is defined as the ratio of the median tumor volumes of treated groups versus vehicle treated group. At the end of the treatment (day 19), the % T/C ratio for the A00790035 Nanobody and the reference compound Temozolomide was 7.3% and 15.2%, respectively. Temozolomide Is the standard of care for glioblastoma and was used as positive control to validate the U87MG xenograft model earlier on.

In conclusion, Nanobodies are more effective than Temozolomide in inhibiting HGF-dependent tumors, and in particular glioblastoma.

Example 10

In Vivo Efficacy of Nanobody 04E09-9GS-Alb11 in a KP4 Xenograft Model

The in vivo efficacy of the 04E09-9GS-Alb111 Nanobody (SEQ ID NO: 7) was further evaluated in a second HGF- and c-Met-dependent xenograft model, in which female nu/nu mice were subcutaneously inoculated with ten million ($10^7$) KP4 pancreatic tumor cells (RCB1005, Riken Biosource Center Cell Bank). KP4 cells also have an autocrine loop for HGF and c-Met. After reaching a mean tumor volume of 125 mm$^3$, the mice were randomized into the 3 treatment groups as outlined in Table 15 and the treatment was initiated for a total duration of 15 days. During the course of the study, the body weight and tumor volume (mm$^3$) (=(length×width$^2$)/2) were monitored and recorded three times a week. All mice were kept alive till the study termination.

TABLE 15

Overview of the treatment groups, number of animals per group, dose, administration route and treatment schedule in the high dose KP4 xenograft study

| Group | No. Animals | Treatment | Dose | Route | Treatment Schedule |
|---|---|---|---|---|---|
| 1 | 10 | Vehicle (PBS) | 0.2 ml/20 g | IP | Q2Dx3; 2 |
| 2 | 10 | Anti-c-Met Nanobody 04E09-9GS-Alb11 | 10 mg/kg/adm. | IP | Q2Dx3; 2 |
| 3 | 10 | Gemcitabine | 100 mg/kg/adm. | IP | Q3Dx2; 2 |

Figure 6:
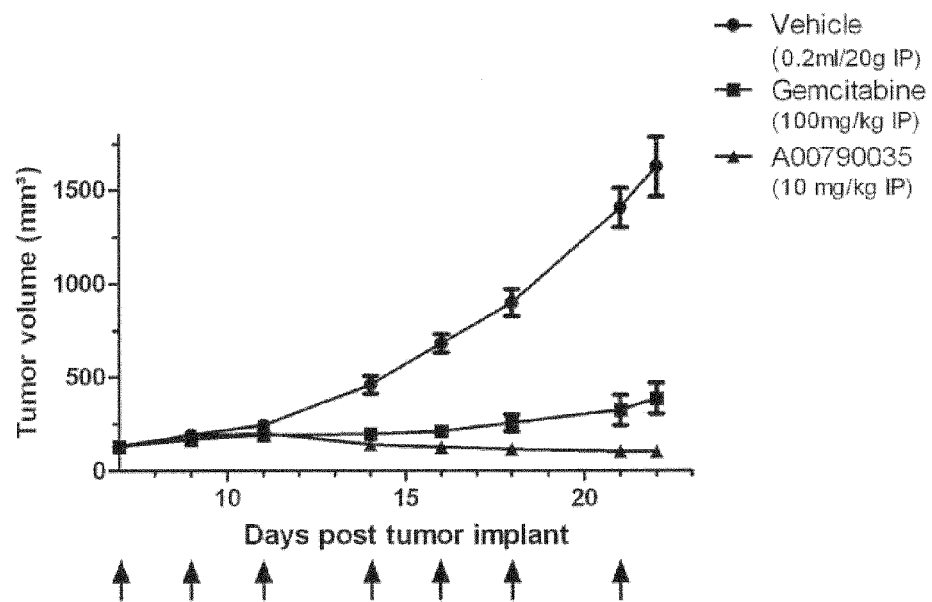
FIG. 6. The effect of A00790035 Nanobody treatment (10 mg/kg; 3x/week IP) on tumor growth in the HGF-dependent KP4 pancreatic xenograft model. Gemcitabine is used as reference compound in the positive control group. The vehicle group is included as negative control group. Arrows represent different A00790035 administrations. Tumor volume is represented as mean tumor volume±SE (mm$^3$). (A00790035 or Nanobody 4E09-9GS-Alb11; SEQ ID NO: 7)

FIG. 6 demonstrates that in this xenograft model the 04E09-9GS-Alb11 Nanobody (indicated by A00790035 in the figure) is capable of inhibiting tumor growth and causing tumor regression. One day after the last administration, a T/C ratio of 6.3% and 23.7% was reached in the 04E09-9GS-Alb11 and gemcitabine treated mice, respectively. Gemcitabine Is the standard of care for pancreatic tumors and was used as positive control to validate the KP4 xenograft model earlier on.

In conclusion, Nanobodies are more effective than Gemcitabine in inhibiting HGF-dependent tumors, and in particular pancreatic tumors. Moreover, Nanobodies facilitate tumor regression.

Example 11

In Vivo Efficacy of Nanobody A00790171

In view of the results provided in Example 10, a sequence optimized variant of 04E09-9GS-Alb11 Nanobody (SEQ ID NO: 7) was constructed, based on A00790105 (cf. Table 12). The sequence optimized variant was denoted A00790171 (A00790105-9GS-Alb11; SEQ ID NO: 113).

The in vivo efficacy of this sequence optimized variant A00790171 is further evaluated in two other HGF autocrine xenograft studies.

Human HGF transgenic C3H-SCID mice are subcutaneously inoculated with human non-small cell lung cancer cells (NSCLC). The A00790171 Nanobody is dosed at a high dose of 10 mg/kg. After onset of cancer, the mice are randomized into the 3 treatment groups: (i) vehicle; (ii) A00790171; and (iii) a positive control. Treatment is initiated for a total duration of 15 days. During the course of the study, the body weight and tumor progression is monitored and recorded three times a week. All mice are kept alive till the study termination.

In order to determine the effective dose of A00790171, a PK/PD study is performed in the KP4 pancreatic xenograft model as detailed in Example 10. The experiments start with a dose ranging from 0.1 to 100 mg/kg to determine the effective dose.

Example 12

Figure 7:
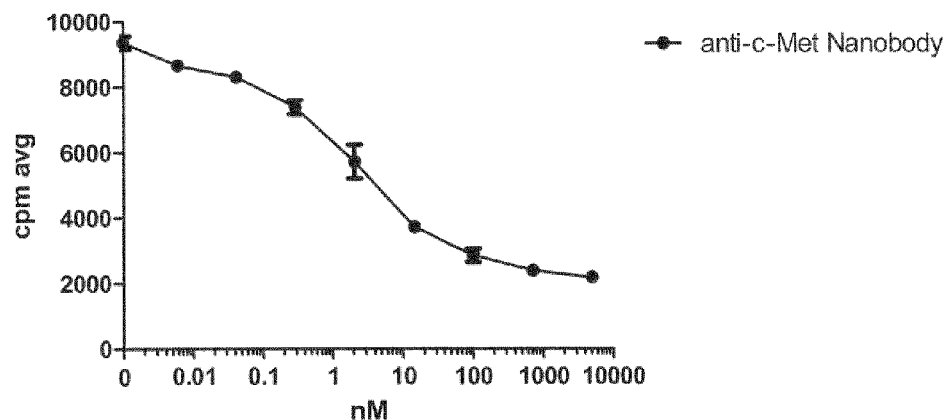
FIG. 7. Complete inhibition of proliferation of ANBL-6 HGF autocrine human multiple myeloma cells following incubation with a dose range series of A00790171. (anti-c-Met Nanobody, A00790171; SEQ ID NO: 113; cpm avg, counts per minute average).
Figure 8:
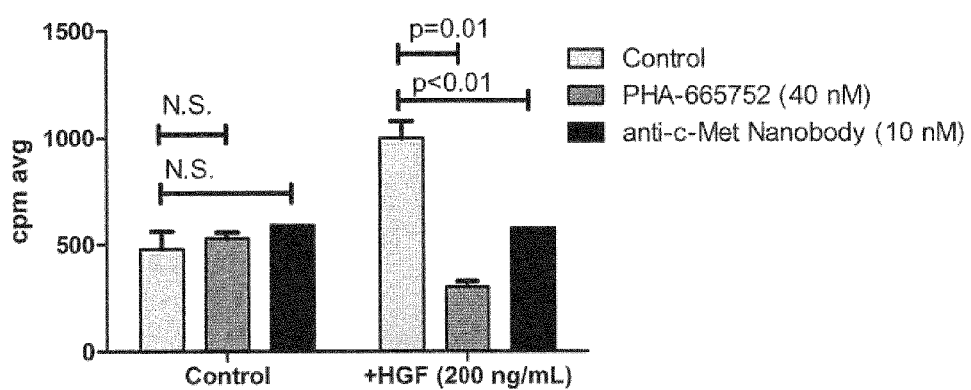
FIG. 8. Complete and specific inhibition of HGF-induced proliferation of INA-6 HGF paracrine human multiple myeloma cells following incubation with 10 nM A00790171. A small molecule c-Met inhibitor PHA-665752 was included as positive control (40 nM). (anti-c-Met Nanobody, A00790171; SEQ ID NO: 113; cpm avg, counts per minute average; p=significance value; N.S., not significant).

In Vitro Efficacy of A00790171 Against HGF-Driven Proliferation and Migration in Multiple Myeloma Cell Lines The in vitro efficacy of A00790171 on HGF induced proliferation and migration was assessed in c-Met positive human multiple myeloma cells. Proliferation experiments were performed according to Hov et al. (Hov et al. 2004; Clin Cancer Res 10, 6686-6694; and Hov et al., 2009; Eur J Haematology 82, 277-287) using HGF autocrine (ANBL-6) as well as paracrine (INA-6 and OH-2) multiple myeloma cell lines. Briefly, cells were cultured (RPMI1640 with 10% fetal calf serum (ANBL-6 and INA-6) or 10% human serum (OH-2), 2 mmol/L L-glutamine and 40 µg/ml gentamicin; 2 ng/ml IL-6 as maintenance factor) and seeded in a 96-well cell culture plate (10.000-30.000 cells/well). After washing the cells in IL-6 free medium, cells were incubated with a dose range series or constant concentration of the A00790171 Nanobody or PHA-665752 as positive control, 30 minutes before addition of HGF (200 ng/ml) (for HGF paracrine cells only). PHA-665752 (Tocris Bioscience) is a small molecule inhibitor of c-Met and other related family members. After 48 hours, cells were pulsed with 1 microCi of methyl-[3H]thymidine per well and harvested 18 hours later to measure the beta irradiation on a Matrix 96 beta counter (Packard). As shown in FIG. 7, complete inhibition of proliferation was observed upon treatment with A00790171 (indicated by anti-c-Met Nanobody in the figure), with an IC50 value of approximately 3 nM and complete inhibition around 1 µM of A00790171. Also in the HGF paracrine cell line INA-6, specific and complete inhibition of HGF-induced proliferation to baseline level was observed upon treatment of the cells with 10 nM of A00790171 (FIG. 8). A00790171 is specific to HGF-induced proliferation and showed no unspecific inhibitory effects at the maximal concentration used (1 µM). Similar experiment in the HGF paracrine OH-2 cell line resulted also in inhibition of a more moderate HGF induced proliferation (data not shown).

Figure 9:
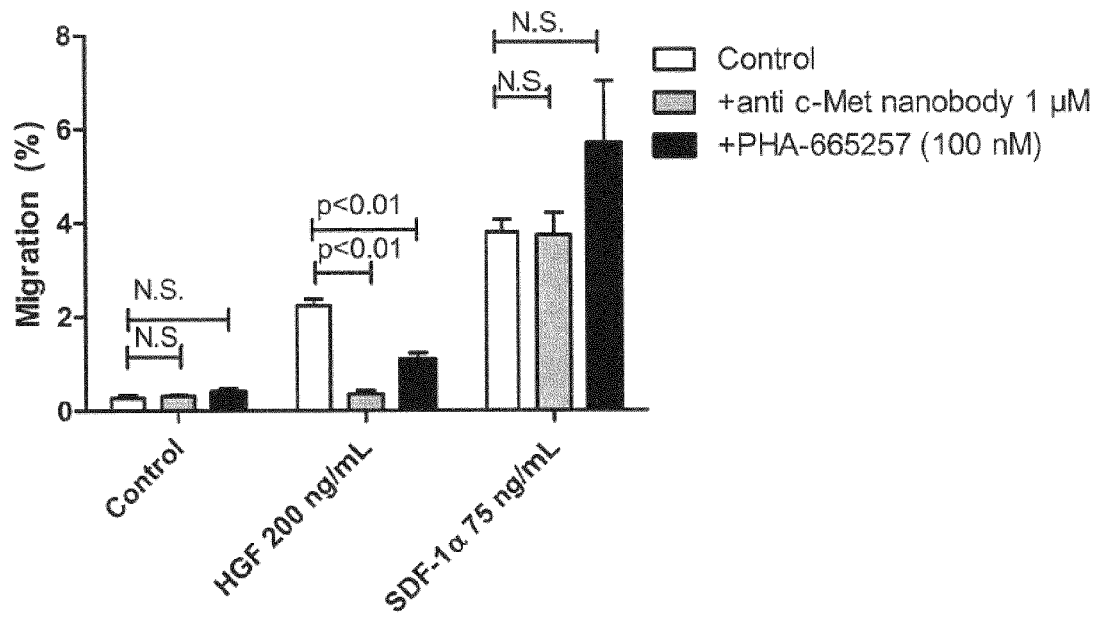
FIG. 9. Complete and specific inhibition of HGF-induced migration of 1NA-6 HGF paracrine human multiple myeloma cells following incubation with 1 μM A00790171. A small molecule c-Met inhibitor PHA-665752 was included as positive control (100 nM). The pro-migratory cytokine SDF-1α was included as positive control for induction of migration. (anti-c-Met Nanobody, A00790171; SEQ ID NO: 113; NS, not significant).

The migration experiments were performed using the INA-6 cells and according to Holt et al. (2008; Haematologica 93, 619-622). Briefly, INA-6 cells were seeded ($4 \times 10^5$ cells) in the upper compartment of a polycarbonate membrane Transwell (Corning; pore size) and incubated with 1 µM A00790171 (indicated by anti-c-Met Nanobody in the figure) or 200 nM of PHA-665752, a small molecule c-Met inhibitor PHA-665752. After 30 minutes, 150 ng/mL HGF was added or 75 ng/mL SDF-1α as positive control promigratory cytokine. After 22-24 hours incubation at 37° C. and 5% $CO_2$, the number of cells that migrated through the membrane to the lower compartment was determined by Coulter Counter Z1 (Beckman Coulter, Fullerton, Calif.). As shown in FIG. 9, A00790171 completely blocked the HGF-induced migration of INA-6 cells. The effect is specific to HGF as SDF-1α-induced migration of INA-6 cells was not inhibited.

In conclusion, A00790171 was able to block proliferation and migration of human HGF autocrine and paracrine multiple myeloma cells in vitro.

Example 13

Analysis of Efficacy of Bispecific c-Met/EGFR Nanobodies on PI3K Signaling

The c-Met as well as the EGFR can signal via the PI3K pathway which conveys mitogenic signals. To demonstrate simultaneous targeting of the EGFR and c-Met receptor phosphorylation of AKT, a downstream target in the PI3K pathway, can be monitored. To this end, unstimulated cells, cells treated with EGF or HGF or cells treated with both cytokines are in parallel incubated with unspecific, parental control or bispecific Nanobodies essentially according to Example 1.6. Alternatively, one can also assess cells which overexpress EGFR and/or have an autocrine HGF loop which activates c-Met signaling. AKT is a major downstream signaling component of the PI3K pathway and phosphorylation of this protein is a key indicator of signaling via this pathway.

Example 14

Analysis of Efficacy of Bispecific c-Met/EGFR Nanobodies on MAPK Signaling

EGFR and c-Met receptor can signal via the MAPK pathway. To demonstrate targeting of the EGFR and c-Met receptor, phosphorylation of ERK1/2, a major downstream target in the MAPK pathway, can be monitored. To this end, unstimulated cells, cells treated with EGF or HGF or cells treated with both cytokines are in parallel incubated with unspecific, monospecific, or bispecific Nanobodies essentially according to Example 1.6. Alternatively, one can also assess cells which overexpress EGFR and/or have an autocrine HGF loop which activates c-Met signaling.

Example 15

Analysis of Efficacy of Bispecific c-Met/EGFR Nanobodies on Inhibiting Proliferation A431 cells display high cell surface levels of EGFR and medium high cell surface expression of c-Met as was independently confirmed in others studies.

Inhibition of A431 proliferation by bispecific c-Met/EGFR Nanobodies can be measured in CellTiterGlow™ assay after 48 hours or essentially as described in Example 2.6.

Example 16

In Vitro Analysis of Migration of Cells after Treatment with Bispecific Nanobodies Active c-Met signaling is involved in cell migration and invasion. Efficacy of the bispecific Nanobody can be determined by measuring inhibition of HGF-induced migration. For this purpose, the HGF-inducible cell line A549 is treated with HGF in the presence or absence of the bispecific Nanobody, monospecific Nanobodies against c-Met and inhibitors of EGFR, essentially as described in Example 2.6. Alternatively, the migration of cells through an 8 μm pore is measured in a time dependent manner on an Acea Real Time analyzer using CIM-plates as a read out.

Example 17

Analysis of Efficacy of Bispecific c-Met/VEGF Nanobodies in a KP4 Pancreatic Xenograft Tumor Model KP4 cells are cultured in growth media that consists of RPMI 1640 media (Invitrogen), 2 mM L-glutamine, and 10% fetal bovine serum. To prepare cells for inoculation into mice, cells are trypsinized and subsequently washed with ten milliliters of sterile IX phosphate buffered saline (PBS). A subset of cells is counted by trypan blue exclusion and the remainder of cells is resuspended in 100 μl of sterile IX PBS to a concentration of $5 \times 10^7$ cells per milliliter. Mice are inoculated subcutaneously in the right sub-scapular region with $5 \times 10^6$ KP4 cells. Tumors are monitored until they reach a mean volume of 230 mm.

Mice are randomized into 5 groups of ten mice each and treatment is initiated. Mice in Group 1 are treated with monospecific c-Met Nanobody. Mice in Group 2 are treated with monospecific VEGF Nanobody. Mice in Group 3 are treated with a bispecific c-Met/VEGF Nanobody. Mice in Group 4 are treated with a monospecific VEGF Nanobody as well as a monospecific c-Met Nanobody. Mice in Group 5 are treated with a negative control (unrelated Nanobody). Tumor volumes are measured twice per week and animals are monitored for 25 days.

Example 18

Analysis of Efficacy of Bispecific c-Met/VEGF Nanobodies in a NSCLC Xenograft Tumor Model Human NSCLC cells (A549, DSMZ, Braunschweig, Germany) are cultured in growth media that consists of RPMI 1640 media (Invitrogen), 2 mM L-glutamine, and 10% fetal bovine serum. To prepare cells for inoculation into mice, cells are trypsinized and subsequently washed with ten milliliters of sterile IX phosphate buffered saline (PBS). A subset of cells is counted by trypan blue exclusion and the remainder of cells is resuspended in 100 μl of sterile IX PBS to a concentration of $5 \times 10^7$ cells per milliliter. Mice are inoculated subcutaneously in the right sub-scapular region with $5 \times 10^6$ human A549 cells. Tumors are monitored until they reach a mean volume of 200 mm.

Mice are randomized into 5 groups of ten mice each and treatment is initiated. Mice in Group 1 are treated with monospecific c-Met Nanobody. Mice in Group 2 are treated with monospecific VEGF Nanobody. Mice in Group 3 are treated with a bispecific c-Met/VEGF Nanobody. Mice in Group 4 are treated with a monospecific VEGF Nanobody as well as a monospecific c-Met Nanobody. Mice in Group 5 are treated with a negative control (unrelated Nanobody). Tumor volumes are measured twice per week and animals are monitored for 25 days.

Example 19

Analysis of Efficacy of Trispecific c-Met/VEGF/EGFR Nanobodies in a NSCLC Xenograft Tumor Model Human NSCLC cells (A549, DSMZ, Braunschweig, Germany) are cultured in growth media that consists of RPMI 1640 media (Invitrogen), 2 mM L-glutamine, and 10% fetal bovine serum. To prepare cells for inoculation into mice, cells are trypsinized and subsequently washed with ten milliliters of sterile IX phosphate buffered saline (PBS). A subset of cells is counted by trypan blue exclusion and the remainder of cells is resuspended in 100 μl of sterile IX PBS to a concentration of $5 \times 10^7$ cells per milliliter. Mice are inoculated subcutaneously in the right sub-scapular region with $5 \times 10^6$ human A549 cells. Tumors are monitored until they reach a mean volume of 200 mm.

Mice are randomized into 6 groups of ten mice each and treatment is initiated. Mice in Group 1 are treated with a monospecific c-Met Nanobody. Mice in Group 2 are treated with monospecific VEGF Nanobody. Mice in Group 3 are treated with a monospecific EGFR Nanobody. Mice in Group 4 are treated with a monospecific VEGF Nanobody, a monospecific EGFR Nanobody as well as a monospecific c-Met Nanobody. Mice in Group 5 are treated with a trispecific c-Met/VEGF/EGFR Nanobody. Mice in Group 6 are treated with a negative control (unrelated Nanobody). Tumor volumes are measured twice per week and animals are monitored for 25 days.

Example 20

Affinity Maturation of a Selected VHH 20.1 33H10 is Subjected to Two Cycles of Affinity Maturation.

In a first cycle, amino acid substitutions were introduced randomly in both framework (FW) and complementary determining regions (CDR) using the error-prone PCR method. Mutagenesis was performed in a two-round PCR-based approach (Genemorph II Random Mutagenesis kit obtained from Stratagene, La Jolla, Calif., USA) using 1 ng of the 33H10 cDNA template, followed by a second error-prone PCR using 0.1 ng of product of round 1. After a polish step, PCR products were inserted via unique restriction sites into a vector designed to facilitate phage display of the VHH library. Consecutive rounds of in-solution selections were performed using decreasing concentrations of biotinylated recombinant cynomolgus cMet (biot-rcycMet) and trypsin elutions. Affinity-driven selections in a third and fourth round using cold rcycMet (at least 100× excess over biot-rcycMet) were also performed. Individual mutants were produced as recombinant protein using an expression vector derived from pUC19, which contained the LacZ promoter, a resistance gene for ampicillin, a multiple cloning site and an ompA leader sequence (pAX50). E. coli TG1 cells were transformed with the expression vector library and plated on agar plates (LB+Amp+2% glucose). Single colonies were picked from the agar plates and grown in 1 mL 96-deep-well plates. VHH expression was induced by adding IPTG (1 mM). Periplasmic extracts (in a volume of ~80 μL) were prepared according to standard methods and screened for binding to recombinant human cMet/Fc in a Nanobody-competition Alphascreen assay (as outlined under 2.3.1) and in a ProteOn (BioRad, Hercules, Calif., USA) off-rate assay. In brief, a GLC ProteOn Sensor chip was coated with recombinant human cMet/Fc on one "ligand channel" (with another "ligand channel" as reference channel). Periplasmic extracts of affinity matured clones were diluted 1/10 and injected across the "analyte channels" A1-A6. An average off-rate was calculated of the parental clones present in the plate and served as a reference to calculate off-rate improvements.

In a second cycle, a combinatorial library was created by simultaneously randomising the susceptible positions identified in cycle one. For this, the full length 33H10 cDNA was synthesized by overlap PCR using oligonucleotides degenerated (NNS) at the randomisation positions and a rescue PCR was performed. The randomised VHH genes were inserted into a phage display vector (pAX212) using specific restriction sites as described above. Preparation of periplasmic extracts of individual VHH clones were performed as described before.

In the TSA assay, Nanobodies were diluted to a concentration of 0.2 mg/ml and melting temperature (Tm) was determined at different pH by stepwise increase in temperature in presence of Sypro Orange, a dye that binds to Trp residues that become exposed upon unfolding of the protein, using the Lightcycler (Roche) for detection. The HGF-competition Alphascreen was performed as described in Example 2 (2.3.1). In SEC analysis, the Nanobodies were analyzed on a Phenomenex matrix to allow detection of multimers or aggregates.

Example 21

Sequence Optimization of 33H10

For sequence optimization, the following mutations were investigated: E1D, A14P, E43K, S71R, S72D, A74S, N82bS, and Q108L. 16 individual mutants were generated as described in Table 16 (SEQ ID NOs: 117-132).

All constructs were cloned in an E. coli expression vector, and expressed in E. coli as 3×FLAG-His$_6$-tagged proteins in a culture volume of 0.5 L to 1.5 L TB medium. Expression was induced by addition of 1 mM IPTG and allowed to continue for 4 hours at 37° C. and 250 rpm. Cells were pelleted, and periplasmic extracts were prepared by freeze-thawing and resuspension in dPBS. These extracts were used as starting material for immobilized metal affinity chromatography (IMAC) using Histrap FF crude columns (GE healthcare). Nanobodies were eluted from the column with 250 mM imidazole and subsequently desalted towards D-PBS. The purity and integrity of Nanobodies was verified by reducing 5D5-PAGE and Western blot using anti-His$_6$ and anti-VHH detection.

TABLE 16

| Clone number | Mutation introduced* | SEQ ID NO |
|---|---|---|
| A007900738 | A14P, A74S | 117 |
| A007900739 | A14P, A74S, N82bS | 118 |
| A007900740 | A14P, S72D, A74S | 119 |
| A007900741 | A14P, S72D, A74S, N82bS | 120 |
| A007900742 | A14P, S71R, A74S | 121 |
| A007900743 | A14P, S72D, A74S | 122 |
| A007900744 | A14P, S71R, A74S, N82bS | 123 |
| A007900745 | A14P, S71R, S72D, A74S, N82bS | 124 |
| A007900746 | A14P, E43K, A74S | 125 |
| A007900747 | A14P, E43K, A74S, N82bS | 126 |
| A007900748 | A14P, E43K, S72D, A74S | 127 |
| A007900749 | A14P, E43K, S72D, A74S, N82bS | 128 |
| A007900750 | A14P, E43K, S71R, A74S | 129 |
| A007900751 | A14P, E43K, S71R, S72D, A74S | 130 |
| A007900752 | A14P, E43K, S71R, A74S, N82bS | 131 |
| A007900753 | A14P, E43K, S71R, S72D, A74S, N82bS | 132 |

*relative to A007900184 (SEQ ID NO: 151).

The purified Nanobodies were tested in three different assays: (i) determination of the melting temperature (Tm) in a Thermal Shift Assay (TSA), (ii) analysis of in vitro potency in HGF-competition Alphascreen, and (iii) analytical size exclusion (SEC) analysis.

In the TSA assay, Nanobodies were diluted to a concentration of 0.2 mg/ml and melting temperature (Tm) was determined at different pH by stepwise increase in temperature in presence of Sypro Orange, a dye that binds to Trp residues that become exposed upon unfolding of the protein, using the Lightcycler (Roche) for detection. The HGF-competition Alphascreen was performed as described in Example 2 (2.3.1). In SEC analysis, the Nanobodies were analyzed on a Phenomenex matrix to allow detection of multimers or aggregates.

As summarized in Table 17, the S71R mutation had a detrimental effect on potency, and will be excluded from the final sequence optimized clone; the Tm slightly increased by ca. 0.5° C. The E43K mutation had a slightly detrimental effect on the potency; the Tm increased by 3 to 4° C. indicating an increased stability of the clone; this mutation will be re-tested in combination with affinity maturation mutations. All other mutations did not affect potency, and will be included in the sequence optimization.

TABLE 17

| Clone | Tm at pH 7.5 [in ° C.] | Alphascreen [in nM] IC$_{50}$ | 95% CI |
|---|---|---|---|
| A007900184 (wt) | 69.9 | 0.78 | 0.59-1.10 |
| A007900738 | 69.8 | 0.69 | 0.52-0.91 |
| A007900739 | 67.7 | 0.58 | 0.44-0.76 |
| A007900740 | 73.6 | 1.10 | 0.80-1.40 |
| A007900741 | 71.9 | 0.85 | 0.64-1.10 |
| A007900742 | 70.2 | 8.30 | 6.30-11.0 |
| A007900743 | 73.6 | 26.0 | 20.0-34.0 |
| A007900744 | 67.7 | 11.0 | 8.10-14.0 |
| A007900745 | 71.1 | 18.0 | 13.0-24.0 |
| A007900746 | 73.6 | 2.50 | 1.80-3.40 |
| A007900747 | 71.1 | 2.50 | 1.90-3.40 |
| A007900748 | 77.3 | 3.50 | 2.60-4.70 |
| A007900749 | 75.7 | 3.40 | 2.50-4.50 |
| A007900750 | 74.0 | 42.0 | 32.0-57.0 |
| A007900751 | 76.5 | 100 | 65.0-150 |
| A007900752 | 72.3 | 31.0 | 23.0-40.0 |
| A007900753 | 74.8 | 100 | 67.0-160 |

Furthermore, the mobility of the clones A007900738 to A007900753 in analytic SEC on Phenomenex matrix was similar to that of the parental clone A007900184. The Nanobodies eluted at the expected molecular weight and no significant aggregation was observed.

In conclusion, Nanobody® sequence optimization resulted in Nanobodies in which protein structure, activity and stability were kept similar vis-à-vis the protein structure, activity and stability of the wildtype clone.

Example 22

Combination of Sequence Optimization and Affinity Maturation Mutations

The mutations identified in Examples 20 and 21 were combined in a set of 9 individual clones as summarized in Table 18.

TABLE 18

| Clone number as 3xFLAG-His$_6$ tagged | Clone number as 9GS-Alb11-Ala format | Mutation introduced* |
|---|---|---|
| A007901245 | A007901255 | A14P; S72D; A74S; N82bS; K83R; E98G; R99L; L100I |
| A007901246 | A007901256 | A14P; T28A; S72D; A74S; N82bS; K83R; E98G; R99L; L100I |
| A007901247 | A007901257 | A14P; E43K; S72D; A74S; N82bS; K83R; E98G; R99L; L100I |
| A007901248 | A007901258 | A14P; T28A; E43K; S72D; A74S; N82bS; K83R; E98G; R99L; L100I |
| A007901249 | A007901259 | A14P; E46L; S72D; A74S; N82bS; K83R; E98G; R99L; L100I |
| A007901250 | A007901260 | A14P; T28A; E46L; S72D; A74S; N82bS; K83R; E98G; R99L; L100I |
| A007901251 | A007901261 | A14P; E43K; E46L; S72D; A74S; N82bS; K83R; E98G; R99L; L100I |
| A007901252 | A007901262 | A14P; T28A; E43K; E46L; S72D; A74S; N82bS; K83R; E98G; R99L; L100I |
| A007901253 | A007901263 | A14P; S62P; S72D; A74S; N82bS; K83R; E98G; R99L; L100I |

*relative to A007900184 (SEQ ID NO: 151).

The constructs A007901245 to A007901253 (SEQ ID NOs: 133-141) were cloned in an *E. coli* expression vector, and expressed in *E. coli* as 3xFLAG-His$_6$-tagged proteins in a culture volume of 0.5 L to 1.5 L TB medium. Expression was induced by addition of 1 mM IPTG and allowed to continue for 4 hours at 37° C. and 250 rpm. Cells were pelleted, and periplasmic extracts were prepared by freeze-thawing and resuspension in dPBS. These extracts were used as starting material for immobilized metal affinity chromatography (IMAC) using Histrap FF crude columns (GE healthcare). Nanobodies were eluted from the column with 250 mM imidazole and subsequently desalted towards D-PBS. The purity and integrity of Nanobodies was verified by reducing 5D5-PAGE and Western blot using anti-His$_6$ and anti-VHH detection.

The purified Nanobodies were tested in three different assays: (i) determination of the melting temperature (Tm) in a Thermal Shift Assay (TSA), (ii) analysis of in vitro potency in HGF-competition Alphascreen, (iii) cell-based cMet phosphorylation assay, (iv) cell-based proliferation assay, and (v) analytical size exclusion (SEC) analysis.

The TSA assay was performed as outlined above. The HGF-competition Alphascreen was performed as described in Example 2 (2.3.1). The cell-based cMet phosphorylation assay was performed as outlined in Example 1.6. The cell-based proliferation assay was performed as outlined in Example 2.5. In SEC analysis, the Nanobodies were analyzed on a Phenomenex matrix to allow detection of multimers or aggregates.

TABLE 19

| Clone number | Tm at pH 7.5 [in ° C.] | Alphascreen [in pM] IC$_{50}$ | 95% CI | c-Met phosphorylation [in nM] IC$_{50}$ | 95% CI | Proliferation assay [in nM] IC$_{50}$ | 95% CI |
|---|---|---|---|---|---|---|---|
| A007900184 | 70.3 | 610 | 560-680 | 79* | | | |
| A007901245 | 69.4 | 92 | 85-100 | 5.41 | 3.71-7.88 | 3.69[A] | 2.57-5.29[A] |
| A007901246 | 69.0 | 89 | 80-99 | 3.44 | 2.31-5.13 | 1.88[A] | 1.29-2.75[A] |
| A007901247 | 72.7 | 270 | 250-300 | 12.8 | 8.91-18.5 | | |
| A007901248 | 72.7 | 170 | 160-190 | 11.5 | 8.30-15.8 | | |
| A007901249 | 68.6 | 80 | 72-90 | 2.81 | 2.07-3.81 | 1.93[B] | 1.09-3.40[B] |
| A007901250 | 68.2 | 81 | 73-91 | 2.34 | 1.64-3.36 | 2.29[A] | 1.58-3.34[A] |
| | | | | | | 1.32[B] | 0.80-2.20[B] |
| A007901251 | 67.3 | 68 | 59-78 | 4.98 | 3.58-6.94 | | |
| A007901252 | 67.3 | 120 | 110-130 | 4.16 | 3.02-5.73 | | |
| A007901253 | 66.5 | 71 | 65-78 | 4.84 | 3.57-6.57 | | |

*IC50 was not correctly determined for missing sufficient amount of top plateau level data points.

[A],[B] data points from 1 or 2, respectively, performed in parallel

A sub-selection of Nanobodies were fused at their C-terminus to an anti-human serum albumin (HSA) binding Nanobody (ALB11), separated by a 9GS-linker. Constructs had an additional C-terminal alanine residue.

Nanobodies were expressed in *P. pastoris* in a culture volume of 5 mL. Nanobody expression was induced by addition of methanol and allowed to continue for 48 hours at 30° C. The cleared supernatants were used as starting material for purification by ProteinA affinity chromatography (MabCapA POROS, Applied Biosystems).

The Nanobodies were tested in a thermal shift assay, by analytical sizing, and in the HGF-competition Alphascreen; the latter was modified (as compared to the initially described set-up) for higher sensitivity by increasing the concentration of biotinylated HGF from 0.1 nM to 0.4 nM, and lowering the concentration of cMet/Fc from 0.1 nM to 0.016 nM (see Table 20).

The mobility of the clones A007901255 to A007901260 in analytic SEC on Phenomenex matrix was similar: The Nanobodies eluted at the expected molecular weight and no significant aggregation was observed.

TABLE 20

| | | Alphascreen [in pM] | | | |
| --- | --- | --- | --- | --- | --- |
| | | monovalent form | | 9GS-Alb11-Ala fusion | |
| Clone number | Tm at pH 7.5 [in ° C.] | $IC_{50}$ | 95% CI | $IC_{50}$ | 95% CI |
| A007901255 | 60.2 | 91 | 82-100 | 93 | 66-130 |
| A007901256 | 59.8 | 48 | 40-58 | 85 | 64-110 |
| A007901259 | 59.4 | 43 | 35-53 | 59 | 46-75 |
| A007901260 | 59.4 | 35 | 27-47 | 64 | 46-89 |

Example 23

Soluble c-Met Response to Nanobody 04E09-9GS-Alb11 in a KP4 Xenograft Model

The response of soluble c-Met to treatment with the 04E09-9GS-Alb11 Nanobody (clone A00790035, SEQ ID NO: 7) was further evaluated in a HGF- and c-Met-dependent xenograft model, in which female nu/nu mice were subcutaneously inoculated with ten million ($10^7$) KP4 pancreatic tumor cells (RCB100S, Riken Biosource Center Cell Bank). KP4 cells also have an autocrine loop for HGF and c-Met. After reaching a mean tumor volume of 125 mm³, the mice were randomized to treatment with the 04E09-9GS-Alb11 Nanobody (10 mg/kg i.p. Q2D×3) or vehicle (PBS, 10 ml/kg i.p.). Mice were treated for 15 days. Twenty-four hours after the final dose (i.e. day 22 following tumour implantation) all of the mice treated with A00790035 or vehicle were euthanized via over exposure to carbon dioxide for blood collection. Whole blood was collected via terminal cardiac puncture. To ensure thorough mixing of the blood and EDTA, the EDTA Microtainer tubes were inverted several times. The samples were then centrifuged (9300 rcf) at 4° C. for 5 minutes to generate plasma. The plasma was drawn off and placed into labeled microcentrifuge tubes. All plasma samples were frozen and stored at ~80° C. until analysis. Samples were analysed for levels of soluble c-Met using a commercially available, ELISA kit (R&D systems) validated fit for purpose. Soluble c-MET levels are indicated for each animal and the average±the standard error of the mean for both treatment groups.

Figure 10:
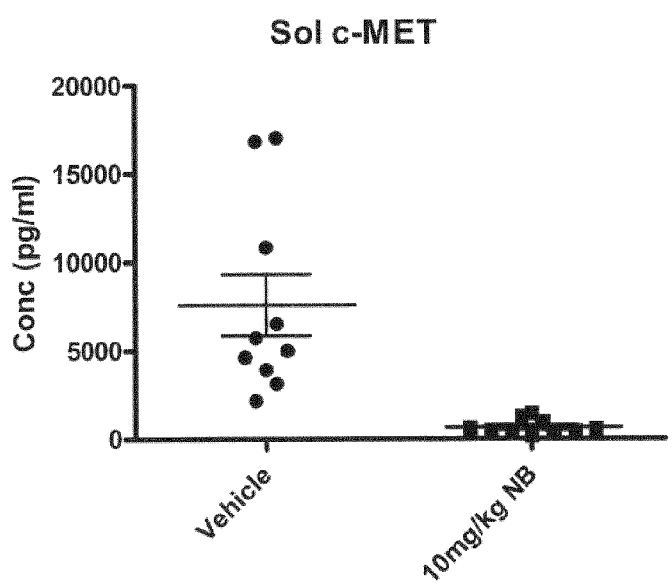
FIG. 10. Soluble c-Met response to Nanobody 04E09-9GS-Alb11 (A00790035, SEQ ID NO: 7) in a KP4 xenograft model. Soluble c-MET levels are indicated for each animal and the average±the standard error of the mean for both treatment groups. Median soluble c-Met levels were greatly reduced in 04E09-9GS-Alb11 Nanobody (NB) treated mice (0.507 ng/ml) as compared to vehicle (PBS, 10 ml/kg i.p.) treated mice (5.348 ng/ml).

As depicted in FIG. 10, median soluble c-Met levels were greatly reduced in 04E09-9GS-Alb11 Nanobody treated mice (0.507 ng/ml) as compared to vehicle treated mice (5.348 ng/ml).

In summary, Nanobodies are effective in reducing soluble c-Met levels. Furthermore, it can be concluded that the amount of soluble c-Met present in a sample provides for a clear indicator of overall tumor burden and highlights the use of this biomarker for monitoring the disease state and the effectiveness of the administered therapy.

Example 24

A00790171 Blocks HGF Mediated Phosphorylation of c-Met and Downstream Signals of MAPK and Akt in INA-6 Multiple Myeloma Cell Line To study the ability of the anti-c-Met Nanobody A00790171 to inhibit HGF mediated signaling through its receptor c-Met, the level of phosphorylation on the c-Met tyrosine epitopes Tyr1234/1235, Tyr1346 and Tyr1003 on c-Met was investigated in the HGF-induced INA-6 multiple myeloma cell line. Also, the phosphorylation of the downstream proteins p44/42 MAPK and Akt (Ser473) was assessed. In parallel, total c-MET, total Akt and GADPH levels were determined. The c-Met tyrosine kinase inhibitor PHA-665752 (200 nM) was used as a positive control (Hov et al. 2004; Clin Cancer Res 10, 6686-6694). Briefly, INA-6 cells were depleted for human serum and IL-6 by four washes Hanks' balanced salt solution (HBSS) (Sigma-Aldrich, St. Louis, Mo., USA), and subsequently starved for 3 hours in a serum-free environment and seeded in 24-well plates (10× 106 cells in 1000 μL RPMI with 0.1% BSA). Cells were preincubated for 20 minutes with A00790171 (0.1, 0.25, 0.5, 1 and 1, 5, 10 and 50 nM in c-Met Tyr phosphorylation experiments; 0.5, 1 and 1 nM in MAPK and Akt phosphorylation experiments) or PHA-665752 (200 nM), and subsequently treated with or without 150-200 ng/mL HGF for 5-7 minutes. After collection and pelleting, cells were resuspended in lysis buffer (1% NP40, 150 mmol/L NaCl, 50 mmol/L TrisHCl 7, 5, 10% glycerol, 1 mmol/L NaF, 2 mmol/L Na3VO4 and a protease-phosphatase inhibitor mixture ((Complete mini tablets, Roche, Basel, Switzerland)). After 30 minutes on ice, the nuclei were pelleted by centrifugation at 12,000×g, 4° C. for 20 minutes. Samples were mixed with lithium dodecyl sulfate sample buffer (Invitrogen, Carslbad, Calif.) with 10 mmol/L dithiothreitol, heated for 2 minutes at 98° C. and separated on 4-12% or 10% Bis-tris gels (Invitrogen). Proteins were then transferred to a nitrocellulose membrane with iBlot® dry blotting system (Invitrogen). Membranes were blocked with 5% BSA or 5% nonfat dried milk in Tris-buffered saline with 0.05% Tween 20 and incubated with antibodies against phosphorylated proteins overnight at 4° C. Detection was performed with horseradish peroxidase-conjugated antibodies (DAKO Cytomation, Copenhagen, Denmark) and Supersignal® West Femto Maxiumum Sensitivity Substrate (Thermo scientific, Rockford, Ill., USA). The membranes were stripped at 60° C. for 30 minutes with gentle rotation in stripping buffer containing 62.5 mmol/L Tris-HCl (pH 6.6), 2% 5D5, and 10 mmol/L 2-mercaptoethanol, then washed in Tris-buffered saline with 0.05% Tween 20, blocked with 5% nonfat dried milk or BSA in Tris-buffered saline with 0.05% Tween 20, and probed with antibodies against non-phospho-epitopes. Antibodies against phosphorylated p44/42 MAPK, total p44/42, phosphorylated Akt, total Akt, phosphorylated c-Met (Tyr1234/1235), phosphorylated C-Met (Tyr1349) and total c-Met were from Cell Signaling Technology (Beverly, Mass.). Antibody recognizing phosphorylated c-Met (Tyr1003) was from Invitrogen (Camarillo, Calif.). Antibody against GAPDH was from Abcam (Cambridge, United Kingdom).

Figure 11:
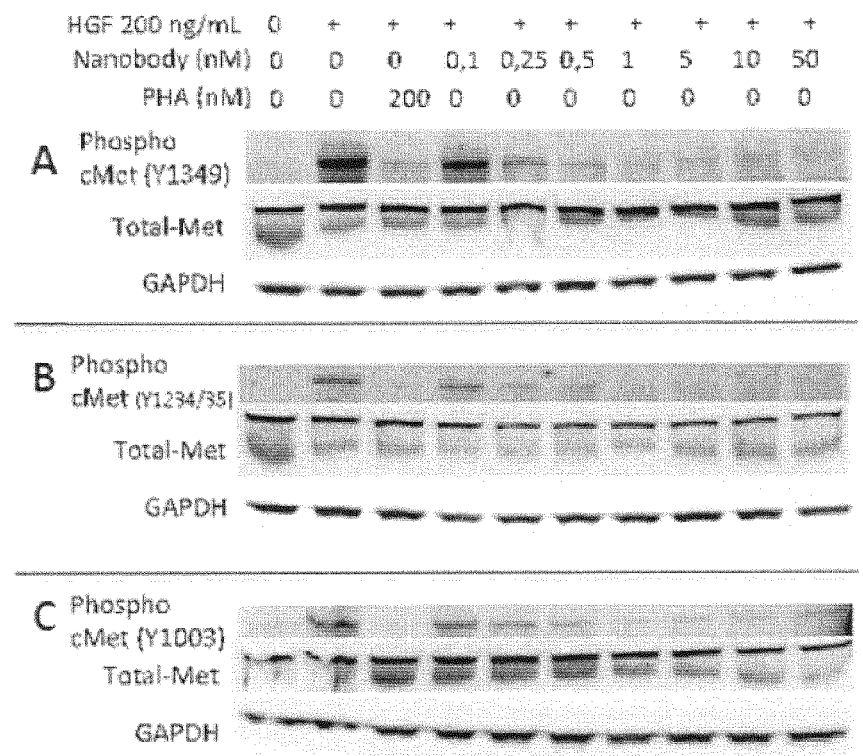
FIG. 11. A00790171 reduces the phosphorylation of the c-Met tyrosine residues Tyr1349 (A), Tyr123435 (B) and Tyr1003 (C) after stimulation with 200 ng/ml HGF in INA-6 cells. PHA-665752 was included as positive control (200 nM). Cells were treated with HGF for 5 minutes before they were lysed and processed for protein gel electrophoresis as total lysates.
Figure 12:
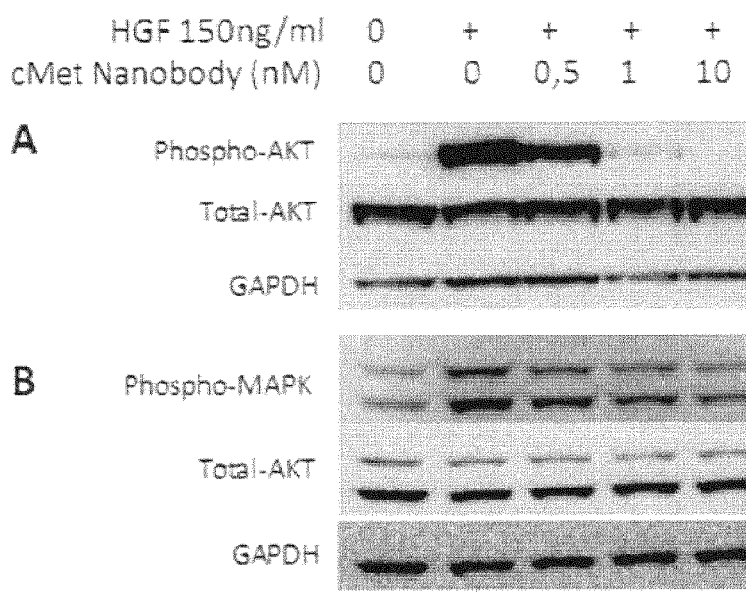
FIG. 12. A00790171 reduces the phosphorylation of Akt (A) and MAPK (B) after stimulation with 150 ng/ml HGF in INA-6 cells. Cells were treated with HGF for 7 minutes before they were lysed and processed for protein gel electrophoresis as total lysates.

As seen in FIG. 11, addition of A00790171 reduced phosphorylation of c-Met at Tyr 1349 (A), Tyr1234/1235 (B) and Tyr1003 (C) after HGF stimulation (200 ng/ml) of INA-6 cells in a dose dependent manner (0.1-1 nM). Nanobody concentrations higher than 1 nM completely blocked c-Met phosphorylation. HGF binding to c-Met is also known to mediate phosphorylation of p44/42 MAPK and Akt. As shown in FIG. 12, A00790171 was able to block the HGF (150 ng/ml) mediated phosphorylation of p44/42 MAPK (FIG. 12A) and Akt (FIG. 12B). In conclusion, A00790171 blocks the phosphorylation of the c-Met Tyrosine residues Tyr 1349, Tyr1234/1235 and Tyr1003 and the phosphorylation of the downstream proteins p44/42 MAPK and Akt (Ser473).

Example 25

Figure 13:
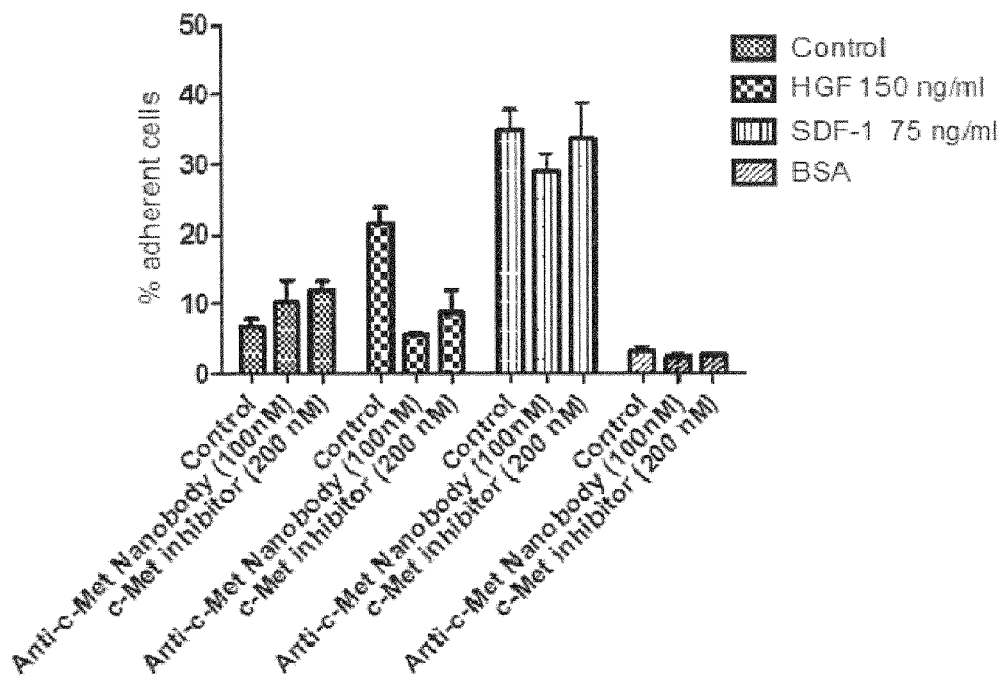
FIG. 13. A00790171 (100 nM) blocks the HGF induced adhesion of 1NA-6 cells to fibronectin. After preincubation with BCECF-AM (a fluorescent dye) 5×10$^4$ cells were incubated for 1 hour with or without the cytokines HGF (150 ng/ml) or SDF-1α (75 ng/ml). Bars represent the mean (+SD) of quadruple samples from one representative of three independent experiments.

Anti-c-Met Nanobody A00790171 Blocks HGF Mediated Adhesion of Human Myeloma Cell Line INA-6 to Fibronectin Adhesion of multiple myeloma cells in the bone marrow is important for growth and survival of myeloma cells. Adhesion of myeloma cells to bone marrow matrix protein is shown to promote drug resistance (Dalton W S, Cancer Treat Rev 2003; 29 Suppl 1:11-9). It was previously shown that HGF stimulates adhesion of myeloma cells to fibronectin (Holt R U et al., 2005, Haematologica, 90(4):479-88). The objective was to investigate what is the effect of A00790171 on the HGF mediated adhesion of INA-6 cells to fibronectin. Briefly, 96-well round-bottomed microplates (Sarstedt, Newston, N.C.) were coated overnight at 4° C. with human plasma fibronectin (20 µg/mL in PBS, 80 µL/well) and blocked with BSA (1 mg/mL, 100 µL/well) for 1 hour at room temperature and finally washed 3 times in HBSS. INA-6 cells were washed three times with HBSS, resuspended in 5 mL RPMI with 0.1% BSA and incubated for 1 hour at 37° C. with 1 µg/mL acetoxymethyl ester-2',7 bis-(2-carboxyethyl)-5-(and 6)-carboxyfluorescein (BCECF-AM), a fluorescent dye, with occasional agitation. After three washes with HBSS, 3-5×10⁴ cells (depending on cell availability) were seeded per well in a total volume of 100 µL and incubated for 2 hours at 37° C. in 5% CO2. Cells were incubated either with BSA as control, HGF (150 ng/ml) or SDF-1α (75 ng/ml) as positive control pro-migratory cytokine. The c-Met tyrosine kinase inhibitor PHA-665752 was used as a positive control. Subsequently plates were carefully washed 4 times in HBSS to remove non-adherent cells. Remaining cells were solubilized in 50 µL/well of 1% Triton X-100. Fluorescence level at 538 nm was determined with VICTOR (PerkinElmer, Waltham, Mass.) fluorescence reader. The HGF (150 ng/ml) induced adhesion to fibronectin is abolished when the INA-6 cells are pre-incubated with 100 nM of A00790171 (FIG. 13). SDF-1α-induced adhesion to fibronectin is not affected significantly by the Nanobody suggesting a c-Met specific effect of the Nanobody. In conclusion, A00790171 blocks the HGF induced adhesion of INA-6 cells to fibronectin.

Example 26

A00790171 Abolishes HGF-Inhibition of Osteoblastogenesis

Osteoblasts and osteoclasts are specialized cells responsible for bone formation and resorption. In myeloma bone disease there is a dysregulation in the bone homeostasis, favoring osteoclastogenesis and inhibition of bone formation. Bone specific alkaline phosphatase (bALP) is produced by osteoblasts. The production of bALP is high during bone formation and bALP is therefore a good indicator of total bone formation activity (van Straalen J P et al., 1991 Clin Chim Acta; 201(1-2):27-33). Histomorphometric studies have shown significant correlations between bALP and the dynamic parameters of bone formation (Abildgaard et al., 2000, Eur J Haematol 2000; 64(2):121-9). HGF is known to have an inhibitory effect on osteoblastogenesis in vitro. bALP activity, which frequently is used as a marker for early osteoblast differentiation, is inhibited by addition of HGF (Standal et al., 2007 Blood; 109(7):3024-30). Also, HGF is known to have an inhibitory effect on the in vitro mineralization of human mesenchymal stem cells (hMSCs). Mineralization of hMSCs can be quantified and visualized by Alizarin Red-S (ARS) staining. In current experiment, the effect of A00790171 on bALP activity and the mineralization of hMSCs was assessed according to the procedures described in Standal et al., 2007 (Blood; 109(7):3024-30).

Figure 14:
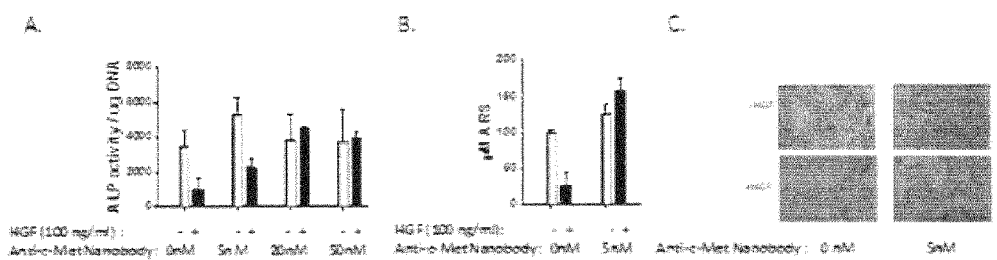
FIG. 14. A00790171 abolishes the inhibiting effect of HGF (100 ng/ml) on BMP-2-induced ALP-activity and mineralization of hMSCs. ALP activity of hMSCs (A). Mineralization of MSCs after 21 days treatment (5 nM A00790171) was quantified (B) or visualized (C) by Alizarin Red-S (ARS) staining.

Anti-c-Met Nanobody A00790171 abolished the inhibiting effect of HGF (100 ng/ml) on BMP_2 induced bALP activity in a dose dependant manner, and at concentrations of 20 nM and higher the inhibitory effect of HGF on bALP activity was completely abolished (FIG. 14A). A00790171 (5 nM) completely reversed the inhibitory effect of HGF (100 ng/ml) on hMSCs mineralization as quantified or visualized after 21 days of treatment (FIG. 14B-C). This supports previous finding. In conclusion, A00790171 abolishes HGF-inhibition of osteoblastogenesis.

The invention claimed is:

1. A method for treatment of pancreatic cancer comprising administering to a subject in need thereof a pharmaceutical composition comprising a polypeptide selected from the group consisting of SEQ ID NO: 7, 104, 106, 108, 110, 113 and 188, wherein tumor volume is reduced.

2. A method for treatment of non-small cell lung cancer (NSCLC) comprising administering to a subject in need thereof a pharmaceutical composition comprising a polypeptide selected from the group consisting of SEQ ID NO: 7, 104, 106, 108, 110, 113 and 188, wherein tumor volume is reduced.

3. A method for treatment of multiple myeloma comprising administering to a subject in need thereof a pharmaceutical composition comprising a polypeptide selected from the group consisting of SEQ ID NO: 7, 104, 106, 108, 110, 113 and 188, wherein myeloma cell proliferation is inhibited.

4. A method for treatment of glioblastoma comprising administering to a subject in need thereof a pharmaceutical composition comprising a polypeptide selected from the group consisting of SEQ ID NO: 7, 104, 106, 108, 110, 113 and 188, wherein tumor volume is reduced.

5. The method of any one of claims 1-4 where the pharmaceutical composition further comprises a pharmaceutically acceptable excipient.

* * * * *

SEQUENCE LISTING

```
<160> NUMBER OF SEQ ID NOS: 190

<210> SEQ ID NO 1
<211> LENGTH: 1390
<212> TYPE: PRT
<213> ORGANISM: Homo sapiens

<400> SEQUENCE: 1

Met Lys Ala Pro Ala Val Leu Ala Pro Gly Ile Leu Val Leu Leu Phe
 1               5                  10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
```

```
                35                  40                  45
Glu Thr Pro Ile Gln Asn Val Ile Leu His Glu His His Ile Phe Leu
 50                  55                  60

Gly Ala Thr Asn Tyr Ile Tyr Val Leu Asn Glu Glu Asp Leu Gln Lys
 65                  70                  75                  80

Val Ala Glu Tyr Lys Thr Gly Pro Val Leu Glu His Pro Asp Cys Phe
                 85                  90                  95

Pro Cys Gln Asp Cys Ser Ser Lys Ala Asn Leu Ser Gly Gly Val Trp
                100                 105                 110

Lys Asp Asn Ile Asn Met Ala Leu Val Val Asp Thr Tyr Tyr Asp Asp
            115                 120                 125

Gln Leu Ile Ser Cys Gly Ser Val Asn Arg Gly Thr Cys Gln Arg His
        130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
        370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
450                 455                 460
```

-continued

```
Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
        755                 760                 765

Ser Val Ser Val Pro Arg Met Val Ile Asn Val His Glu Ala Gly Arg
    770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
        835                 840                 845

Met Ile Ser Met Gly Asn Glu Asn Val Leu Glu Ile Lys Gly Asn Asp
    850                 855                 860

Ile Asp Pro Glu Ala Val Lys Gly Glu Val Leu Lys Val Gly Asn Lys
865                 870                 875                 880
```

```
Ser Cys Glu Asn Ile His Leu His Ser Glu Ala Val Leu Cys Thr Val
            885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
            915                 920                 925

Gln Asn Phe Thr Gly Leu Ile Ala Gly Val Val Ser Ile Ser Thr Ala
            930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
                965                 970                 975

Thr Pro His Leu Asp Arg Leu Val Ser Ala Arg Ser Val Ser Pro Thr
            980                 985                 990

Thr Glu Met Val Ser Asn Glu Ser Val Asp Tyr Arg Ala Thr Phe Pro
            995                 1000                1005

Glu Asp Gln Phe Pro Asn Ser Gln Asn Gly Ser Cys Arg Gln
    1010                1015                1020

Val Gln Tyr Pro Leu Thr Asp Met Ser Pro Ile Leu Thr Ser Gly
    1025                1030                1035

Asp Ser Asp Ile Ser Ser Pro Leu Leu Gln Asn Thr Val His Ile
    1040                1045                1050

Asp Leu Ser Ala Leu Asn Pro Glu Leu Val Gln Ala Val Gln His
    1055                1060                1065

Val Val Ile Gly Pro Ser Ser Leu Ile Val His Phe Asn Glu Val
    1070                1075                1080

Ile Gly Arg Gly His Phe Gly Cys Val Tyr His Gly Thr Leu Leu
    1085                1090                1095

Asp Asn Asp Gly Lys Lys Ile His Cys Ala Val Lys Ser Leu Asn
    1100                1105                1110

Arg Ile Thr Asp Ile Gly Glu Val Ser Gln Phe Leu Thr Glu Gly
    1115                1120                1125

Ile Ile Met Lys Asp Phe Ser His Pro Asn Val Leu Ser Leu Leu
    1130                1135                1140

Gly Ile Cys Leu Arg Ser Glu Gly Ser Pro Leu Val Val Leu Pro
    1145                1150                1155

Tyr Met Lys His Gly Asp Leu Arg Asn Phe Ile Arg Asn Glu Thr
    1160                1165                1170

His Asn Pro Thr Val Lys Asp Leu Ile Gly Phe Gly Leu Gln Val
    1175                1180                1185

Ala Lys Gly Met Lys Tyr Leu Ala Ser Lys Lys Phe Val His Arg
    1190                1195                1200

Asp Leu Ala Ala Arg Asn Cys Met Leu Asp Glu Lys Phe Thr Val
    1205                1210                1215

Lys Val Ala Asp Phe Gly Leu Ala Arg Asp Met Tyr Asp Lys Glu
    1220                1225                1230

Tyr Tyr Ser Val His Asn Lys Thr Gly Ala Lys Leu Pro Val Lys
    1235                1240                1245

Trp Met Ala Leu Glu Ser Leu Gln Thr Gln Lys Phe Thr Thr Lys
    1250                1255                1260

Ser Asp Val Trp Ser Phe Gly Val Leu Leu Trp Glu Leu Met Thr
    1265                1270                1275

Arg Gly Ala Pro Pro Tyr Pro Asp Val Asn Thr Phe Asp Ile Thr
```

-continued

```
            1280                1285                1290

Val Tyr Leu Leu Gln Gly Arg Arg Leu Leu Gln Pro Glu Tyr Cys
            1295                1300                1305

Pro Asp Pro Leu Tyr Glu Val Met Leu Lys Cys Trp His Pro Lys
            1310                1315                1320

Ala Glu Met Arg Pro Ser Phe Ser Glu Leu Val Ser Arg Ile Ser
            1325                1330                1335

Ala Ile Phe Ser Thr Phe Ile Gly Glu His Tyr Val His Val Asn
            1340                1345                1350

Ala Thr Tyr Val Asn Val Lys Cys Val Ala Pro Tyr Pro Ser Leu
            1355                1360                1365

Leu Ser Ser Glu Asp Asn Ala Asp Asp Glu Val Asp Thr Arg Pro
            1370                1375                1380

Ala Ser Phe Trp Glu Thr Ser
            1385                1390

<210> SEQ ID NO 2
<211> LENGTH: 1152
<212> TYPE: PRT
<213> ORGANISM: Artificial Sequence
<220> FEATURE:
<223> OTHER INFORMATION: chimera

<400> SEQUENCE: 2

Glu Cys Lys Glu Ala Leu Ala Lys Ser Glu Met Asn Val Asn Met Lys
1               5                   10                  15

Tyr Gln Leu Pro Asn Phe Thr Ala Glu Thr Pro Ile Gln Asn Val Ile
            20                  25                  30

Leu His Glu His His Ile Phe Leu Gly Ala Thr Asn Tyr Ile Tyr Val
        35                  40                  45

Leu Asn Glu Glu Asp Leu Gln Lys Val Ala Glu Tyr Lys Thr Gly Pro
    50                  55                  60

Val Leu Glu His Pro Asp Cys Phe Pro Cys Gln Asp Cys Ser Ser Lys
65                  70                  75                  80

Ala Asn Leu Ser Gly Gly Val Trp Lys Asp Asn Ile Asn Met Ala Leu
                85                  90                  95

Val Val Asp Thr Tyr Tyr Asp Asp Gln Leu Ile Ser Cys Gly Ser Val
            100                 105                 110

Asn Arg Gly Thr Cys Gln Arg His Val Phe Pro His Asn His Thr Ala
        115                 120                 125

Asp Ile Gln Ser Glu Val His Cys Ile Phe Ser Pro Gln Ile Glu Glu
    130                 135                 140

Pro Ser Gln Cys Pro Asp Cys Val Val Ser Ala Leu Gly Ala Lys Val
145                 150                 155                 160

Leu Ser Ser Val Lys Asp Arg Phe Ile Asn Phe Phe Val Gly Asn Thr
                165                 170                 175

Ile Asn Ser Ser Tyr Phe Pro Asp His Pro Leu His Ser Ile Ser Val
            180                 185                 190

Arg Arg Leu Lys Glu Thr Lys Asp Gly Phe Met Phe Leu Thr Asp Gln
        195                 200                 205

Ser Tyr Ile Asp Val Leu Pro Glu Phe Arg Asp Ser Tyr Pro Ile Lys
    210                 215                 220

Tyr Val His Ala Phe Glu Ser Asn Asn Phe Ile Tyr Phe Leu Thr Val
225                 230                 235                 240

Gln Arg Glu Thr Leu Asp Ala Gln Thr Phe His Thr Arg Ile Ile Arg
```

```
                    245                 250                 255
        Phe Cys Ser Ile Asn Ser Gly Leu His Ser Tyr Met Glu Met Pro Leu
                        260                 265                 270

Glu Cys Ile Leu Thr Glu Lys Arg Lys Lys Arg Ser Thr Lys Lys Glu
                        275                 280                 285

Val Phe Asn Ile Leu Gln Ala Ala Tyr Val Ser Lys Pro Gly Ala Gln
                        290                 295                 300

Leu Ala Arg Gln Ile Gly Ala Ser Leu Asn Asp Asp Ile Leu Phe Gly
        305                 310                 315                 320

Val Phe Ala Gln Ser Lys Pro Asp Ser Ala Glu Pro Met Asp Arg Ser
                        325                 330                 335

Ala Met Cys Ala Phe Pro Ile Lys Tyr Val Asn Asp Phe Phe Asn Lys
                        340                 345                 350

Ile Val Asn Lys Asn Asn Val Arg Cys Leu Gln His Phe Tyr Gly Pro
                        355                 360                 365

Asn His Glu His Cys Phe Asn Arg Thr Leu Leu Arg Asn Ser Ser Gly
                        370                 375                 380

Cys Glu Ala Arg Arg Asp Glu Tyr Arg Thr Glu Phe Thr Thr Ala Leu
        385                 390                 395                 400

Gln Arg Val Asp Leu Phe Met Gly Gln Phe Ser Glu Val Leu Leu Thr
                        405                 410                 415

Ser Ile Ser Thr Phe Ile Lys Gly Asp Leu Thr Ile Ala Asn Leu Gly
                        420                 425                 430

Thr Ser Glu Gly Arg Phe Met Gln Val Val Val Ser Arg Ser Gly Pro
                        435                 440                 445

Ser Thr Pro His Val Asn Phe Leu Leu Asp Ser His Pro Val Ser Pro
                        450                 455                 460

Glu Val Ile Val Glu His Thr Leu Asn Gln Asn Gly Tyr Thr Leu Val
        465                 470                 475                 480

Ile Thr Gly Lys Lys Ile Thr Lys Ile Pro Leu Asn Gly Leu Gly Cys
                        485                 490                 495

Arg His Phe Gln Ser Cys Ser Gln Cys Leu Ser Ala Pro Pro Phe Val
                        500                 505                 510

Gln Cys Gly Trp Cys His Asp Lys Cys Val Arg Ser Glu Glu Cys Leu
                        515                 520                 525

Ser Gly Thr Trp Thr Gln Gln Ile Cys Leu Pro Ala Ile Tyr Lys Val
                        530                 535                 540

Phe Pro Asn Ser Ala Pro Leu Glu Gly Gly Thr Arg Leu Thr Ile Cys
        545                 550                 555                 560

Gly Trp Asp Phe Gly Phe Arg Arg Asn Asn Lys Phe Asp Leu Lys Lys
                        565                 570                 575

Thr Arg Val Leu Leu Gly Asn Glu Ser Cys Thr Leu Thr Leu Ser Glu
                        580                 585                 590

Ser Thr Met Asn Thr Leu Lys Cys Thr Val Gly Pro Ala Met Asn Lys
                        595                 600                 605

His Phe Asn Met Ser Ile Ile Ile Ser Asn Gly His Gly Thr Thr Gln
                        610                 615                 620

Tyr Ser Thr Phe Ser Tyr Val Asp Pro Val Ile Thr Ser Ile Ser Pro
        625                 630                 635                 640

Lys Tyr Gly Pro Met Ala Gly Gly Thr Leu Leu Thr Leu Thr Gly Asn
                        645                 650                 655

Tyr Leu Asn Ser Gly Asn Ser Arg His Ile Ser Ile Gly Gly Lys Thr
                        660                 665                 670
```

```
Cys Thr Leu Lys Ser Val Ser Asn Ser Ile Leu Glu Cys Tyr Thr Pro
            675                 680                 685

Ala Gln Thr Ile Ser Thr Glu Phe Ala Val Lys Leu Lys Ile Asp Leu
        690                 695                 700

Ala Asn Arg Glu Thr Ser Ile Phe Ser Tyr Arg Glu Asp Pro Ile Val
705                 710                 715                 720

Tyr Glu Ile His Pro Thr Lys Ser Phe Ile Ser Gly Gly Ser Thr Ile
                725                 730                 735

Thr Gly Val Gly Lys Asn Leu Asn Ser Val Ser Val Pro Arg Met Val
            740                 745                 750

Ile Asn Val His Glu Ala Gly Arg Asn Phe Thr Val Ala Cys Gln His
        755                 760                 765

Arg Ser Asn Ser Glu Ile Ile Cys Cys Thr Thr Pro Ser Leu Gln Gln
770                 775                 780

Leu Asn Leu Gln Leu Pro Leu Lys Thr Lys Ala Phe Phe Met Leu Asp
785                 790                 795                 800

Gly Ile Leu Ser Lys Tyr Phe Asp Leu Ile Tyr Val His Asn Pro Val
                805                 810                 815

Phe Lys Pro Phe Glu Lys Pro Val Met Ile Ser Met Gly Asn Glu Asn
            820                 825                 830

Val Leu Glu Ile Lys Gly Asn Asp Ile Asp Pro Glu Ala Val Lys Gly
        835                 840                 845

Glu Val Leu Lys Val Gly Asn Lys Ser Cys Glu Asn Ile His Leu His
850                 855                 860

Ser Glu Ala Val Leu Cys Thr Val Pro Asn Asp Leu Leu Lys Leu Asn
865                 870                 875                 880

Ser Glu Leu Asn Ile Glu Trp Lys Gln Ala Ile Ser Ser Thr Val Leu
                885                 890                 895

Gly Lys Val Ile Val Gln Pro Asp Gln Asn Phe Thr His Ile Glu Gly
            900                 905                 910

Arg Met Asp Pro Lys Ser Cys Asp Lys Thr His Thr Cys Pro Pro Cys
        915                 920                 925

Pro Ala Pro Glu Leu Leu Gly Gly Pro Ser Val Phe Leu Phe Pro Pro
930                 935                 940

Lys Pro Lys Asp Thr Leu Met Ile Ser Arg Thr Pro Glu Val Thr Cys
945                 950                 955                 960

Val Val Val Asp Val Ser His Glu Asp Pro Glu Val Lys Phe Asn Trp
                965                 970                 975

Tyr Val Asp Gly Val Glu Val His Asn Ala Lys Thr Lys Pro Arg Glu
            980                 985                 990

Glu Gln Tyr Asn Ser Thr Tyr Arg Val Val Ser Val Leu Thr Val Leu
        995                 1000                1005

His Gln Asp Trp Leu Asn Gly Lys Glu Tyr Lys Cys Lys Val Ser
    1010                1015                1020

Asn Lys Ala Leu Pro Ala Pro Ile Glu Lys Thr Ile Ser Lys Ala
    1025                1030                1035

Lys Gly Gln Pro Arg Glu Pro Gln Val Tyr Thr Leu Pro Pro Ser
    1040                1045                1050

Arg Asp Glu Leu Thr Lys Asn Gln Val Ser Leu Thr Cys Leu Val
    1055                1060                1065

Lys Gly Phe Tyr Pro Ser Asp Ile Ala Val Glu Trp Glu Ser Asn
    1070                1075                1080
```

```
Gly Gln Pro Glu Asn Asn Tyr Lys Thr Thr Pro Pro Val Leu Asp
    1085                1090                1095

Ser Asp Gly Ser Phe Phe Leu Tyr Ser Lys Leu Thr Val Asp Lys
    1100                1105                1110

Ser Arg Trp Gln Gln Gly Asn Val Phe Ser Cys Ser Val Met His
    1115                1120                1125

Glu Ala Leu His Asn His Tyr Thr Gln Lys Ser Leu Ser Leu Ser
    1130                1135                1140

Pro Gly Lys His His His His His His
    1145                1150

<210> SEQ ID NO 3
<211> LENGTH: 1381
<212> TYPE: PRT
<213> ORGANISM: Macaca fascicularis

<400> SEQUENCE: 3

Met Lys Ala Pro Ala Val Leu Val Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Ala Ile Gln Asn Val Ile Leu His Glu His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Asn Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro His
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Ile His Ala Phe Glu Ser Asn
                245                 250                 255

Asn Phe Ile Tyr Phe Leu Thr Val Gln Arg Glu Thr Leu Asn Ala Gln
            260                 265                 270

Thr Phe His Thr Arg Ile Ile Arg Phe Cys Ser Leu Asn Ser Gly Leu
        275                 280                 285

His Ser Tyr Met Glu Met Pro Leu Glu Cys Ile Leu Thr Glu Lys Arg
    290                 295                 300
```

```
Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Ala Glu Phe Thr Thr Ala Leu Gln Arg Val Asp Leu Phe Met Gly
            420                 425                 430

Gln Phe Ser Glu Val Leu Leu Thr Ser Ile Ser Thr Phe Val Lys Gly
        435                 440                 445

Asp Leu Thr Ile Ala Asn Leu Gly Thr Ser Glu Gly Arg Phe Met Gln
450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Pro Leu
                485                 490                 495

Asn Gln Asn Gly Tyr Thr Leu Val Val Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
530                 535                 540

Cys Val Arg Ser Glu Glu Cys Pro Ser Gly Thr Trp Thr Gln Gln Ile
545                 550                 555                 560

Cys Leu Pro Ala Ile Tyr Lys Val Phe Pro Thr Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Ile Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
690                 695                 700

Ser Ile Leu Glu Cys Tyr Thr Pro Ala Gln Thr Ile Ser Thr Glu Phe
705                 710                 715                 720
```

-continued

```
Ala Val Lys Leu Lys Ile Asp Leu Ala Asn Arg Glu Thr Ser Ile Phe
            725                 730                 735
Ser Tyr Arg Glu Asp Pro Ile Val Tyr Glu Ile His Pro Thr Lys Ser
            740                 745                 750
Phe Ile Ser Gly Gly Ser Thr Ile Thr Gly Val Gly Lys Asn Leu His
            755                 760                 765
Ser Val Ser Val Pro Arg Met Val Ile Asn Val His Glu Ala Gly Arg
            770                 775                 780
Asn Phe Thr Val Ala Cys Gln His Arg Ser Asn Ser Glu Ile Ile Cys
785                 790                 795                 800
Cys Thr Thr Pro Ser Leu Gln Gln Leu Asn Leu Gln Leu Pro Leu Lys
                805                 810                 815
Thr Lys Ala Phe Phe Met Leu Asp Gly Ile Leu Ser Lys Tyr Phe Asp
            820                 825                 830
Leu Ile Tyr Val His Asn Pro Val Phe Lys Pro Phe Glu Lys Pro Val
            835                 840                 845
Met Ile Ser Met Gly Asn Glu Asn Val Leu Glu Ile Lys Gly Asn Asp
            850                 855                 860
Ile Asp Pro Glu Ala Val Lys Gly Glu Val Leu Lys Val Gly Asn Lys
865                 870                 875                 880
Ser Cys Glu Asn Ile His Leu His Ser Glu Ala Val Leu Cys Thr Val
                885                 890                 895
Pro Asn Asp Leu Leu Lys Leu Asn Ser Glu Leu Asn Ile Glu Trp Lys
            900                 905                 910
Gln Ala Ile Ser Ser Thr Val Leu Gly Lys Val Ile Val Gln Pro Asp
            915                 920                 925
Gln Asn Phe Thr Gly Leu Ile Ala Gly Val Val Ser Ile Ser Ile Ala
            930                 935                 940
Leu Leu Leu Leu Leu Gly Leu Phe Leu Trp Leu Lys Lys Arg Lys Gln
945                 950                 955                 960
Ile Lys Asp Leu Gly Ser Glu Leu Val Arg Tyr Asp Ala Arg Val His
            965                 970                 975
Thr Pro His Leu Asp Arg Leu Val Ser Ala Arg Ser Val Ser Pro Thr
            980                 985                 990
Thr Glu Met Val Ser Asn Glu Ser Val Asp Tyr Arg Ala Thr Phe Pro
            995                1000                1005
Glu Asp Gln Phe Pro Asn Ser Ser Gln Asn Gly Ser Cys Arg Gln
           1010                1015                1020
Val Gln Tyr Pro Leu Thr Asp Met Ser Pro Ile Leu Thr Ser Gly
           1025                1030                1035
Asp Ser Asp Ile Ser Ser Pro Leu Leu Gln Asn Thr Val His Ile
           1040                1045                1050
Asp Leu Ser Ala Leu Asn Pro Glu Leu Val Gln Ala Val Gln His
           1055                1060                1065
Val Val Ile Gly Pro Ser Ser Leu Ile Val His Phe Asn Glu Val
           1070                1075                1080
Ile Gly Arg Gly His Phe Gly Cys Val Tyr His Gly Thr Leu Leu
           1085                1090                1095
Asp Asn Asp Gly Lys Lys Ile His Cys Ala Val Lys Ser Leu Asn
           1100                1105                1110
Arg Ile Thr Asp Ile Gly Glu Val Ser Gln Phe Leu Thr Glu Gly
           1115                1120                1125
Ile Ile Met Lys Asp Phe Ser His Pro Asn Val Leu Ser Leu Leu
```

```
                    1130                1135                1140

Gly Ile Cys Leu Arg Ser Glu Gly Ser Pro Leu Val Val Leu Pro
    1145                1150                1155

Tyr Met Lys His Gly Asp Leu Arg Asn Phe Ile Arg Asn Glu Thr
    1160                1165                1170

His Asn Pro Thr Val Lys Asp Leu Ile Gly Phe Gly Leu Gln Val
    1175                1180                1185

Ala Lys Gly Met Lys Tyr Leu Ala Ser Lys Lys Phe Val His Arg
    1190                1195                1200

Asp Leu Ala Ala Arg Asn Cys Met Leu Asp Glu Lys Phe Thr Val
    1205                1210                1215

Lys Val Ala Asp Phe Gly Leu Ala Arg Asp Met Tyr Asp Lys Glu
    1220                1225                1230

Tyr Tyr Ser Val His Asn Lys Thr Gly Ala Lys Leu Pro Val Lys
    1235                1240                1245

Trp Met Ala Leu Glu Ser Leu Gln Thr Gln Lys Phe Thr Thr Lys
    1250                1255                1260

Ser Asp Val Trp Ser Phe Gly Val Leu Leu Trp Glu Leu Met Thr
    1265                1270                1275

Arg Gly Ala Pro Pro Tyr Pro Asp Val Asn Thr Phe Asp Ile Thr
    1280                1285                1290

Val Tyr Leu Leu Gln Gly Arg Arg Leu Leu Gln Pro Glu Tyr Cys
    1295                1300                1305

Pro Asp Pro Leu Tyr Glu Val Met Leu Lys Cys Trp His Pro Lys
    1310                1315                1320

Ala Glu Met Arg Pro Ser Phe Ser Glu Leu Val Ser Arg Ile Ser
    1325                1330                1335

Ala Ile Phe Ser Thr Phe Ile Gly Glu His Tyr Val His Val Asn
    1340                1345                1350

Ala Thr Tyr Val Asn Val Lys Cys Val Ala Pro Tyr Pro Ser Leu
    1355                1360                1365

Leu Ser Ser Glu Asp Asn Ala Asp Asp Glu Val Asp Thr
    1370                1375                1380

<210> SEQ ID NO 4
<211> LENGTH: 1176
<212> TYPE: PRT
<213> ORGANISM: Artificial Sequence
<220> FEATURE:
<223> OTHER INFORMATION: chimera

<400> SEQUENCE: 4

Met Lys Ala Pro Ala Val Leu Val Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Ala Ile Gln Asn Val Ile Leu His Glu His His Ile Phe Leu
    50                  55                  60

Gly Ala Thr Asn Tyr Ile Tyr Val Leu Asn Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
```

```
                100             105             110
Lys Asp Asn Ile Asn Met Ala Leu Val Val Asp Thr Tyr Tyr Asp Asp
            115                 120                 125
Gln Leu Ile Ser Cys Gly Ser Val Asn Arg Gly Thr Cys Gln Arg His
            130                 135                 140
Val Phe Pro His Asn His Thr Ala Asp Ile Gln Ser Glu Val His Cys
145                 150                 155                 160
Ile Phe Ser Pro Gln Ile Glu Glu Pro Asn Gln Cys Pro Asp Cys Val
                165                 170                 175
Val Ser Ala Leu Gly Ala Lys Val Leu Ser Val Lys Asp Arg Phe
                180                 185                 190
Ile Asn Phe Phe Val Gly Asn Thr Ile Asn Ser Ser Tyr Phe Pro His
                195                 200                 205
His Pro Leu His Ser Ile Ser Val Arg Arg Leu Lys Glu Thr Lys Asp
            210                 215                 220
Gly Phe Met Phe Leu Thr Asp Gln Ser Tyr Ile Asp Val Leu Pro Glu
225                 230                 235                 240
Phe Arg Asp Ser Tyr Pro Ile Lys Tyr Ile His Ala Phe Glu Ser Asn
                245                 250                 255
Asn Phe Ile Tyr Phe Leu Thr Val Gln Arg Glu Thr Leu Asn Ala Gln
                260                 265                 270
Thr Phe His Thr Arg Ile Ile Arg Phe Cys Ser Leu Asn Ser Gly Leu
            275                 280                 285
His Ser Tyr Met Glu Met Pro Leu Glu Cys Ile Leu Thr Glu Lys Arg
            290                 295                 300
Lys Lys Arg Ser Thr Lys Lys Glu Val Phe Asn Ile Leu Gln Ala Ala
305                 310                 315                 320
Tyr Val Ser Lys Pro Gly Ala Gln Leu Ala Arg Gln Ile Gly Ala Ser
                325                 330                 335
Leu Asn Asp Asp Ile Leu Phe Gly Val Phe Ala Gln Ser Lys Pro Asp
            340                 345                 350
Ser Ala Glu Pro Met Asp Arg Ser Ala Met Cys Ala Phe Pro Ile Lys
            355                 360                 365
Tyr Val Asn Asp Phe Phe Asn Lys Ile Val Asn Lys Asn Asn Val Arg
370                 375                 380
Cys Leu Gln His Phe Tyr Gly Pro Asn His Glu His Cys Phe Asn Arg
385                 390                 395                 400
Thr Leu Leu Arg Asn Ser Ser Gly Cys Glu Ala Arg Arg Asp Glu Tyr
            405                 410                 415
Arg Ala Glu Phe Thr Thr Ala Leu Gln Arg Val Asp Leu Phe Met Gly
            420                 425                 430
Gln Phe Ser Glu Val Leu Leu Thr Ser Ile Ser Thr Phe Val Lys Gly
            435                 440                 445
Asp Leu Thr Ile Ala Asn Leu Gly Thr Ser Glu Gly Arg Phe Met Gln
            450                 455                 460
Val Val Val Ser Arg Ser Gly Pro Ser Thr Pro His Val Asn Phe Leu
465                 470                 475                 480
Leu Asp Ser His Pro Val Ser Pro Glu Val Ile Val Glu His Pro Leu
                485                 490                 495
Asn Gln Asn Gly Tyr Thr Leu Val Val Thr Gly Lys Lys Ile Thr Lys
            500                 505                 510
Ile Pro Leu Asn Gly Leu Gly Cys Arg His Phe Gln Ser Cys Ser Gln
            515                 520                 525
```

```
Cys Leu Ser Ala Pro Pro Phe Val Gln Cys Gly Trp Cys His Asp Lys
            530                 535                 540

Cys Val Arg Ser Glu Glu Cys Pro Ser Gly Thr Trp Thr Gln Gln Ile
545                 550                 555                 560

Cys Leu Pro Ala Ile Tyr Lys Val Phe Pro Thr Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Ile Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu His
        755                 760                 765

Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
        835                 840                 845

Met Ile Ser Met Gly Asn Glu Asn Val Leu Glu Ile Lys Gly Asn Asp
    850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
        915                 920                 925

Gln Asn Phe Thr His Ile Glu Gly Arg Met Asp Pro Lys Ser Cys Asp
    930                 935                 940
```

```
Lys Thr His Thr Cys Pro Cys Pro Ala Pro Glu Leu Leu Gly Gly
945                 950                 955                 960

Pro Ser Val Phe Leu Phe Pro Pro Lys Pro Lys Asp Thr Leu Met Ile
                965                 970                 975

Ser Arg Thr Pro Glu Val Thr Cys Val Val Val Asp Val Ser His Glu
            980                 985                 990

Asp Pro Glu Val Lys Phe Asn Trp Tyr Val Asp Gly Val Glu Val His
        995                 1000                1005

Asn Ala Lys Thr Lys Pro Arg Glu Glu Gln Tyr Asn Ser Thr Tyr
    1010                1015                1020

Arg Val Val Ser Val Leu Thr Val Leu His Gln Asp Trp Leu Asn
    1025                1030                1035

Gly Lys Glu Tyr Lys Cys Lys Val Ser Asn Lys Ala Leu Pro Ala
    1040                1045                1050

Pro Ile Glu Lys Thr Ile Ser Lys Ala Lys Gly Gln Pro Arg Glu
    1055                1060                1065

Pro Gln Val Tyr Thr Leu Pro Pro Ser Arg Asp Glu Leu Thr Lys
    1070                1075                1080

Asn Gln Val Ser Leu Thr Cys Leu Val Lys Gly Phe Tyr Pro Ser
    1085                1090                1095

Asp Ile Ala Val Glu Trp Glu Ser Asn Gly Gln Pro Glu Asn Asn
    1100                1105                1110

Tyr Lys Thr Thr Pro Pro Val Leu Asp Ser Asp Gly Ser Phe Phe
    1115                1120                1125

Leu Tyr Ser Lys Leu Thr Val Asp Lys Ser Arg Trp Gln Gln Gly
    1130                1135                1140

Asn Val Phe Ser Cys Ser Val Met His Glu Ala Leu His Asn His
    1145                1150                1155

Tyr Thr Gln Lys Ser Leu Ser Leu Ser Pro Gly Lys His His His
    1160                1165                1170

His His His
    1175

<210> SEQ ID NO 5
<211> LENGTH: 115
<212> TYPE: PRT
<213> ORGANISM: Artificial Sequence
<220> FEATURE:
<223> OTHER INFORMATION: Nanobody sequence

<400> SEQUENCE: 5

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110
```

```
Val Ser Ser
        115

<210> SEQ ID NO 6
<211> LENGTH: 34
<212> TYPE: PRT
<213> ORGANISM: Artificial Sequence
<220> FEATURE:
<223> OTHER INFORMATION: tag

<400> SEQUENCE: 6

Gly Ala Ala Asp Tyr Lys Asp His Asp Gly Asp Tyr Lys Asp His Asp
1               5                   10                  15

Ile Asp Tyr Lys Asp Asp Asp Lys Gly Ala Ala His His His His
            20                  25                  30

His His

<210> SEQ ID NO 7
<211> LENGTH: 249
<212> TYPE: PRT
<213> ORGANISM: Artificial Sequence
<220> FEATURE:
<223> OTHER INFORMATION: Nanobody sequence

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45

Leu Cys Ile Asp Ala Ser Asp Asp Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Gly Val Tyr Tyr Cys
                85                  90                  95

Ala Thr Pro Ile Gly Leu Ser Ser Cys Leu Leu Glu Tyr Asp Tyr
            100                 105                 110

Asp Tyr Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser
                245
```

```
<210> SEQ ID NO 8
<211> LENGTH: 254
<212> TYPE: PRT
<213> ORGANISM: Artificial Sequence
<220> FEATURE:
<223> OTHER INFORMATION: Nanobody sequence

<400> SEQUENCE: 8

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Ile Ser Arg Tyr
            20                  25                  30

Thr Met Gly Trp Phe Arg Gln Ala Pro Gly Lys Glu Arg Glu Phe Val
        35                  40                  45

Ala Ala Ile Ser Trp Ser Gly Asp Asn Thr Asn Tyr Ala Asp Ser Val
    50                  55                  60

Lys Gly Arg Phe Thr Ile Ser Arg Pro Asn Thr Lys Asn Thr Met Tyr
65                  70                  75                  80

Leu Gln Met Asn Ser Leu Lys Pro Glu Asp Thr Ala Val Tyr Tyr Cys
                85                  90                  95

Ala Ala Asp Tyr Arg Ser Gly Ser Tyr Tyr Gln Ala Ser Glu Trp Thr
            100                 105                 110

Arg Pro Ser Gly Tyr Asp Tyr Trp Gly Gln Gly Thr Leu Val Thr Val
        115                 120                 125

Ser Ser Gly Gly Gly Gly Ser Gly Gly Gly Ser Glu Val Gln Leu Val
    130                 135                 140

Glu Ser Gly Gly Gly Leu Val Gln Pro Gly Asn Ser Leu Arg Leu Ser
145                 150                 155                 160

Cys Ala Ala Ser Gly Phe Thr Phe Ser Ser Phe Gly Met Ser Trp Val
                165                 170                 175

Arg Gln Ala Pro Gly Lys Gly Leu Glu Trp Val Ser Ser Ile Ser Gly
            180                 185                 190

Ser Gly Ser Asp Thr Leu Tyr Ala Asp Ser Val Lys Gly Arg Phe Thr
        195                 200                 205

Ile Ser Arg Asp Asn Ala Lys Thr Thr Leu Tyr Leu Gln Met Asn Ser
    210                 215                 220

Leu Arg Pro Glu Asp Thr Ala Val Tyr Tyr Cys Thr Ile Gly Gly Ser
225                 230                 235                 240

Leu Ser Arg Ser Ser Gln Gly Thr Leu Val Thr Val Ser Ser
                245                 250

<210> SEQ ID NO 9
<211> LENGTH: 249
<212> TYPE: PRT
<213> ORGANISM: Artificial Sequence
<220> FEATURE:
<223> OTHER INFORMATION: Nanobody sequence

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asp Tyr Phe
            20                  25                  30

Ala Ile Gly Trp Phe Arg Gln Ala Pro Gly Lys Glu Arg Glu Glu Ile
        35                  40                  45

Ser Cys Ile Ser Asn Ser Asp Gly Ser Thr Tyr Tyr Ala Asn Ser Val
    50                  55                  60
```

```
Lys Gly Arg Phe Thr Ile Ser Ile Asp Asn Ala Lys Asn Thr Val Tyr
 65                  70                  75                  80

Leu Gln Met Thr Ser Leu Lys Pro Glu Asp Thr Ala Val Tyr Tyr Cys
             85                  90                  95

Ala Thr Pro Val Gly Leu Gly Pro Phe Cys Lys Thr Thr Asn Asp Tyr
            100                 105                 110

Asp Tyr Ser Gly Gln Gly Thr Leu Val Thr Val Ser Ser Gly Gly Gly
            115                 120                 125

Gly Ser Gly Gly Gly Ser Glu Val Gln Leu Val Glu Ser Gly Gly Gly
        130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser
                245

<210> SEQ ID NO 10
<211> LENGTH: 248
<212> TYPE: PRT
<213> ORGANISM: Artificial Sequence
<220> FEATURE:
<223> OTHER INFORMATION: Nanobody sequence

<400> SEQUENCE: 10

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Leu Asp Tyr Tyr
             20                  25                  30

Ala Ile Asn Trp Phe Arg Gln Ala Pro Gly Lys Glu Arg Glu Gly Val
         35                  40                  45

Ser Cys Ile Ser Gly Gly Asp Gly Ser Thr Tyr Tyr Ala Asp Ser Val
     50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
             85                  90                  95

Ala Thr Ala Leu Gly Leu Ser Ser Ser Cys His Gly Asp Gly Tyr Asp
            100                 105                 110

Tyr Trp Gly Gln Gly Thr Leu Val Thr Val Ser Ser Gly Gly Gly Gly
            115                 120                 125

Ser Gly Gly Gly Ser Glu Val Gln Leu Val Glu Ser Gly Gly Gly Leu
        130                 135                 140

Val Gln Pro Gly Asn Ser Leu Arg Leu Ser Cys Ala Ala Ser Gly Phe
145                 150                 155                 160

Thr Phe Ser Ser Phe Gly Met Ser Trp Val Arg Gln Ala Pro Gly Lys
                165                 170                 175
```

```
Gly Leu Glu Trp Val Ser Ser Ile Ser Gly Gly Ser Asp Thr Leu
            180                 185                 190

Tyr Ala Asp Ser Val Lys Gly Arg Phe Thr Ile Ser Arg Asp Asn Ala
        195                 200                 205

Lys Thr Thr Leu Tyr Leu Gln Met Asn Ser Leu Arg Pro Glu Asp Thr
210                 215                 220

Ala Val Tyr Tyr Cys Thr Ile Gly Gly Ser Leu Ser Arg Ser Ser Gln
225                 230                 235                 240

Gly Thr Leu Val Thr Val Ser Ser
                245

<210> SEQ ID NO 11
<211> LENGTH: 275
<212> TYPE: PRT
<213> ORGANISM: Artificial Sequence
<220> FEATURE:
<223> OTHER INFORMATION: Nanobody sequence

<400> SEQUENCE: 11

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Ser Gly Gly Gly
        115                 120                 125

Gly Ser Gly Gly Gly Ser Gly Gly Gly Ser Gly Gly Gly
    130                 135                 140

Ser Gly Gly Gly Ser Glu Val Gln Leu Val Glu Ser Gly Gly Gly
145                 150                 155                 160

Leu Val Gln Pro Gly Gly Ser Leu Arg Leu Ser Cys Ala Ala Ser Gly
                165                 170                 175

Phe Ile Leu Asp Tyr Tyr Ala Ile Gly Trp Phe Arg Gln Ala Pro Gly
            180                 185                 190

Lys Glu Arg Glu Gly Val Leu Cys Ile Asp Ala Ser Asp Ile Thr
        195                 200                 205

Tyr Tyr Ala Asp Ser Val Lys Gly Arg Phe Thr Ile Ser Arg Asp Asn
210                 215                 220

Ala Lys Asn Thr Val Tyr Leu Gln Met Asn Ser Leu Lys Pro Glu Asp
225                 230                 235                 240

Thr Gly Val Tyr Tyr Cys Ala Thr Pro Ile Gly Leu Ser Ser Ser Cys
                245                 250                 255

Leu Leu Glu Tyr Asp Tyr Asp Tyr Trp Gly Gln Gly Thr Leu Val Thr
            260                 265                 270

Val Ser Ser
    275
```

```
<210> SEQ ID NO 12
<211> LENGTH: 249
<212> TYPE: PRT
<213> ORGANISM: Artificial Sequence
<220> FEATURE:
<223> OTHER INFORMATION: Nanobody sequence

<400> SEQUENCE: 12

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Ser Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Ile Leu Asp Tyr Tyr Ala Ile Gly Trp
145                 150                 155                 160

Phe Arg Gln Ala Pro Gly Lys Glu Arg Glu Gly Val Leu Cys Ile Asp
                165                 170                 175

Ala Ser Asp Asp Ile Thr Tyr Tyr Ala Asp Ser Val Lys Gly Arg Phe
            180                 185                 190

Thr Ile Ser Arg Asp Asn Ala Lys Asn Thr Val Tyr Leu Gln Met Asn
        195                 200                 205

Ser Leu Lys Pro Glu Asp Thr Gly Val Tyr Tyr Cys Ala Thr Pro Ile
    210                 215                 220

Gly Leu Ser Ser Ser Cys Leu Leu Glu Tyr Asp Tyr Asp Tyr Trp Gly
225                 230                 235                 240

Gln Gly Thr Leu Val Thr Val Ser Ser
                245

<210> SEQ ID NO 13
<211> LENGTH: 5
<212> TYPE: PRT
<213> ORGANISM: Artificial Sequence
<220> FEATURE:
<223> OTHER INFORMATION: linker

<400> SEQUENCE: 13

Gly Gly Gly Gly Ser
1               5

<210> SEQ ID NO 14
<211> LENGTH: 7
<212> TYPE: PRT
<213> ORGANISM: Artificial Sequence
<220> FEATURE:
<223> OTHER INFORMATION: linker
```

```
<400> SEQUENCE: 14

Ser Gly Gly Ser Gly Gly Ser
1               5

<210> SEQ ID NO 15
<211> LENGTH: 9
<212> TYPE: PRT
<213> ORGANISM: Artificial Sequence
<220> FEATURE:
<223> OTHER INFORMATION: linker

<400> SEQUENCE: 15

Gly Gly Gly Gly Ser Gly Gly Gly Ser
1               5

<210> SEQ ID NO 16
<211> LENGTH: 10
<212> TYPE: PRT
<213> ORGANISM: Artificial Sequence
<220> FEATURE:
<223> OTHER INFORMATION: linker

<400> SEQUENCE: 16

Gly Gly Gly Gly Ser Gly Gly Gly Gly Ser
1               5                   10

<210> SEQ ID NO 17
<211> LENGTH: 15
<212> TYPE: PRT
<213> ORGANISM: Artificial Sequence
<220> FEATURE:
<223> OTHER INFORMATION: linker

<400> SEQUENCE: 17

Gly Gly Gly Gly Ser Gly Gly Gly Ser Gly Gly Gly Gly Ser
1               5                   10                  15

<210> SEQ ID NO 18
<211> LENGTH: 18
<212> TYPE: PRT
<213> ORGANISM: Artificial Sequence
<220> FEATURE:
<223> OTHER INFORMATION: linker

<400> SEQUENCE: 18

Gly Gly Gly Gly Ser Gly Gly Gly Ser Gly Gly Gly Gly Gly
1               5                   10                  15

Gly Ser

<210> SEQ ID NO 19
<211> LENGTH: 20
<212> TYPE: PRT
<213> ORGANISM: Artificial Sequence
<220> FEATURE:
<223> OTHER INFORMATION: linker

<400> SEQUENCE: 19

Gly Gly Gly Gly Ser Gly Gly Gly Gly Ser Gly Gly Gly Ser Gly
1               5                   10                  15

Gly Gly Gly Ser
            20

<210> SEQ ID NO 20
<211> LENGTH: 25
```

-continued

```
<212> TYPE: PRT
<213> ORGANISM: Artificial Sequence
<220> FEATURE:
<223> OTHER INFORMATION: linker

<400> SEQUENCE: 20

Gly Gly Gly Gly Ser Gly Gly Gly Ser Gly Gly Gly Gly Ser Gly
1               5                   10                  15

Gly Gly Gly Ser Gly Gly Gly Gly Ser
            20                  25

<210> SEQ ID NO 21
<211> LENGTH: 30
<212> TYPE: PRT
<213> ORGANISM: Artificial Sequence
<220> FEATURE:
<223> OTHER INFORMATION: linker

<400> SEQUENCE: 21

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 22
<211> LENGTH: 35
<212> TYPE: PRT
<213> ORGANISM: Artificial Sequence
<220> FEATURE:
<223> OTHER INFORMATION: linker

<400> SEQUENCE: 22

Gly Gly Gly Gly Ser Gly Gly Gly Ser Gly Gly Gly Gly Ser Gly
1               5                   10                  15

Gly Gly Gly Ser Gly Gly Gly Ser Gly Gly Gly Ser Gly Gly
            20                  25                  30

Gly Gly Ser
        35

<210> SEQ ID NO 23
<211> LENGTH: 125
<212> TYPE: PRT
<213> ORGANISM: Artificial Sequence
<220> FEATURE:
<223> OTHER INFORMATION: Nanobody sequence

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45

Ser Cys Ile Asp Ala Ser Asp Asp Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Gly Val Tyr Tyr Cys
                85                  90                  95

Ala Thr Pro Ile Gly Leu Ser Ser Cys Leu Leu Gly Tyr Asp Tyr
            100                 105                 110
```

```
Asp Tyr Trp Gly Gln Gly Thr Leu Val Thr Val Ser Ser
        115                 120                 125

<210> SEQ ID NO 24
<211> LENGTH: 125
<212> TYPE: PRT
<213> ORGANISM: Artificial Sequence
<220> FEATURE:
<223> OTHER INFORMATION: Nanobody sequence

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45

Leu Ser Ile Asp Ala Ser Asp Asp Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Gly Val Tyr Tyr Cys
                85                  90                  95

Ala Thr Pro Ile Gly Leu Ser Ser Gly Leu Leu Glu Tyr Asp Tyr
            100                 105                 110

Asp Tyr Trp Gly Gln Gly Thr Leu Val Thr Val Ser Ser
        115                 120                 125

<210> SEQ ID NO 25
<211> LENGTH: 125
<212> TYPE: PRT
<213> ORGANISM: Artificial Sequence
<220> FEATURE:
<223> OTHER INFORMATION: Nanobody sequence

<400> SEQUENCE: 25

Glu Val Gln Leu Val Glu Ser Gly Gly Gly Leu Val Gln Pro Gly Gly
1               5                   10                  15

Ser Leu Arg Leu Ser Ala Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45

Leu Cys Ile Asp Ala Ser Asp Asp Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Gly Val Tyr Tyr Ser
                85                  90                  95

Ala Thr Pro Ile Gly Leu Ser Ser Cys Leu Leu Glu Tyr Asp Tyr
            100                 105                 110

Asp Tyr Trp Gly Gln Gly Thr Leu Val Thr Val Ser Ser
        115                 120                 125

<210> SEQ ID NO 26
<211> LENGTH: 125
<212> TYPE: PRT
<213> ORGANISM: Artificial Sequence
<220> FEATURE:
<223> OTHER INFORMATION: Nanobody sequence
```

```
<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45

Leu Cys Ile Asp Ala Ser Asp Asp Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Gly Val Tyr Tyr Cys
                85                  90                  95

Ala Thr Pro Ile Gly Leu Ser Ser Cys Leu Leu Gly Tyr Asp Tyr
            100                 105                 110

Asp Tyr Trp Gly Gln Gly Thr Leu Val Thr Val Ser Ser
        115                 120                 125

<210> SEQ ID NO 27
<211> LENGTH: 130
<212> TYPE: PRT
<213> ORGANISM: Artificial Sequence
<220> FEATURE:
<223> OTHER INFORMATION: Nanobody sequence

<400> SEQUENCE: 27

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Ile Ser Arg Tyr
            20                  25                  30

Thr Met Gly Trp Phe Arg Gln Ala Pro Gly Lys Glu Arg Glu Phe Val
        35                  40                  45

Ala Ala Ile Ser Trp Ser Gly Asp Asn Thr Asn Tyr Ala Asp Ser Val
    50                  55                  60

Lys Gly Arg Phe Thr Ile Ser Arg Pro Asn Thr Lys Asn Thr Met Tyr
65                  70                  75                  80

Leu Gln Met Asn Ser Leu Lys Pro Glu Asp Thr Ala Val Tyr Tyr Cys
                85                  90                  95

Ala Ala Asp Tyr Arg Ser Gly Ser Tyr Tyr Gln Ala Ser Glu Trp Thr
            100                 105                 110

Arg Pro Ser Gly Tyr Asp Tyr Trp Gly Gln Gly Thr Leu Val Thr Val
        115                 120                 125

Ser Ser
130

<210> SEQ ID NO 28
<211> LENGTH: 125
<212> TYPE: PRT
<213> ORGANISM: Artificial Sequence
<220> FEATURE:
<223> OTHER INFORMATION: Nanobody sequence

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asp Tyr Phe
            20                  25                  30
```

Ala Ile Gly Trp Phe Arg Gln Ala Pro Gly Lys Glu Arg Glu Ile
            35                  40                  45

Ser Cys Ile Ser Asn Ser Asp Gly Ser Thr Tyr Tyr Ala Asn Ser Val
 50                  55                  60

Lys Gly Arg Phe Thr Ile Ser Ile Asp Asn Ala Lys Asn Thr Val Tyr
 65                  70                  75                  80

Leu Gln Met Thr Ser Leu Lys Pro Glu Asp Thr Ala Val Tyr Tyr Cys
                 85                  90                  95

Ala Thr Pro Val Gly Leu Gly Pro Phe Cys Lys Thr Thr Asn Asp Tyr
            100                 105                 110

Asp Tyr Ser Gly Gln Gly Thr Leu Val Thr Val Ser Ser
            115                 120                 125

<210> SEQ ID NO 29
<211> LENGTH: 124
<212> TYPE: PRT
<213> ORGANISM: Artificial Sequence
<220> FEATURE:
<223> OTHER INFORMATION: Nanobody sequence

<400> SEQUENCE: 29

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Leu Asp Tyr Tyr
             20                  25                  30

Ala Ile Asn Trp Phe Arg Gln Ala Pro Gly Lys Glu Arg Glu Gly Val
             35                  40                  45

Ser Cys Ile Ser Gly Gly Asp Gly Ser Thr Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Thr Ala Leu Gly Leu Ser Ser Ser Cys His Gly Asp Gly Tyr Asp
            100                 105                 110

Tyr Trp Gly Gln Gly Thr Leu Val Thr Val Ser Ser
            115                 120

<210> SEQ ID NO 30
<211> LENGTH: 375
<212> TYPE: DNA
<213> ORGANISM: Artificial Sequence
<220> FEATURE:
<223> OTHER INFORMATION: Nanobody sequence

<400> SEQUENCE: 30
gaggtgcaat tggtggagtc tgggggaggc ttggtgcagc ctggggggtc cctgagactc      60
tcctgtgcag cctctggatt cattttggat tattatgcca taggctggtt ccgccaggcc     120
ccagggaagg agcgcgaggg ggtcttatgt attgatgcta gtgatgatat tacatactat     180
gcagactccg tgaagggccg attcaccatc tccagagaca tgccaagaa cacggtgtat     240 ctgcaaatga acagcctgaa acctgaggac acgggcgttt attactgtgc gaccccccatc     300 ggactgagta gtagctgcct acttgaatat gattatgact actggggcca ggggaccctg     360
gtcacggtct cctcc     375

<210> SEQ ID NO 31
<211> LENGTH: 390

```
<212> TYPE: DNA
<213> ORGANISM: Artificial Sequence
<220> FEATURE:
<223> OTHER INFORMATION: Nanobody sequence

<400> SEQUENCE: 31
gaggtgcaat tggtggagtc tgggggagga ttggtgcagg ctgggggctc tctgagactc      60
tcctgtgcag cctctggacg caccatcagt aggtatacca tgggctggtt ccgccaggct     120
ccagggaagg agcgtgagtt tgtagcagct attagctgga gtggtgataa cacaaactat     180
gcagactccg tgaagggccg attcaccatc tccagaccca acaccaagaa cacgatgtat     240
ctgcaaatga acagcctgaa acctgaggac acggccgttt attactgtgc agcagattac     300
cgaagtggta gttactacca ggcatcagag tggacacggc atcggggta tgactactgg      360 ggccagggga ccctggtcac ggtctcctcc                                       390

<210> SEQ ID NO 32
<211> LENGTH: 375
<212> TYPE: DNA
<213> ORGANISM: Artificial Sequence
<220> FEATURE:
<223> OTHER INFORMATION: Nanobody sequence

<400> SEQUENCE: 32
gaggtgcaat tggtggagtc tgggggaggc ttggtgcagc ctgggggtc tctgagactc       60 tcctgtgcag cctctggatt ctctttggat tattttgcca taggctggtt ccgccaggcc     120
ccagggaagg agcgcgagga aatctcatgt attagtaaca gtgatggtag cacatactat     180
gcaaactccg tgaagggccg attcaccatc tccatagaca atgccaagaa cacggtgtat     240
ctgcaaatga caagcctgaa acctgaggac acggccgttt attactgtgc gaccccgtg      300 gggttggggc cattctgtaa gacgaccaat gactatgact acagcggcca ggggaccctg     360
gtcacggtct cctcc                                                      375

<210> SEQ ID NO 33
<211> LENGTH: 372
<212> TYPE: DNA
<213> ORGANISM: Artificial Sequence
<220> FEATURE:
<223> OTHER INFORMATION: Nanobody sequence

<400> SEQUENCE: 33
gaggtgcaat tggtggagtc tgggggaggc ttggtgcagc ctgggggtc tctgagactc       60 tcctgtgcag cctctggatt cactttggat tattatgcca taaactggtt ccgccaggcc     120
ccagggaagg agcgcgaggg ggtctcatgt attagtggtg gtgatggtag cacatactat     180
gcagactccg tgaagggccg attcaccatc tccagagaca atgccaagaa cacggtgtat     240
ctgcaaatga acagcctgaa acctgaggac acggccgttt attactgtgc gacagcctta     300
ggattatcaa gtagctgcca cggagacgga tatgactact ggggccaggg gaccctggtc     360
acggtctcct cc                                                         372

<210> SEQ ID NO 34
<211> LENGTH: 375
<212> TYPE: DNA
<213> ORGANISM: Artificial Sequence
<220> FEATURE:
<223> OTHER INFORMATION: Nanobody sequence

<400> SEQUENCE: 34
```

```
gaggtgcaat tggtggagtc tggggtggt tggttcaac caggtggttc tttgagattg    60
tcctgtgctg cttccggttt catcttggac tactacgcta tcggttggtt cagacaggct   120
ccaggtaaag aaagagaggg agtttcctgt atcgacgctt ccgacgacat cacttactac   180
gctgactccg ttaagggtag attcactatc tccagagaca acgctaagaa cactgtttac   240
ttgcagatga actccttgaa gccagaggac actggtgttt actactgtgc tactccaatc   300
ggtttgtcct cctcctgttt gttggaatac gactacgact actggggtca agggaccctg   360
gtcaccgtct cctca                                                    375

<210> SEQ ID NO 35
<211> LENGTH: 375
<212> TYPE: DNA
<213> ORGANISM: Artificial Sequence
<220> FEATURE:
<223> OTHER INFORMATION: Nanobody sequence

<400> SEQUENCE: 35
gaggtgcaat tggtggagtc tggggtggt tggttcaac caggtggttc tttgagattg    60
tcctgtgctg cttccggttt catcttggac tactacgcta tcggttggtt cagacaggct   120
ccaggtaaag aaagagaggg agttttgtcc atcgacgctt ccgacgacat cacttactac   180
gctgactccg ttaagggtag attcactatc tccagagaca acgctaagaa cactgtttac   240
ttgcagatga actccttgaa gccagaggac actggtgttt actactgtgc tactccaatc   300
ggtttgtcct cctccggttt gttggaatac gactacgact actggggtca agggaccctg   360
gtcaccgtct cctca                                                    375

<210> SEQ ID NO 36
<211> LENGTH: 375
<212> TYPE: DNA
<213> ORGANISM: Artificial Sequence
<220> FEATURE:
<223> OTHER INFORMATION: Nanobody sequence

<400> SEQUENCE: 36
gaggtgcaat tggtggagtc tggggtggt tggttcaac caggtggttc tttgagattg    60
tctgctgctg cttccggttt catcttggac tactacgcta tcggttggtt cagacaggct   120
ccaggtaaag aaagagaagg tgttttgtgt atcgacgctt ccgacgacat cacttactac   180
gctgactccg ttaagggtag attcactatc tccagagaca acgctaagaa cactgtttac   240
ttgcagatga actccttgaa gccagaggac actggtgttt actactccgc tactccaatc   300
ggtttgtcct cctcctgttt gttggaatac gactacgact actggggtca agggaccctg   360
gtcaccgtct cctca                                                    375

<210> SEQ ID NO 37
<211> LENGTH: 747
<212> TYPE: DNA
<213> ORGANISM: Artificial Sequence
<220> FEATURE:
<223> OTHER INFORMATION: Nanobody sequence

<400> SEQUENCE: 37
gaggtgcaat tggtggagtc tgggggaggc ttggtgcagc ctggggggtc cctgagactc    60
tcctgtgcag cctctggatt cattttggat tattatgcca taggctggtt ccgccaggcc   120 cagggaagg agcgcgaggg ggtcttatgt attgatgcta gtgatgatat tacatactat   180
gcagactccg tgaagggccg attcaccatc tccagagaca atgccaagaa cacggtgtat   240
```

```
ctgcaaatga acagcctgaa acctgaggac acgggcgttt attactgtgc gaccccatc      300 ggactgagta gtagctgcct acttgaatat gattatgact actggggcca ggggaccctg     360
gtcacggtct cctccggagg cggtggatct ggcggtggat ccgaggtgca gttggtggag     420
tctgggggtg gcttggtgca accgggtaac agtctgcgcc ttagctgcgc agcgtctggc     480
tttaccttca gctcctttgg catgagctgg gttcgccagg ctccgggaaa aggactggaa     540
tgggtttcgt ctattagcgg cagtggtagc gatacgctct acgcggactc cgtgaagggc     600
cgtttcacca tctcccgcga taacgccaaa actacactgt atctgcaaat gaatagcctg     660
cgtcctgaag acacggccgt ttattactgt actattggtg gctcgttaag ccgttcttca     720
caggggaccc tggtcaccgt ctcctca                                         747

<210> SEQ ID NO 38
<211> LENGTH: 762
<212> TYPE: DNA
<213> ORGANISM: Artificial Sequence
<220> FEATURE:
<223> OTHER INFORMATION: Nanobody sequence

<400> SEQUENCE: 38
gaggtgcaat tggtggagtc tgggggagga ttggtgcagg ctggggggctc tctgagactc     60 tcctgtgcag cctctggacg caccatcagt aggtatacca tggctggtt ccgccaggct     120 ccagggaagg agcgtgagtt tgtagcagct attagctgga gtggtgataa cacaaactat     180
gcagactccg tgaagggccg attcaccatc tccagaccca acaccaagaa cacgatgtat     240
ctgcaaatga acagcctgaa acctgaggac acggccgttt attactgtgc agcagattac     300
cgaagtggta gttactacca ggcatcagag tggacacggc catcggggta tgactactgg     360
ggccagggga ccctggtcac ggtctcctcc ggaggcggtg gatctggcgg tggatccgag     420
gtgcagttgg tggagtctgg gggtggcttg gtgcaaccgg gtaacagtct gcgccttagc     480
tgcgcagcgt ctggctttac cttcagctcc tttggcatga gctgggttcg ccaggctccg     540
ggaaaaggac tggaatgggt ttcgtctatt agcggcagtg gtagcgatac gctctacgcg     600
gactccgtga agggccgttt caccatctcc cgcgataacg ccaaaactac actgtatctg     660
caaatgaata gcctgcgtcc tgaagacacg gccgtttatt actgtactat tggtggctcg     720
ttaagccgtt cttcacaggg gaccctggtc accgtctcct ca                        762

<210> SEQ ID NO 39
<211> LENGTH: 747
<212> TYPE: DNA
<213> ORGANISM: Artificial Sequence
<220> FEATURE:
<223> OTHER INFORMATION: Nanobody sequence

<400> SEQUENCE: 39
gaggtgcaat tggtggagtc tgggggaggc ttggtgcagc ctggggggtc tctgagactc     60
tcctgtgcag cctctggatt ctctttggat tattttgcca taggctggtt ccgccaggcc    120
ccagggaagg agcgcgagga aatctcatgt attagtaaca gtgatggtag cacatactat    180
gcaaactccg tgaagggccg attcaccatc tccatagaca atgccaagaa cacggtgtat    240
ctgcaaatga caagcctgaa acctgaggac acggccgttt attactgtgc gaccccgtg    300 gggttgggc cattctgtaa gacgaccaat gactatgact acagcggcca ggggaccctg    360
gtcacggtct cctccggagg cggtggatct ggcggtggat ccgaggtgca gttggtggag    420
```

```
tctgggggtg gcttggtgca accgggtaac agtctgcgcc ttagctgcgc agcgtctggc    480
tttaccttca gctcctttgg catgagctgg gttcgccagg ctccgggaaa aggactggaa    540
tgggtttcgt ctattagcgg cagtggtagc gatacgctct acgcggactc cgtgaagggc    600
cgtttcacca tctcccgcga taacgccaaa actacactgt atctgcaaat gaatagcctg    660
cgtcctgaag acacggccgt ttattactgt actattggtg gctcgttaag ccgttcttca    720
caggggaccc tggtcaccgt ctcctca                                        747

<210> SEQ ID NO 40
<211> LENGTH: 744
<212> TYPE: DNA
<213> ORGANISM: Artificial Sequence
<220> FEATURE:
<223> OTHER INFORMATION: Nanobody sequence

<400> SEQUENCE: 40
gaggtgcaat tggtggagtc tggggggaggc ttggtgcagc ctgggggtc tctgagactc     60 tcctgtgcag cctctggatt cactttggat tattatgcca taaactggtt ccgccaggcc   120
ccagggaagg agcgcgaggg ggtctcatgt attagtggtg gtgatggtag cacatactat   180
gcagactccg tgaagggccg attcaccatc tccagagaca tgccaagaa cacggtgtat    240 ctgcaaatga cagcctgaa acctgaggac acggccgttt attactgtgc gacagcctta    300
ggattatcaa gtagctgcca ggagacgga tatgactact ggggccaggg gaccctggtc    360
acggtctcct ccggaggcgg tggatctggc ggtggatccg aggtgcagtt ggtggagtct   420
gggggtggct tggtgcaacc gggtaacagt ctgcgcctta gctgcgcagc gtctggcttt   480
accttcagct cctttggcat gagctgggtt cgccaggctc cgggaaaagg actggaatgg   540
gtttcgtcta ttagcggcag tggtagcgat acgctctacg cggactccgt gaagggccgt   600 tcaccatct cccgcgataa cgccaaaact acactgtatc tgcaaatgaa tagcctgcgt    660
cctgaagaca cggccgttta ttactgtact attggtggct cgttaagccg ttcttcacag   720
gggaccctgg tcaccgtctc ctca                                          744

<210> SEQ ID NO 41
<211> LENGTH: 825
<212> TYPE: DNA
<213> ORGANISM: Artificial Sequence
<220> FEATURE:
<223> OTHER INFORMATION: Nanobody sequence

<400> SEQUENCE: 41
gaggtgcaat tggtggagtc tgggggtggc ttggtgcaac cgggtaacag tctgcgcctt     60
agctgcgcag cgtctggctt taccttcagc tcctttggca tgagctgggt tcgccaggct   120
ccgggaaaag gactggaatg ggtttcgtct attagcggca gtggtagcga tacgctctac   180
gcggactccg tgaagggccg tttcaccatc tcccgcgata cgccaaaac tacactgtat    240 ctgcaaatga atagcctgcg tcctgaagac acggccgttt attactgtac tattggtggc   300
tcgttaagcc gttcttcaca ggggaccctg gtcacggtct cctccggagg cggtgggtca   360
ggtggcggag gcagcggtgg aggaggtagt ggcggtggcg gtagtggggg tggaggcagc   420
ggaggcggag gcagtggggg cggtggatcc gaggtgcagt tggtggagtc tggggagg    480 ttggtgcagc ctgggggtc cctgagactc tcctgtgcag cctctggatt cattttggat   540
tattatgcca taggctggtt ccgccaggcc ccagggaagg agcgcgaggg ggtcttatgt   600
attgatgcta gtgatgatat tacatactat gcagactccg tgaagggccg attcaccatc   660
```

```
tccagagaca atgccaagaa cacggtgtat ctgcaaatga acagcctgaa acctgaggac    720
acgggcgttt attactgtgc gacccccatc ggactgagta gtagctgcct acttgaatat    780
gattatgact actggggcca ggggaccctg gtcaccgtct cctca                    825
```

<210> SEQ ID NO 42
<211> LENGTH: 747
<212> TYPE: DNA
<213> ORGANISM: Artificial Sequence
<220> FEATURE:
<223> OTHER INFORMATION: Nanobody sequence

<400> SEQUENCE: 42

```
gaggtgcaat tggtggagtc tgggggtggc ttggtgcaac cgggtaacag tctgcgcctt    60
agctgcgcag cgtctggctt taccttcagc tcctttggca tgagctgggt tcgccaggct    120
ccgggaaaag gactggaatg ggtttcgtct attagcggca gtggtagcga tacgctctac    180
gcggactccg tgaagggccg tttcaccatc tcccgcgata cgccaaaaac tacactgtat    240
ctgcaaatga atagcctgcg tcctgaagac acggccgttt attactgtac tattggtggc    300
tcgttaagcc gttcttcaca ggggaccctg gtcacggtct cctccggagg cggtggatct    360
ggcggtggat ccgaggtgca gttggtggag tctgggggag gcttggtgca gcctggggg    420 tccctgagac tctcctgtgc agcctctgga ttcatttttgg attattatgc cataggctgg    480
ttccgccagg ccccagggaa ggagcgcgag ggggtcttat gtattgatgc tagtgatgat    540
attacatact atgcagactc cgtgaagggc cgattcacca tctccagaga caatgccaag    600
aacacggtgt atctgcaaat gaacagcctg aaacctgagg acacgggcgt ttattactgt    660
gcgaccccca tcggactgag tagtagctgc tacttgaat atgattatga ctactggggc    720
caggggaccc tggtcaccgt ctcctca                                        747
```

<210> SEQ ID NO 43
<211> LENGTH: 30
<212> TYPE: PRT
<213> ORGANISM: Artificial Sequence
<220> FEATURE:
<223> OTHER INFORMATION: framework 1 sequence

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp
            20                  25                  30

<210> SEQ ID NO 44
<211> LENGTH: 30
<212> TYPE: PRT
<213> ORGANISM: Artificial Sequence
<220> FEATURE:
<223> OTHER INFORMATION: framework 1 sequence

<400> SEQUENCE: 44

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Ile Ser
            20                  25                  30

<210> SEQ ID NO 45
<211> LENGTH: 30
<212> TYPE: PRT

<213> ORGANISM: Artificial Sequence
<220> FEATURE:
<223> OTHER INFORMATION: framework 1 sequence

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asp
            20                  25                  30

<210> SEQ ID NO 46
<211> LENGTH: 30
<212> TYPE: PRT
<213> ORGANISM: Artificial Sequence
<220> FEATURE:
<223> OTHER INFORMATION: framework 1 sequence

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp
            20                  25                  30

<210> SEQ ID NO 47
<211> LENGTH: 30
<212> TYPE: PRT
<213> ORGANISM: Artificial Sequence
<220> FEATURE:
<223> OTHER INFORMATION: framework 1 sequence

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp
            20                  25                  30

<210> SEQ ID NO 48
<211> LENGTH: 30
<212> TYPE: PRT
<213> ORGANISM: Artificial Sequence
<220> FEATURE:
<223> OTHER INFORMATION: framework 1 sequence

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp
            20                  25                  30

<210> SEQ ID NO 49
<211> LENGTH: 30
<212> TYPE: PRT
<213> ORGANISM: Artificial Sequence
<220> FEATURE:
<223> OTHER INFORMATION: framework 1 sequence

<400> SEQUENCE: 49

Glu Val Gln Leu Val Glu Ser Gly Gly Gly Leu Val Gln Pro Gly Gly
1               5                   10                  15

Ser Leu Arg Leu Ser Ala Ala Ala Ser Gly Phe Ile Leu Asp
            20                  25                  30

<210> SEQ ID NO 50
<211> LENGTH: 30

```
<212> TYPE: PRT
<213> ORGANISM: Artificial Sequence
<220> FEATURE:
<223> OTHER INFORMATION: framework 1 sequence

<400> SEQUENCE: 50

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser
            20                  25                  30

<210> SEQ ID NO 51
<211> LENGTH: 5
<212> TYPE: PRT
<213> ORGANISM: Artificial Sequence
<220> FEATURE:
<223> OTHER INFORMATION: CDR1 sequence

<400> SEQUENCE: 51

Tyr Tyr Ala Ile Gly
1               5

<210> SEQ ID NO 52
<211> LENGTH: 5
<212> TYPE: PRT
<213> ORGANISM: Artificial Sequence
<220> FEATURE:
<223> OTHER INFORMATION: CDR1 sequence

<400> SEQUENCE: 52

Arg Tyr Thr Met Gly
1               5

<210> SEQ ID NO 53
<211> LENGTH: 5
<212> TYPE: PRT
<213> ORGANISM: Artificial Sequence
<220> FEATURE:
<223> OTHER INFORMATION: CDR1 sequence

<400> SEQUENCE: 53

Tyr Phe Ala Ile Gly
1               5

<210> SEQ ID NO 54
<211> LENGTH: 5
<212> TYPE: PRT
<213> ORGANISM: Artificial Sequence
<220> FEATURE:
<223> OTHER INFORMATION: CDR1 sequence

<400> SEQUENCE: 54

Tyr Tyr Ala Ile Asn
1               5

<210> SEQ ID NO 55
<211> LENGTH: 5
<212> TYPE: PRT
<213> ORGANISM: Artificial Sequence
<220> FEATURE:
<223> OTHER INFORMATION: CDR1 sequence

<400> SEQUENCE: 55

Tyr Tyr Ala Ile Gly
1               5
```

```
<210> SEQ ID NO 56
<211> LENGTH: 5
<212> TYPE: PRT
<213> ORGANISM: Artificial Sequence
<220> FEATURE:
<223> OTHER INFORMATION: CDR1 sequence

<400> SEQUENCE: 56

Tyr Tyr Ala Ile Gly
1               5

<210> SEQ ID NO 57
<211> LENGTH: 5
<212> TYPE: PRT
<213> ORGANISM: Artificial Sequence
<220> FEATURE:
<223> OTHER INFORMATION: CDR1 sequence

<400> SEQUENCE: 57

Tyr Tyr Ala Ile Gly
1               5

<210> SEQ ID NO 58
<211> LENGTH: 5
<212> TYPE: PRT
<213> ORGANISM: Artificial Sequence
<220> FEATURE:
<223> OTHER INFORMATION: CDR1 sequence

<400> SEQUENCE: 58

Ser Phe Gly Met Ser
1               5

<210> SEQ ID NO 59
<211> LENGTH: 14
<212> TYPE: PRT
<213> ORGANISM: Artificial Sequence
<220> FEATURE:
<223> OTHER INFORMATION: framework 2 sequence

<400> SEQUENCE: 59

Trp Phe Arg Gln Ala Pro Gly Lys Glu Arg Glu Gly Val Leu
1               5                   10

<210> SEQ ID NO 60
<211> LENGTH: 14
<212> TYPE: PRT
<213> ORGANISM: Artificial Sequence
<220> FEATURE:
<223> OTHER INFORMATION: framework 2 sequence

<400> SEQUENCE: 60

Trp Phe Arg Gln Ala Pro Gly Lys Glu Arg Glu Phe Val Ala
1               5                   10

<210> SEQ ID NO 61
<211> LENGTH: 14
<212> TYPE: PRT
<213> ORGANISM: Artificial Sequence
<220> FEATURE:
<223> OTHER INFORMATION: framework 2 sequence

<400> SEQUENCE: 61

Trp Phe Arg Gln Ala Pro Gly Lys Glu Arg Glu Glu Ile Ser
1               5                   10

<210> SEQ ID NO 62
```

```
<211> LENGTH: 14
<212> TYPE: PRT
<213> ORGANISM: Artificial Sequence
<220> FEATURE:
<223> OTHER INFORMATION: framework 2 sequence

<400> SEQUENCE: 62

Trp Phe Arg Gln Ala Pro Gly Lys Glu Arg Glu Gly Val Ser
1               5                   10

<210> SEQ ID NO 63
<211> LENGTH: 14
<212> TYPE: PRT
<213> ORGANISM: Artificial Sequence
<220> FEATURE:
<223> OTHER INFORMATION: framework 2 sequence

<400> SEQUENCE: 63

Trp Phe Arg Gln Ala Pro Gly Lys Glu Arg Glu Gly Val Ser
1               5                   10

<210> SEQ ID NO 64
<211> LENGTH: 14
<212> TYPE: PRT
<213> ORGANISM: Artificial Sequence
<220> FEATURE:
<223> OTHER INFORMATION: framework 2 sequence

<400> SEQUENCE: 64

Trp Phe Arg Gln Ala Pro Gly Lys Glu Arg Glu Gly Val Leu
1               5                   10

<210> SEQ ID NO 65
<211> LENGTH: 14
<212> TYPE: PRT
<213> ORGANISM: Artificial Sequence
<220> FEATURE:
<223> OTHER INFORMATION: framework 2 sequence

<400> SEQUENCE: 65

Trp Phe Arg Gln Ala Pro Gly Lys Glu Arg Glu Gly Val Leu
1               5                   10

<210> SEQ ID NO 66
<211> LENGTH: 14
<212> TYPE: PRT
<213> ORGANISM: Artificial Sequence
<220> FEATURE:
<223> OTHER INFORMATION: framework 2 sequence

<400> SEQUENCE: 66

Trp Val Arg Gln Ala Pro Gly Lys Gly Leu Glu Trp Val Ser
1               5                   10

<210> SEQ ID NO 67
<211> LENGTH: 17
<212> TYPE: PRT
<213> ORGANISM: Artificial Sequence
<220> FEATURE:
<223> OTHER INFORMATION: CDR2 sequence

<400> SEQUENCE: 67

Cys Ile Asp Ala Ser Asp Asp Ile Thr Tyr Tyr Ala Asp Ser Val Lys
1               5                   10                  15

Gly
```

```
<210> SEQ ID NO 68
<211> LENGTH: 17
<212> TYPE: PRT
<213> ORGANISM: Artificial Sequence
<220> FEATURE:
<223> OTHER INFORMATION: CDR2 sequence

<400> SEQUENCE: 68

Ala Ile Ser Trp Ser Gly Asp Asn Thr Asn Tyr Ala Asp Ser Val Lys
1               5                   10                  15
Gly

<210> SEQ ID NO 69
<211> LENGTH: 17
<212> TYPE: PRT
<213> ORGANISM: Artificial Sequence
<220> FEATURE:
<223> OTHER INFORMATION: CDR2 sequence

<400> SEQUENCE: 69

Cys Ile Ser Asn Ser Asp Gly Ser Thr Tyr Tyr Ala Asn Ser Val Lys
1               5                   10                  15
Gly

<210> SEQ ID NO 70
<211> LENGTH: 17
<212> TYPE: PRT
<213> ORGANISM: Artificial Sequence
<220> FEATURE:
<223> OTHER INFORMATION: CDR2 sequence

<400> SEQUENCE: 70

Cys Ile Ser Gly Gly Asp Gly Ser Thr Tyr Tyr Ala Asp Ser Val Lys
1               5                   10                  15
Gly

<210> SEQ ID NO 71
<211> LENGTH: 17
<212> TYPE: PRT
<213> ORGANISM: Artificial Sequence
<220> FEATURE:
<223> OTHER INFORMATION: CDR2 sequence

<400> SEQUENCE: 71

Cys Ile Asp Ala Ser Asp Asp Ile Thr Tyr Tyr Ala Asp Ser Val Lys
1               5                   10                  15
Gly

<210> SEQ ID NO 72
<211> LENGTH: 17
<212> TYPE: PRT
<213> ORGANISM: Artificial Sequence
<220> FEATURE:
<223> OTHER INFORMATION: CDR2 sequence

<400> SEQUENCE: 72

Ser Ile Asp Ala Ser Asp Asp Ile Thr Tyr Tyr Ala Asp Ser Val Lys
1               5                   10                  15
Gly

<210> SEQ ID NO 73
<211> LENGTH: 17
<212> TYPE: PRT
<213> ORGANISM: Artificial Sequence
```

```
<220> FEATURE:
<223> OTHER INFORMATION: CDR2 sequence

<400> SEQUENCE: 73

Cys Ile Asp Ala Ser Asp Ile Thr Tyr Tyr Ala Asp Ser Val Lys
1               5                   10                  15

Gly

<210> SEQ ID NO 74
<211> LENGTH: 17
<212> TYPE: PRT
<213> ORGANISM: Artificial Sequence
<220> FEATURE:
<223> OTHER INFORMATION: CDR2 sequence

<400> SEQUENCE: 74

Ser Ile Ser Gly Ser Gly Ser Asp Thr Leu Tyr Ala Asp Ser Val Lys
1               5                   10                  15

Gly

<210> SEQ ID NO 75
<211> LENGTH: 32
<212> TYPE: PRT
<213> ORGANISM: Artificial Sequence
<220> FEATURE:
<223> OTHER INFORMATION: framework 3 sequence

<400> SEQUENCE: 75

Arg Phe Thr Ile Ser Arg Asp Asn Ala Lys Asn Thr Val Tyr Leu Gln
1               5                   10                  15

Met Asn Ser Leu Lys Pro Glu Asp Thr Gly Val Tyr Tyr Cys Ala Thr
                20                  25                  30

<210> SEQ ID NO 76
<211> LENGTH: 32
<212> TYPE: PRT
<213> ORGANISM: Artificial Sequence
<220> FEATURE:
<223> OTHER INFORMATION: framework 3 sequence

<400> SEQUENCE: 76

Arg Phe Thr Ile Ser Arg Pro Asn Thr Lys Asn Thr Met Tyr Leu Gln
1               5                   10                  15

Met Asn Ser Leu Lys Pro Glu Asp Thr Ala Val Tyr Tyr Cys Ala Ala
                20                  25                  30

<210> SEQ ID NO 77
<211> LENGTH: 32
<212> TYPE: PRT
<213> ORGANISM: Artificial Sequence
<220> FEATURE:
<223> OTHER INFORMATION: Nanobody sequence

<400> SEQUENCE: 77

Arg Phe Thr Ile Ser Ile Asp Asn Ala Lys Asn Thr Val Tyr Leu Gln
1               5                   10                  15

Met Thr Ser Leu Lys Pro Glu Asp Thr Ala Val Tyr Tyr Cys Ala Thr
                20                  25                  30

<210> SEQ ID NO 78
<211> LENGTH: 32
<212> TYPE: PRT
<213> ORGANISM: Artificial Sequence
<220> FEATURE:
```

<223> OTHER INFORMATION: framework 3 sequence

<400> SEQUENCE: 78

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Thr
            20                  25                  30

<210> SEQ ID NO 79
<211> LENGTH: 32
<212> TYPE: PRT
<213> ORGANISM: Artificial Sequence
<220> FEATURE:
<223> OTHER INFORMATION: framework 3 sequence

<400> SEQUENCE: 79

Arg Phe Thr Ile Ser Arg Asp Asn Ala Lys Asn Thr Val Tyr Leu Gln
1               5                   10                  15

Met Asn Ser Leu Lys Pro Glu Asp Thr Gly Val Tyr Tyr Cys Ala Thr
            20                  25                  30

<210> SEQ ID NO 80
<211> LENGTH: 32
<212> TYPE: PRT
<213> ORGANISM: Artificial Sequence
<220> FEATURE:
<223> OTHER INFORMATION: framework 3 sequence

<400> SEQUENCE: 80

Arg Phe Thr Ile Ser Arg Asp Asn Ala Lys Asn Thr Val Tyr Leu Gln
1               5                   10                  15

Met Asn Ser Leu Lys Pro Glu Asp Thr Gly Val Tyr Tyr Cys Ala Thr
            20                  25                  30

<210> SEQ ID NO 81
<211> LENGTH: 32
<212> TYPE: PRT
<213> ORGANISM: Artificial Sequence
<220> FEATURE:
<223> OTHER INFORMATION: framework 3 sequence

<400> SEQUENCE: 81

Arg Phe Thr Ile Ser Arg Asp Asn Ala Lys Asn Thr Val Tyr Leu Gln
1               5                   10                  15

Met Asn Ser Leu Lys Pro Glu Asp Thr Gly Val Tyr Tyr Ser Ala Thr
            20                  25                  30

<210> SEQ ID NO 82
<211> LENGTH: 32
<212> TYPE: PRT
<213> ORGANISM: Artificial Sequence
<220> FEATURE:
<223> OTHER INFORMATION: framework 3 sequence

<400> SEQUENCE: 82

Arg Phe Thr Ile Ser Arg Asp Asn Ala Lys Thr Thr Leu Tyr Leu Gln
1               5                   10                  15

Met Asn Ser Leu Arg Pro Glu Asp Thr Ala Val Tyr Tyr Cys Thr Ile
            20                  25                  30

<210> SEQ ID NO 83
<211> LENGTH: 16
<212> TYPE: PRT
<213> ORGANISM: Artificial Sequence

```
<220> FEATURE:
<223> OTHER INFORMATION: CDR3 sequence

<400> SEQUENCE: 83

Pro Ile Gly Leu Ser Ser Ser Cys Leu Leu Glu Tyr Asp Tyr Asp Tyr
1               5                   10                  15

<210> SEQ ID NO 84
<211> LENGTH: 21
<212> TYPE: PRT
<213> ORGANISM: Artificial Sequence
<220> FEATURE:
<223> OTHER INFORMATION: CDR3 sequence

<400> SEQUENCE: 84

Asp Tyr Arg Ser Gly Ser Tyr Tyr Gln Ala Ser Glu Trp Thr Arg Pro
1               5                   10                  15

Ser Gly Tyr Asp Tyr
            20

<210> SEQ ID NO 85
<211> LENGTH: 16
<212> TYPE: PRT
<213> ORGANISM: Artificial Sequence
<220> FEATURE:
<223> OTHER INFORMATION: CDR3 sequence

<400> SEQUENCE: 85

Pro Val Gly Leu Gly Pro Phe Cys Lys Thr Thr Asn Asp Tyr Asp Tyr
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: CDR3 sequence

<400> SEQUENCE: 86

Ala Leu Gly Leu Ser Ser Ser Cys His Gly Asp Gly Tyr Asp Tyr
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: CDR3 sequence

<400> SEQUENCE: 87

Pro Ile Gly Leu Ser Ser Ser Cys Leu Leu Glu Tyr Asp Tyr Asp Tyr
1               5                   10                  15

<210> SEQ ID NO 88
<211> LENGTH: 16
<212> TYPE: PRT
<213> ORGANISM: Artificial Sequence
<220> FEATURE:
<223> OTHER INFORMATION: CDR3 sequence

<400> SEQUENCE: 88

Pro Ile Gly Leu Ser Ser Ser Gly Leu Leu Glu Tyr Asp Tyr Asp Tyr
1               5                   10                  15

<210> SEQ ID NO 89
<211> LENGTH: 16
```

```
<212> TYPE: PRT
<213> ORGANISM: Artificial Sequence
<220> FEATURE:
<223> OTHER INFORMATION: CDR3 sequence

<400> SEQUENCE: 89

Pro Ile Gly Leu Ser Ser Ser Cys Leu Leu Glu Tyr Asp Tyr Asp Tyr
1               5                   10                  15

<210> SEQ ID NO 90
<211> LENGTH: 6
<212> TYPE: PRT
<213> ORGANISM: Artificial Sequence
<220> FEATURE:
<223> OTHER INFORMATION: CDR3 sequence

<400> SEQUENCE: 90

Gly Gly Ser Leu Ser Arg
1               5

<210> SEQ ID NO 91
<211> LENGTH: 11
<212> TYPE: PRT
<213> ORGANISM: Artificial Sequence
<220> FEATURE:
<223> OTHER INFORMATION: framework 4 sequence

<400> SEQUENCE: 91

Trp Gly Gln Gly Thr Leu Val Thr Val Ser Ser
1               5                   10

<210> SEQ ID NO 92
<211> LENGTH: 11
<212> TYPE: PRT
<213> ORGANISM: Artificial Sequence
<220> FEATURE:
<223> OTHER INFORMATION: framework 4 sequence

<400> SEQUENCE: 92

Trp Gly Gln Gly Thr Leu Val Thr Val Ser Ser
1               5                   10

<210> SEQ ID NO 93
<211> LENGTH: 11
<212> TYPE: PRT
<213> ORGANISM: Artificial Sequence
<220> FEATURE:
<223> OTHER INFORMATION: framework 4 sequence

<400> SEQUENCE: 93

Ser Gly Gln Gly Thr Leu Val Thr Val Ser Ser
1               5                   10

<210> SEQ ID NO 94
<211> LENGTH: 11
<212> TYPE: PRT
<213> ORGANISM: Artificial Sequence
<220> FEATURE:
<223> OTHER INFORMATION: framework 4 sequence

<400> SEQUENCE: 94

Trp Gly Gln Gly Thr Leu Val Thr Val Ser Ser
1               5                   10

<210> SEQ ID NO 95
<211> LENGTH: 11
<212> TYPE: PRT
```

<213> ORGANISM: Artificial Sequence
<220> FEATURE:
<223> OTHER INFORMATION: framework 4 sequence

<400> SEQUENCE: 95

Trp Gly Gln Gly Thr Leu Val Thr Val Ser Ser
1               5                   10

<210> SEQ ID NO 96
<211> LENGTH: 11
<212> TYPE: PRT
<213> ORGANISM: Artificial Sequence
<220> FEATURE:
<223> OTHER INFORMATION: framework 4 sequence

<400> SEQUENCE: 96

Trp Gly Gln Gly Thr Leu Val Thr Val Ser Ser
1               5                   10

<210> SEQ ID NO 97
<211> LENGTH: 11
<212> TYPE: PRT
<213> ORGANISM: Artificial Sequence
<220> FEATURE:
<223> OTHER INFORMATION: framework 4 sequence

<400> SEQUENCE: 97

Trp Gly Gln Gly Thr Leu Val Thr Val Ser Ser
1               5                   10

<210> SEQ ID NO 98
<211> LENGTH: 11
<212> TYPE: PRT
<213> ORGANISM: Artificial Sequence
<220> FEATURE:
<223> OTHER INFORMATION: framework 4 sequence

<400> SEQUENCE: 98

Ser Ser Gln Gly Thr Leu Val Thr Val Ser Ser
1               5                   10

<210> SEQ ID NO 99
<211> LENGTH: 98
<212> TYPE: PRT
<213> ORGANISM: Artificial Sequence
<220> FEATURE:
<223> OTHER INFORMATION: Nanobody sequence

<400> SEQUENCE: 99

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Ala Ile Gly Trp Phe Arg Gln Ala Pro Gly Lys Glu Arg Glu Gly Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala

<210> SEQ ID NO 100
<211> LENGTH: 763
<212> TYPE: PRT
<213> ORGANISM: Artificial Sequence
<220> FEATURE:
<223> OTHER INFORMATION: chimera

<400> SEQUENCE: 100

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
```

```
                  370                375                380
Cys Leu Gln His Phe Tyr Gly Pro Asn His Glu His Cys Phe Asn Arg
385                390                395                400

Thr Leu Leu Arg Asn Ser Ser Gly Cys Glu Ala Arg Arg Asp Glu Tyr
                405                410                415

Arg Thr Glu Phe Thr Thr Ala Leu Gln Arg Val Asp Leu Phe Met Gly
                420                425                430

Gln Phe Ser Glu Val Leu Leu Thr Ser Ile Ser Thr Phe Ile Lys Gly
                435                440                445

Asp Leu Thr Ile Ala Asn Leu Gly Thr Ser Glu Gly Arg Phe Met Gln
            450                455                460

Val Val Val Ser Arg Ser Gly Pro Ser Thr Pro His Val Asn Phe Leu
465                470                475                480

Leu Asp Ser His Pro Val Ser Pro Glu Val Ile Val Glu His Thr Leu
                485                490                495

Asn Gln Asn Gly Tyr Thr Leu Val Ile Thr Gly Lys Lys Ile Thr Lys
                500                505                510

Ile Pro Leu Asn Gly Leu Gly His Ile Glu Gly Arg Met Asp Pro Lys
            515                520                525

Ser Cys Asp Lys Thr His Thr Cys Pro Pro Cys Pro Ala Pro Glu Leu
530                535                540

Leu Gly Gly Pro Ser Val Phe Leu Phe Pro Pro Lys Pro Lys Asp Thr
545                550                555                560

Leu Met Ile Ser Arg Thr Pro Glu Val Thr Cys Val Val Val Asp Val
                565                570                575

Ser His Glu Asp Pro Glu Val Lys Phe Asn Trp Tyr Val Asp Gly Val
            580                585                590

Glu Val His Asn Ala Lys Thr Lys Pro Arg Glu Glu Gln Tyr Asn Ser
                595                600                605

Thr Tyr Arg Val Val Ser Val Leu Thr Val Leu His Gln Asp Trp Leu
                610                615                620

Asn Gly Lys Glu Tyr Lys Cys Lys Val Ser Asn Lys Ala Leu Pro Ala
625                630                635                640

Pro Ile Glu Lys Thr Ile Ser Lys Ala Lys Gly Gln Pro Arg Glu Pro
                645                650                655

Gln Val Tyr Thr Leu Pro Pro Ser Arg Asp Glu Leu Thr Lys Asn Gln
                660                665                670

Val Ser Leu Thr Cys Leu Val Lys Gly Phe Tyr Pro Ser Asp Ile Ala
            675                680                685

Val Glu Trp Glu Ser Asn Gly Gln Pro Glu Asn Asn Tyr Lys Thr Thr
            690                695                700

Pro Pro Val Leu Asp Ser Asp Gly Ser Phe Phe Leu Tyr Ser Lys Leu
705                710                715                720

Thr Val Asp Lys Ser Arg Trp Gln Gln Gly Asn Val Phe Ser Cys Ser
                725                730                735

Val Met His Glu Ala Leu His Asn His Tyr Thr Gln Lys Ser Leu Ser
                740                745                750

Leu Ser Pro Gly Lys His His His His
            755                760

<210> SEQ ID NO 101
<211> LENGTH: 115
<212> TYPE: PRT
<213> ORGANISM: Artificial Sequence
```

```
<220> FEATURE:
<223> OTHER INFORMATION: Nanobody sequence

<400> SEQUENCE: 101

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 102
<211> LENGTH: 125
<212> TYPE: PRT
<213> ORGANISM: Artificial Sequence
<220> FEATURE:
<223> OTHER INFORMATION: Nanobody sequence

<400> SEQUENCE: 102

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45

Leu Cys Ile Asp Ala Ser Asp Asp Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Thr Pro Ile Gly Leu Ser Ser Cys Leu Leu Tyr Asp Tyr
            100                 105                 110

Asp Tyr Trp Gly Gln Gly Thr Leu Val Thr Val Ser Ser
        115                 120                 125

<210> SEQ ID NO 103
<211> LENGTH: 249
<212> TYPE: PRT
<213> ORGANISM: Artificial Sequence
<220> FEATURE:
<223> OTHER INFORMATION: Nanobody sequence

<400> SEQUENCE: 103

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30
```

```
Gly Met Ser Trp Val Arg Gln Ala Pro Gly Lys Pro Glu Trp Val
            35                  40                  45
Ser Ser Ile Ser Gly Ser Gly Ser Asp Thr Leu Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Pro Glu Asp Thr Ala Val Tyr Tyr Cys
                85                  90                  95
Thr Ile Gly Gly Ser Leu Ser Arg Ser Ser Gln Gly Thr Leu Val Thr
            100                 105                 110
Val Ser Ser Gly Gly Gly Gly Ser Gly Gly Gly Ser Glu Val Gln Leu
            115                 120                 125
Val Glu Ser Gly Gly Gly Leu Val Gln Pro Gly Gly Ser Leu Arg Leu
            130                 135                 140
Ser Cys Ala Ala Ser Gly Phe Ile Leu Asp Tyr Tyr Ala Ile Gly Trp
145                 150                 155                 160
Phe Arg Gln Ala Pro Gly Lys Glu Arg Glu Gly Val Leu Cys Ile Asp
                165                 170                 175
Ala Ser Asp Asp Ile Thr Tyr Tyr Ala Asp Ser Val Lys Gly Arg Phe
            180                 185                 190
Thr Ile Ser Arg Asp Asn Ala Lys Asn Thr Val Tyr Leu Gln Met Asn
            195                 200                 205
Ser Leu Lys Pro Glu Asp Thr Gly Val Tyr Tyr Cys Ala Thr Pro Ile
            210                 215                 220
Gly Leu Ser Ser Ser Cys Leu Leu Glu Tyr Asp Tyr Asp Tyr Trp Gly
225                 230                 235                 240
Gln Gly Thr Leu Val Thr Val Ser Ser
                245

<210> SEQ ID NO 104
<211> LENGTH: 249
<212> TYPE: PRT
<213> ORGANISM: Artificial Sequence
<220> FEATURE:
<223> OTHER INFORMATION: Nanobody sequence

<400> SEQUENCE: 104

Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Ile Leu Asp Tyr Tyr
                20                  25                  30
Ala Ile Gly Trp Phe Arg Gln Ala Pro Gly Lys Glu Arg Glu Gly Val
            35                  40                  45
Leu Cys Ile Asp Ala Ser Asp Asp Ile Thr Tyr Tyr Ala Asp Ser Val
 50                  55                  60
Lys Gly Arg Phe Thr Ile Ser Arg Asp Asn Ala Lys Asn Thr Val Tyr
 65                  70                  75                  80
Leu Gln Met Asn Ser Leu Lys Pro Glu Asp Thr Gly Val Tyr Tyr Cys
                85                  90                  95
Ala Thr Pro Ile Gly Leu Ser Ser Ser Cys Leu Leu Glu Tyr Asp Tyr
            100                 105                 110
Asp Tyr Trp Gly Gln Gly Thr Leu Val Thr Val Ser Ser Gly Gly Gly
            115                 120                 125
Gly Ser Gly Gly Gly Ser Glu Val Gln Leu Leu Glu Ser Gly Gly Gly
            130                 135                 140
```

```
Leu Val Gln Pro Gly Gly Ser Leu Arg Leu Ser Cys Ala Ala Ser Gly
145                 150                 155                 160

Phe Thr Phe Arg Ser Phe Gly Met Ser Trp Val Arg Gln Ala Pro Gly
            165                 170                 175

Lys Gly Pro Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
            195                 200                 205

Ser Lys Asn Thr Leu Tyr Leu Gln Met Asn Ser Leu Arg Pro Glu Asp
            210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser
                245
```

<210> SEQ ID NO 105
<211> LENGTH: 249
<212> TYPE: PRT
<213> ORGANISM: Artificial Sequence
<220> FEATURE:
<223> OTHER INFORMATION: Nanobody sequence

<400> SEQUENCE: 105

```
Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Arg Ser Phe
                20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Ser Asp Val Gln Leu
        115                 120                 125

Val Glu Ser Gly Gly Gly Leu Val Gln Pro Gly Gly Ser Leu Arg Leu
130                 135                 140

Ser Cys Ala Ala Ser Gly Phe Ile Leu Asp Tyr Tyr Ala Ile Gly Trp
145                 150                 155                 160

Phe Arg Gln Ala Pro Gly Lys Glu Arg Glu Gly Val Leu Cys Ile Asp
            165                 170                 175

Ala Ser Asp Asp Ile Thr Tyr Tyr Ala Asp Ser Val Lys Gly Arg Phe
            180                 185                 190

Thr Ile Ser Arg Asp Asn Ser Lys Asn Thr Val Tyr Leu Gln Met Asn
            195                 200                 205

Ser Leu Arg Pro Glu Asp Thr Ala Val Tyr Tyr Cys Ala Thr Pro Ile
            210                 215                 220

Gly Leu Ser Ser Cys Leu Leu Glu Tyr Asp Tyr Asp Tyr Trp Gly
225                 230                 235                 240

Gln Gly Thr Leu Val Thr Val Ser Ser
                245
```

```
<210> SEQ ID NO 106
<211> LENGTH: 249
<212> TYPE: PRT
<213> ORGANISM: Artificial Sequence
<220> FEATURE:
<223> OTHER INFORMATION: Nanobody sequence

<400> SEQUENCE: 106

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45

Leu Cys Ile Asp Ala Ser Asp Asp Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Thr Pro Ile Gly Leu Ser Ser Cys Leu Leu Gly Tyr Asp Tyr
            100                 105                 110

Asp Tyr Trp Gly Gln Gly Thr Leu Val Thr Val Ser Ser Gly Gly Gly
        115                 120                 125

Gly Ser Gly Gly Gly Ser Glu Val Gln Leu Leu Glu Ser Gly Gly Gly
    130                 135                 140

Leu Val Gln Pro Gly Gly Ser Leu Arg Leu Ser Cys Ala Ala Ser Gly
145                 150                 155                 160

Phe Thr Phe Arg Ser Phe Gly Met Ser Trp Val Arg Gln Ala Pro Gly
                165                 170                 175

Lys Gly Pro Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ser Lys Asn Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser
                245

<210> SEQ ID NO 107
<211> LENGTH: 275
<212> TYPE: PRT
<213> ORGANISM: Artificial Sequence
<220> FEATURE:
<223> OTHER INFORMATION: Nanobody sequence

<400> SEQUENCE: 107

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Gln Gly Thr Leu Val Thr
            100                 105                 110

Val Ser Ser Gly Gly Gly Gly Ser Gly Gly Gly Gly Ser Gly Gly Gly
            115                 120                 125

Gly Ser Gly Gly Gly Gly Ser Gly Gly Gly Gly Ser Gly Gly Gly Gly
            130                 135                 140

Ser Gly Gly Gly Gly Ser Glu Val Gln Leu Val Glu Ser Gly Gly Gly
145                 150                 155                 160

Leu Val Gln Pro Gly Gly Ser Leu Arg Leu Ser Cys Ala Ala Ser Gly
                165                 170                 175

Phe Ile Leu Asp Tyr Tyr Ala Ile Gly Trp Phe Arg Gln Ala Pro Gly
            180                 185                 190

Lys Glu Arg Glu Gly Val Leu Cys Ile Asp Ala Ser Asp Ile Thr
            195                 200                 205

Tyr Tyr Ala Asp Ser Val Lys Gly Arg Phe Thr Ile Ser Arg Asp Asn
210                 215                 220

Ala Lys Asn Thr Val Tyr Leu Gln Met Asn Ser Leu Lys Pro Glu Asp
225                 230                 235                 240

Thr Gly Val Tyr Tyr Cys Ala Thr Pro Ile Gly Leu Ser Ser Cys
            245                 250                 255

Leu Leu Glu Tyr Asp Tyr Asp Tyr Trp Gly Gln Gly Thr Leu Val Thr
                260                 265                 270

Val Ser Ser
        275

<210> SEQ ID NO 108
<211> LENGTH: 275
<212> TYPE: PRT
<213> ORGANISM: Artificial Sequence
<220> FEATURE:
<223> OTHER INFORMATION: Nanobody sequence

<400> SEQUENCE: 108

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Ile Leu Asp Tyr Tyr
                 20                  25                  30

Ala Ile Gly Trp Phe Arg Gln Ala Pro Gly Lys Glu Arg Glu Gly Val
             35                  40                  45

Leu Cys Ile Asp Ala Ser Asp Ile Thr Tyr Tyr Ala Asp Ser Val
         50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Gly Val Tyr Tyr Cys
                 85                  90                  95

Ala Thr Pro Ile Gly Leu Ser Ser Cys Leu Leu Glu Tyr Asp Tyr
            100                 105                 110

Asp Tyr Trp Gly Gln Gly Thr Leu Val Thr Val Ser Ser Gly Gly Gly
            115                 120                 125

Gly Ser Gly Gly Gly Gly Ser Gly Gly Gly Gly Ser Gly Gly Gly Gly
            130                 135                 140
```

```
Ser Gly Gly Gly Gly Ser Gly Gly Gly Ser Gly Gly Gly Ser
145                 150                 155                 160

Glu Val Gln Leu Leu Glu Ser Gly Gly Gly Leu Val Gln Pro Gly Gly
            165                 170                 175

Ser Leu Arg Leu Ser Cys Ala Ala Ser Gly Phe Thr Phe Arg Ser Phe
            180                 185                 190

Gly Met Ser Trp Val Arg Gln Ala Pro Gly Lys Gly Pro Glu Trp Val
            195                 200                 205

Ser Ser Ile Ser Gly Ser Gly Ser Asp Thr Leu Tyr Ala Asp Ser Val
            210                 215                 220

Lys Gly Arg Phe Thr Ile Ser Arg Asp Asn Ser Lys Asn Thr Leu Tyr
225                 230                 235                 240

Leu Gln Met Asn Ser Leu Arg Pro Glu Asp Thr Ala Val Tyr Tyr Cys
            245                 250                 255

Thr Ile Gly Gly Ser Leu Ser Arg Ser Ser Gln Gly Thr Leu Val Thr
            260                 265                 270

Val Ser Ser
        275

<210> SEQ ID NO 109
<211> LENGTH: 275
<212> TYPE: PRT
<213> ORGANISM: Artificial Sequence
<220> FEATURE:
<223> OTHER INFORMATION: Nanobody sequence

<400> SEQUENCE: 109

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Ser Gly Gly Gly
            115                 120                 125

Gly Ser Gly Gly Gly Gly Ser Gly Gly Gly Ser Gly Gly Gly Gly
        130                 135                 140

Ser Gly Gly Gly Gly Ser Asp Val Gln Leu Val Glu Ser Gly Gly Gly
145                 150                 155                 160

Leu Val Gln Pro Gly Gly Ser Leu Arg Leu Ser Cys Ala Ala Ser Gly
            165                 170                 175

Phe Ile Leu Asp Tyr Tyr Ala Ile Gly Trp Phe Arg Gln Ala Pro Gly
            180                 185                 190

Lys Glu Arg Glu Gly Val Leu Cys Ile Asp Ala Ser Asp Asp Ile Thr
            195                 200                 205

Tyr Tyr Ala Asp Ser Val Lys Gly Arg Phe Thr Ile Ser Arg Asp Asn
        210                 215                 220
```

```
Ser Lys Asn Thr Val Tyr Leu Gln Met Asn Ser Leu Arg Pro Glu Asp
225                 230                 235                 240

Thr Ala Val Tyr Tyr Cys Ala Thr Pro Ile Gly Leu Ser Ser Ser Cys
                245                 250                 255

Leu Leu Glu Tyr Asp Tyr Asp Tyr Trp Gly Gln Gly Thr Leu Val Thr
            260                 265                 270

Val Ser Ser
        275

<210> SEQ ID NO 110
<211> LENGTH: 275
<212> TYPE: PRT
<213> ORGANISM: Artificial Sequence
<220> FEATURE:
<223> OTHER INFORMATION: Nanobody sequence

<400> SEQUENCE: 110

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45

Leu Cys Ile Asp Ala Ser Asp Asp Ile Thr Tyr Tyr Ala Asp Ser Val
50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Thr Pro Ile Gly Leu Ser Ser Ser Cys Leu Leu Glu Tyr Asp Tyr
            100                 105                 110

Asp Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Glu Val Gln Leu Leu Glu Ser Gly Gly Gly Leu Val Gln Pro Gly Gly
                165                 170                 175

Ser Leu Arg Leu Ser Cys Ala Ala Ser Gly Phe Thr Phe Arg Ser Phe
            180                 185                 190

Gly Met Ser Trp Val Arg Gln Ala Pro Gly Lys Gly Pro Glu Trp Val
        195                 200                 205

Ser Ser Ile Ser Gly Ser Gly Ser Asp Thr Leu Tyr Ala Asp Ser Val
    210                 215                 220

Lys Gly Arg Phe Thr Ile Ser Arg Asp Asn Ser Lys Asn Thr Leu Tyr
225                 230                 235                 240

Leu Gln Met Asn Ser Leu Arg Pro Glu Asp Thr Ala Val Tyr Tyr Cys
                245                 250                 255

Thr Ile Gly Gly Ser Leu Ser Arg Ser Ser Gln Gly Thr Leu Val Thr
            260                 265                 270

Val Ser Ser
        275

<210> SEQ ID NO 111
```

<211> LENGTH: 383
<212> TYPE: PRT
<213> ORGANISM: Artificial Sequence
<220> FEATURE:
<223> OTHER INFORMATION: Nanobody sequence

<400> SEQUENCE: 111

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45

Leu Cys Ile Asp Ala Ser Asp Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Thr Pro Ile Gly Leu Ser Ser Cys Leu Leu Glu Tyr Asp Tyr
            100                 105                 110

Asp Tyr Trp Gly Gln Gly Thr Leu Val Thr Val Ser Ser Gly Gly Gly
        115                 120                 125

Gly Ser Gly Gly Gly Ser Asp Val Gln Leu Val Glu Ser Gly Gly Gly
130                 135                 140

Leu Val Gln Pro Gly Gly Ser Leu Arg Leu Ser Cys Ala Ala Ser Gly
145                 150                 155                 160

Phe Ile Leu Asp Tyr Tyr Ala Ile Gly Trp Phe Arg Gln Ala Pro Gly
                165                 170                 175

Lys Glu Arg Glu Gly Val Leu Cys Ile Asp Ala Ser Asp Ile Thr
            180                 185                 190

Tyr Tyr Ala Asp Ser Val Lys Gly Arg Phe Thr Ile Ser Arg Asp Asn
        195                 200                 205

Ser Lys Asn Thr Val Tyr Leu Gln Met Asn Ser Leu Arg Pro Glu Asp
210                 215                 220

Thr Ala Val Tyr Tyr Cys Ala Thr Pro Ile Gly Leu Ser Ser Ser Cys
225                 230                 235                 240

Leu Leu Glu Tyr Asp Tyr Asp Tyr Trp Gly Gln Gly Thr Leu Val Thr
                245                 250                 255

Val Ser Ser Gly Gly Gly Gly Ser Gly Gly Gly Ser Glu Val Gln Leu
            260                 265                 270

Leu Glu Ser Gly Gly Gly Leu Val Gln Pro Gly Gly Ser Leu Arg Leu
        275                 280                 285

Ser Cys Ala Ala Ser Gly Phe Thr Phe Arg Ser Phe Gly Met Ser Trp
290                 295                 300

Val Arg Gln Ala Pro Gly Lys Gly Pro Glu Trp Val Ser Ser Ile Ser
305                 310                 315                 320

Gly Ser Gly Ser Asp Thr Leu Tyr Ala Asp Ser Val Lys Gly Arg Phe
                325                 330                 335

Thr Ile Ser Arg Asp Asn Ser Lys Asn Thr Leu Tyr Leu Gln Met Asn
            340                 345                 350

Ser Leu Arg Pro Glu Asp Thr Ala Val Tyr Tyr Cys Thr Ile Gly Gly
        355                 360                 365

Ser Leu Ser Arg Ser Ser Gln Gly Thr Leu Val Thr Val Ser Ser
370                 375                 380

<210> SEQ ID NO 112
<211> LENGTH: 283
<212> TYPE: PRT
<213> ORGANISM: Artificial Sequence
<220> FEATURE:
<223> OTHER INFORMATION: Nanobody sequence

<400> SEQUENCE: 112

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45

Leu Cys Ile Asp Ala Ser Asp Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Gly Val Tyr Tyr Cys
                85                  90                  95

Ala Thr Pro Ile Gly Leu Ser Ser Ser Cys Leu Leu Glu Tyr Asp Tyr
            100                 105                 110

Asp Tyr Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Ala Ala Asp Tyr Lys Asp
                245                 250                 255

His Asp Gly Asp Tyr Lys Asp His Asp Ile Asp Tyr Lys Asp Asp Asp
            260                 265                 270

Asp Lys Gly Ala Ala His His His His His His
        275                 280
```

<210> SEQ ID NO 113
<211> LENGTH: 249
<212> TYPE: PRT
<213> ORGANISM: Artificial Sequence
<220> FEATURE:
<223> OTHER INFORMATION: Nanobody sequence

<400> SEQUENCE: 113

```
Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
```

```
                    20                  25                  30
Ala Ile Gly Trp Phe Arg Gln Ala Pro Gly Lys Glu Arg Glu Gly Val
                35                  40                  45

Leu Cys Ile Asp Ala Ser Asp Asp Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Thr Pro Ile Gly Leu Ser Ser Cys Leu Leu Glu Tyr Asp Tyr
                100                 105                 110

Asp Tyr Trp Gly Gln Gly Thr Leu Val Thr Val Ser Ser Gly Gly Gly
            115                 120                 125

Gly Ser Gly Gly Gly Ser Glu Val Gln Leu Val Glu Ser Gly Gly Gly
        130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
                180                 185                 190

Leu Tyr Ala Asp Ser Val Lys Gly Arg Phe Thr Ile Ser Arg Asp Asn
            195                 200                 205

Ala Lys Thr Thr Leu Tyr Leu Gln Met Asn Ser Leu Arg Pro Glu Asp
        210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser
                245

<210> SEQ ID NO 114
<211> LENGTH: 158
<212> TYPE: PRT
<213> ORGANISM: Artificial Sequence
<220> FEATURE:
<223> OTHER INFORMATION: Nanobody sequence

<400> SEQUENCE: 114

Val Gln Leu Val Glu Ser Gly Gly Gly Leu Val Gln Pro Gly Gly Ser
1               5                   10                  15

Leu Arg Leu Ser Cys Ala Ala Ser Gly Phe Ile Leu Asp Tyr Tyr Ala
                20                  25                  30

Ile Gly Trp Phe Arg Gln Ala Pro Gly Lys Glu Arg Glu Gly Val Leu
                35                  40                  45

Cys Ile Asp Ala Ser Asp Asp Ile Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Gly Val Tyr Tyr Cys Ala
                85                  90                  95

Thr Pro Ile Gly Leu Ser Ser Cys Leu Leu Glu Tyr Asp Tyr Asp
            100                 105                 110

Tyr Trp Gly Gln Gly Thr Leu Val Thr Val Ser Ser Ala Ala Ala Asp
            115                 120                 125

Tyr Lys Asp His Asp Gly Asp Tyr Lys Asp His Asp Ile Asp Tyr Lys
```

```
                130               135               140
Asp Asp Asp Lys Gly Ala Ala His His His His His
145                 150               155

<210> SEQ ID NO 115
<211> LENGTH: 159
<212> TYPE: PRT
<213> ORGANISM: Artificial Sequence
<220> FEATURE:
<223> OTHER INFORMATION: Nanobody sequence

<400> SEQUENCE: 115

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45

Leu Cys Ile Asp Ala Ser Asp Asp Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Gly Val Tyr Tyr Cys
                85                  90                  95

Ala Thr Pro Ile Gly Leu Ser Ser Cys Leu Leu Glu Tyr Asp Tyr
            100                 105                 110

Asp Tyr Trp Gly Gln Gly Thr Leu Val Thr Val Ser Ser Ala Ala Ala
        115                 120                 125

Asp Tyr Lys Asp His Asp Gly Asp Tyr Lys Asp His Asp Ile Asp Tyr
        130                 135                 140

Lys Asp Asp Asp Asp Lys Gly Ala Ala His His His His His His
145                 150                 155

<210> SEQ ID NO 116
<211> LENGTH: 159
<212> TYPE: PRT
<213> ORGANISM: Artificial Sequence
<220> FEATURE:
<223> OTHER INFORMATION: Nanobody sequence

<400> SEQUENCE: 116

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45

Leu Cys Ile Asp Ala Ser Asp Asp Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Thr Pro Ile Gly Leu Ser Ser Cys Leu Leu Glu Tyr Asp Tyr
            100                 105                 110

Asp Tyr Trp Gly Gln Gly Thr Leu Val Thr Val Ser Ser Ala Ala Ala
        115                 120                 125
```

Asp Tyr Lys Asp His Asp Gly Asp Tyr Lys Asp His Asp Ile Asp Tyr
            130                 135                 140

Lys Asp Asp Asp Lys Gly Ala Ala His His His His His His
145                 150                 155

<210> SEQ ID NO 117
<211> LENGTH: 158
<212> TYPE: PRT
<213> ORGANISM: Artificial Sequence
<220> FEATURE:
<223> OTHER INFORMATION: Nanobody sequence

<400> SEQUENCE: 117

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Glu Glu Arg Glu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asn Ser Lys Asn Thr Val Tyr
65                  70                  75                  80

Leu Gln Met Asn Asn Leu Lys Pro Glu Asp Thr Ala Val Tyr Tyr Cys
                85                  90                  95

Ala Ala Thr Pro Ile Glu Arg Leu Gly Leu Asp Ala Tyr Glu Tyr Asp
            100                 105                 110

Tyr Trp Gly Gln Gly Thr Leu Val Thr Val Ser Ser Ala Ala Ala Asp
        115                 120                 125

Tyr Lys Asp His Asp Gly Asp Tyr Lys Asp His Asp Ile Asp Tyr Lys
    130                 135                 140

Asp Asp Asp Asp Lys Gly Ala Ala His His His His His His
145                 150                 155

<210> SEQ ID NO 118
<211> LENGTH: 158
<212> TYPE: PRT
<213> ORGANISM: Artificial Sequence
<220> FEATURE:
<223> OTHER INFORMATION: Nanobody sequence

<400> SEQUENCE: 118

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Glu Glu Arg Glu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asn Ser Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Thr Pro Ile Glu Arg Leu Gly Leu Asp Ala Tyr Glu Tyr Asp
            100                 105                 110

Tyr Trp Gly Gln Gly Thr Leu Val Thr Val Ser Ser Ala Ala Ala Asp
        115                 120                 125

Tyr Lys Asp His Asp Gly Asp Tyr Lys Asp His Asp Ile Asp Tyr Lys
        130                 135                 140

Asp Asp Asp Asp Lys Gly Ala Ala His His His His His His
145                 150                 155

<210> SEQ ID NO 119
<211> LENGTH: 158
<212> TYPE: PRT
<213> ORGANISM: Artificial Sequence
<220> FEATURE:
<223> OTHER INFORMATION: Nanobody sequence

<400> SEQUENCE: 119

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Glu Glu Arg Glu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asp Asn Ser Lys Asn Thr Val Tyr
65                  70                  75                  80

Leu Gln Met Asn Asn Leu Lys Pro Glu Asp Thr Ala Val Tyr Tyr Cys
                85                  90                  95

Ala Ala Thr Pro Ile Glu Arg Leu Gly Leu Asp Ala Tyr Glu Tyr Asp
            100                 105                 110

Tyr Trp Gly Gln Gly Thr Leu Val Thr Val Ser Ser Ala Ala Ala Asp
        115                 120                 125

Tyr Lys Asp His Asp Gly Asp Tyr Lys Asp His Asp Ile Asp Tyr Lys
        130                 135                 140

Asp Asp Asp Asp Lys Gly Ala Ala His His His His His His
145                 150                 155

<210> SEQ ID NO 120
<211> LENGTH: 158
<212> TYPE: PRT
<213> ORGANISM: Artificial Sequence
<220> FEATURE:
<223> OTHER INFORMATION: Nanobody sequence

<400> SEQUENCE: 120

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Glu Glu Arg Glu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Thr Pro Ile Glu Arg Leu Gly Leu Asp Ala Tyr Glu Tyr Asp
            100                 105                 110

Tyr Trp Gly Gln Gly Thr Leu Val Thr Val Ser Ser Ala Ala Ala Asp

```
            115                 120                 125
Tyr Lys Asp His Asp Gly Asp Tyr Lys Asp His Asp Ile Asp Tyr Lys
        130                 135                 140

Asp Asp Asp Asp Lys Gly Ala Ala His His His His His His
145                 150                 155
```

<210> SEQ ID NO 121
<211> LENGTH: 158
<212> TYPE: PRT
<213> ORGANISM: Artificial Sequence
<220> FEATURE:
<223> OTHER INFORMATION: Nanobody sequence

<400> SEQUENCE: 121

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Glu Glu Arg Glu Gly Val
        35                  40                  45

Ser Ser Ile Ser Ser Thr Tyr Gly Leu Thr Tyr Tyr Ala Asp Ser Val
50                  55                  60

Lys Gly Arg Phe Thr Ile Ser Arg Ser Asn Ser Lys Asn Thr Val Tyr
65                  70                  75                  80

Leu Gln Met Asn Asn Leu Lys Pro Glu Asp Thr Ala Val Tyr Tyr Cys
                85                  90                  95

Ala Ala Thr Pro Ile Glu Arg Leu Gly Leu Asp Ala Tyr Glu Tyr Asp
            100                 105                 110

Tyr Trp Gly Gln Gly Thr Leu Val Thr Val Ser Ser Ala Ala Ala Asp
        115                 120                 125

Tyr Lys Asp His Asp Gly Asp Tyr Lys Asp His Asp Ile Asp Tyr Lys
        130                 135                 140

Asp Asp Asp Asp Lys Gly Ala Ala His His His His His His
145                 150                 155
```

<210> SEQ ID NO 122
<211> LENGTH: 158
<212> TYPE: PRT
<213> ORGANISM: Artificial Sequence
<220> FEATURE:
<223> OTHER INFORMATION: Nanobody sequence

<400> SEQUENCE: 122

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Glu Glu Arg Glu Gly Val
        35                  40                  45

Ser Ser Ile Ser Ser Thr Tyr Gly Leu Thr Tyr Tyr Ala Asp Ser Val
50                  55                  60

Lys Gly Arg Phe Thr Ile Ser Arg Asp Asn Ser Lys Asn Thr Val Tyr
65                  70                  75                  80

Leu Gln Met Asn Asn Leu Lys Pro Glu Asp Thr Ala Val Tyr Tyr Cys
                85                  90                  95

Ala Ala Thr Pro Ile Glu Arg Leu Gly Leu Asp Ala Tyr Glu Tyr Asp
            100                 105                 110
```

```
Tyr Trp Gly Gln Gly Thr Leu Val Thr Val Ser Ser Ala Ala Ala Asp
            115                 120                 125

Tyr Lys Asp His Asp Gly Asp Tyr Lys Asp His Asp Ile Asp Tyr Lys
        130                 135                 140

Asp Asp Asp Asp Lys Gly Ala Ala His His His His His His
145                 150                 155

<210> SEQ ID NO 123
<211> LENGTH: 157
<212> TYPE: PRT
<213> ORGANISM: Artificial Sequence
<220> FEATURE:
<223> OTHER INFORMATION: Nanobody sequence

<400> SEQUENCE: 123

Val Gln Leu Val Glu Ser Gly Gly Gly Leu Val Gln Pro Gly Gly Ser
1               5                   10                  15

Leu Arg Leu Ser Cys Ala Ala Ser Gly Phe Thr Phe Asp Asp Tyr Ala
            20                  25                  30

Ile Gly Trp Phe Arg Gln Ala Pro Gly Glu Glu Arg Glu Gly Val Ser
        35                  40                  45

Ser Ile Ser Ser Thr Tyr Gly Leu Thr Tyr Tyr Ala Asp Ser Val Lys
50                  55                  60

Gly Arg Phe Thr Ile Ser Arg Ser Asn Ser Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Thr Pro Ile Glu Arg Leu Gly Leu Asp Ala Tyr Glu Tyr Asp Tyr
            100                 105                 110

Trp Gly Gln Gly Thr Leu Val Thr Val Ser Ser Ala Ala Ala Asp Tyr
        115                 120                 125

Lys Asp His Asp Gly Asp Tyr Lys Asp His Asp Ile Asp Tyr Lys Asp
    130                 135                 140

Asp Asp Asp Lys Gly Ala Ala His His His His His His
145                 150                 155

<210> SEQ ID NO 124
<211> LENGTH: 158
<212> TYPE: PRT
<213> ORGANISM: Artificial Sequence
<220> FEATURE:
<223> OTHER INFORMATION: Nanobody sequence

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Glu Glu Arg Glu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Thr Pro Ile Glu Arg Leu Gly Leu Asp Ala Tyr Glu Tyr Asp
            100                 105                 110
```

Tyr Trp Gly Gln Gly Thr Leu Val Thr Val Ser Ser Ala Ala Ala Asp
            115                 120                 125

Tyr Lys Asp His Asp Gly Asp Tyr Lys Asp His Asp Ile Asp Tyr Lys
    130                 135                 140

Asp Asp Asp Asp Lys Gly Ala Ala His His His His His His
145                 150                 155

<210> SEQ ID NO 125
<211> LENGTH: 158
<212> TYPE: PRT
<213> ORGANISM: Artificial Sequence
<220> FEATURE:
<223> OTHER INFORMATION: Nanobody sequence

<400> SEQUENCE: 125

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asn Ser Lys Asn Thr Val Tyr
65                  70                  75                  80

Leu Gln Met Asn Asn Leu Lys Pro Glu Asp Thr Ala Val Tyr Tyr Cys
                85                  90                  95

Ala Ala Thr Pro Ile Glu Arg Leu Gly Leu Asp Ala Tyr Glu Tyr Asp
            100                 105                 110

Tyr Trp Gly Gln Gly Thr Leu Val Thr Val Ser Ser Ala Ala Ala Asp
            115                 120                 125

Tyr Lys Asp His Asp Gly Asp Tyr Lys Asp His Asp Ile Asp Tyr Lys
    130                 135                 140

Asp Asp Asp Asp Lys Gly Ala Ala His His His His His His
145                 150                 155

<210> SEQ ID NO 126
<211> LENGTH: 158
<212> TYPE: PRT
<213> ORGANISM: Artificial Sequence
<220> FEATURE:
<223> OTHER INFORMATION: Nanobody sequence

<400> SEQUENCE: 126

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asn Ser Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Thr Pro Ile Glu Arg Leu Gly Leu Asp Ala Tyr Glu Tyr Asp

```
            100                 105                 110
Tyr Trp Gly Gln Gly Thr Leu Val Thr Val Ser Ser Ala Ala Ala Asp
        115                 120                 125

Tyr Lys Asp His Asp Gly Asp Tyr Lys Asp His Asp Ile Asp Tyr Lys
        130                 135                 140

Asp Asp Asp Asp Lys Gly Ala Ala His His His His His His
145                 150                 155
```

<210> SEQ ID NO 127
<211> LENGTH: 158
<212> TYPE: PRT
<213> ORGANISM: Artificial Sequence
<220> FEATURE:
<223> OTHER INFORMATION: Nanobody sequence

<400> SEQUENCE: 127

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asp Asn Ser Lys Asn Thr Val Tyr
65                  70                  75                  80

Leu Gln Met Asn Asn Leu Lys Pro Glu Asp Thr Ala Val Tyr Tyr Cys
                85                  90                  95

Ala Ala Thr Pro Ile Glu Arg Leu Gly Leu Asp Ala Tyr Glu Tyr Asp
            100                 105                 110

Tyr Trp Gly Gln Gly Thr Leu Val Thr Val Ser Ser Ala Ala Ala Asp
        115                 120                 125

Tyr Lys Asp His Asp Gly Asp Tyr Lys Asp His Asp Ile Asp Tyr Lys
        130                 135                 140

Asp Asp Asp Asp Lys Gly Ala Ala His His His His His His
145                 150                 155
```

<210> SEQ ID NO 128
<211> LENGTH: 158
<212> TYPE: PRT
<213> ORGANISM: Artificial Sequence
<220> FEATURE:
<223> OTHER INFORMATION: Nanobody sequence

<400> SEQUENCE: 128

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Lys Pro Glu Asp Thr Ala Val Tyr Tyr Cys
                85                  90                  95
```

```
Ala Ala Thr Pro Ile Glu Arg Leu Gly Leu Asp Ala Tyr Glu Tyr Asp
            100                 105                 110

Tyr Trp Gly Gln Gly Thr Leu Val Thr Val Ser Ser Ala Ala Ala Asp
        115                 120                 125

Tyr Lys Asp His Asp Gly Asp Tyr Lys Asp His Asp Ile Asp Tyr Lys
    130                 135                 140

Asp Asp Asp Asp Lys Gly Ala Ala His His His His His His
145                 150                 155
```

<210> SEQ ID NO 129
<211> LENGTH: 158
<212> TYPE: PRT
<213> ORGANISM: Artificial Sequence
<220> FEATURE:
<223> OTHER INFORMATION: Nanobody sequence

<400> SEQUENCE: 129

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Arg Ser Asn Ser Lys Asn Thr Val Tyr
65                  70                  75                  80

Leu Gln Met Asn Asn Leu Lys Pro Glu Asp Thr Ala Val Tyr Tyr Cys
                85                  90                  95

Ala Ala Thr Pro Ile Glu Arg Leu Gly Leu Asp Ala Tyr Glu Tyr Asp
            100                 105                 110

Tyr Trp Gly Gln Gly Thr Leu Val Thr Val Ser Ser Ala Ala Ala Asp
        115                 120                 125

Tyr Lys Asp His Asp Gly Asp Tyr Lys Asp His Asp Ile Asp Tyr Lys
    130                 135                 140

Asp Asp Asp Asp Lys Gly Ala Ala His His His His His His
145                 150                 155
```

<210> SEQ ID NO 130
<211> LENGTH: 158
<212> TYPE: PRT
<213> ORGANISM: Artificial Sequence
<220> FEATURE:
<223> OTHER INFORMATION: Nanobody sequence

<400> SEQUENCE: 130

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Asn Leu Lys Pro Glu Asp Thr Ala Val Tyr Tyr Cys
                85                  90                  95
```

Ala Ala Thr Pro Ile Glu Arg Leu Gly Leu Asp Ala Tyr Glu Tyr Asp
                100                 105                 110

Tyr Trp Gly Gln Gly Thr Leu Val Thr Val Ser Ser Ala Ala Ala Asp
            115                 120                 125

Tyr Lys Asp His Asp Gly Asp Tyr Lys Asp His Asp Ile Asp Tyr Lys
        130                 135                 140

Asp Asp Asp Asp Lys Gly Ala Ala His His His His His His
145                 150                 155

<210> SEQ ID NO 131
<211> LENGTH: 158
<212> TYPE: PRT
<213> ORGANISM: Artificial Sequence
<220> FEATURE:
<223> OTHER INFORMATION: Nanobody sequence

<400> SEQUENCE: 131

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Arg Ser Asn Ser Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Thr Pro Ile Glu Arg Leu Gly Leu Asp Ala Tyr Glu Tyr Asp
                100                 105                 110

Tyr Trp Gly Gln Gly Thr Leu Val Thr Val Ser Ser Ala Ala Ala Asp
            115                 120                 125

Tyr Lys Asp His Asp Gly Asp Tyr Lys Asp His Asp Ile Asp Tyr Lys
        130                 135                 140

Asp Asp Asp Asp Lys Gly Ala Ala His His His His His His
145                 150                 155

<210> SEQ ID NO 132
<211> LENGTH: 158
<212> TYPE: PRT
<213> ORGANISM: Artificial Sequence
<220> FEATURE:
<223> OTHER INFORMATION: Nanobody sequence

<400> SEQUENCE: 132

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Lys Pro Glu Asp Thr Ala Val Tyr Tyr Cys

```
                    85                  90                  95
Ala Ala Thr Pro Ile Glu Arg Leu Gly Leu Asp Ala Tyr Glu Tyr Asp
                100                 105                 110

Tyr Trp Gly Gln Gly Thr Leu Val Thr Val Ser Ser Ala Ala Ala Asp
            115                 120                 125

Tyr Lys Asp His Asp Gly Asp Tyr Lys Asp His Asp Ile Asp Tyr Lys
        130                 135                 140

Asp Asp Asp Asp Lys Gly Ala Ala His His His His His His
145                 150                 155

<210> SEQ ID NO 133
<211> LENGTH: 158
<212> TYPE: PRT
<213> ORGANISM: Artificial Sequence
<220> FEATURE:
<223> OTHER INFORMATION: Nanobody sequence

<400> SEQUENCE: 133

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Glu Glu Arg Glu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Thr Pro Ile Gly Leu Ile Gly Leu Asp Ala Tyr Glu Tyr Asp
                100                 105                 110

Tyr Trp Gly Gln Gly Thr Leu Val Thr Val Ser Ser Ala Ala Ala Asp
            115                 120                 125

Tyr Lys Asp His Asp Gly Asp Tyr Lys Asp His Asp Ile Asp Tyr Lys
        130                 135                 140

Asp Asp Asp Asp Lys Gly Ala Ala His His His His His His
145                 150                 155

<210> SEQ ID NO 134
<211> LENGTH: 158
<212> TYPE: PRT
<213> ORGANISM: Artificial Sequence
<220> FEATURE:
<223> OTHER INFORMATION: Nanobody sequence

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asp Asp Tyr
            20                  25                  30

Ala Ile Gly Trp Phe Arg Gln Ala Pro Gly Glu Glu Arg Glu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Asp Asn Ser Lys Asn Thr Val Tyr
65                  70                  75                  80
```

Leu Gln Met Asn Ser Leu Arg Pro Glu Asp Thr Ala Val Tyr Tyr Cys
                85                  90                  95

Ala Ala Thr Pro Ile Gly Leu Ile Gly Leu Asp Ala Tyr Glu Tyr Asp
            100                 105                 110

Tyr Trp Gly Gln Gly Thr Leu Val Thr Val Ser Ser Ala Ala Ala Asp
        115                 120                 125

Tyr Lys Asp His Asp Gly Asp Tyr Lys Asp His Asp Ile Asp Tyr Lys
    130                 135                 140

Asp Asp Asp Asp Lys Gly Ala Ala His His His His His His
145                 150                 155

<210> SEQ ID NO 135
<211> LENGTH: 158
<212> TYPE: PRT
<213> ORGANISM: Artificial Sequence
<220> FEATURE:
<223> OTHER INFORMATION: Nanobody sequence

<400> SEQUENCE: 135

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Thr Pro Ile Gly Leu Ile Gly Leu Asp Ala Tyr Glu Tyr Asp
            100                 105                 110

Tyr Trp Gly Gln Gly Thr Leu Val Thr Val Ser Ser Ala Ala Ala Asp
        115                 120                 125

Tyr Lys Asp His Asp Gly Asp Tyr Lys Asp His Asp Ile Asp Tyr Lys
    130                 135                 140

Asp Asp Asp Asp Lys Gly Ala Ala His His His His His His
145                 150                 155

<210> SEQ ID NO 136
<211> LENGTH: 158
<212> TYPE: PRT
<213> ORGANISM: Artificial Sequence
<220> FEATURE:
<223> OTHER INFORMATION: Nanobody sequence

<400> SEQUENCE: 136

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asp Asp Tyr
            20                  25                  30

Ala Ile Gly Trp Phe Arg Gln Ala Pro Gly Lys Glu Arg Glu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asp Asn Ser Lys Asn Thr Val Tyr
65                  70                  75                  80

```
Leu Gln Met Asn Ser Leu Arg Pro Glu Asp Thr Ala Val Tyr Tyr Cys
                85                  90                  95

Ala Ala Thr Pro Ile Gly Leu Ile Gly Leu Asp Ala Tyr Glu Tyr Asp
            100                 105                 110

Tyr Trp Gly Gln Gly Thr Leu Val Thr Val Ser Ser Ala Ala Ala Asp
        115                 120                 125

Tyr Lys Asp His Asp Gly Asp Tyr Lys Asp His Asp Ile Asp Tyr Lys
    130                 135                 140

Asp Asp Asp Asp Lys Gly Ala Ala His His His His His His
145                 150                 155

<210> SEQ ID NO 137
<211> LENGTH: 158
<212> TYPE: PRT
<213> ORGANISM: Artificial Sequence
<220> FEATURE:
<223> OTHER INFORMATION: Nanobody sequence

<400> SEQUENCE: 137

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Glu Glu Arg Leu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Thr Pro Ile Gly Leu Ile Gly Leu Asp Ala Tyr Glu Tyr Asp
            100                 105                 110

Tyr Trp Gly Gln Gly Thr Leu Val Thr Val Ser Ser Ala Ala Ala Asp
        115                 120                 125

Tyr Lys Asp His Asp Gly Asp Tyr Lys Asp His Asp Ile Asp Tyr Lys
    130                 135                 140

Asp Asp Asp Asp Lys Gly Ala Ala His His His His His His
145                 150                 155

<210> SEQ ID NO 138
<211> LENGTH: 158
<212> TYPE: PRT
<213> ORGANISM: Artificial Sequence
<220> FEATURE:
<223> OTHER INFORMATION: Nanobody sequence

<400> SEQUENCE: 138

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asp Asp Tyr
            20                  25                  30

Ala Ile Gly Trp Phe Arg Gln Ala Pro Gly Glu Glu Arg Leu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asp Asn Ser Lys Asn Thr Val Tyr
```

```
                65                  70                  75                  80
Leu Gln Met Asn Ser Leu Arg Pro Glu Asp Thr Ala Val Tyr Tyr Cys
                    85                  90                  95

Ala Ala Thr Pro Ile Gly Leu Ile Gly Leu Asp Ala Tyr Glu Tyr Asp
                100                 105                 110

Tyr Trp Gly Gln Gly Thr Leu Val Thr Val Ser Ser Ala Ala Ala Asp
            115                 120                 125

Tyr Lys Asp His Asp Gly Asp Tyr Lys Asp His Asp Ile Asp Tyr Lys
        130                 135                 140

Asp Asp Asp Asp Lys Gly Ala Ala His His His His His His
145                 150                 155

<210> SEQ ID NO 139
<211> LENGTH: 158
<212> TYPE: PRT
<213> ORGANISM: Artificial Sequence
<220> FEATURE:
<223> OTHER INFORMATION: Nanobody sequence

<400> SEQUENCE: 139

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Leu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Thr Pro Ile Gly Leu Ile Gly Leu Asp Ala Tyr Glu Tyr Asp
                100                 105                 110

Tyr Trp Gly Gln Gly Thr Leu Val Thr Val Ser Ser Ala Ala Ala Asp
            115                 120                 125

Tyr Lys Asp His Asp Gly Asp Tyr Lys Asp His Asp Ile Asp Tyr Lys
        130                 135                 140

Asp Asp Asp Asp Lys Gly Ala Ala His His His His His His
145                 150                 155

<210> SEQ ID NO 140
<211> LENGTH: 158
<212> TYPE: PRT
<213> ORGANISM: Artificial Sequence
<220> FEATURE:
<223> OTHER INFORMATION: Nanobody sequence

<400> SEQUENCE: 140

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asp Asp Tyr
            20                  25                  30

Ala Ile Gly Trp Phe Arg Gln Ala Pro Gly Lys Glu Arg Leu Gly Val
        35                  40                  45

Ser Ser Ile Ser Ser Thr Tyr Gly Leu Thr Tyr Tyr Ala Asp Ser Val
    50                  55                  60
```

Lys Gly Arg Phe Thr Ile Ser Ser Asp Asn Ser Lys Asn Thr Val Tyr
65                  70                  75                  80

Leu Gln Met Asn Ser Leu Arg Pro Glu Asp Thr Ala Val Tyr Tyr Cys
            85                  90                  95

Ala Ala Thr Pro Ile Gly Leu Ile Gly Leu Asp Ala Tyr Glu Tyr Asp
            100                 105                 110

Tyr Trp Gly Gln Gly Thr Leu Val Thr Val Ser Ser Ala Ala Ala Asp
            115                 120                 125

Tyr Lys Asp His Asp Gly Asp Tyr Lys Asp His Asp Ile Asp Tyr Lys
            130                 135                 140

Asp Asp Asp Asp Lys Gly Ala Ala His His His His His His
145                 150                 155

<210> SEQ ID NO 141
<211> LENGTH: 158
<212> TYPE: PRT
<213> ORGANISM: Artificial Sequence
<220> FEATURE:
<223> OTHER INFORMATION: Nanobody sequence

<400> SEQUENCE: 141

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Glu Glu Arg Glu Gly Val
            35                  40                  45

Ser Ser Ile Ser Ser Thr Tyr Gly Leu Thr Tyr Tyr Ala Asp Pro Val
50                  55                  60

Lys Gly Arg Phe Thr Ile Ser Ser Asp Asn Ser Lys Asn Thr Val Tyr
65                  70                  75                  80

Leu Gln Met Asn Ser Leu Arg Pro Glu Asp Thr Ala Val Tyr Tyr Cys
            85                  90                  95

Ala Ala Thr Pro Ile Gly Leu Ile Gly Leu Asp Ala Tyr Glu Tyr Asp
            100                 105                 110

Tyr Trp Gly Gln Gly Thr Leu Val Thr Val Ser Ser Ala Ala Ala Asp
            115                 120                 125

Tyr Lys Asp His Asp Gly Asp Tyr Lys Asp His Asp Ile Asp Tyr Lys
            130                 135                 140

Asp Asp Asp Asp Lys Gly Ala Ala His His His His His His
145                 150                 155

<210> SEQ ID NO 142
<211> LENGTH: 249
<212> TYPE: PRT
<213> ORGANISM: Artificial Sequence
<220> FEATURE:
<223> OTHER INFORMATION: Nanobody sequence

<400> SEQUENCE: 142

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Glu Glu Arg Glu Gly Val
            35                  40                  45

Ser Ser Ile Ser Ser Thr Tyr Gly Leu Thr Tyr Tyr Ala Asp Ser Val
50                  55                  60

Lys Gly Arg Phe Thr Ile Ser Ser Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Thr Pro Ile Gly Leu Ile Gly Leu Asp Ala Tyr Glu Tyr Asp
            100                 105                 110

Tyr Trp Gly Gln Gly Thr Leu Val Thr Val Ser Ser Gly Gly Gly Gly
            115                 120                 125

Ser Gly Gly Gly Ser Glu Val Gln Leu Val Glu Ser Gly Gly Gly Leu
130                 135                 140

Val Gln Pro Gly Asn Ser Leu Arg Leu Ser Cys Ala Ala Ser Gly Phe
145                 150                 155                 160

Thr Phe Ser Ser Phe Gly Met Ser Trp Val Arg Gln Ala Pro Gly Lys
            165                 170                 175

Gly Leu Glu Trp Val Ser Ser Ile Ser Gly Ser Gly Ser Asp Thr Leu
            180                 185                 190

Tyr Ala Asp Ser Val Lys Gly Arg Phe Thr Ile Ser Arg Asp Asn Ala
            195                 200                 205

Lys Thr Thr Leu Tyr Leu Gln Met Asn Ser Leu Arg Pro Glu Asp Thr
210                 215                 220

Ala Val Tyr Tyr Cys Thr Ile Gly Gly Ser Leu Ser Arg Ser Ser Gln
225                 230                 235                 240

Gly Thr Leu Val Thr Val Ser Ser Ala
                245

<210> SEQ ID NO 143
<211> LENGTH: 249
<212> TYPE: PRT
<213> ORGANISM: Artificial Sequence
<220> FEATURE:
<223> OTHER INFORMATION: Nanobody sequence

<400> SEQUENCE: 143

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asp Asp Tyr
                20                  25                  30

Ala Ile Gly Trp Phe Arg Gln Ala Pro Gly Glu Glu Arg Glu Gly Val
            35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Thr Pro Ile Gly Leu Ile Gly Leu Asp Ala Tyr Glu Tyr Asp
            100                 105                 110

Tyr Trp Gly Gln Gly Thr Leu Val Thr Val Ser Ser Gly Gly Gly Gly
            115                 120                 125

Ser Gly Gly Gly Ser Glu Val Gln Leu Val Glu Ser Gly Gly Gly Leu
130                 135                 140

Val Gln Pro Gly Asn Ser Leu Arg Leu Ser Cys Ala Ala Ser Gly Phe
145                 150                 155                 160

Thr Phe Ser Ser Phe Gly Met Ser Trp Val Arg Gln Ala Pro Gly Lys
            165                 170                 175

```
Gly Leu Glu Trp Val Ser Ser Ile Ser Gly Ser Gly Ser Asp Thr Leu
            180                 185                 190

Tyr Ala Asp Ser Val Lys Gly Arg Phe Thr Ile Ser Arg Asp Asn Ala
            195                 200                 205

Lys Thr Thr Leu Tyr Leu Gln Met Asn Ser Leu Arg Pro Glu Asp Thr
210                 215                 220

Ala Val Tyr Tyr Cys Thr Ile Gly Gly Ser Leu Ser Arg Ser Ser Gln
225                 230                 235                 240

Gly Thr Leu Val Thr Val Ser Ser Ala
                245
```

<210> SEQ ID NO 144
<211> LENGTH: 249
<212> TYPE: PRT
<213> ORGANISM: Artificial Sequence
<220> FEATURE:
<223> OTHER INFORMATION: Nanobody sequence

<400> SEQUENCE: 144

```
Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
            35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Thr Pro Ile Gly Leu Ile Gly Leu Asp Ala Tyr Glu Tyr Asp
            100                 105                 110

Tyr Trp Gly Gln Gly Thr Leu Val Thr Val Ser Ser Gly Gly Gly Gly
        115                 120                 125

Ser Gly Gly Gly Ser Glu Val Gln Leu Val Glu Ser Gly Gly Gly Leu
    130                 135                 140

Val Gln Pro Gly Asn Ser Leu Arg Leu Ser Cys Ala Ala Ser Gly Phe
145                 150                 155                 160

Thr Phe Ser Ser Phe Gly Met Ser Trp Val Arg Gln Ala Pro Gly Lys
                165                 170                 175

Gly Leu Glu Trp Val Ser Ser Ile Ser Gly Ser Gly Ser Asp Thr Leu
            180                 185                 190

Tyr Ala Asp Ser Val Lys Gly Arg Phe Thr Ile Ser Arg Asp Asn Ala
            195                 200                 205

Lys Thr Thr Leu Tyr Leu Gln Met Asn Ser Leu Arg Pro Glu Asp Thr
210                 215                 220

Ala Val Tyr Tyr Cys Thr Ile Gly Gly Ser Leu Ser Arg Ser Ser Gln
225                 230                 235                 240

Gly Thr Leu Val Thr Val Ser Ser Ala
                245
```

<210> SEQ ID NO 145
<211> LENGTH: 249
<212> TYPE: PRT
<213> ORGANISM: Artificial Sequence

```
<220> FEATURE:
<223> OTHER INFORMATION: Nanobody sequence

<400> SEQUENCE: 145

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asp Asp Tyr
            20                  25                  30

Ala Ile Gly Trp Phe Arg Gln Ala Pro Gly Lys Glu Arg Glu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Pro Glu Asp Thr Ala Val Tyr Tyr Cys
            85                  90                  95

Ala Ala Thr Pro Ile Gly Leu Ile Gly Leu Asp Ala Tyr Glu Tyr Asp
        100                 105                 110

Tyr Trp Gly Gln Gly Thr Leu Val Thr Val Ser Ser Gly Gly Gly Gly
    115                 120                 125

Ser Gly Gly Gly Ser Glu Val Gln Leu Val Glu Ser Gly Gly Gly Leu
    130                 135                 140

Val Gln Pro Gly Asn Ser Leu Arg Leu Ser Cys Ala Ala Ser Gly Phe
145                 150                 155                 160

Thr Phe Ser Ser Phe Gly Met Ser Trp Val Arg Gln Ala Pro Gly Lys
            165                 170                 175

Gly Leu Glu Trp Val Ser Ser Ile Ser Gly Ser Gly Ser Asp Thr Leu
        180                 185                 190

Tyr Ala Asp Ser Val Lys Gly Arg Phe Thr Ile Ser Arg Asp Asn Ala
    195                 200                 205

Lys Thr Thr Leu Tyr Leu Gln Met Asn Ser Leu Arg Pro Glu Asp Thr
210                 215                 220

Ala Val Tyr Tyr Cys Thr Ile Gly Gly Ser Leu Ser Arg Ser Ser Gln
225                 230                 235                 240

Gly Thr Leu Val Thr Val Ser Ser Ala
            245

<210> SEQ ID NO 146
<211> LENGTH: 249
<212> TYPE: PRT
<213> ORGANISM: Artificial Sequence
<220> FEATURE:
<223> OTHER INFORMATION: Nanobody sequence

<400> SEQUENCE: 146

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Glu Glu Arg Leu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Pro Glu Asp Thr Ala Val Tyr Tyr Cys
```

```
                        85                  90                  95
Ala Ala Thr Pro Ile Gly Leu Ile Gly Leu Asp Ala Tyr Glu Tyr Asp
                100                 105                 110

Tyr Trp Gly Gln Gly Thr Leu Val Thr Val Ser Ser Gly Gly Gly Gly
            115                 120                 125

Ser Gly Gly Gly Ser Glu Val Gln Leu Val Glu Ser Gly Gly Gly Leu
        130                 135                 140

Val Gln Pro Gly Asn Ser Leu Arg Leu Ser Cys Ala Ala Ser Gly Phe
145                 150                 155                 160

Thr Phe Ser Ser Phe Gly Met Ser Trp Val Arg Gln Ala Pro Gly Lys
                165                 170                 175

Gly Leu Glu Trp Val Ser Ser Ile Ser Gly Ser Gly Ser Asp Thr Leu
            180                 185                 190

Tyr Ala Asp Ser Val Lys Gly Arg Phe Thr Ile Ser Arg Asp Asn Ala
        195                 200                 205

Lys Thr Thr Leu Tyr Leu Gln Met Asn Ser Leu Arg Pro Glu Asp Thr
210                 215                 220

Ala Val Tyr Tyr Cys Thr Ile Gly Gly Ser Leu Ser Arg Ser Ser Gln
225                 230                 235                 240

Gly Thr Leu Val Thr Val Ser Ser Ala
                245

<210> SEQ ID NO 147
<211> LENGTH: 249
<212> TYPE: PRT
<213> ORGANISM: Artificial Sequence
<220> FEATURE:
<223> OTHER INFORMATION: Nanobody sequence

<400> SEQUENCE: 147

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asp Asp Tyr
            20                  25                  30

Ala Ile Gly Trp Phe Arg Gln Ala Pro Gly Glu Glu Arg Leu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Thr Pro Ile Gly Leu Ile Gly Leu Asp Ala Tyr Glu Tyr Asp
                100                 105                 110

Tyr Trp Gly Gln Gly Thr Leu Val Thr Val Ser Ser Gly Gly Gly Gly
            115                 120                 125

Ser Gly Gly Gly Ser Glu Val Gln Leu Val Glu Ser Gly Gly Gly Leu
        130                 135                 140

Val Gln Pro Gly Asn Ser Leu Arg Leu Ser Cys Ala Ala Ser Gly Phe
145                 150                 155                 160

Thr Phe Ser Ser Phe Gly Met Ser Trp Val Arg Gln Ala Pro Gly Lys
                165                 170                 175

Gly Leu Glu Trp Val Ser Ser Ile Ser Gly Ser Gly Ser Asp Thr Leu
            180                 185                 190

Tyr Ala Asp Ser Val Lys Gly Arg Phe Thr Ile Ser Arg Asp Asn Ala
```

```
                  195                 200                 205
Lys Thr Thr Leu Tyr Leu Gln Met Asn Ser Leu Arg Pro Glu Asp Thr
    210                 215                 220

Ala Val Tyr Tyr Cys Thr Ile Gly Gly Ser Leu Ser Arg Ser Ser Gln
225                 230                 235                 240

Gly Thr Leu Val Thr Val Ser Ser Ala
                245

<210> SEQ ID NO 148
<211> LENGTH: 249
<212> TYPE: PRT
<213> ORGANISM: Artificial Sequence
<220> FEATURE:
<223> OTHER INFORMATION: Nanobody sequence

<400> SEQUENCE: 148

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Leu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Thr Pro Ile Gly Leu Ile Gly Leu Asp Ala Tyr Glu Tyr Asp
            100                 105                 110

Tyr Trp Gly Gln Gly Thr Leu Val Thr Val Ser Ser Gly Gly Gly Gly
        115                 120                 125

Ser Gly Gly Gly Ser Glu Val Gln Leu Val Glu Ser Gly Gly Gly Leu
    130                 135                 140

Val Gln Pro Gly Asn Ser Leu Arg Leu Ser Cys Ala Ala Ser Gly Phe
145                 150                 155                 160

Thr Phe Ser Ser Phe Gly Met Ser Trp Val Arg Gln Ala Pro Gly Lys
                165                 170                 175

Gly Leu Glu Trp Val Ser Ser Ile Ser Gly Ser Gly Ser Asp Thr Leu
            180                 185                 190

Tyr Ala Asp Ser Val Lys Gly Arg Phe Thr Ile Ser Arg Asp Asn Ala
        195                 200                 205

Lys Thr Thr Leu Tyr Leu Gln Met Asn Ser Leu Arg Pro Glu Asp Thr
    210                 215                 220

Ala Val Tyr Tyr Cys Thr Ile Gly Gly Ser Leu Ser Arg Ser Ser Gln
225                 230                 235                 240

Gly Thr Leu Val Thr Val Ser Ser Ala
                245

<210> SEQ ID NO 149
<211> LENGTH: 249
<212> TYPE: PRT
<213> ORGANISM: Artificial Sequence
<220> FEATURE:
<223> OTHER INFORMATION: Nanobody sequence

<400> SEQUENCE: 149
```

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asp Asp Tyr
            20                  25                  30

Ala Ile Gly Trp Phe Arg Gln Ala Pro Gly Lys Glu Arg Leu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Thr Pro Ile Gly Leu Ile Gly Leu Asp Ala Tyr Glu Tyr Asp
            100                 105                 110

Tyr Trp Gly Gln Gly Thr Leu Val Thr Val Ser Ser Gly Gly Gly Gly
        115                 120                 125

Ser Gly Gly Gly Ser Glu Val Gln Leu Val Glu Ser Gly Gly Gly Leu
    130                 135                 140

Val Gln Pro Gly Asn Ser Leu Arg Leu Ser Cys Ala Ala Ser Gly Phe
145                 150                 155                 160

Thr Phe Ser Ser Phe Gly Met Ser Trp Val Arg Gln Ala Pro Gly Lys
            165                 170                 175

Gly Leu Glu Trp Val Ser Ser Ile Ser Gly Ser Gly Ser Asp Thr Leu
        180                 185                 190

Tyr Ala Asp Ser Val Lys Gly Arg Phe Thr Ile Ser Arg Asp Asn Ala
    195                 200                 205

Lys Thr Thr Leu Tyr Leu Gln Met Asn Ser Leu Arg Pro Glu Asp Thr
210                 215                 220

Ala Val Tyr Tyr Cys Thr Ile Gly Gly Ser Leu Ser Arg Ser Ser Gln
225                 230                 235                 240

Gly Thr Leu Val Thr Val Ser Ser Ala
                245

<210> SEQ ID NO 150
<211> LENGTH: 249
<212> TYPE: PRT
<213> ORGANISM: Artificial Sequence
<220> FEATURE:
<223> OTHER INFORMATION: Nanobody sequence

<400> SEQUENCE: 150

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Glu Glu Arg Glu Gly Val
        35                  40                  45

Ser Ser Ile Ser Ser Thr Tyr Gly Leu Thr Tyr Tyr Ala Asp Pro Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Thr Pro Ile Gly Leu Ile Gly Leu Asp Ala Tyr Glu Tyr Asp
            100                 105                 110

Tyr Trp Gly Gln Gly Thr Leu Val Thr Val Ser Ser Gly Gly Gly
            115                 120                 125

Ser Gly Gly Ser Glu Val Gln Leu Val Glu Ser Gly Gly Gly Leu
        130                 135                 140

Val Gln Pro Gly Asn Ser Leu Arg Leu Ser Cys Ala Ala Ser Gly Phe
145                 150                 155                 160

Thr Phe Ser Ser Phe Gly Met Ser Trp Val Arg Gln Ala Pro Gly Lys
                165                 170                 175

Gly Leu Glu Trp Val Ser Ser Ile Gly Ser Gly Ser Asp Thr Leu
            180                 185                 190

Tyr Ala Asp Ser Val Lys Gly Arg Phe Thr Ile Ser Arg Asp Asn Ala
            195                 200                 205

Lys Thr Thr Leu Tyr Leu Gln Met Asn Ser Leu Arg Pro Glu Asp Thr
210                 215                 220

Ala Val Tyr Tyr Cys Thr Ile Gly Gly Ser Leu Ser Arg Ser Ser Gln
225                 230                 235                 240

Gly Thr Leu Val Thr Val Ser Ser Ala
            245

<210> SEQ ID NO 151
<211> LENGTH: 158
<212> TYPE: PRT
<213> ORGANISM: Artificial Sequence
<220> FEATURE:
<223> OTHER INFORMATION: Nanobody sequence

<400> SEQUENCE: 151

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Glu Glu Arg Glu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Ala Ala Thr Pro Ile Glu Arg Leu Gly Leu Asp Ala Tyr Glu Tyr Asp
            100                 105                 110

Tyr Trp Gly Gln Gly Thr Leu Val Thr Val Ser Ser Ala Ala Ala Asp
        115                 120                 125

Tyr Lys Asp His Asp Gly Asp Tyr Lys Asp His Asp Ile Asp Tyr Lys
    130                 135                 140

Asp Asp Asp Asp Lys Gly Ala Ala His His His His His His
145                 150                 155

<210> SEQ ID NO 152
<211> LENGTH: 30
<212> TYPE: PRT
<213> ORGANISM: Artificial Sequence
<220> FEATURE:
<223> OTHER INFORMATION: framework 1 sequence

<400> SEQUENCE: 152

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg
            20                  25                  30

<210> SEQ ID NO 153
<211> LENGTH: 30
<212> TYPE: PRT
<213> ORGANISM: Artificial Sequence
<220> FEATURE:
<223> OTHER INFORMATION: framework 1 sequence

<400> SEQUENCE: 153

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp
            20                  25                  30

<210> SEQ ID NO 154
<211> LENGTH: 30
<212> TYPE: PRT
<213> ORGANISM: Artificial Sequence
<220> FEATURE:
<223> OTHER INFORMATION: framework 1 sequence

<400> SEQUENCE: 154

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asp
            20                  25                  30

<210> SEQ ID NO 155
<211> LENGTH: 30
<212> TYPE: PRT
<213> ORGANISM: Artificial Sequence
<220> FEATURE:
<223> OTHER INFORMATION: framework 1 sequence

<400> SEQUENCE: 155

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp
            20                  25                  30

<210> SEQ ID NO 156
<211> LENGTH: 30
<212> TYPE: PRT
<213> ORGANISM: Artificial Sequence
<220> FEATURE:
<223> OTHER INFORMATION: framework 1 sequence

<400> SEQUENCE: 156

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asp
            20                  25                  30

<210> SEQ ID NO 157
<211> LENGTH: 5
<212> TYPE: PRT
<213> ORGANISM: Artificial Sequence
<220> FEATURE:
<223> OTHER INFORMATION: CDR1 sequence

<400> SEQUENCE: 157

Ser Phe Gly Met Ser

```
1               5

<210> SEQ ID NO 158
<211> LENGTH: 5
<212> TYPE: PRT
<213> ORGANISM: Artificial Sequence
<220> FEATURE:
<223> OTHER INFORMATION: CDR1 sequence

<400> SEQUENCE: 158

Asp Tyr Ala Ile Gly
1               5

<210> SEQ ID NO 159
<211> LENGTH: 5
<212> TYPE: PRT
<213> ORGANISM: Artificial Sequence
<220> FEATURE:
<223> OTHER INFORMATION: CDR1 sequence

<400> SEQUENCE: 159

Asp Tyr Ala Ile Gly
1               5

<210> SEQ ID NO 160
<211> LENGTH: 5
<212> TYPE: PRT
<213> ORGANISM: Artificial Sequence
<220> FEATURE:
<223> OTHER INFORMATION: CDR1 sequence

<400> SEQUENCE: 160

Asp Tyr Ala Ile Gly
1               5

<210> SEQ ID NO 161
<211> LENGTH: 5
<212> TYPE: PRT
<213> ORGANISM: Artificial Sequence
<220> FEATURE:
<223> OTHER INFORMATION: CDR1 sequence

<400> SEQUENCE: 161

Asp Tyr Ala Ile Gly
1               5

<210> SEQ ID NO 162
<211> LENGTH: 14
<212> TYPE: PRT
<213> ORGANISM: Artificial Sequence
<220> FEATURE:
<223> OTHER INFORMATION: framework 2 sequence

<400> SEQUENCE: 162

Trp Val Arg Gln Ala Pro Gly Lys Gly Pro Glu Trp Val Ser
1               5                   10

<210> SEQ ID NO 163
<211> LENGTH: 14
<212> TYPE: PRT
<213> ORGANISM: Artificial Sequence
<220> FEATURE:
<223> OTHER INFORMATION: framework 2 sequence

<400> SEQUENCE: 163

Trp Phe Arg Gln Ala Pro Gly Glu Glu Arg Glu Gly Val Ser
1               5                   10
```

<210> SEQ ID NO 164
<211> LENGTH: 14
<212> TYPE: PRT
<213> ORGANISM: Artificial Sequence
<220> FEATURE:
<223> OTHER INFORMATION: framework 2 sequence

<400> SEQUENCE: 164

Trp Phe Arg Gln Ala Pro Gly Glu Glu Arg Glu Gly Val Ser
1               5                   10

<210> SEQ ID NO 165
<211> LENGTH: 14
<212> TYPE: PRT
<213> ORGANISM: Artificial Sequence
<220> FEATURE:
<223> OTHER INFORMATION: framework 2 sequence

<400> SEQUENCE: 165

Trp Phe Arg Gln Ala Pro Gly Glu Glu Arg Leu Gly Val Ser
1               5                   10

<210> SEQ ID NO 166
<211> LENGTH: 14
<212> TYPE: PRT
<213> ORGANISM: Artificial Sequence
<220> FEATURE:
<223> OTHER INFORMATION: framework 2 sequence

<400> SEQUENCE: 166

Trp Phe Arg Gln Ala Pro Gly Glu Glu Arg Leu Gly Val Ser
1               5                   10

<210> SEQ ID NO 167
<211> LENGTH: 17
<212> TYPE: PRT
<213> ORGANISM: Artificial Sequence
<220> FEATURE:
<223> OTHER INFORMATION: CDR2 sequence

<400> SEQUENCE: 167

Ser Ile Ser Gly Ser Gly Ser Asp Thr Leu Tyr Ala Asp Ser Val Lys
1               5                   10                  15

Gly

<210> SEQ ID NO 168
<211> LENGTH: 17
<212> TYPE: PRT
<213> ORGANISM: Artificial Sequence
<220> FEATURE:
<223> OTHER INFORMATION: CDR2 sequence

<400> SEQUENCE: 168

Ser Ile Ser Ser Thr Tyr Gly Leu Thr Tyr Tyr Ala Asp Ser Val Lys
1               5                   10                  15

Gly

<210> SEQ ID NO 169
<211> LENGTH: 17
<212> TYPE: PRT
<213> ORGANISM: Artificial Sequence
<220> FEATURE:
<223> OTHER INFORMATION: CDR2 sequence

<400> SEQUENCE: 169

Ser Ile Ser Ser Thr Tyr Gly Leu Thr Tyr Tyr Ala Asp Ser Val Lys
1               5                   10                  15

Gly

<210> SEQ ID NO 170
<211> LENGTH: 17
<212> TYPE: PRT
<213> ORGANISM: Artificial Sequence
<220> FEATURE:
<223> OTHER INFORMATION: CDR2 sequence

<400> SEQUENCE: 170

Ser Ile Ser Ser Thr Tyr Gly Leu Thr Tyr Tyr Ala Asp Ser Val Lys
1               5                   10                  15

Gly

<210> SEQ ID NO 171
<211> LENGTH: 17
<212> TYPE: PRT
<213> ORGANISM: Artificial Sequence
<220> FEATURE:
<223> OTHER INFORMATION: CDR2 sequence

<400> SEQUENCE: 171

Ser Ile Ser Ser Thr Tyr Gly Leu Thr Tyr Tyr Ala Asp Ser Val Lys
1               5                   10                  15

Gly

<210> SEQ ID NO 172
<211> LENGTH: 32
<212> TYPE: PRT
<213> ORGANISM: Artificial Sequence
<220> FEATURE:
<223> OTHER INFORMATION: framework 3 sequence

<400> SEQUENCE: 172

Arg Phe Thr Ile Ser Arg Asp Asn Ser Lys Asn Thr Leu Tyr Leu Gln
1               5                   10                  15

Met Asn Ser Leu Arg Pro Glu Asp Thr Ala Val Tyr Tyr Cys Thr Ile
                20                  25                  30

<210> SEQ ID NO 173
<211> LENGTH: 32
<212> TYPE: PRT
<213> ORGANISM: Artificial Sequence
<220> FEATURE:
<223> OTHER INFORMATION: framework 3 sequence

<400> SEQUENCE: 173

Arg Phe Thr Ile Ser Ser Ser Asn Ala Lys Asn Thr Val Tyr Leu Gln
1               5                   10                  15

Met Asn Asn Leu Lys Pro Glu Asp Thr Ala Val Tyr Tyr Cys Ala Ala
                20                  25                  30

<210> SEQ ID NO 174
<211> LENGTH: 32
<212> TYPE: PRT
<213> ORGANISM: Artificial Sequence
<220> FEATURE:
<223> OTHER INFORMATION: framework 3 sequence

<400> SEQUENCE: 174

Arg Phe Thr Ile Ser Ser Asp Asn Ser Lys Asn Thr Val Tyr Leu Gln

```
                1               5                   10                  15
Met Asn Ser Leu Arg Pro Glu Asp Thr Ala Val Tyr Tyr Cys Ala Ala
                20                  25                  30

<210> SEQ ID NO 175
<211> LENGTH: 32
<212> TYPE: PRT
<213> ORGANISM: Artificial Sequence
<220> FEATURE:
<223> OTHER INFORMATION: framework 3 sequence

<400> SEQUENCE: 175

Arg Phe Thr Ile Ser Ser Asp Asn Ser Lys Asn Thr Val Tyr Leu Gln
1               5                   10                  15

Met Asn Ser Leu Arg Pro Glu Asp Thr Ala Val Tyr Tyr Cys Ala Ala
                20                  25                  30

<210> SEQ ID NO 176
<211> LENGTH: 32
<212> TYPE: PRT
<213> ORGANISM: Artificial Sequence
<220> FEATURE:
<223> OTHER INFORMATION: framework 3 sequence

<400> SEQUENCE: 176

Arg Phe Thr Ile Ser Ser Asp Asn Ser Lys Asn Thr Val Tyr Leu Gln
1               5                   10                  15

Met Asn Ser Leu Arg Pro Glu Asp Thr Ala Val Tyr Tyr Cys Ala Ala
                20                  25                  30

<210> SEQ ID NO 177
<211> LENGTH: 6
<212> TYPE: PRT
<213> ORGANISM: Artificial Sequence
<220> FEATURE:
<223> OTHER INFORMATION: CDR3 sequence

<400> SEQUENCE: 177

Gly Gly Ser Leu Ser Arg
1               5

<210> SEQ ID NO 178
<211> LENGTH: 15
<212> TYPE: PRT
<213> ORGANISM: Artificial Sequence
<220> FEATURE:
<223> OTHER INFORMATION: CDR3 sequence

<400> SEQUENCE: 178

Thr Pro Ile Glu Arg Leu Gly Leu Asp Ala Tyr Glu Tyr Asp Tyr
1               5                   10                  15

<210> SEQ ID NO 179
<211> LENGTH: 15
<212> TYPE: PRT
<213> ORGANISM: Artificial Sequence
<220> FEATURE:
<223> OTHER INFORMATION: CDR3 sequence

<400> SEQUENCE: 179

Thr Pro Ile Gly Leu Ile Gly Leu Asp Ala Tyr Glu Tyr Asp Tyr
1               5                   10                  15

<210> SEQ ID NO 180
<211> LENGTH: 15
```

```
<212> TYPE: PRT
<213> ORGANISM: Artificial Sequence
<220> FEATURE:
<223> OTHER INFORMATION: CDR3 sequence

<400> SEQUENCE: 180

Thr Pro Ile Gly Leu Ile Gly Leu Asp Ala Tyr Glu Tyr Asp Tyr
1               5                   10                  15

<210> SEQ ID NO 181
<211> LENGTH: 15
<212> TYPE: PRT
<213> ORGANISM: Artificial Sequence
<220> FEATURE:
<223> OTHER INFORMATION: CDR3 sequence

<400> SEQUENCE: 181

Thr Pro Ile Gly Leu Ile Gly Leu Asp Ala Tyr Glu Tyr Asp Tyr
1               5                   10                  15

<210> SEQ ID NO 182
<211> LENGTH: 11
<212> TYPE: PRT
<213> ORGANISM: Artificial Sequence
<220> FEATURE:
<223> OTHER INFORMATION: framework 4 sequence

<400> SEQUENCE: 182

Ser Ser Gln Gly Thr Leu Val Thr Val Ser Ser
1               5                   10

<210> SEQ ID NO 183
<211> LENGTH: 11
<212> TYPE: PRT
<213> ORGANISM: Artificial Sequence
<220> FEATURE:
<223> OTHER INFORMATION: framework 4 sequence

<400> SEQUENCE: 183

Trp Gly Gln Gly Thr Gln Val Thr Val Ser Ser
1               5                   10

<210> SEQ ID NO 184
<211> LENGTH: 11
<212> TYPE: PRT
<213> ORGANISM: Artificial Sequence
<220> FEATURE:
<223> OTHER INFORMATION: framework 4 sequence

<400> SEQUENCE: 184

Trp Gly Gln Gly Thr Leu Val Thr Val Ser Ser
1               5                   10

<210> SEQ ID NO 185
<211> LENGTH: 11
<212> TYPE: PRT
<213> ORGANISM: Artificial Sequence
<220> FEATURE:
<223> OTHER INFORMATION: framework 4 sequence

<400> SEQUENCE: 185

Trp Gly Gln Gly Thr Leu Val Thr Val Ser Ser
1               5                   10

<210> SEQ ID NO 186
<211> LENGTH: 11
<212> TYPE: PRT
```

<213> ORGANISM: Artificial Sequence
<220> FEATURE:
<223> OTHER INFORMATION: framework 4 sequence

<400> SEQUENCE: 186

Trp Gly Gln Gly Thr Leu Val Thr Val Ser Ser
1               5                   10

<210> SEQ ID NO 187
<211> LENGTH: 124
<212> TYPE: PRT
<213> ORGANISM: Artificial Sequence
<220> FEATURE:
<223> OTHER INFORMATION: Nanobody sequence

<400> SEQUENCE: 187

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Glu Arg Glu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asn Ala Lys Asn Thr Val Tyr
65                  70                  75                  80

Leu Gln Met Asn Asn Leu Lys Pro Glu Asp Thr Ala Val Tyr Tyr Cys
            85                  90                  95

Ala Ala Thr Pro Ile Glu Arg Leu Gly Leu Ala Tyr Glu Tyr Asp
            100                 105                 110

Tyr Trp Gly Gln Gly Thr Gln Val Thr Val Ser Ser
        115                 120

<210> SEQ ID NO 188
<211> LENGTH: 250
<212> TYPE: PRT
<213> ORGANISM: Artificial Sequence
<220> FEATURE:
<223> OTHER INFORMATION: Nanobody sequence

<400> SEQUENCE: 188

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45

Leu Cys Ile Asp Ala Ser Asp Ile Thr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
            85                  90                  95

Ala Thr Pro Ile Gly Leu Ser Ser Cys Leu Leu Tyr Asp Tyr
            100                 105                 110

Asp Tyr Trp Gly Gln Gly Thr Leu Val Thr Val Ser Ser Gly Gly Gly
        115                 120                 125

Gly Ser Gly Gly Gly Ser Glu Val Gln Leu Leu Glu Ser Gly Gly Gly
        130                 135                 140

-continued

```
Leu Val Gln Pro Gly Gly Ser Leu Arg Leu Ser Cys Ala Ala Ser Gly
145                 150                 155                 160

Phe Thr Phe Arg Ser Phe Gly Met Ser Trp Val Arg Gln Ala Pro Gly
                165                 170                 175

Lys Gly Pro Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ser Lys Asn Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Ala
                245                 250

<210> SEQ ID NO 189
<211> LENGTH: 30
<212> TYPE: PRT
<213> ORGANISM: Artificial Sequence
<220> FEATURE:
<223> OTHER INFORMATION: framework 1 sequence

<400> SEQUENCE: 189

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp
            20                  25                  30

<210> SEQ ID NO 190
<211> LENGTH: 32
<212> TYPE: PRT
<213> ORGANISM: Artificial Sequence
<220> FEATURE:
<223> OTHER INFORMATION: framework 3 sequence

<400> SEQUENCE: 190

Arg Phe Thr Ile Ser Arg Asp Asn Ser Lys Asn Thr Val Tyr Leu Gln
1               5                   10                  15

Met Asn Ser Leu Arg Pro Glu Asp Thr Ala Val Tyr Tyr Cys Ala Thr
            20                  25                  30
```